United States Patent
Myers et al.

(10) Patent No.: US 6,809,099 B2
(45) Date of Patent: Oct. 26, 2004

(54) SAFRAMYCINS, ANALOGUES AND USES THEREOF

(75) Inventors: Andrew G. Myers, Boston, MA (US); Alleyn T. Plowright, Didsbury (GB); Daniel W. Kung, Salem, CT (US); Brian Lanman, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/011,466

(22) Filed: Nov. 5, 2001

(65) Prior Publication Data

US 2003/0008873 A1 Jan. 9, 2003

Related U.S. Application Data

(60) Provisional application No. 60/245,888, filed on Nov. 3, 2000.

(51) Int. Cl.[7] .................. A61K 31/4985; C07D 471/18
(52) U.S. Cl. ...................................... 514/250; 544/342
(58) Field of Search .......................... 544/342; 514/250

(56) References Cited

U.S. PATENT DOCUMENTS

| | | | |
|---|---|---|---|
| 4,248,863 A | 2/1981 | Arai ........................ | 424/121 |
| 4,372,947 A | 2/1983 | Arai et al. ................ | 424/121 |
| 4,837,149 A | 6/1989 | Arai et al. ................ | 435/119 |
| 5,023,184 A | 6/1991 | Reichenbach et al. ... | 435/252.1 |
| 5,721,362 A | 2/1998 | Corey et al. ............. | 540/466 |
| 5,834,228 A | 11/1998 | Becker et al. ........... | 435/23 |
| 6,124,292 A | 9/2000 | Corey ...................... | 514/250 |
| 6,124,293 A | 9/2000 | Rinehart et al. ......... | 514/250 |
| 6,316,214 B1 | 11/2001 | Rinehart et al. ......... | 435/25 |
| 6,348,467 B1 | 2/2002 | Corey ...................... | 514/250 |
| 6,569,859 B1 | 5/2003 | Corey ...................... | 514/250 |

FOREIGN PATENT DOCUMENTS

| | | |
|---|---|---|
| DE | 28 39 668 | 3/1979 |
| EP | 0 173 649 | 8/1985 |
| EP | 0 233841 | 12/1987 |
| EP | 0 329 606 | 2/1989 |
| JP | 56-135486 | 10/1981 |
| JP | 57-50896 | 3/1982 |
| JP | 61-58593 | 3/1986 |
| JP | 63-2991 | 1/1988 |
| WO | WO 98/12198 | 3/1998 |
| WO | WO 00/18233 | 4/2000 |
| WO | WO 00/69862 | 11/2000 |
| WO | WO 01/19824 | 3/2001 |
| WO | WO 01/53299 | 7/2001 |
| WO | WO 01/87894 | 11/2001 |
| WO | WO 01/87895 | 11/2001 |

OTHER PUBLICATIONS

Arai, et al., "Increased Production of Saframycin A and Isolation of Saframycin S", *the Journal of Antibiotics*, XXXIII (9): 951–960, 1980.

Arai, Directed Biosynthesis of New Saframycin Derivatives with Resting Cells of Streptomyces Lavendulae, *Antimicrobial Agents and Chemotherapy*, 28(1): 5–11, 1985.

Bodian et al., "Inhibition of Fusion–Inducing Conformational Change of Influenza Hemagglutinin by Benzoquinones and Hydroquinones", *Biochemistry*, 32:2967–2978, 1993.

Davidson, B., "Renieramycin G, A New Alkaloid from the Sponge Xestospongia Caycedoi", *Tetrahedron Letters*, 33(26): 3721–3724, 1992.

Eisen, et al., "Binding of the Influenza A Virus to Cell–Surface Receptors: Structures of Five Hemagglutinin–Sialyloligosaccharide Complexes Determined by X–Ray Crystallography", *Virology*, 232:19–31, 1997.

Ekambareswara, et al., "DNA Sequence Selectivities in the Covalent Bonding of Antibiotic Saframycins Mx1, Mx3, A, and S Deduced from MPE-Fe(II) Footprinting and Exonuclease III Stop Assays", *Biochemisry*, 31: 12076–12082, 1992.

Ekambareswara, et al., "Mode of Action of Saframycin Antitumor Antibiotics: Sequence Selectivities in the Covalent Binding of Saframycins A and S to Deoxyribonucleic Acid", *Chem. Res. Toxicol.* 3:262–267, 1990.

Evans, et al., "Stereoselective Synthesis of (±)–Cyanocycline", *J. Am. Chem. Soc.* 108: 2478–2479, 1986.

(List continued on next page.)

*Primary Examiner*—Richard L. Raymond
(74) *Attorney, Agent, or Firm*—Choate, Hall & Stewart; Brenda H. Jarrell; C. Hunter Baker

(57) ABSTRACT

In recognition of the need to develop novel therapeutic agents and efficient methods for the synthesis thereof, the present invention provides novel compounds of general formula (I), and methods for the synthesis thereof.

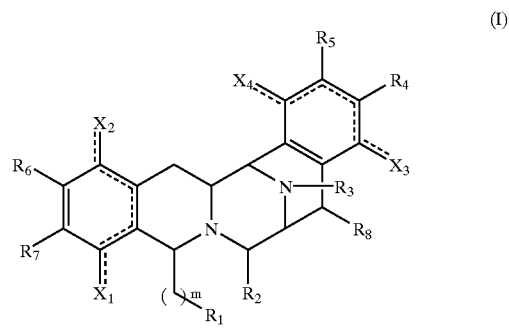

(I)

In another aspect, the present invention provides pharmaceutical compositions comprising a compound of formula (I) and a pharmaceutically acceptable carrier. In yet another aspect, the present invention provides methods for treating cancer comprising administering a therapeutically effective amount of a compound of formula (I) to a subject in need thereof.

33 Claims, 15 Drawing Sheets

OTHER PUBLICATIONS

Flanagan, et al., "Synthetic Studies on Quinocarcin: Total Synthesis of (±)–Quinocarcinamide Via Dipole Cycloaddition of an Azomethine Ylide Generated by NPS Oxidation", *J. Org. Chem.* 60: 6791–6797, 1995.

Fukuyama, et al., "Total Synthesis of (±)–Saframycin A", *J. Am. Chem. Soc.* 112: 3712–3713, 1990.

Fukuyama, et al., "Stereocontrolled Total Sunthesis of (±)–Saframycin B", *J. Am. Chem. Soc.*, 104: 4957–4958, 1982.

Fukuyama, et al., A Stereocontrolled Total Synthesis of (±)–Renieramycin A, *Tetrahedron Letters,* 31(42): 5989–5992, 1990.

Ha, et al., X–Ray Structures of H5 Avian and H9 Swine Influenza Virus Hemagglutinins Bound to Avian and Human Receptor Analogs, *PNAS,* 98(20): 11181–11186, 2001.

Hoffman, et al., "Structure–Based Identification of an Inducer of the Low–pH Conformational Change in the Influenza Virus Hemagglutinin: Irreversible Inhibition of Infectivity", *Journal of Virology,* 71(11): 8808–8820, 1997.

Ishiguro, et al., "Binding of Saframycin A, a Heterocyclic Quinone Anti–Tumor Antibiotic to DNA as Revealed by the Use of the Antibiotic Labeled with [$^{14}$C]Tyrosine of [$^{14}$C] Cyanide", *The Journal of Biological Chemistry,* 256(5): 2162–2167, 1981.

Ishiguro, et al., "Mode of Action of Saframycin A, A Novel Heterocyclic Quinone Antibiotic. Inhibition of RNA Synthesis in Vivo and In Vitro", *Biochemistry,* 17(13): 2545–2550, 1978.

Kaneda, et al., "Antitumor Activity of New Semisynthetic Saframycin Derivatives", *Jpn. J. Cancer Res. (Gann),* 77: 1043–1049, 1986.

Kishi, et al., "Structure–Activity Relationships of Saframycins", *The Journal of Antibiotics,* XXXVII(8): 847–852, 1984.

Kubo, et al., "A Synthesis of the Derivatives of 1,2,3,5,10, 10a–Hexahydrobanz[f]Indolizine–6,9–Dione Having Antifungal Activity as a Simple Model of Saframycin A", *Heterocycles,* 42(1): 195–211, 1996.

Kubo, et al., "Stereoselective Total Synthesis of (±)–Saframycin B", *J. Org. Chem.* 53: 4295–4310, 1988.

Kurihara, et al., "Studies Directed Towards Total Synthesis of Saframycin: I. A Synthesis of Hexahydro–1, 5–Imino–3–Benzazocin–7,10–Dione", *Tetrahedron Letters,* 23(35): 3639–3640, 1982.

Lown, et al., "Molecular Mechanisms of Binding and Single–Strand Scission of Deoxyribonucleic Acid by the Antitumor Antibiotics Saframycins A and C", *Biochemistry,* 21(3): 419–428, 1982.

Luo, et al., "Molecular Mechanism Underlying the Action of a Novel Fusion Inhibitor of Influenza A Virus",*Journal of Virology,* 71(5): 4062–4070, 1997.

Martinez, et al., "Enantioselective Synthesis of Saframycin A and Evaluation of Antitumor Activity Relative to Ecteinascidin/Saframycin Hybrids", *Organic Letters,* 1(1): 75–77, 1999.

Martinez, et al., "Phthalascidin, A Synthetic Antitumor Agent with Potency and Mode of Action Comparable to Ecteinascidin 743", *Proc. Natl. Acad Sci. USA,* 96: 3496–3501, 1999.

Matrosovich, et al., "The Surface Glycoproteins of H5 Influenza Viruses Isolated from Humans, Chickens, and Wild Aquatic Birds Have Distinguishable Properties",*Journal of Virology,* 73(2): 1146–1155, 1999.

Mikami, et al., "Biosynthetic Studies on Saframycin A, A Quinone Antitumor Antibiotic Produced by Streptomyces Lavendulae", *The Journal of Biological Chemistry,* 260(1): 344–348, 1985.

Myers, et al., "A Concise, Stereocontrolled Synthesis of (–)—Saframycin A by the Directed Condensation of α–Amino Aldehyde Precursors", *Journal of the American Chemical Society,* 121(46): 10828–10829, 1999.

Myers, et al., "Synthesis and Evaluation of Bishydroquinone Derivatives of (–)—Saframycin A: Indentification of a Versatile Molecular Template Imparting Potent Antiproliferative Activity", *J. Am. Chem. Soc.* 123:5114–5115, 2001.

Myers, et al., "Synthesis of Highly Epimerizable N–Protected α–Amino Aldehydes of High Enantiomeric Excess", *Tetrahedron Letters,* 41: 1359–1362, 2000.

Myers, et al., "Greatly Simplified Procedures for the Synthesis of α–Amino Acids by the Direct Alkylation of Pseudoephedrine Glycinamide Hydrate", *J. Org. Chem.* 64: 3322–3327, 1999.

Myers, et al., "One–Step Construction of the Pentacyclic Skeleton of Saframycin A from a "Trimer" of a α–Amino Aldehydes", *Organic Letters,* 2(19): 3019–3022, 2000.

Myers, et al., "Preparation of Chiral, C–Protected α–Amino Aldehydes of High Optical Purity and Their Use as Condensation Components in a Linear Synthesis Strategy", *J. Am Chem. Soc.* 121:8401–8402, 1999.

Myers, et al., "Synthesis of C–Protected α–Amino Aldeydes of High Enantiomeric Excess from Highly Epimerizable N–Protected α–Amino Aldehydes", *Organic Letters,* 2(21): 3337–3340, 2000.

Myers, et al., "Asymmetric Synthesis of Chrial Organofluorine Compounds: Use of Nonracemic Fluoroiodoacetic Acid as a Practical Electrophile and Its Application to the Synthesis of Monofluoro Hydroxyethylene Dipeptide Isosteres within a Novel Series of HIV ProteaseInhibitors",*Journal of the American Chemical Society,* 123(30): 7207–7219, 2001.

Nobusawa, et al., "Comparison of Complete Amino Acid Sequences and Receptor–Binding Properties Among 13 Serotypes of Hemagglutinins of Influenza A Viruses", *Virology,* 182: 475–485, 1991.

Parker, et al., "Approaches to the Isoquinoline Quinone Antibiotics. 1. Additions of an Amino Acid Derivative to Quinone Monoacetal", *Tetrahedron Letters,* 25(33): 3543–3546, 1984.

Parker, et al., "Isoquinoline Quinones. Preparation of Aframycin Intermediates and a Total Synthesis of Mimosamycin", *J. Org. Chem.* 53:2847–2850, 1988.

Podhorez, David., "Stepwise Approach to the 2,3–Dihydroimidazo[1,2–a]Pyridine and 5–Oxo–1,2,3,5–Tetrahydroimidazo[1,2–a] Pyridine Ring Systems",*J. Heterocyclic Chem.* 28: 971, 1991.

Pospiech, et al., "Two Multifunctional Peptide Synthetases and an O–Methyltransferase are Involved in the Biosynthesis of the DNA–Binding Antibiotic and Antitumour Agent Saframycin Mx1 from Myxococcus Xanthus", *Microbiology,* 142: 741–746, 1996.

Pospiech, et al., "A New Myxococcus Xanthus Gene Cluster for the Biosynthesis of the Antibiotic Saframycin Mx1 Encoding a Peptide Synthetase", *Microbiology,* 141:1793–1803, 1995.

Rosenthal, et al., "Structure of the Haemagglutinin–Esterase–Fusion Glycoprotein of Influenza C Virus", *Nature,* 396:92–96, 1998.

Saito, et al., "Synthesis of Saframycins VIII. 1. Synthesis of the ABC Ring of Safracins", *Chem, Pharm. Bull.* 40(10): 2620–2626, 1992.

Saito, et al., "Synthesis of Saframycins. 3. Preparation of a Key Tricyclic Lactam Intermediate to Saframycin A", *J. Org. Chem.,* 54: 5391–5395, 1989.

Saito, et al., "Synthesis of Saframycins, VII. The Synthesis of Novel Renieramycin Congeners", *Heterocycles,* 32(6):1203–1214, 1991.

Saito, et al., "Synthesis of Saframycins. XII. 1 Total Synthesis of (–)–N–Acetylsaframycin Mx 2 and its epi–(+)–Enantiomer", *Tetrahedrons,* 51(30): 8231–8246, 1995.

Saito, et al., "Synthesis of Saframycins. X. 1) Transformation of (–) Saframycin A to (–)–Saframycin Mx Type Compound with the Structure Proposed for Saframycin E", *Chem. Pharm. Gull.* 43(5): 777–782, 1995.

Saito, et al., "Synthesis of Saframycins. V. Selenium Oxide Oxidation of Hexahydro–1,5–Imino–3–Benzazocin–7, 10–Dione; A Useful Method for Constructing Saframycins C and D From Saframycin B",*Tetrahedron,* 46(23): 7711–7728, 1990.

Sauter, et al., "Binding of Influenza Virus Hemagglutinin to Analogs of Its Cell–Surface Receptor, Sialic Acid: Analysis by Proton Nuclear Magnetic Resonance Spectroscopy and X–Ray Crystallography", *Biochemistry,* 31: 9609–9621, 1992.

Staschke, et al., "Inhibition of Influenza Virus Hemagglutinin–Mediated Membrane Fusion by a Compound Related to Podocarpic Acid" *Virology,* 248:264–274, 1998.

Shawe, et al., "Saframycin Synthetic Studies", *Tetrahedron,* 47(30): 5643–5666, 1991.

Webster, et al., "Evolution and Ecology of Influenza A Viruses", *Microbiological Reviews,* 56(1): 152–179, 1992.

Weis, et al., "Structure of the Influenza Virus Haemagglutinin Complexed with its Receptor, Sialic Acid", *Nature,* 333(2): 426–431, 1988.

Winquist, et al., "Neuraminidase inhibitors for Treatment of Influenza A and B Infections", *MMWR Morbidity and Mortality Weekly Report/Recommendations and Reports,* 48(RR14): 1–11, 1999.

Zhou, et al., "A Novel Face Specific Mannich Closure Providing Access to the Saframycin–Ecteinascidin Series of Piperazine Based Alkaloids", *Tetrahedron Letters,* 41:2043–2046, 2000.

Zhou, et al., "Synthetic Explorations in the Saframycin–Ecteinascidin Series: Construction of Major Chiral Subunits Through Catalytic Asymmetric Induction", *Tetrahedron Letters,* 41:2039–2042, 2000.

SAFRAMYCINS, ANALOGUES AND USES THEREOF

PRIORITY INFORMATION

The present application claims priority under 35 U.S.C. § 119(e) to provisional application No. 60/245,888, filed Nov. 3, 2000, entitled "Synthesis of Saframycins, Analogues and Uses Thereof", the entire contents of which are hereby incorporated by reference.

GOVERNMENT SUPPORT

This invention was made in part with a grant from the National Institutes of Health (Grant Number: 7 R37 CA47148-12). Therefore, the government has certain rights in the invention.

BACKGROUND OF THE INVENTION

The discovery of novel therapeutic agents has traditionally relied on the identification of biologically active secondary metabolites of microorganisms. These compounds have provided a rich source of natural products that have either been utilized directly as effective therapeutic agents, or have provided leads for novel therapeutic agents to be developed through synthetic techniques.

One disease for which the development of novel therapeutics is particularly important is cancer, which not only has eluded a "cure", but is also one of the leading disease-related causes of death of the human population. Examples of anticancer agents that have been identified from or developed from natural sources include paclitaxel, mitomycin C, and adriamycin to name a few. One drawback to the use of secondary metabolites from natural resources, however, has been that these agents are generally only present in minute quantities. Fortunately, in an effort to make these agents more available for use, and to enable further pharmaceutical research, synthetic chemists have developed elegant and efficient synthetic strategies to enable the production of either the natural products themselves, or useful derivatives thereof.

Although these therapeutic agents, and others developed from natural sources, through the efforts of synthetic chemistry, are currently in use for the treatment of individuals having cancer, many of these agents, as well as other common treatments such as surgery and radiation, are often unselective for tumor cells and/or are so toxic as to render the individual significantly immunocompromised. Thus, although many strides have been made in the development of novel treatments, there remains a need for the identification of additional therapeutics, preferably those that are more selective and less toxic.

One particular family of natural products that has generated significant interest is the saframycins. The saframycins are a class of antibiotics with activity against gram-positive bacteria and also against several kinds of tumor. Specifically, several saframycin analogues have been isolated and characterized in recent years (see, DE 2839668; U.S. Pat. Nos. 4,248,863; 4,372,947; 5,023,184; 4,837,149; and EP 329606). For example saframycins A–H, R and S have been isolated from the culture broths of *Streptomyces lavendulae*, and saframycins $M_{x1}$ and $M_{x2}$, have been isolated from the culture broths of the myxobacterium, *Myxococcus xanthus*, each of the saframycins varying in the oxidation state of the ring system and in substitution of the core structure (see, for example, Saito et al. *Chem. Pharm. Bull.* 1995, 43, 777). It has been suggested that certain saframycins, namely A and C exhibit extreme cytotoxicity toward culture cells and toward several experimental tumors including leukemias L1210 and P388 and Ehrlich carcinoma. Specifically, saframycin A has been shown to block RNA synthesis in cultured cells, and it has been suggested that saframycins A and C exhibit this potency because of their ability to bind and cleave DNA (for a discussion of the biological activity of saframycins see, for example, Lown et al. *Biochemistry* 1982, 21, 419; Ishiguro et al. *Biochemistry* 1978, 17, 2545; Rao et al. *Chem. Res. Toxicol* 1990, 3, 262; Ishiguro et al *J Biol. Chem.* 1981, 256, 2162). Although this class of natural products has shown promising biological activity, there have been few investigations into the synthesis and development of novel analogues of this family of natural products (see, EP 233841; EP 173649; Fukuyama et al. *J. Am. Chem. Soc.* 1982, 104, 4957–4958; Kubo et al. *J. Org. Chem.* 1988, 53, 4295–4310; Fukuyama et al. *J. Am. Chem. Soc.* 1990, 112, 3712–3713).

Clearly, there remains a need to further investigate the potential of this class of natural products, and analogues thereof, to develop novel, more potent and more selective therapeutics. Additionally, because of the complexity of the structure of this class of natural products, there also remains a need to develop additional synthetic techniques to rapidly access novel compounds based upon the general core structure of the saframycins, and other related compounds.

SUMMARY OF THE INVENTION

In recognition of the need to develop novel therapeutic agents and efficient methods for the synthesis thereof, the present invention provides novel compounds of general formula (I), and methods for the synthesis thereof.

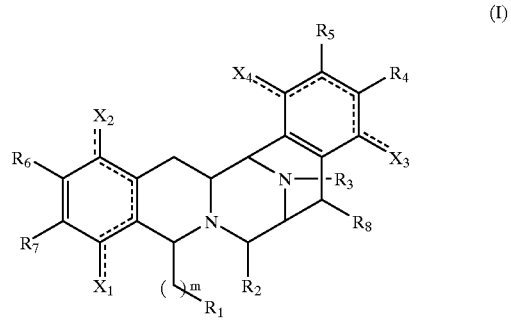

(I)

The present invention additionally provides pharmaceutical compositions comprising a compound of formula (I) and a pharmaceutically acceptable carrier. In yet another aspect, the present invention provides methods for treating cancer comprising administering a therapeutically effective amount of a compound of formula (I) to a subject in need thereof.

DETAILED DESCRIPTION OF THE INVENTION

Figure 1:
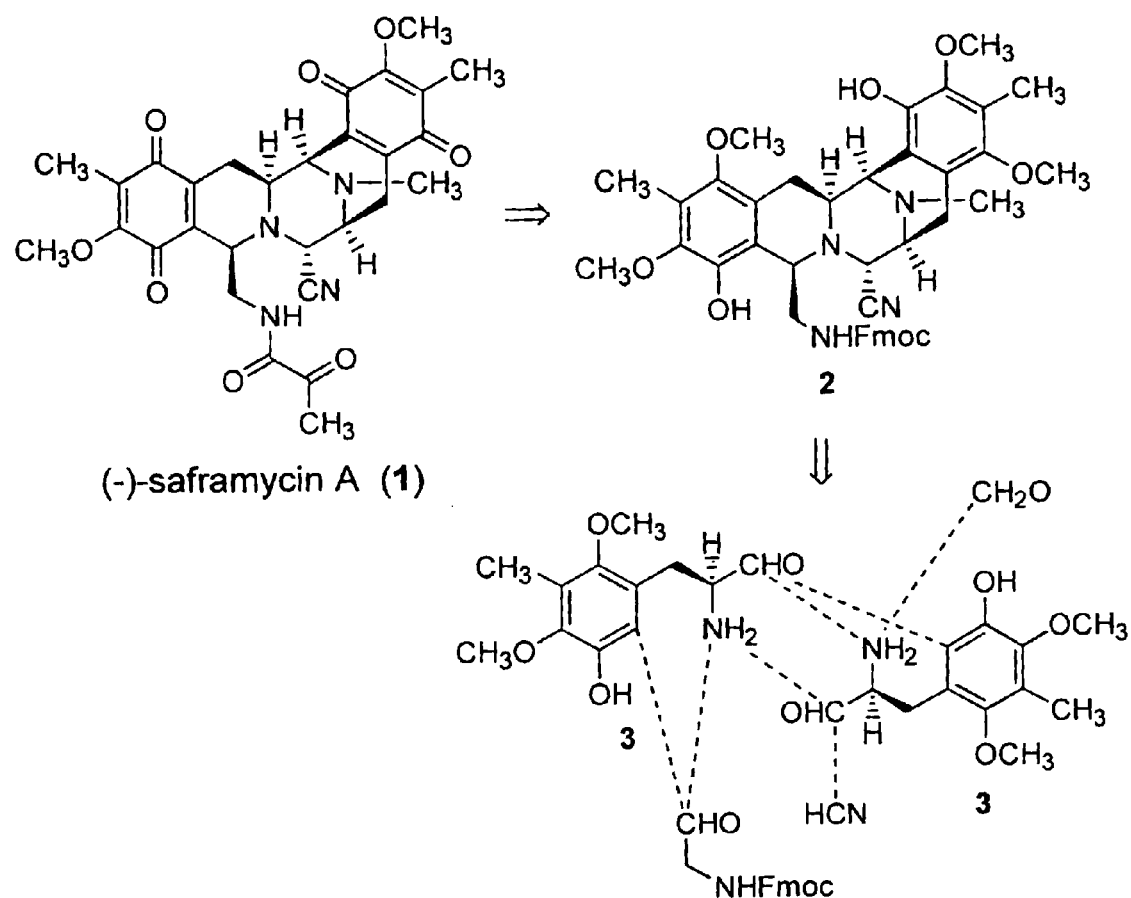
FIG. 1 depicts a retrosynthetic analysis of saframycin A.

In recognition of the need to develop novel anticancer therapeutics and more efficient processes for the preparation of such therapeutics, the present invention provides novel compounds and methods for the preparation thereof. In general, in one aspect, the present invention provides novel analogues of the saframycin antitumor antibiotics having anticancer activity. In yet another aspect, the present invention provides efficient methods for the generation of these compounds, and alkaloids in general, involving the directed condensation of substituted aldehyde precursors. Significantly, the methodology provided by the present invention enables the efficient production of these novel compounds in significant quantities for therapeutic use.

1) General Description of Compounds of the Invention

As mentioned above, in one aspect of the invention, novel analogues of the saframycin antitumor antibiotics are provided. In general, compounds having the structure (I) are provided:

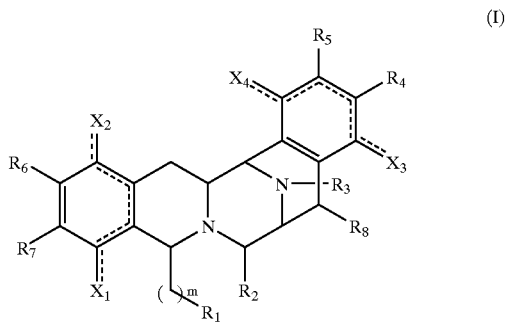

(I)

wherein R$_1$ is NR$_A$R$_B$, —OR$_A$, —SR$_A$, —C(=O)R$_A$, —C(=S)R$_A$, —S(O)$_2$R$_A$, or an aliphatic, heteroaliphatic, aryl, heteroaryl, (aliphatic)aryl, (aliphatic)heteroaryl, (heteroaliphatic)aryl, or (heteroaliphatic)heteroaryl moiety, wherein each occurrence of R$_A$ and R$_B$ is independently hydrogen, —(C=O)R$_C$, —NHR$_C$, —(SO$_2$)R$_C$, —OR$_C$, or an aliphatic, heteroaliphatic, aryl, or heteroaryl moiety, or R$_A$ and R$_B$, when taken together form an aryl, heteroaryl, cycloaliphatic, or cycloheteroaliphatic moiety, wherein each occurrence of R$_C$ is independently hydrogen, —OR$_D$, —SR$_D$, —NHR$_D$, —(C=O)R$_D$, or an aliphatic, heteroaliphatic, aryl, or heteroaryl moiety, wherein each occurrence of R$_D$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;

wherein R$_2$ is hydrogen, —OR$_E$, =O, —C(=O)R$_E$, —CO$_2$R$_E$, —CN, —SCN, halogen, —SR$_E$, —SOR$_E$, —SO$_2$R$_E$, —NO$_2$, —N(R$_E$)$_2$, —NHC(O)R$_E$, or an aliphatic, heteroaliphatic, aryl, or heteroaryl moiety, wherein each occurrence of R$_E$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;

wherein R$_3$ is hydrogen, a nitrogen protecting group, —COOR$_F$, —COR$_F$, —CN, or an aliphatic, heteroaliphatic, aryl, or heteroaryl moiety, wherein each occurrence of R$_F$ is independently hydrogen, a protecting group, or an aliphatic, heteroaliphatic, aryl, heteroaryl, alkoxy, aryloxy, alkylthio, arylthio, heteroaryloxy, or heteroarylthio moiety;

wherein R$_4$ and R$_6$ are each independently hydrogen, or an aliphatic, heteroaliphatic, aryl, heteroaryl, acyl, alkoxy, aryloxy, alkylthio, arylthio, heteroaryloxy, or heteroarylthio moiety;

wherein R$_5$ and R$_7$ are each independently hydrogen, —OR$_G$, —C(=O)R$_G$, —CO$_2$R$_G$, —CN, —SCN, halogen, —SR$_G$, —SOR$_G$, —SO$_2$R$_G$, —NO$_2$, —N(R$_G$)$_2$, —NHC(O)R$_G$, or an aliphatic, heteroaliphatic, aryl or heteroaryl moiety, wherein each occurrence of R$_G$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;

wherein R$_8$ is hydrogen, alkyl, —OH, protected hydroxyl, =O, —CN, —SCN, halogen, —SH, protected thio, alkoxy, thioalkyl, amino, protected amino, or alkylamino;

wherein m is 0–5;

wherein $X_1$, $X_2$, $X_3$ and $X_4$ are each independently hydrogen, —$OR_H$, =O, —C(=O)$R_H$, —$CO_2R_H$, —CN, —SCN, halogen, —$SR_H$, —$SOR_H$, —$SO_2R_H$, —$NO_2$, —$N(R_H)_2$, —NHC(O)$R_H$, or an aliphatic, heteroaliphatic, aryl, or heteroaryl moiety, wherein each occurrence of $R_H$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;

whereby if at least either $X_1$ and $X_2$ or $X_3$ and $X_4$ are doubly bonded to the 6-membered ring, then the dotted bonds in either or both of the 6-membered rings represent two single bonds and one double bond, and a quinone moiety is generated, or if at least either $X_1$ and $X_2$ or $X_3$ and $X_4$ are singly bonded to the 6-membered ring, then the dotted bonds in either or both of the 6-membered rings represent two double bonds and one single bond, and a hydroquinone moiety is generated;

whereby each of the foregoing aliphatic, heteroaliphatic and alkyl moieties may independently be substituted or unsubstituted, branched or unbranched, or cyclic or acyclic, and each of the foregoing aryl or heteroaryl moieties may independently be substituted or unsubstituted; and pharmaceutically acceptable derivatives thereof.

In certain embodiments of the invention, compounds of formula (I) have the following stereochemistry and structure as shown in formula (Ia):

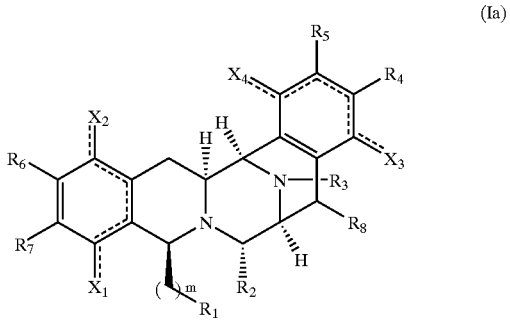

(Ia)

It will be appreciated that, in certain embodiments of the compounds as described generally above and in classes and subclasses herein certain naturally occurring saframycins and other related natural products are excluded including:

saframycins A, B, C, D, E, F, G, H, R, $S_1$, $Y_3$, $Y_{d1}$, $A_{d1}$, $Y_{d2}$, $Y_{2b}$, $Y_{2b-d}$, $AH_2$, $AH_2Ac$, $AH_1$, $AH_1Ac$, $AR_3$, $M_{x-1}$ and $M_{x-2}$; safracins A and B; reineramycins A, B, D, E, and F; and xestomycin.

In certain other embodiments, for compounds as described above and in subclasses herein, when m is 1, $R_1$ excludes any one or more of the following groups: —NH(protecting group), —$NH_2$, —NHCOCOMe, —NHCOC(Me)(OMe)(OMe), —NHCOCH($NH_2$)$CH_3$, —NHCOCH(NH(acyl))$CH_3$ —NHCOCH($NH_2$)AC, or NHCOCH(NHCOOBn)(Me); —O(C=O)C($CH_3$)=C($CH_3$)H; —OH, —O(protecting group), —O(COCH$_3$), —O(C=O)$CH_2CH_3$.

In still other embodiments, for certain of the compounds as described above and herein, when m is 1; when $X_1$, $X_2$, $X_3$ and $X_4$ are each =O; when $R_2$ is —CN or —OH; when $R_4$ and $R_6$ are each —$CH_3$; when $R_5$ and $R_7$ are each —$OCH_3$; when $R_8$ is H; and $R_1$ is —NH(C=O)$R_C$, then $R_C$ is not —CH(NR$_W$R$_Y$)(CH$_2$R$_Z$) where R$_W$ and R$_Y$ are each independently hydrogen or $C_{1-7}$ alkyl, aryl($C_{1-4}$)alkyl, ($C_{1-4}$)alkylaryl, a substituted sulfonyl (—S(O)$_2$—) group, or a substituted acyl group, and where R$_Z$ is hydrogen or $C_{1-4}$ alkyl.

In yet other embodiments, for certain of the compounds as described above and herein, when m is 1; when $X_1$, $X_2$, $X_3$ and $X_4$ are each =O; when $R_2$ is —CN; when $R_4$ and $R_6$ are each —$CH_3$; when $R_5$ and $R_7$ are each —$OCH_3$; when $R_8$ is H; and $R_1$ is —NH(C=O)$R_C$, then $R_C$ is not —C(OH)(Me)CH$_2$(C=O)Me.

In still other embodiments, for certain of the compounds as described above and herein, when m is 1 and when $R_2$ is H; and $R_1$ is —NH(C=O)$R_C$, then $R_C$ is not —CH(Me)NH(C=O)O(CH$_2$)Ph.

In yet other embodiments, for certain of the compounds as described above and herein, when m is 0; $R_2$ is H; $X_3$ is H; and $R_1$ is —C(=O)$R_A$, then $R_A$ is not —O(alkyl). Alternatively, in certain other embodiments, when $R_2$ is H; m is 1; and $R_1$ is —$OR_A$, then $R_A$ is not —C(=O)$R_C$, or S(O)$_2R_C$, wherein $R_C$ is an alkyl moiety.

2) Featured Classes of Compounds

It will be appreciated that for compounds as generally described above, certain classes of compounds are of special interest. For example, one class of compounds of special interest includes those compounds of the invention as described above and in certain subclasses herein, wherein the compounds have the general structure (II):

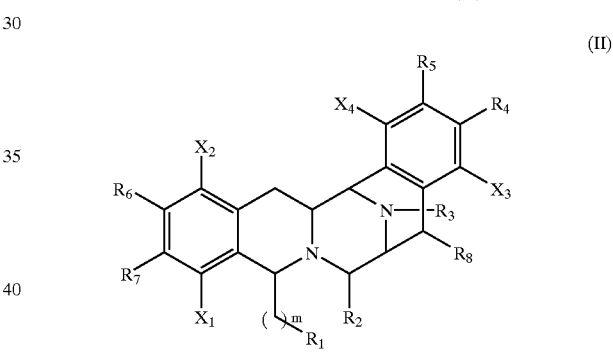

(II)

wherein $R_1$–$R_8$, $X_1$–$X_4$ and m are as defined above and in subclasses herein.

Another class of compounds of special interest includes those compounds of the invention as described above and in certain subclasses herein, wherein the compounds have the general structure (III):

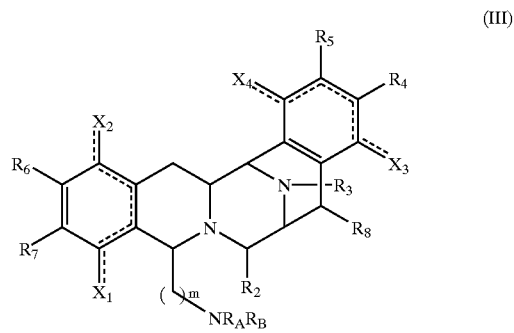

(III)

wherein $R_2$–$R_8$, $X_1$–$X_4$, m, $R_A$ and $R_B$ are as defined above and in subclasses herein.

Yet another class of compounds of special interest includes those compounds of the invention as described above and in certain subclasses herein, wherein the compounds have the general structure (IV):

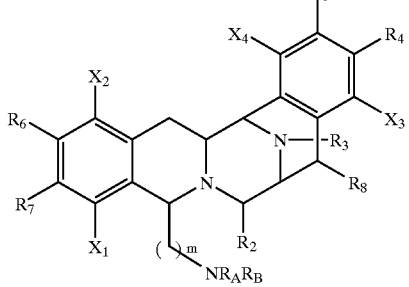

(IV)

wherein $R_2$–$R_8$, $X_1$–$X_4$, m, $R_A$ and $R_B$ are as defined above and in subclasses herein.

Yet another class of compounds of special interest includes those compounds of the invention as described above and in certain subclasses herein, wherein the compounds have the general structure (V):

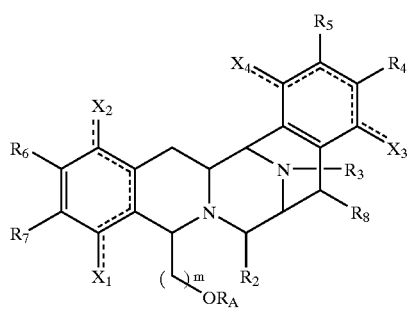

(V)

wherein $R_2$–$R_8$, $X_1$–$X_4$, m, and $R_A$ are as defined above and in subclasses herein.

Yet another class of compounds of special interest includes those compounds of the invention as described above and in certain subclasses herein, wherein the compounds have the general structure (VI):

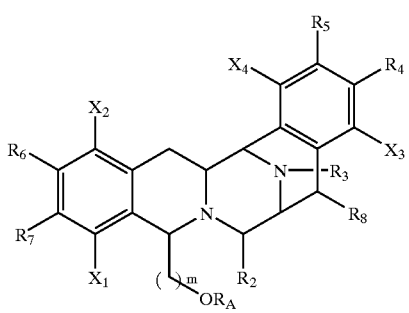

(VI)

wherein $R_2$–$R_8$, $X_1$–$X_4$, m, and $R_A$ are as defined above and in subclasses herein.

Yet another class of compounds of special interest includes those compounds of the invention as described above and in certain subclasses herein, wherein the compounds have the general structure (VII):

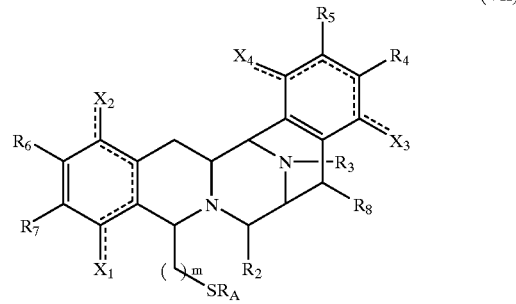

(VII)

wherein $R_2$–$R_8$, $X_1$–$X_4$, m, and $R_A$ are as defined above and in subclasses herein.

Yet another class of compounds of special interest includes those compounds of the invention as described above and in certain subclasses herein, wherein the compounds have the general structure (VIII):

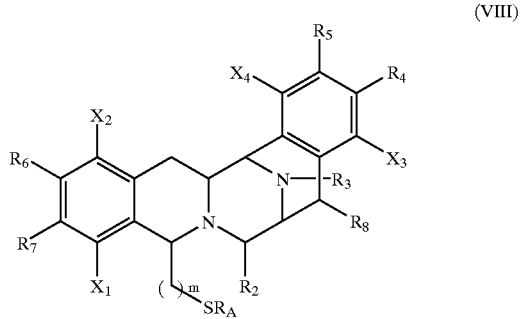

(VIII)

wherein $R_2$–$R_8$, $X_1$–$X_4$, m, and $R_A$ are as defined above and in subclasses herein.

Still another class of compounds of special interest includes those compounds of the invention as described above and in certain subclasses herein, wherein the compounds have the general structure (IX):

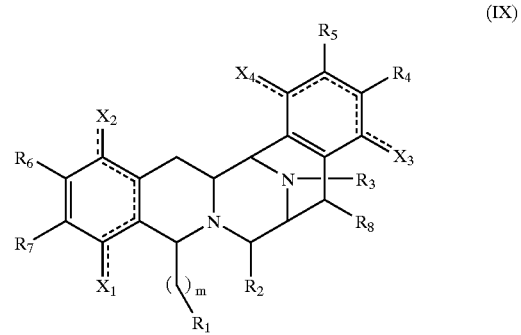

(IX)

wherein $R_2$–$R_8$ $X_1$–$X_4$, and m are as defined above and in subclasses herein, and wherein $R_1$ is a substituted or unsubstituted, cyclic or acyclic, branched or unbranched aliphatic or heteroaliphatic moiety, or is a substituted or unsubstituted aryl or heteroaryl moiety.

Yet another class of compounds of special interest includes those compounds of the invention as described above and in certain subclasses herein, wherein the compounds have the general structure (X):

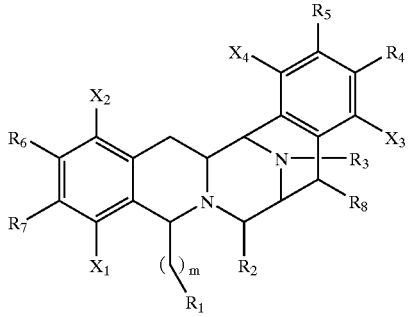

wherein $R_2$–$R_8$, $X_1$–$X_4$, and m are as defined above and in subclasses herein, and wherein $R_1$ is a substituted or unsubstituted, cyclic or acyclic, branched or unbranched aliphatic or heteroaliphatic moiety, or is a substituted or unsubstituted aryl or heteroaryl moiety.

The following compounds are illustrative of certain of the compounds described generally and in classes and subclasses herein:

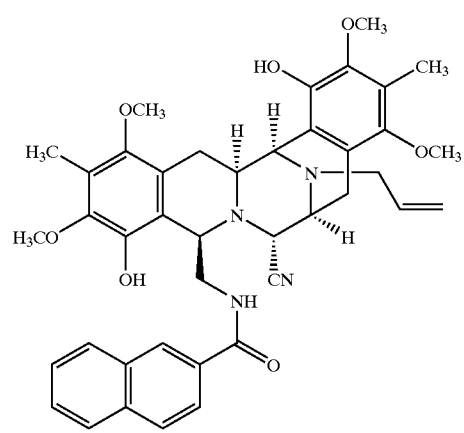

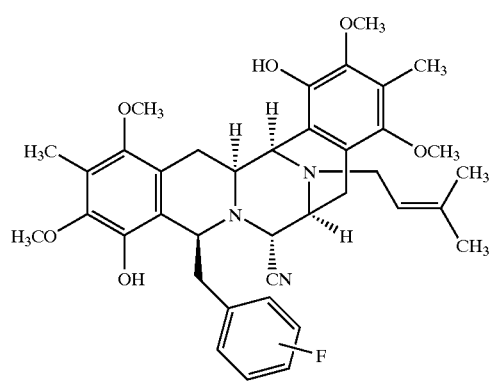

-continued

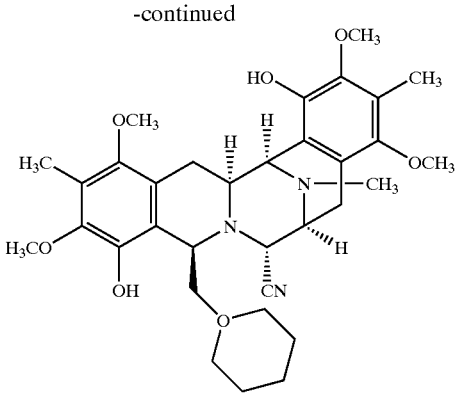

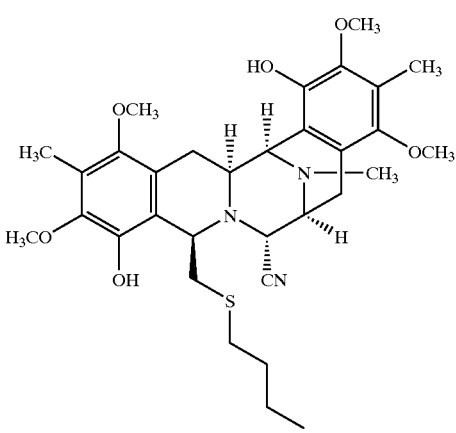

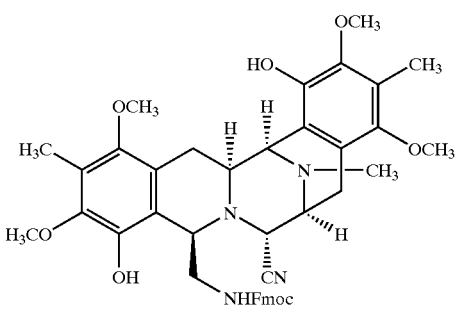

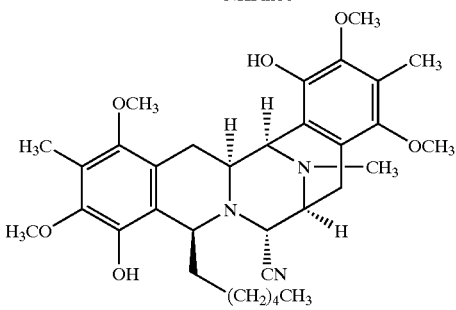

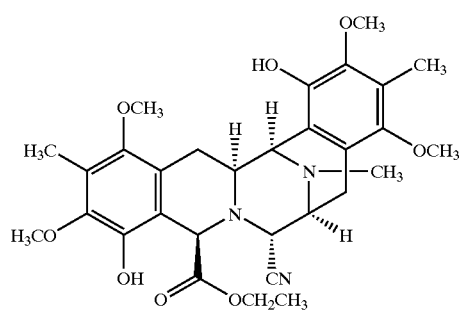
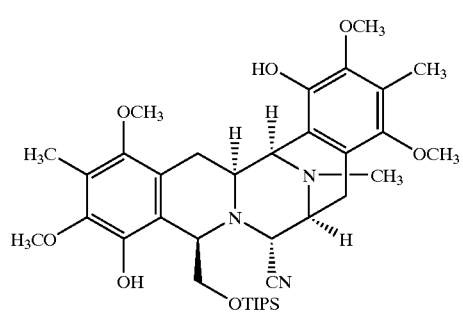
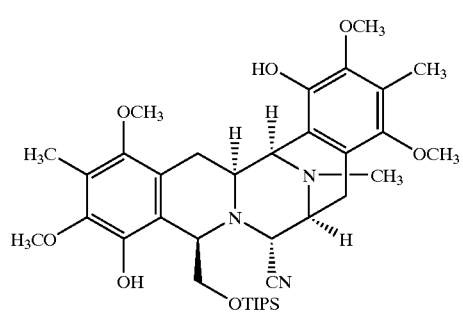
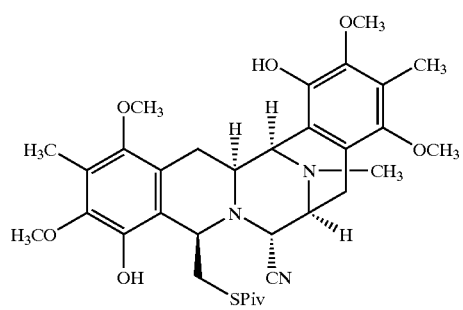
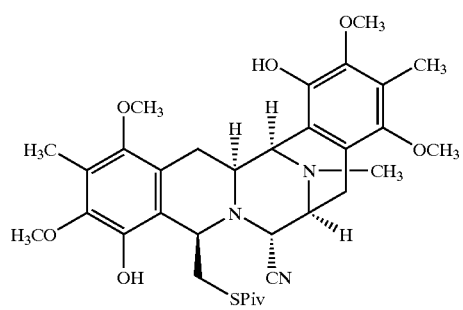
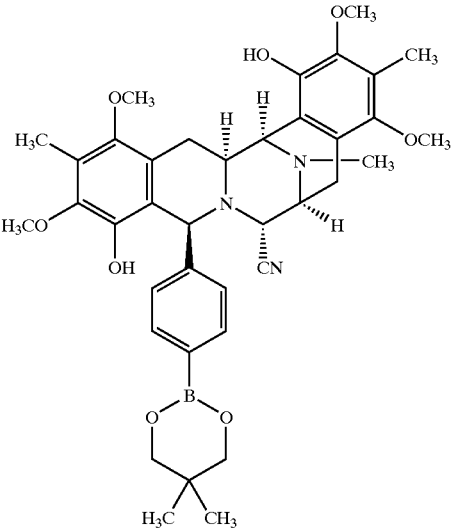
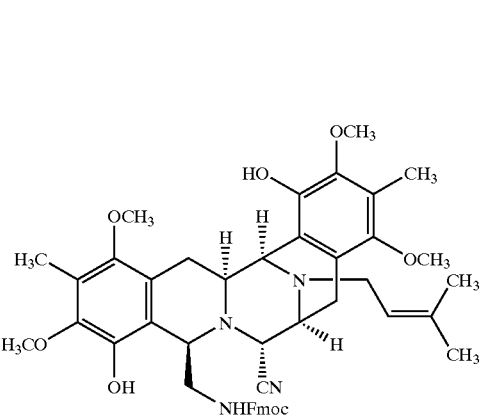
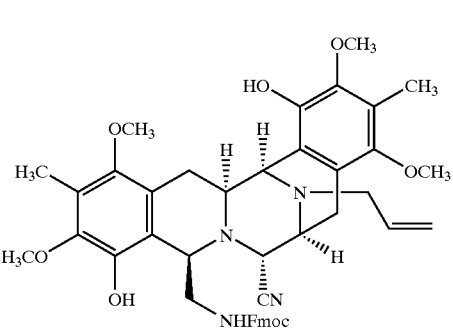
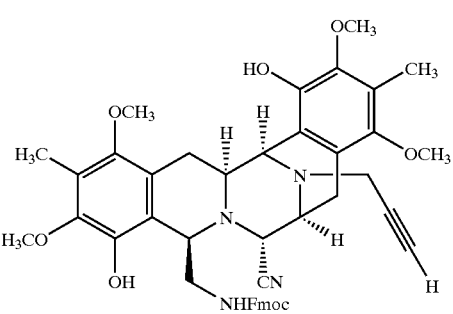

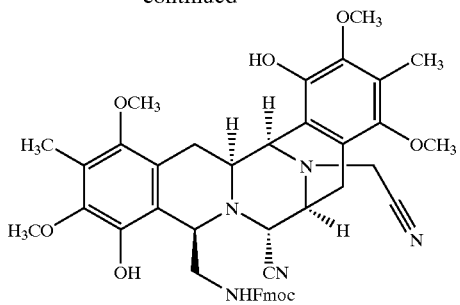

A number of important subclasses of each of the foregoing classes deserve separate mention; these subclasses include subclasses of each of the foregoing classes in which:

i) compounds of the invention as described above and herein are enantiopure;

ii) compounds as described above and in subclasses herein, wherein when m is 1, $R_1$ excludes any one or more of the following groups: —NH(protecting group), —NH$_2$, —NHCOCOMe, —NHCOC(Me)(OMe)(OMe), —NHCOCH(NH$_2$)CH$_3$, —NHCOCH(NH(acyl))CH$_3$—NHCOCH(NH$_2$)Ac, or NHCOCH(NHCOOBn)(Me); —O(C=O)C(CH$_3$)=C(CH$_3$)H; —OH, —O(protecting group), —O(COCH$_3$), —O(C=O)CH$_2$CH$_3$;

iii) compounds as described above and in subclasses herein, wherein when m is 1; when $X_1$, $X_2$, $X_3$ and $X_4$ are each =O; when $R_2$ is —CN or —OH; when $R_4$ and $R_6$ are each —CH$_3$; when $R_5$ and $R_7$ are each —OCH$_3$; when $R_8$ is H; and $R_1$ is —NH(C=O)$R_C$, then $R_C$ is not —CH(NR$_W$R$_Y$)(CH$_2$R$_Z$) where $R_W$ and $R_Y$ are each independently hydrogen or C$_{1-7}$ alkyl, aryl(C$_{1-4}$)alkyl, (C$_{1-4}$)alkylaryl, a substituted sulfonyl (—S(O)$_2$—) group, or a substituted acyl group, and where $R_Z$ is hydrogen or C$_{1-4}$ alkyl;

iv) compounds as described above and in subclasses herein, wherein when m is 1; when $X_1$, $X_2$, $X_3$ and $X_4$ are each =O; when $R_2$ is —CN; when $R_4$ and $R_6$ are each —CH$_3$; when $R_5$ and $R_7$ are each —OCH$_3$; when $R_8$ is H; and $R_1$ is —NH(C=O)$R_C$, then $R_C$ is not —C(OH)(Me)CH$_2$(C=O)Me;

v) compounds as described above and in subclasses herein, wherein when m is 1 and when $R_2$ is H; and $R_1$ is —NH(C=O)$R_C$, then $R_C$ is not —CH(Me)NH(C=O)O(CH$_2$)Ph;

vi) compounds as described above and in subclasses herein, wherein when m is 0; $R_2$ is H; $X_3$ is H; and $R_1$ is —C(=O)$R_A$, then $R_A$ is not —O(alkyl). Alternatively, in certain other embodiments, when $R_2$ is H; m is 1; and $R_1$ is —OR$_A$, then $R_A$ is not —C(=O)$R_C$, or S(O)$_2R_C$, wherein $R_C$ is an alkyl moiety.

vii) m is 0 or 1;

viii) $R_2$ is CN, —SCN, =O, OH, protected hydroxyl, H, or alkoxy;

ix) $R_2$ is hydrogen, hydroxyl, —CN or —SCN;

x) $R_3$ is hydrogen, a nitrogen protecting group, —CN, —CH$_2$CN, aliphatic or aryl;

xi) $R_4$ and $R_6$ are each alkyl;

xii) $R_5$ and $R_7$ are each alkyloxy or thioalkyl;

xiii) $R_8$ is hydrogen, alkyl, —OH, protected hydroxyl, =O, —CN, —SCN, halogen, —SH, protected thio, alkoxy, thioalkyl, amino, protected amino, or alkylamino;

xiv) $R_8$ is hydrogen;

xv) $X_1$, $X_2$, $X_3$, and $X_4$ are each independently alkoxy, —OH, protected hydroxyl, or =O;

xvi) $R_2$ is CN, —SCN, =O, OH, protected hydroxyl, H, or alkoxy; $R_3$ is hydrogen, a nitrogen protecting group, —CN, —CH$_2$CN, aliphatic, or aryl; $R_4$ and $R_6$ are each alkyl; $R_5$ and $R_7$ are each alkyloxy or thioalkyl; $R_8$ is hydrogen, alkyl, —OH, protected hydroxyl, =O, CN, halogen, SH, alkoxy, thioalkyl, amino, or alkylamino; and $X_1$, $X_2$, $X_3$, and $X_4$ are each independently alkoxy, OH or =O;

xvii) $R_2$ is —CN, —SCN, —OH, protected hydroxyl, H, or alkoxy; $R_3$ is hydrogen, a nitrogen protecting group, aliphatic, or aryl; $R_4$ and $R_6$ are each alkyl; $R_5$ and $R_7$ are each alkyloxy or thioalkyl; $X_1$ and $X_4$ are each —OH; $R_8$ is hydrogen, alkyl, OH, protected hydroxyl, =O, CN, halogen, SH, alkoxy, thioalkyl, amino, or alkylamino; and $X_2$ and $X_3$ are each alkyloxy or thioalkyl;

xviii) $X_1$ is OH, $X_2$ is OCH$_3$, $X_3$ is OCH$_3$, $X_4$ is OH, $R_2$ is CN, H or OH, $R_3$ is Me, $R_4$ is CH$_3$, $R_5$ is OCH$_3$, $R_6$ is CH$_3$, $R_7$ is OCH$_3$, and $R_8$ is H;

xix) $R_1$ is OR$_A$, SR$_A$, or NR$_A$R$_B$, wherein $R_A$ and $R_B$ are each independently hydrogen, —(C=O)R$_C$ or an aliphatic, heteroaliphatic, aryl, or heteroaryl moiety, wherein $R_C$ is —(C=O)R$_D$, or an aliphatic, heteroaliphatic, aryl or heteroaryl moiety, and wherein $R_D$ is an aliphatic, heteroaliphatic, aryl, or heteroaryl moiety, or wherein $R_A$ and $R_B$, taken together, form a heterocyclic moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted;

xx) $R_1$ is OR$_A$, SR$_A$, or NR$_A$R$_B$, wherein $R_A$ and $R_B$ are each independently hydrogen, —(C=O)R$_C$, or an aryl, (aliphatic)aryl, (heteroaliphatic)aryl, heteroaryl, (aliphatic)heteroaryl, or (heteroaliphatic)heteroaryl moiety, wherein $R_C$ is an aryl, (aliphatic)aryl, (heteroaliphatic)aryl, heteroaryl, (aliphatic)heteroaryl, or (heteroaliphatic)heteroaryl moiety, or wherein $R_A$ and $R_B$ taken together form a heterocyclic moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted;

xxi) $R_1$ is —NR$_A$C(=O)R$_C$, wherein $R_A$ is hydrogen or lower alkyl, and $R_C$ is a substituted or unsubstituted, branched or unbranched, cyclic or acyclic aliphatic or heteroaliphatic moiety, or a substituted or unsubstituted aryl or heteroaryl moiety, or wherein $R_A$ and $R_C$ taken together form a heterocyclic or heteroaryl moiety;

xxii) $R_1$ is NR$_A$C(=O)R$_C$, wherein $R_A$ is hydrogen or lower alkyl, and $R_C$ is an aryl, (aliphatic)aryl, (aliphatic)heteroaryl, heteroaryl, (heteroaliphatic)aryl, or (heteroaliphatic)heteroaryl moiety, or wherein $R_A$ and $R_C$ taken together form a heterocyclic or heteroaryl moiety;

whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted;

xxiii) $R_1$ is a substituted or unsubstituted, branched or unbranched, cyclic or acyclic aliphatic or heteroaliphatic moiety, or a substituted or unsubstituted aryl or heteroaryl moiety;

xxiv) $R_1$ is an aryl, (aliphatic)aryl, (aliphatic)heteroaryl, heteroaryl, (heteroaliphatic)aryl, or (heteroaliphatic)heteroaryl moiety;

whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted;

xxv) any one or more of $R_1$, $R_A$, $R_B$, $R_C$, or $R_D$ is independently any one of the following groups:

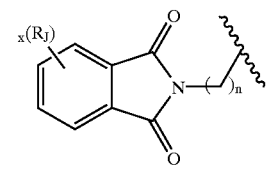
i

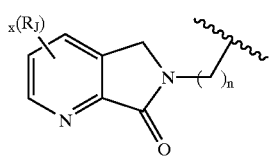
ii

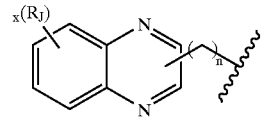
iii

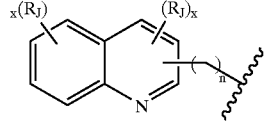
iv

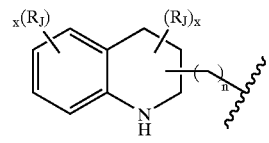
v

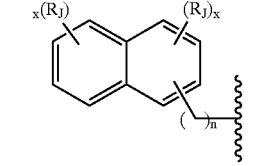
vi

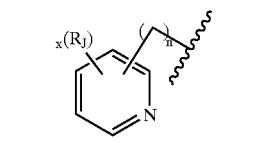
vii

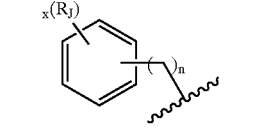
viii

-continued

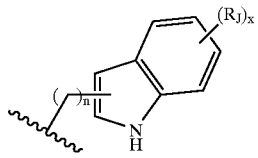
ix

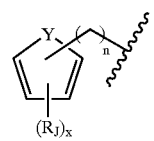
x

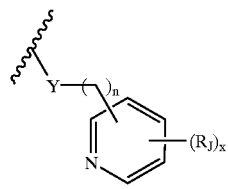
xi

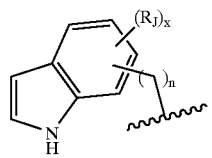
xii

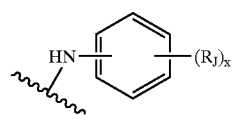
xiii

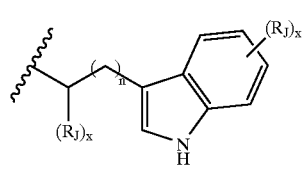
xiv

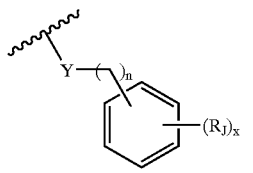
xv

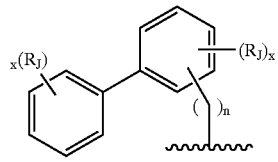
xvi

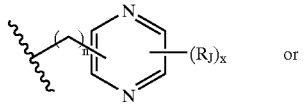
xvii or

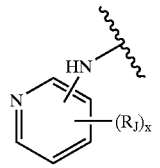
xviii wherein each occurrence of $R_J$ is independently hydrogen, a protecting group, $-OR_K$, $=O$, $-C(=O)R_K$, $-CO_2R_K$, $-CN$, $-SCN$, halogen, $-SR_K$, $-SOR_K$, $-SO_2R_K$, $-NO_2$, $-N(R_K)_2$, $-NHC(O)R_K$, $-B(OR_K)_2$, or an aliphatic, heteroaliphatic, aryl, or heteroaryl moiety, wherein each occurrence of $R_K$ is independently hydrogen, or an aliphatic, heteroaliphatic, aryl, or heteroaryl moiety, or wherein two occurrences of $R_K$, taken together form a cyclic aliphatic or heteroaliphatic moiety; wherein each occurrence of Y is independently O, S or NH; wherein each occurrence of x is independently 0–5; and wherein each occurrence of n is independently 0–3, or wherein $R_J$ is a labeling reagent, whereby each of said aliphatic and heteroaliphatic moieties are independently substituted or unsubstituted, branched or unbranched or cyclic or acyclic, and each of said aryl and heteroaryl moieties is independently substituted or unsubstituted;

xxvi) $R_A$ is hydrogen, $R_B$ is $-(C=O)R_C$, and $R_C$ is iii, iv, vii, viii, ix, x, xv, or xvii, or $R_A$ and $R_C$ taken together form the structure of i or ii;

xxvii) $R_A$ is hydrogen, $R_B$ is $-(C=O)R_C$, and $R_C$ is

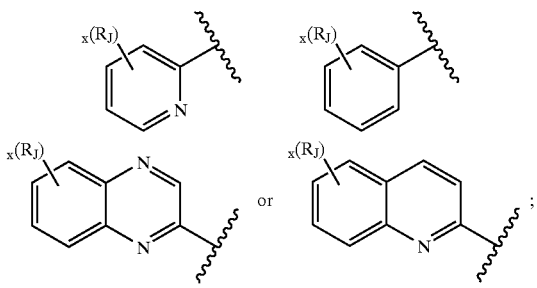

xxviii) $R_J$ is hydrogen, halogen, $-OH$, lower alkyl or lower alkoxy;

xxix) $R_J$ is a linker-biotin or a linker-fluorescein moiety; and xxx) x is 1 or 2.

As the reader will appreciate, compounds of particular interest include, among others, those which share the attributes of one or more of the foregoing subclasses. Some of those subclasses are illustrated by the following sorts of compounds:

I) Compounds of the Formula:

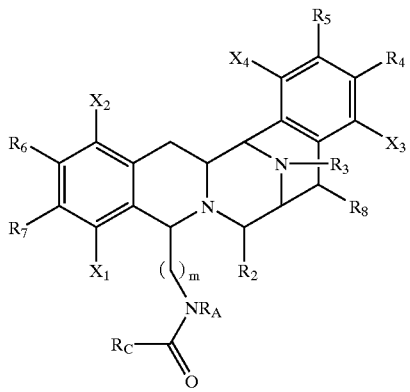

as described generally above and in classes and subclasses herein.

In certain embodiments, for compounds as described directly above, $R_A$ is hydrogen, m is 1 and $R_C$ is an aryl, (aliphatic)aryl, (aliphatic)heteroaryl, heteroaryl, (heteroaliphatic)aryl, or (heteroaliphatic)heteroaryl moiety, or wherein $R_A$ and $R_C$ taken together form a heterocyclic or heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In certain other embodiments for compounds as described directly above $R_A$ is hydrogen and $R_C$ is any one of groups iii–xviii as described herein, or $R_A$ and $R_C$ taken together are a structure of group i or ii.

In still other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_A$ is hydrogen, m is 1 and $R_C$ is an aryl, (aliphatic)aryl, (aliphatic)heteroaryl, heteroaryl, (heteroaliphatic)aryl, or (heteroaliphatic)heteroaryl moiety, or wherein $R_A$ and $R_C$ taken together form a heterocyclic or heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In yet other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_A$ is hydrogen and $R_C$ is any one of groups iii–xviii as described herein, or $R_A$ and $R_C$ taken together are a structure of group i or ii.

II) Compounds of the Formula:

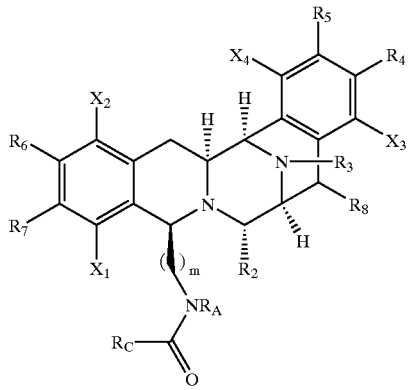

as described generally above and in classes and subclasses herein.

In certain embodiments, for compounds as described directly above, $R_A$ is hydrogen, m is 1 and $R_C$ is an aryl, (aliphatic)aryl, (aliphatic)heteroaryl, heteroaryl, (heteroaliphatic)aryl, or (heteroaliphatic)heteroaryl moiety, or wherein $R_A$ and $R_C$ taken together form a heterocyclic or heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In certain other embodiments for compounds as described directly above $R_A$ is hydrogen and $R_C$ is any one of groups iii–xviii as described herein, or $R_A$ and $R_C$ taken together are a structure of group i or ii.

In still other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_A$ is hydrogen, m is 1 and $R_C$ is an aryl, (aliphatic)aryl, (aliphatic)heteroaryl, heteroaryl, (heteroaliphatic)aryl, or (heteroaliphatic)heteroaryl moiety, or wherein $R_A$ and $R_C$ taken together form a heterocyclic or heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In yet other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_A$ is hydrogen and $R_C$ is any one of groups iii–xviii as described herein, or $R_A$ and $R_C$ taken together are a structure of group i or ii.

III) Compounds of the Formula:

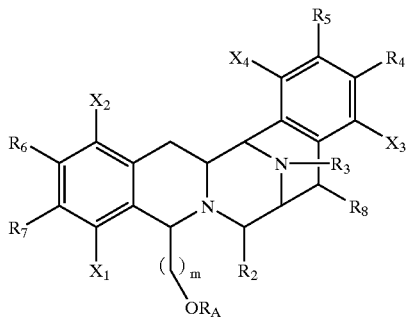

as described generally above and in classes and subclasses herein.

In certain embodiments, for compounds as described directly above, m is 1 and $R_A$ is an aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In certain other embodiments for compounds as described directly above $R_A$ is any one of groups iii–xviii as described herein.

In still other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, m is 1 and $R_A$ is an aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In yet other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_A$ is any one of groups iii–xviii as described herein.

IV) Compounds of the Formula:

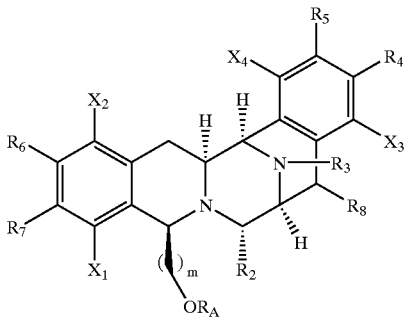

as described generally above and in classes and subclasses herein.

In certain embodiments, for compounds as described directly above, m is 1 and $R_A$ is an aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In certain other embodiments for compounds as described directly above $R_A$ is any one of groups iii–xviii as described herein.

In still other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, m is 1 and $R_A$ is an aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In yet other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_A$ is any one of groups iii–xviii as described herein.

V, Compounds of the Formula:

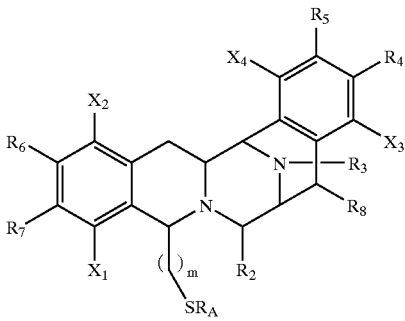

as described generally above and in classes and subclasses herein.

In certain embodiments, for compounds as described directly above, m is 1 and $R_A$ is an aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In certain other embodiments for compounds as described directly above $R_A$ is any one of groups iii–xviii as described herein.

In still other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, m is 1 and $R_A$ is an aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In yet other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_A$ is any one of groups iii–xviii as described herein.

VI, Compounds of the Formula:

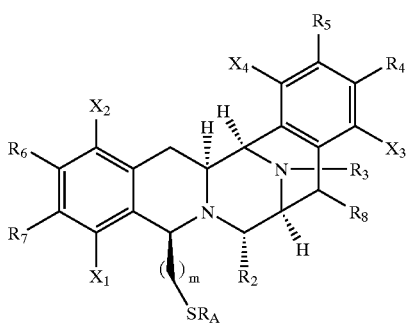

as described generally above and in classes and subclasses herein.

In certain embodiments, for compounds as described directly above, m is 1 and $R_A$ is an aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In certain other embodiments for compounds as described directly above $R_A$ is any one of groups iii–xviii as described herein.

In still other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, m is 1 and $R_A$ is an aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In yet other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_A$ is any one of groups iii–xviii as described herein.

VII, Compounds of the Formula:

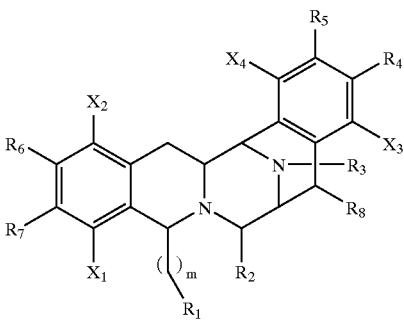

wherein $R_1$ is an aliphatic, heteroaliphatic, aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In certain other embodiments for compounds as described directly above $R_1$ is any one of groups iii–xviii as described herein.

In still other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, m is 0 or 1 and $R_1$ is an aliphatic, heteroaliphatic, aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In yet other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_1$ is any one of groups iii–xviii as described herein.

VIII, Compounds of the Formula:

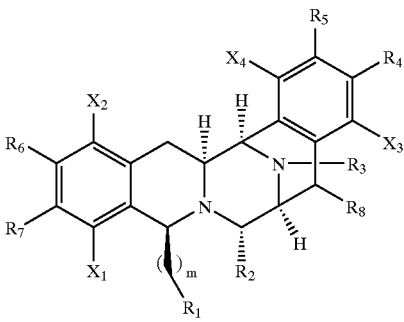

wherein $R_1$ is an aliphatic, heteroaliphatic, aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In certain other embodiments for compounds as described directly above $R_1$ is any one of groups iii–xviii as described herein.

In still other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, m is 0 or 1 and $R_1$ is an aliphatic, heteroaliphatic, aryl, (aliphatic)aryl, (aliphatic)heteroaryl, heteroaryl, (heteroaliphatic)aryl, or (heteroaliphatic)heteroaryl moiety, whereby each of said aliphatic and heteroaliphatic moieties is independently substituted or unsubstituted, branched or unbranched, or cyclic or acyclic, and each of said aryl, heteroaryl and heterocyclic moieties is independently substituted or unsubstituted.

In yet other embodiments, for compounds as described directly above, $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, $R_8$ is H, $R_1$ is any one of groups iii–xviii as described herein.

It will be appreciated that some of the foregoing classes and subclasses of compounds can exist in various isomeric forms. The invention encompasses the compounds as individual isomers substantially free of other isomers and alternatively, as mixtures of various isomers, e.g., racemic mixtures of stereoisomers. Additionally, the invention encompasses both (Z) and (E) double bond isomers unless otherwise specifically designated. The invention also encompasses tautomers of specific compounds as described above. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of this invention which are of particular interest include those which:

exhibit cytotoxic or growth inhibitory effect on cancer cell lines maintained in vitro or in animal studies using a scientifically acceptable cancer cell xenograft model;

exhibit enhanced water solubility over existing chemotherapetuic agents, or additionally or alternatively exhibit sufficient solubility to be formulated in an aqueous medium; and exhibit a therapeutic profile (e.g., optimum safety and curative effect) that is superior to existing chemotherapeutic agents.

This invention also provides a pharmaceutical preparation comprising at least one of the compounds as described above and herein, or a pharmaceutically acceptable derivative thereof, which compounds are capable of inhibiting the growth of or killing cancer cells, and, in certain embodiments of special interest are capable of inhibiting the growth of or killing multidrug resistant cancer cells.

The invention further provides a method for inhibiting tumor growth and/or tumor metastasis. In certain embodiments of special interest, the invention provides a method of treating cancers by inhibiting tumor growth and/or tumor metastasis for tumors multidrug resistant cancer cells. The method involves the administration of a therapeutically effective amount of the compound or a pharmaceutically acceptable derivative thereof to a subject (including, but not limited to a human or animal) in need of it. In certain embodiments, specifically for treating cancers comprising multidrug resistant cancer cells, the therapeutically effective amount is an amount sufficient to kill or inhibit the growth of multidrug resistant cancer cell lines. In certain embodiments, the inventive compounds are useful for the treatment of solid tumors.

3) Compounds and Definitions

As discussed above, the present invention provides a novel class of compounds useful for the treatment of cancer and other proliferative conditions related thereto. Compounds of this invention comprise those, as set forth above and described herein, and are illustrated in part by the various classes, subgenera and species disclosed elsewhere herein.

It will be appreciated by one of ordinary skill in the art that numerous asymmetric centers exist in the compounds of the present invention. Thus, inventive compounds and pharmaceutical compositions thereof may be in the form of an individual enantiomer, diastereomer or geometric isomer, or may be in the form of a mixture of stereoisomers. Additionally, in certain embodiments, as detailed herein, the method of the present invention provides for the stereoselective synthesis of alkaloids and analogues thereof. Thus, in certain embodiments, the compounds of the invention are enantiopure.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester that is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., C, O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference. Furthermore, a variety of carbon protecting groups are described in Myers, A.; Kung, D. W.; Zhong, B.; Movassaghi, M.; Kwon, S. J. Am. Chem. Soc. 1999, 121, 8401–8402, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "acyl", as used herein, refers to a carbonyl-containing functionality, e.g., —C(=O)$R_x$, wherein $R_x$ is an aliphatic, heteroaliphatic, aryl, heteroaryl, (aliphatic)aryl, (heteroaliphatic)aryl, heteroaliphatic(aryl) or heteroaliphatic (heteroaryl) moiety, whereby each of the aliphatic, heteroaliphatic, aryl, or heteroaryl moieties is substituted or unsubstituted, or is a substituted (e.g., hydrogen or alipahtic, heteroaliphatic, aryl, or heteroaryl moieties) oxygen or nitrogen containing functionality (e.g., forming a carboxylic acid, ester, or amide functionality).

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1–6 carbon atoms.

In certain embodiments, the alkyl, alkenyl and alkynyl groups employed in the invention contain 1–20 aliphatic carbon atoms. In certain other embodiments, the alkyl, alkenyl, and alkynyl groups employed in the invention contain 1–10 aliphatic carbon atoms. In yet other embodiments, the alkyl, alkenyl, and alkynyl groups employed in the invention contain 1–8 aliphatic carbon atoms. In still other embodiments, the alkyl, alkenyl, and alkynyl groups employed in the invention contain 1–6 aliphatic carbon atoms. In yet other embodiments, the alkyl, alkenyl, and alkynyl groups employed in the invention contain 1–4 carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. In certain embodiments, the alkyl group contains 1–20 alipahtic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. In certain embodiments, the alkyl group contains 1–20 aliphatic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —SCN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ or —B(OR$_x$)$_2$, wherein each occurrence of R$_x$ independently includes, but is not limited to, aliphatic, heteroaliphatic, aryl, heteroaryl, alkylaryl, or alkylheteroaryl, or wherein any two of R$_x$, taken together is a cyclic aliphatic, heteroaliphatic, aryl or heteroaryl moiety, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —SCN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ or —B(OR$_x$)$_2$, wherein each occurrence of R$_x$ independently includes, but is not limited to, aliphatic, heteroaliphatic, aryl, heteroaryl, alkylaryl, or alkylheteroaryl, or wherein any two of R$_x$, taken together is a cyclic aliphatic, heteroaliphatic, aryl or heteroaryl moiety, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —SCN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ or —B(OR$_x$)$_2$, wherein each occurrence of R$_x$, independently includes, but is not limited to, aliphatic, heteroaliphatic, aryl, heteroaryl, alkylaryl, or alkylheteroaryl, or wherein any two of R$_x$, taken together is a cyclic aliphatic, heteroaliphatic, aryl or heteroaryl moiety, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties that contain one or more oxygen, sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —SCN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ or —B(OR$_x$)$_2$, wherein each occurrence of R$_x$ independently includes, but is not limited to, aliphatic, heteroaliphatic, aryl, heteroaryl, alkylaryl, or alkylheteroaryl, or wherein any two of R$_x$, taken together is a cyclic aliphatic, heteroaliphatic, aryl or heteroaryl moiety, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —SCN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$ R$_x$; —NR$_x$(CO)R$_x$, or —B(OR$_x$)$_2$, wherein each occurrence of R$_x$ independently includes, but is not limited to, aliphatic, heteroaliphatic, aryl, heteroaryl, alkylaryl, or alkylheteroaryl, or wherein any two of R$_x$, taken together is a cyclic aliphatic, heteroaliphatic, aryl or heteroaryl moiety, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

"Labeled": As used herein, the term "labeled" is intended to mean that a compound has at least one element, isotope or chemical compound attached to enable the detection of the compound. It will be appreciated that certain of the inventive compounds are substituted with a labeling reagent, that, as used herein, is intended to mean an element, isotope or chemical compound attached to the inventive compound directly or through a suitable linker (e.g., substituted or unsubstituted, branched or unbranched, cyclic or acyclic, aliphatic, heteroaliphatic, aryl, heteroaryl moiety). Certain exemplary labeling reagents are described in the Exemplification herein; however, it will be appreciated that the present invention is not intended to be limited to these examples. Rather, a variety of labeling reagents can be employed as substituents for the inventive compounds.

4.) Synthetic Methodology:

It will be appreciated that each of the compounds as described above and herein can be synthesized according to the pioneering methodology described in more detail herein; however, the synthesis of these compounds is not limited to the methodology described herein. Rather, any methods available in the art of synthetic organic chemistry can be utilized to provide the inventive compounds, including combinatorial techniques. Significantly, the methodology as described herein (and as also described in Myers, A. G., Plowright, A. T. *J. Am Chem. Soc.* 2001, 123, 5114–5115; and Myers, A. G., Kung, D. W. *J. Am. Chem. Soc.* 1999, 121, 10828–10829, the entire contents of which are hereby incorporated by reference (including Supplemental Materials available via the internet at http://publ.acs.org)) enables the efficient production of significant quantities of alkaloid structures that can be utilized directly or modified to generate other modified alkaloid structures.

In general, the pioneering method of the present invention provides a general method for the rapid synthesis of alkaloids comprising (1) providing a desired number of substituted aldehyde precursors; and (2) reacting said desired number of substituted aldehyde precursors under suitable conditions to effect the directed condensation of said desired substituted aldehyde precursors, whereby an alkaloid is generated. It will be appreciated that the alkaloid structures generated may, in certain embodiments, be natural product precursors, and thus the subsequent reaction of said precursors with suitable reagents yields a natural product or derivatives thereof (e.g., saframycins or derivatives thereof). In certain other embodiments, the alkaloid structures generated represent core structures that can subsequently be functionalized to generate a variety of structures of interest for biological testing and therapeutic use. In certain embodiments of special interest, inventive compounds are prepared using solid phase methodologies as described herein, for the efficient synthesis of large numbers of exemplary compounds. In general, in certain exemplary embodiments, the step of reacting said desired number of substituted aldehyde precursors comprises reacting said precursors under conditions to effect the directed condensation of said desired substituted aldehyde precursors, whereby an alkaloid is generated. In certain embodiments, the substituted aldehyde precursors are α-amino aldehyde precursors. In certain other embodiments, any combination of α-amino aldehyde and other substituted aldehyde precursors may be utilized (see, e.g., Exemplification, Section IV) to diversify the core pentacyclic structures.

In certain other embodiments of special interest, particularly those related to the synthesis of saframycins and derivatives thereof, the step of providing said desired number of precursors comprises providing a first N-protected precursor, a second C-protected precursor and a third substituted aldehyde precursor, and the step of reacting said precursors under suitable conditions further comprises: (1) reacting said first N-protected and said second C-protected aldehyde precursor under suitable conditions to generate a tetrahydroisoquinoline core structure; (2) reacting said third substituted aldehyde precursor with said tetrahydroisoquinoline core structure under suitable conditions to generate a trimer of aldehydes; (3) reacting said trimer of aldehydes under suitable conditions to generate an alkaloid; and (4) optionally further reacting the alkaloid generated in step (3) to generate a diversified alkaloid. Additionally, in certain embodiments, the tetrahydroisoquinoline core structure generated in step (1) can be diversified prior to reaction in step (2) with the third aldehyde precursor to generate additional diversity. In certain embodiments, as detailed herein, the third substituted aldehyde precursor is an N-protected α-amino aldehyde precursor. In certain other embodiments, the third aldehyde precursor is an alternate substituted aldehyde precursor, as defined generally. For example, the term "substituted aldehyde precursor", as used herein, refers generally to structures of the formula R$_9$(CH$_2$)$_m$CHO, wherein m is 0–5 and R$_9$ is NR$_L$R$_M$, —OR$_L$, —SR$_L$, —C(=O)R$_L$, —C(=S)R$_L$, —S(O)$_2$R$_L$, or an aliphatic, heteroaliphatic, aryl, heteroaryl, (aliphatic)aryl, (aliphatic)heteroaryl, (heteroaliphatic)aryl, or (heteroaliphatic)heteroaryl moiety, wherein each occurrence of R$_L$ and R$_M$ is independently hydrogen, —(C=O)R$_N$, —NHR$_N$, —(SO$_2$)R$_N$, —OR$_N$, or an aliphatic, heteroaliphatic, aryl, or heteroaryl moiety, or $R_L$ and $R_M$, when taken together form an aryl, heteroaryl, cycloaliphatic, or cycloheteroaliphatic moiety, wherein each occurrence of $R_N$ is independently hydrogen, —$OR_P$, —$SR_P$, —$NHR_P$, —(C=O)$R_P$, or an aliphatic, heteroaliphatic, aryl, or heteroaryl moiety, wherein each occurrence of $R_P$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety. It will be appreciated that N-protected a-amino aldehyde precursors are encompassed by the generic term "substituted aldehyde precursors". Certain exemplary embodiments are discussed in more detail below and in the exemplification herein.

As described in more detail in the Exemplification section herein, the methodology described generally above takes advantage of the ability to generate a series of imine structures and subsequently subject these imines to suitable reaction conditions to effect cyclization reactions, thus generating the desired alkaloid structures. Thus, in one embodiment of special interest, a first N-protected α-amino aldehyde precursor (XI) is provided, and reacted with a second C-protected α-amino aldehyde precursor (XII) under suitable conditions to generate a tetrahydroisoquinoline core structure (XIII), which reaction comprises first reacting said precursors to effect Schiff-base formation and Pictet-Spengler cyclization and generate a tetrahydroisoquinoline core of structure (XIII); and optionally reacting the tetrahydroisoquinoline core structure (XIII) to further functionalize the core structure at $R_3$; and wherein the step of reacting said third aldehyde precursor with said tetrahydrisoquinoline core structure comprises reacting under suitable conditions to effect another Pictet-Spengler cyclization to generate a trimer of aldehydes (XIV) and reacting said trimer (XIV) under suitable conditions to effect cyclization and generate an alkaloid structure (XV).

In certain embodiments of special interest, said first N-protected α-amino aldehyde precursor, and said second C-protected α-amino aldehyde precursor have the general structures:

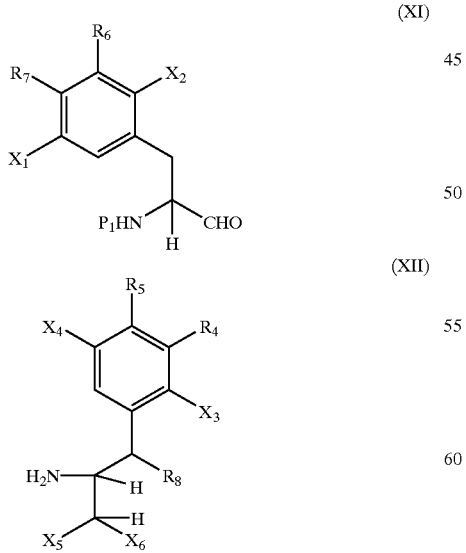

wherein said tetrohydroisoquinoline core has the structure (XIII):

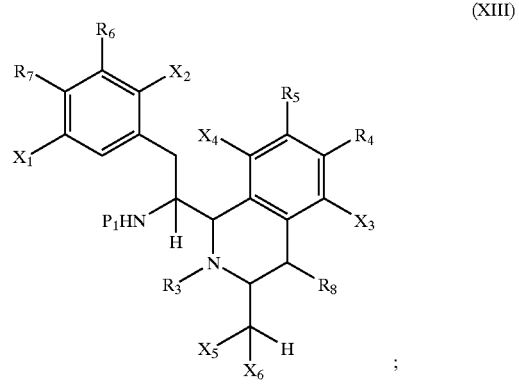

wherein said third aldehyde precursor is $R_9(CH_2)_mCHO$; wherein said trimer of amino aldehydes has the structure (XIV):

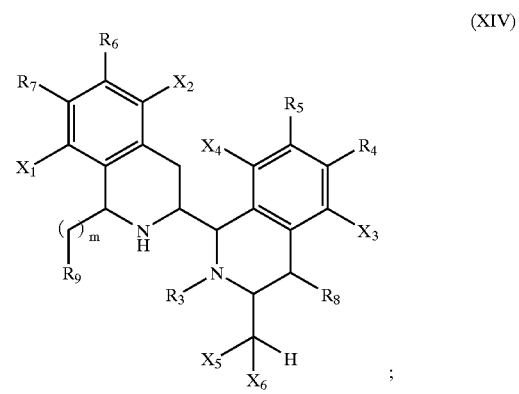

and wherein the alkaloid generated upon reaction of said trimer under suitable conditions has the structure (XV):

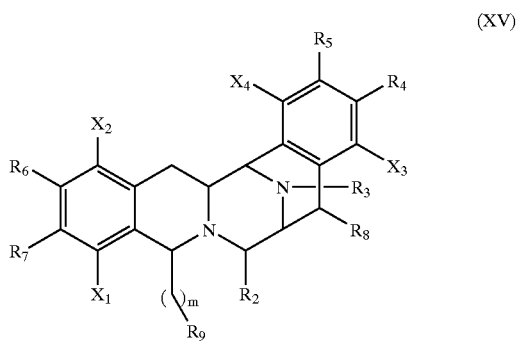

wherein $X_1$–$X_4$, $R_2$–$R_8$ and m are as defined generally and in subclasses herein;
$P_1$ is hydrogen or a nitrogen protecting group;
$X_5$ and $X_6$ taken together represent a carbon protecting group, optionally substituted with a solid support unit; and
$R_9$ is $NR_LR_M$, —$OR_L$, —$SR_L$, —C(=O)$R_L$, —C(=S)$R_L$, —S(O)$_2R_L$, or an aliphatic, heteroaliphatic, aryl, heteroaryl, (aliphatic)aryl, (aliphatic)heteroaryl, (heteroaliphatic)aryl, or (heteroaliphatic)heteroaryl moiety, wherein each occurrence of $R_L$ and $R_M$ is independently hydrogen, —(C=O)$R_N$, —$NHR_N$, —(SO₂)R_N, —OR_N, or an aliphatic, heteroaliphatic, aryl, or heteroaryl moiety, or R_L and R_M, when taken together form an aryl, heteroaryl, cycloaliphatic, or cycloheteroaliphatic moiety, wherein each occurrence of R_N is independently hydrogen, —OR_P, —SR_P, —NHR_P, —(C=O)R_P, or an aliphatic, heteroaliphatic, aryl, or heteroaryl moiety, wherein each occurrence of R_P is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety.

It will be appreciated that, in addition to the synthesis of compounds as described herein, the novel method can be utilized to generate a variety of compounds. For example, the present invention also contemplates the synthesis of ecteinascidin analogues where X₁ and R₇ taken together are a heterocyclic moiety.

In certain embodiments of special interest herein for the intermediates (XIV) and (XV) R₉ is —NHP₂, wherein P₂ is a nitrogen protecting group, and thus the intermediates have the structures (XIVa) and (XVa):

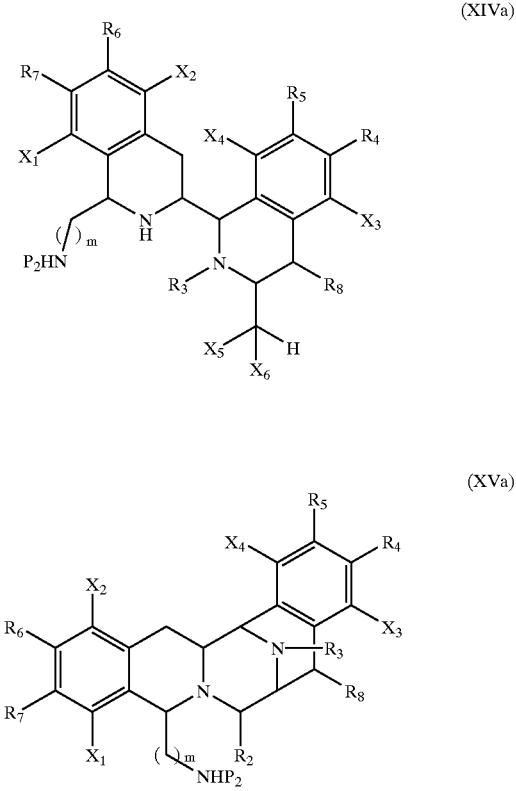

As mentioned above, in certain other embodiments of the invention, compounds of formula (XV) and (XVa) can be further modified to generate compounds of general formula (I) including classes and subclasses thereof, as described in more detail herein.

In certain other embodiments for methods as described herein, the third substituted aldehyde precursor, R₉(CH₂)_m CHO is (aliphatic)(C=O)(CH₂)_m CHO, (heteroaliphatic)(C=O)(CH₂)_m CHO, (aliphatic)(CH₂)_m CHO, (heteroaliphatic)(CH₂)_m CHO, aryl(aliphatic)(CH₂)_m CHO, aryl(heteroaliphatic)(CH₂)_m CHO, -heteroaryl(aliphatic)(CH₂)_m CHO, or heteroaryl(heteroaliphatic)(CH₂)_m CHO, wherein each of the aliphatic, heteroaliphatic, aryl, and heteroaryl moieties is independently substituted or unsubstituted. In certain embodiments, any one or more of the aliphatic, heteroaliphatic, aryl or heteroaryl moieties is substituted with one or more of substituted or unsubstituted amino, substituted or unsubstituted thiol, or substituted or unsubstituted hydroxyl. In certain exemplary embodiments, as described in more detail in the exemplification herein, the third substituted aldehyde precursor is CH₃(CH₂)₁₋₆CHO; (protecting group)O(CH₂)₁₋₆CHO; (protecting group)NH (CH₂)₁₋₆CHO; (protecting group)S(CH₂)₁₋₆CHO; (alkyl)O (C=O)CHO; (aryl)(alkenyl)CHO; (heteroaryl)(alkenyl) CHO; (aryl)CHO; or (heteroaryl)CHO, wherein any one or more of the aryl, heteroaryl, alkenyl or alkyl moieties is substituted or unsubstituted.

In still other exemplary embodiments as described herein X₅ is CN and X₆ is a heterocyclic moiety optionally substituted with a solid support unit.

Thus, the present invention additionally provides a method for the synthesis of compounds of structure (I) as described above and in classes and subclasses herein, which method comprises:

(a) providing a compound of formula (XV)

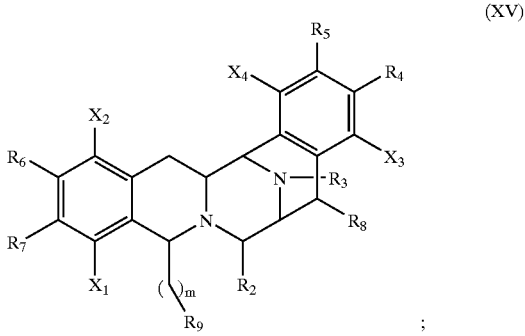

and (b) reacting said compound of formula (XV) under suitable conditions to generate a compound of formula (I):

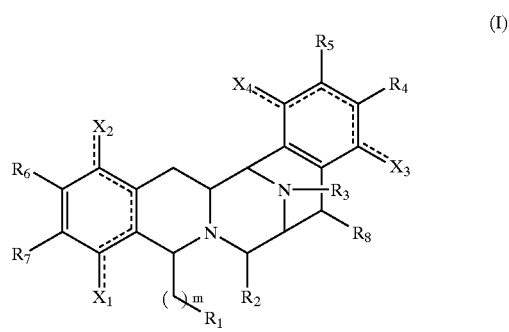

wherein X₁–X₄, R₁–R₈, and m are as described above and in classes and subclasses herein, and wherein the step of providing a compound of formula (XV) further comprises:

(1) reacting a first N-protected and a second C-protected α-amino aldehyde precursor having the structures:

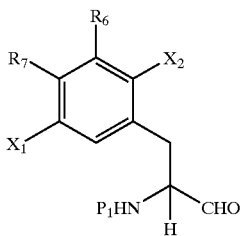

(XI)

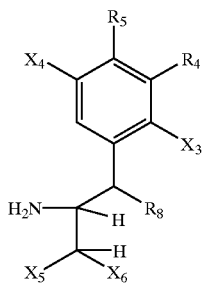

(XII)

under suitable conditions to generate a tetrahydroisoquinoline core having the structure (IX):

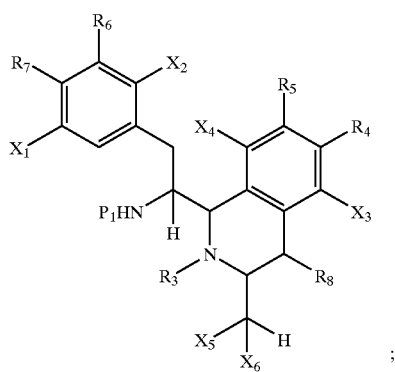

(XIII)

(2) optionally reacting said tetrahydroisoquinoline core under suitable conditions to diversify $R_3$;

(3) reacting a third aldehyde precursor having the structure: $R_9(CH_2)_m CHO$, with said tetrahydroisoquinoline core structure (XIV) under suitable conditions to generate a trimer of aldehydes having the structure:

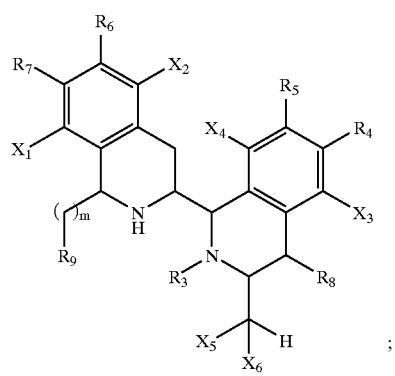

(XIV)

and (4) reacting said trimer of aldehydes under suitable conditions to generate a compound of structure (XV).

In certain embodiments of special interest herein for the intermediates (XIV) and (XV) $R_9$ is —$NHP_2$, wherein $P_2$ is a nitrogen protecting group, and thus the intermediates have the structures (XIVa) and (XVa):

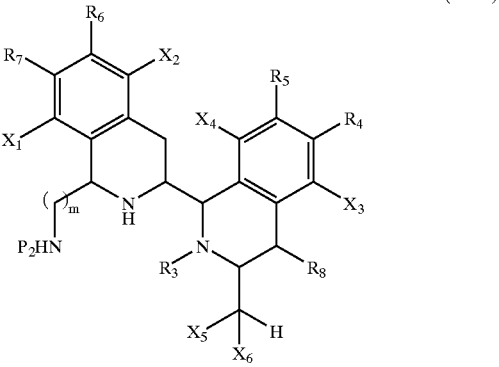

(XIVa)

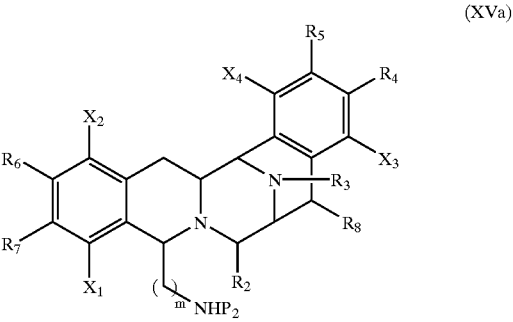

(XVa)

As described above, in certain embodiments, the alkaloid structures generated by the method of the present invention represent natural product precursors. Thus, subsequent reaction of these precursors enables the production of the desired natural products, and, in certain embodiments, the methods of the present invention enables the stereoselective production of the desired natural product precursors and natural products. In certain embodiments of special interest, the methods as described herein are utilized for the synthesis of an alkaloid structure, wherein the alkaloid structure (I) generated is that of saframycin A or derivatives thereof. In certain other particularly preferred embodiments, the method is stereoselective and the alkaloid structure (I) generated is that of-(−) saframycin A and derivatives thereof.

It will be appreciated, however, that the method of the present invention can be utilized for the synthesis of any of the compounds as described herein and for classes and subclasses thereof. Additionally, the method of the present invention can be utilized for the synthesis of naturally occurring saframycins and related compounds (e.g., for ecteinascidins and analogues thereof, where $R_7$ and $X_1$ taken together are a heterocyclic moiety (methylenedioxy, in certain embodiments)).

Figure 14A:
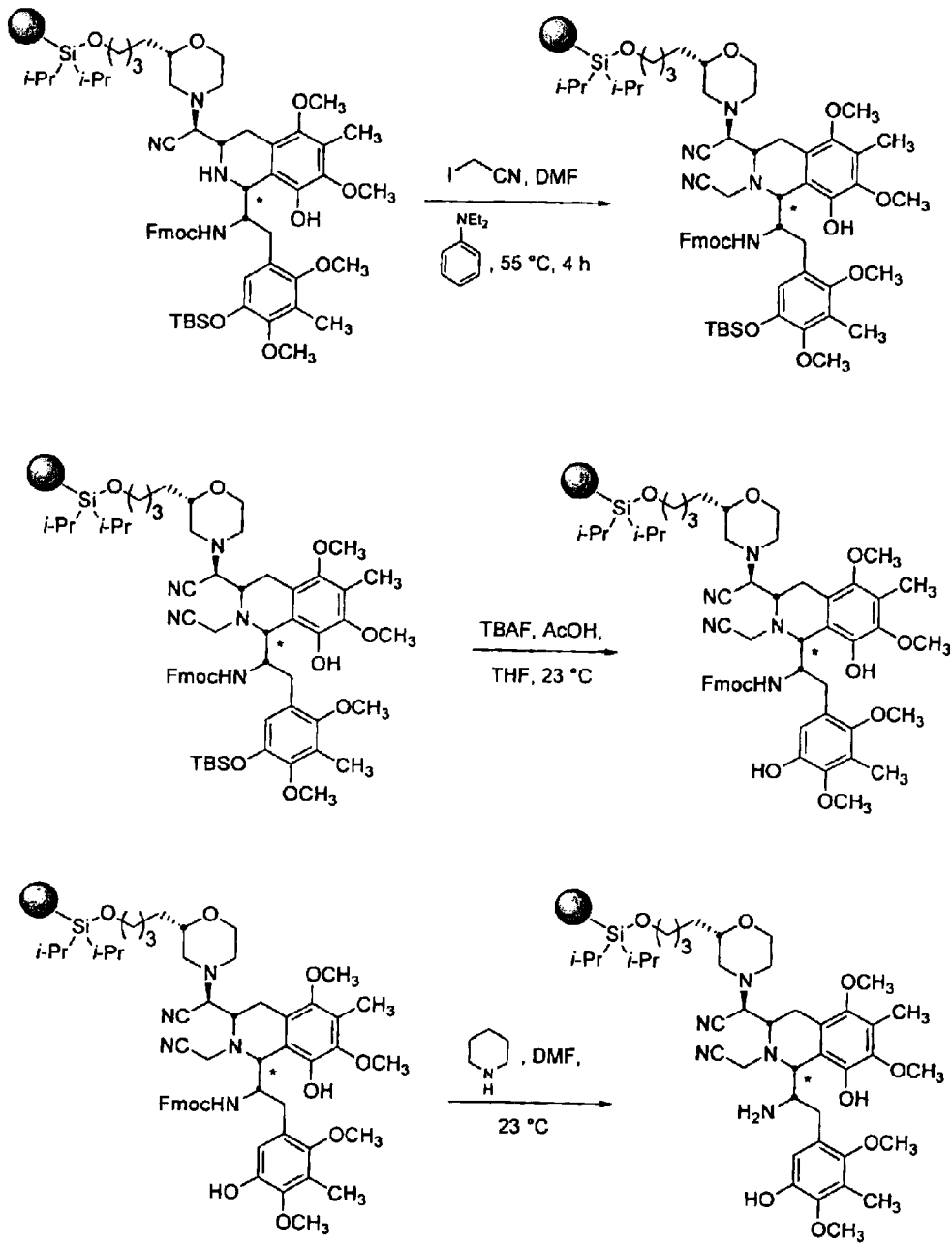
FIGS. 14A and 14B depict a synthetic scheme illustrating the generation of diversity in the R$_3$ position of generic structure (I) (via alternate N-alkylation reaction).
Figure 14B:
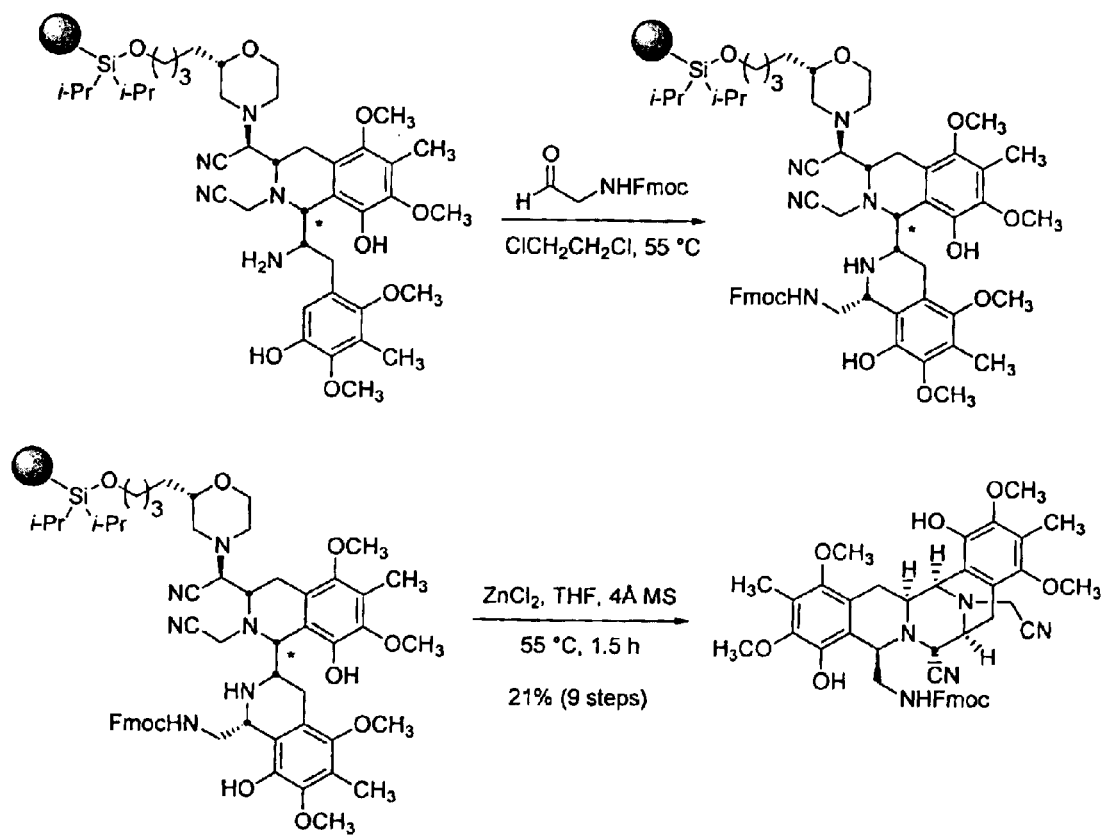

It will be appreciated that a variety of experimental conditions can be utilized to effect the synthetic transformations as described generally above. The Exemplification sections describe certain experimental conditions in more detail to enable the production of the compounds of the present invention. It will be appreciated however, that although certain reagents are specifically described in the experimentals, a variety of equivalent reagents can also be utilized. In but one example, although LiBr was utilized to effect activation of the imine functionality to initiate Pictet-Spengler cyclization, it will be appreciated that a variety of other suitable Lewis acids known in the art may be utilized for the activation of the imine functionality as described in the methodology herein. In certain preferred embodiments, those Lewis acids that will not ionise the amino nitrile are utilized in the method of the present invention. Additionally, as described herein, the compounds of the present invention can be diversified at a variety of functional sites (e.g., $R_1$, $R_2$, $R_3$, $R_9$, oxidation of one or more aromatic rings to quinone moieties, to name a few) either after synthesis of the core structure (XV) or during the synthesis of the compounds. As shown in the Exemplification herein, compounds where $R_9$ is —$NHP_1$ can be diversified to generate a variety of analogues as described. Additionally, use of a variety of third aldehyde precursors in the method of the present invention yields analogues in which the core ring structure is altered (e.g., —C—C linkages, —C—N linkages, —C—C(=O) linkages etc.). Additionally, as shown in FIGS. 14A and 14B, and as described herein, the N-alkylation reaction can be varied to yield exemplary analogues diversified at $R_3$.

It will be appreciated that the general synthetic method described above can be utilized with solid support techniques. Thus, in certain embodiments of the invention, compounds of the invention are prepared using a solid support. As described herein, the desired alkaloid precursors may be modified or reacted directly to effect attachment to the solid support. The use of a solid support bound component enables the use of more rapid combinatorial (parallel or split-pool) techniques to generate large numbers of compounds more easily. In general, as described in the Exemplification herein, the carbon protected aldehyde can be modified by attachment of a linker moiety (generally an aliphatic or heteroaliphatic moiety) to facilitate attachment of the solid support. The solid support bound carbon protected aldehyde is then reacted under suitable conditions with the first α-amino aldehyde described generally above to generate a solid support bound tetrahydroisoquinoline derivative. Finally, reaction under suitable conditions with a third aldehyde precursor results in the cleavage of the solid support unit and generation of the desired compound.

A solid support, for the purposes of this invention, is defined as an insoluble material to which compounds are attached during a synthesis sequence. The use of a solid support is advantageous for the synthesis of libraries because the isolation of support-bound reaction products can be accomplished simply by washing away reagents from the support-bound material and therefore the reaction can be driven to completion by the use of excess reagents. Additionally, the use of a solid support also enables the use of specific encoding techniques to "track" the identity of the inventive compounds in the library. A solid support can be any material which is an insoluble matrix and can have a rigid or semi-rigid surface. Exemplary solid supports include, but are not limited to, pellets, disks, capillaries, hollow fibers, needles, pins, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally crosslinked with N–N'-bis-acryloylethylenediamine, and glass particles coated with a hydrophobic polymer. One of ordinary skill in the art will realize that the choice of particular solid support will be limited by the compatability of the support with the reaction chemistry being utilized.

It will be appreciated that specific compounds may be attached directly to the solid support or may be attached to the solid support through a linking reagent. Direct attachment to the solid support may be useful if it is desired not to detach the library member from the solid support. For example, for direct on-bead analysis of biological/pharmacological activitiy or analysis of the compound structure, a stronger interaction between the library member and the solid support may be desirable. Alternatively, the use of a linking reagent may be useful if more facile cleavage of the inventive library members from the solid support is desired.

Furthermore, any linking reagent used in the present invention may comprise a single linking molecule, or alternatively may comprise a linking molecule and one or more spacer molecules. A spacer molecule is particularly useful when the particular reaction conditions require that the linking molecule be separated from the library member, or if additional distance between the solid support/linking unit and the library member is desired.

Thus, in certain embodiments, libraries of inventive alkaloids can be prepared using established combinatorial methods for solution phase, solid phase, or a combination of solution phase and solid phase synthesis techniques. The synthesis of combinatorial libraries is well known in the art and has been reviewed (see, e.g., "Combinatorial Chemistry", Chemical and Engineering News, Feb. 24, 1997, p. 43; Thompson, L. A., Ellman, J. A., *Chem. Rev.* 1996, 96, 555.) I0n certain embodiments, the use of solid phase techniques may be desired and thus encoding techniques may also be employed. Specific encoding techniques have been reviewed by Czarnik. (Czarnik, A. W., *Current Opinion in Chemical Biology*, 1997, 1, 60.) One of ordinary skill in the art will realize that the choice of method will depend upon the specific number of compounds to be synthesized, the specific reaction chemistry, and the availability of specific instrumentation, such as robotic instrumentation for the preparation and analysis of libraries. In particularly preferred embodiments, the reactions to be performed on the compound precursors are selected for their ability to proceed in high yield, and in a stereoselective fashion, if desired.

Figure 10:
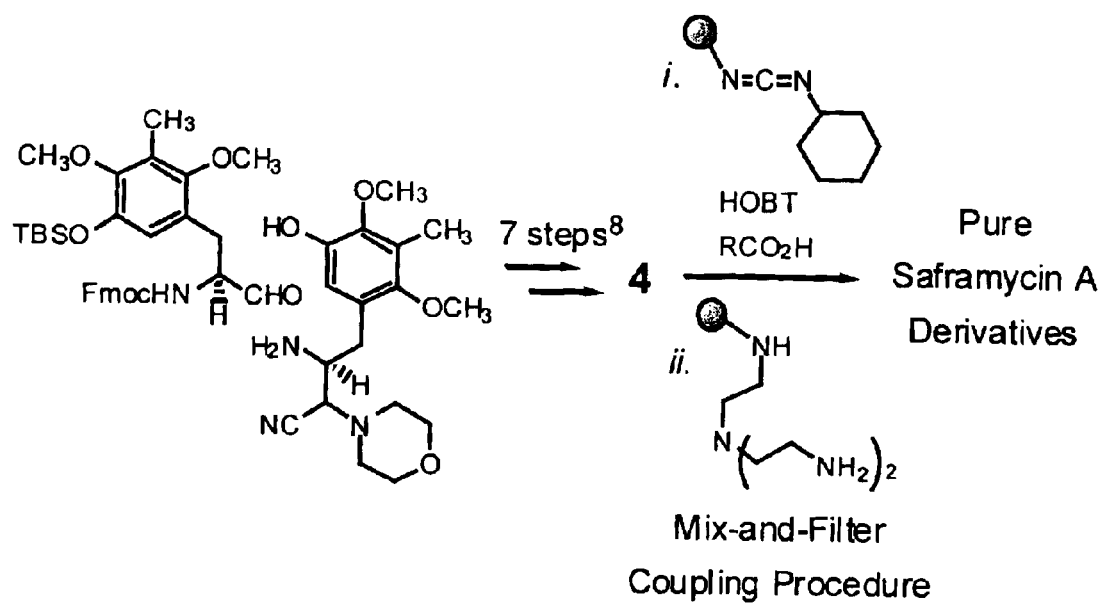
FIG. 10 depicts a general method for the rapid synthesis of large numbers of potent derivatives of saframycin A.
Figure 11:
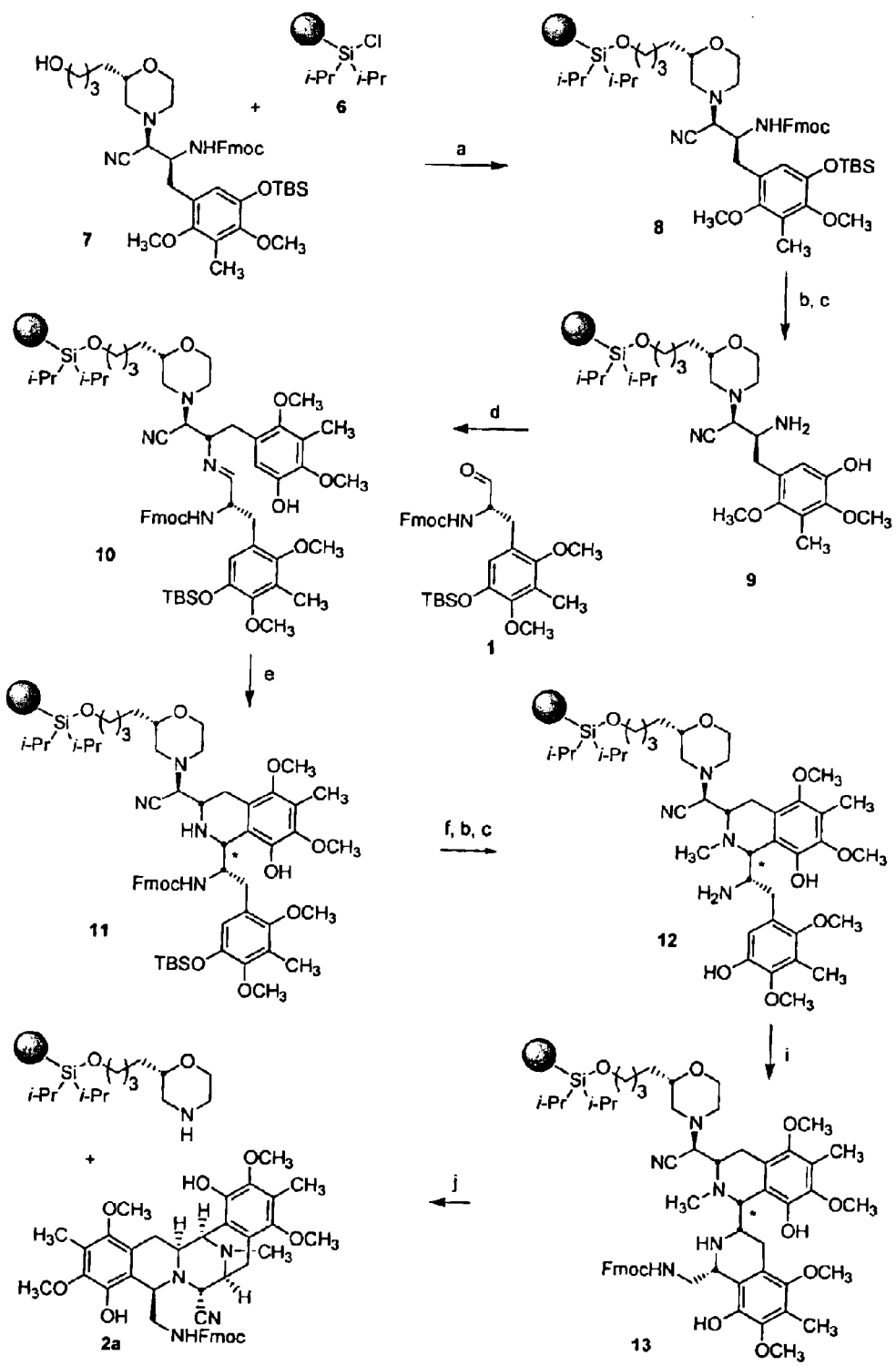
FIG. 11 depicts the solid phase synthesis of derivatives of saframycin A. Reaction conditions: (a) Imidazole, DMF, 23° C.; CH$_3$OH, Imidazole, 23° C., 100% (2 steps). (b) TBAF, AcOH, THF, 23° C. (c) Piperidine, DMF, 23° C. (d) aldehyde 1, DMF, 23° C. (e) LiBr, DME, 35° C., 83% (4 steps). (f) CH$_2$O—H$_2$O, NaBH(OAc)$_3$, DMF, 23° C., 95%. (g) Fmoc-glycinal, DCE, 40° C., 80% (3 steps). (h) ZnCl$_2$, TMSCN, CF$_3$CH$_2$OH—THF, 23° C., 48%. (*=4.5:1 mixture of diastereomers (cis- is major))
Figure 12:
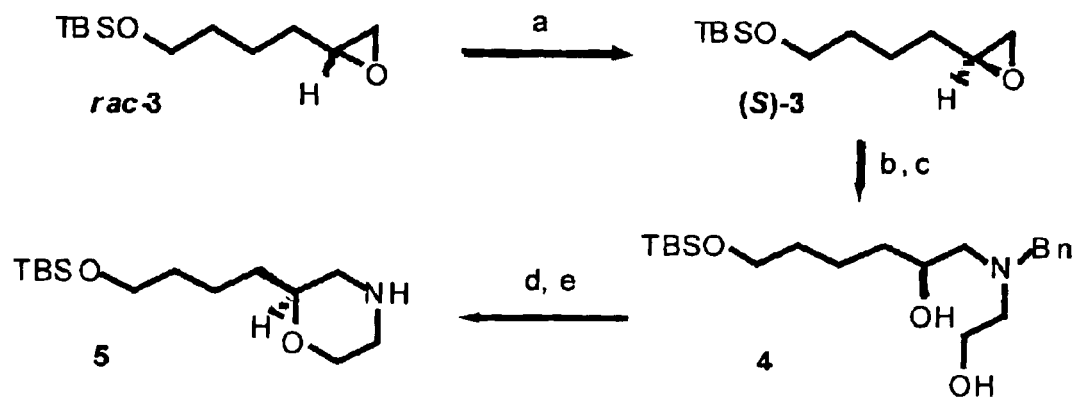
FIG. 12 depicts the synthesis of the siloxymorpholine reagent (5). Reaction conditions: (a) Jacobsen H K R (Tokunaga, M.; Larrow, J. F.; Kakiuchi, F.; Jacobsen, E. N. *Science.* 1997, 277, 936–938). 23° C., 100% (98% ee). (b) 2-aminoethanol, EtOH, 0→70° C., 100%. (c) Bnbr, KHCO$_3$, DMF, 50° C., 97%. (d) NaH, THF, 0→23° C.; TsIm, THF, 0→23° C., 70% (2 steps, >95% ee). (e) 10% Pd/C, H$_2$, CH3OH, AcOH, 23° C., 96%.
Figure 13:
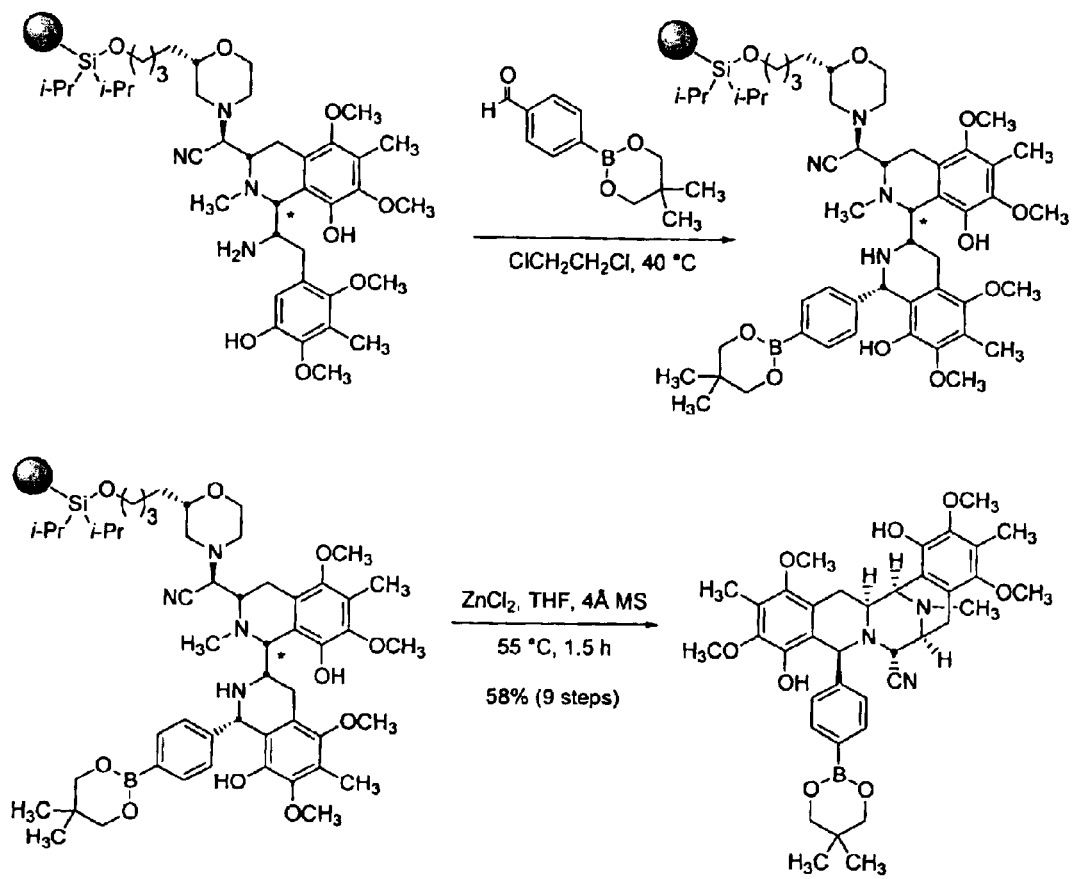
FIG. 13 depicts reaction with a substituted aldehyde reagent (via Pictet-Spengler reaction) to generate diversified pentacyclic core structures.

As described in the Exemplification herein, and as shown in FIG. 10, in one embodiment of particular interest, the inventive compounds are preparing using a modular solid-supported synthesis. As described generally above, the C-protected aldehyde precursor can be further modified with a solid support unit. As used herein, the term "solid support unit" includes a solid support, as defined herein, and additionally optionally includes a linker moiety which may be an aliphatic, heteroaliphatic, aryl or heteroaryl moiety that facilitates attachment of the solid support to the intermediate of interest. In certain embodiments, herein, a solid support unit is attached to the carbon protecting group (by preparation of a modified group, e.g., preparation of a siloxymorpholine moiety as described in the Exemplification section herein) through a linker unit. It will be appreciated that a variety of linkages and solid supports can be utilized in the method of the invention.

5) Uses, Formulation and Administration

Pharmaceutical Compositions

As discussed above, the present invention provides novel compounds having antitumor and antiproliferative activity, and thus the inventive compounds are useful for the treatment of cancer. Accordingly, in another aspect of the present invention, pharmaceutical compositions are provided, wherein these compositions comprise any one of the compounds as described herein, and optionally comprise a pharmaceutically acceptable carrier. In certain embodiments, these compositions optionally further comprise one or more additional therapeutic agents. In certain other embodiments, the additional therapeutic agent is an anticancer agent, as discussed in more detail herein.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

In yet another aspect, according to the methods of treatment of the present invention, tumor cells are killed, or their growth is inhibited by contacting said tumor cells with an inventive compound or composition, as described herein. Thus, in still another aspect of the invention, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells", as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. The anticancer compounds of the invention are preferably formulated in dosage unit form for ease of administration and uniformity of dosage. The expression "dosage unit form" as used herein refers to a physically discrete unit of anticancer agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, the compounds of the present invention are useful as anticancer agents, and thus may be useful in the treatment of cancer, by effecting tumor cell death or inhibiting the growth of tumor cells. In general, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors and also kill and/or inhibit the growth of multidrug resistant cells (MDR cells).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Equivalents

Figure 2:
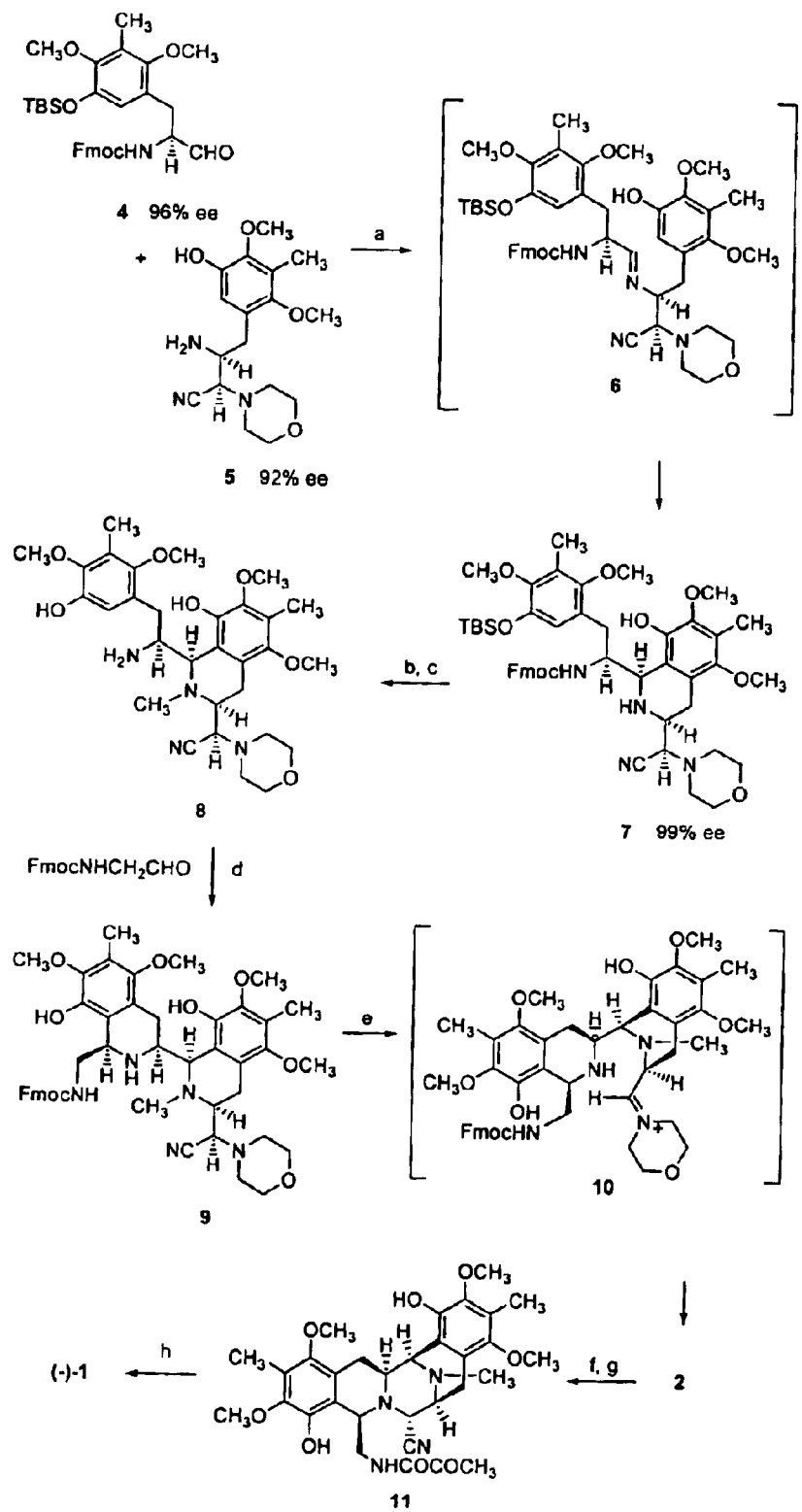
FIG. 2 depicts the synthesis of saframycin A and precursors. Reaction conditions: (a) $Na_2SO_4$, $CH_2Cl_2$, 23° C., >90%; LiBr, DME, 35 C, 65–72%. (b) $CH_2O$—$H_2O$, NaBH(OAc)$_3$, $CH_3CN$, 23° C., 94%. (c) HOAc, TBAF, THF, 23° C.; DBU, $CH_2Cl_2$, 23° C., 92%. (d) $Na_2SO_4$, $CH_2Cl_2$, 23° C., 66%. (e) $ZnCl_2$, TMSCN, $CF_3CH_2OH$—THF, 23° C., 86%. (f) DBU, $CH_2Cl_2$, 23° C., 88%. (g) $ClCOCOCH_3$, $PhNEt_2$, $CH_2Cl_2$, 0° C., 89%. (h) PhIO, $CH_3CN$—$H_2O$, 0° C., 66%.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and the equivalents thereof.

Exemplification I. Synthesis of Alkaloids:

A. As discussed above, in one aspect of the invention, novel synthetic methodology for the preparation of alkaloids is provided. In but one embodiment, this methodology involves the directed condensation of α-amino aldehyde precursors. As described in more detail below, the synthesis of saframycin A and intermediates thereof is described.

i) General Description:

Referring to FIGS. 1 and 2, and Scheme 1, a short and enantioselective synthetic route to the potent antitumor agent (−)-saframycin A (1), a bisquinone alkaloid of microbial origin is provided (for reviews, see, (a) Arai, et al. In *The Alkaloids*; Brossi, A., Ed.; Academic Press: New York, 1983; Vol. 21, Chapter 3. (b) Remers, W. A. In *The Chemistry of Antitumor Antibiotics*; Wiley-Interscience: New York, 1988; Vol. 2, Chapter 3). The route employs a new and powerful synthetic strategy involving the directed condensation of optically active α-amino aldehydes. This strategy evolved from retrosynthetic analysis of 1, as shown, where a series of transformations initiated by the condensation of an aldehyde with an amine (e.g., reductive amination, Pictet-Spengler, and Strecker reactions), was envisioned to assemble the target 1 from five simple components: hydrogen cyanide, formaldehyde, and three α-amino aldehydes, two of which (structure 3) are the same-hence the latent symmetry of 1. The complexity of the analysis arises in the determination of the precise order and stereochemistry of bonding events that ultimately links the precursors (seven bonds must be formed), and upon consideration of the fundamental issues of stability, reactivity, and protection strategies surrounding the proposed use of optically active α-amino aldehydes as synthetic intermediates. Recently, a series of "C-protected" optically active α-amino aldehydes were reported that incorporate an amino nitrile group as a masked aldehyde (Myers et al. *J. Am. Chem. Soc.* 1999, 121, 8401). Morpholino nitrile derivatives, exemplified by structure 5, were found to be particularly useful synthetic intermediates, undergoing condensation reactions with optically active N-protected α-amino aldehydes with little to no epimerization of either component, thus establishing the basis for the directed assembly of (−)-saframycin A detailed herein.

Compounds 4 and 5, N- and C-protected versions of the same chiral α-amino aldehyde (3), were prepared in high enantiomeric excess from the same product of asymmetric alkylation of (−)-pseudoephedrine glycinamide, as previously described (Myers et al. *J. Am. Chem. Soc.* 1999, 121, 8401; Myers et al. *J. Org. Chem.* 1999, 64, 3322). Addition of N-protected α-amino aldehyde 4 (96% ee, 1.05 equiv) to C-protected α-amino aldehyde 5 (92% ee, 1 equiv) in dichloromethane at 23° C. in the presence of sodium sulfate cleanly provided the imine 6 (presumed trans) without detectable epimerization of either α-stereocenter ($^1$H NMR analysis, >90% yield, dr~95:5). Addition of a saturated solution of anhydrous lithium bromide in dimethoxyethane to the imine intermediate and warming to 35° C. brought about Pictet-Spengler cyclization to provide a ~5:1 mixture of cis and trans tetrahydroisoquinolines, respectively. Flash column chromatography afforded the desired cis product (7) in 65–72% yield and 99% ee. The optical purity of 7 was assayed by HPLC analysis (Chiralcel OD) of the corresponding bis(benzoyl) derivative against an authentic sample of its enantiomer, derived from (+)-pseudoephedrine via ent-4 and ent-5. Lithium ion proved to be optimal for mild and selective Lewis-acid activation of the imine function without reaction of the morpholino nitrile. The cis-trans selectivity of the cyclization reaction varied markedly as a function of solvent and activating agent; for example, use of lithium perchlorate in diethyl ether provided the trans product exclusively. It is also noteworthy that the transformation of 6 to 7 is the only step in the synthetic route that was conducted above ambient temperature.

Introduction of the N-methyl group at this stage of the synthesis was found to be optimal. Stirring 7 at 23° C. in the presence of formalin (2.0 equiv) and sodium triacetoxyborohydride (1.5 equiv) in acetonitrile provided the corresponding N-methylated compound in 94% yield; the morpholino nitrile function was unaffected by the reductive conditions. The N-Fmoc and OTBS protective groups were then cleaved. While these deprotections could be performed simultaneously by the action of fluoride or hydroxide, sequential removal of the silyl ether with acetic acid-buffered tetrabutylammonium fluoride (2.4 and 1.1 equiv, respectively) followed by cleavage of the carbamate with DBU (1.3 equiv) provided 8 with greater efficiency (92%). Notably, compound 8 showed no propensity for the primary amine to add to the masked aldehyde under such conditions as exposure to silica gel or upon standing in the protic medium 2,2,2-trifluoroethanol, further highlighting the stability of the morpholino nitrile protective group.

Addition of the third and final α-amino aldehyde component, N-Fmoc glycinal (1.5 equiv), to amine 8 (1 equiv) in the presence of sodium sulfate in deoxygenated dichloromethane at 23° C. produced an imine intermediate which underwent Pictet-Spengler cyclization, also at 23° C., to provide a ≧9:1 mixture of cis and trans tetrahydroisoquinolines, respectively. The desired cis isomer (9) was isolated in 66% yield. The reaction solvent was again critical for selective formation of the desired cis tetrahydroisoquinoline; protic solvents afforded predominantly the trans diastereomer (e.g., in methanol, trans:cis >5:1). With the "trimer" of α-amino aldehydes assembled (9), the C-terminus morpholino nitrile blocking group was then cleaved with anhydrous zinc chloride (Guibe, F. et al. *Tetrahedron Lett.* 1982, 23, 5055) (3.0 equiv) in a mixture of trifluoroethanol and tetrahydrofuran (2:1) at 23° C., producing the key pentacyclic intermediate 2 in 86% yield. This transformation presumably proceeded by the sequential formation of iminium ion 10, cyclization (addition of the secondary amine to the iminium ion), expulsion of morpholine, and trapping of the resultant iminium ion by cyanide. It was necessary to introduce exogenous cyanide (trimethylsilyl cyanide, 2.0 equiv) to ensure complete amino nitrile formation; in the absence of added cyanide, small amounts (5–10%) of the hemiaminal corresponding to hydrolysis of amino nitrile 2 were observed, presumably due to adventitious water. Finally, the N-Fmoc protective group of 2 was cleaved with DBU (1.3 equiv) at 23° C. in 88% yield, and the resulting primary amine was acylated with pyruvoyl chloride (3.0 equiv) in the presence of N,N-diethylaniline (1.1 equiv) at 0° C. to afford 11 (89%). Oxidative demethylation of the hydroquinones with iodosobenzene (2.5 equiv) in acetonitrile-water (1:1, 0° C.) furnished synthetic (−)-saframycin A in 66% yield (127 mg of (−)-1). The synthetic material was found to be identical in all respects ($^1$H NMR, $^{13}$C NMR, IR, HPLC, tlc analysis, and optical rotation) with an authentic sample of natural saframycin A, kindly provided by Professor T. Arai.

In summary, a practical and efficient synthesis of (−)-saframycin A has been developed that proceeds in just 8 steps from the α-amino aldehyde precursors 4 and 5, in ~15% overall yield. Significantly, this synthesis illustrates a simple strategy for alkaloid assembly that can be applied more generally, and that involves the directed condensation of α-amino aldehyde precursors in a manner not unlike oligopeptide synthesis (here, with C→N directionality). The present route is suitable for the production of 1 in quantity; to date, more than 1 g of 2 and 200 mg of (−)-1 have been prepared. Additionally, this synthetic methodology can also be utilized for the generation of 2 in significant quantities and this compound can be further functionalized, as described herein, to generate the compounds as described herein in suitable quantities for therapeutic utility.

ii) Experimental Data:

The N- and C-protected α-amino aldehyde derivatives 4 and 5 were prepared as previously described (Myers et al. *J. Am. Chem. Soc.* 1999, 121, 8401) from amide 12, the product of alkylation (Myers et al. *J. Org. Chem.* 1999, 64, 3322) of (−)-pseudoephedrine glycinamide with benzylic bromide 13. Bromide 13 was synthesized from 2,4-dimethoxy-3-methylphenol (Godfrey, I. M.; Sargent, M. V.; Elix, J. A. *J. Chem. Soc., Perkin Trans.* 1 1974, 1353–1354) as shown in Scheme 1 below.

Scheme 1

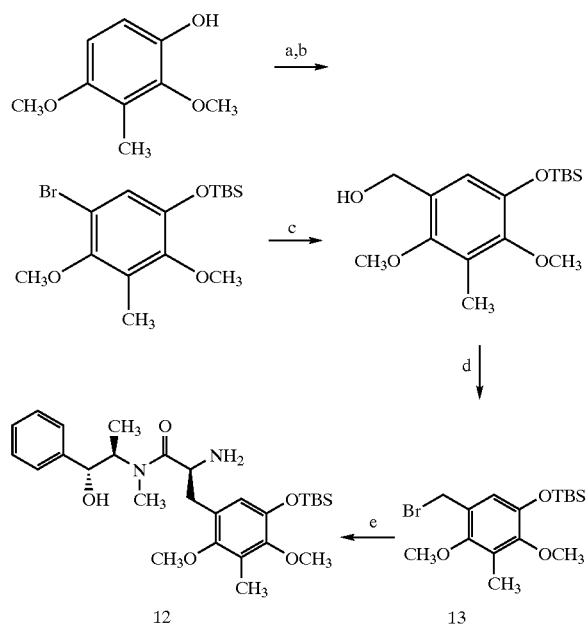

(a) TBSCl, imidazole, DMF, 23° C., 99%.
(b) Br$_2$, pyridine, DMF, 23° C., 90%.
(c) t-BuLi, THF, -90° C.; DMF, -90 →23° C.; NaBH$_4$, EtOH, 0° C., 77%.
(d) PPh$_3$, Br$_2$, imidazole, CH$_2$Cl$_2$, 0° C., 78%.
(e) (−)-pseudoephedrine glycinamide hydrate, LHMDS, LiCl, THF, 0° C., 74%.

Tetrahydroisoguinoline 7

A solution of aldehyde 4 (433 mg, 0.752 mmol, 1.05 equiv) in dichloromethane (7.2 mL) was added to a solid mixture of amine 5 (240 mg, 0.716 mmol, 1 equiv) and sodium sulfate (2.03 g, 14.3 mmol, 20.0 equiv). The resulting suspension was stirred rapidly for 75 min at 23° C., then was filtered through a plug of cotton. The filtrate was concentrated and the residue was dried azeotropically by concentration from a 3-mL portion of toluene to afford a white foam. $^1$H NMR analysis (CDCl$_3$) showed two diastereomers of imine 6 to be present in a ratio of ~95:5. Anhydrous lithium bromide (1.62 g, 18.7 mmol, 26 equiv) and 1,2-dimethoxyethane (14.3 mL) were then added sequentially to the imine residue, and the mixture was held in a sonicator for 5 min. The resultant suspension was warmed to 35° C. and was held at that temperature for 17.5 h before being cooled to 23° C. The mixture was diluted with ethyl acetate (20 mL) and was washed with three 20-mL portions of 4:1 saturated aqueous sodium chloride solution-saturated aqueous sodium bicarbonate solution. The organic layer was dried over sodium sulfate and was concentrated. $^1$H NMR analysis (CDCl$_3$) of the residue showed a ~5:1 mixture of cis:trans tetrahydroisoquinolines to be present. The crude product was purified by flash column chromatography (100:1 dichloromethane-methanol) to afford tetrahydroisoquinoline 7 as an off-white solid (460 mg, 72%). HPLC analysis (Chiralcel OD, 4% 2-propanol-0.3% diethylamine-hexanes, 0.30 mL/min, 254 nm detection, ~0.1 mg injection) of bis(benzoyl)-7 (PhCOCl, Et$_3$N, DMAP, CH$_2$Cl$_2$, 23° C.) established an enantiomeric excess of 99% (t$_r$(7): 79.2 min, t$_r$(ent-7):89.2 min).

(R)-Morpholino nitrile diastereomer, 7: $^1$H NMR (400 MHz, CDCl$_3$), δ 7.75 (d, 2 H, J=7.7 Hz, ArH), 7.51 (d, 1 H, J=8.4 Hz, ArH), 7.44 (d, 1 H, J=7.3 Hz, ArH), 7.40–7.36 (m, 2 H, ArH), 7.30–7.24 (m, 2 H, ArH), 6.35 (s, 1 H, ArH), 6.20 (s, 1 H, ArOH), 5.70 (d, 1 H, J=7.0 Hz, NHFmoc), 4.82 (br s, 1 H, ArCHN), 4.58 (m, 1 H, CHNHFmoc), 4.43 (dd, 1 H, J=9.7, 6.8 Hz, OCH$_2$CH), 4.19–4.06 (m, 2 H, OCH$_2$CH), 3.83–3.74 (m, 4 H, CH$_2$OCH$_2$), 3.79 (s, 3 H, ArOCH$_3$), 3.69 (s, 3 H, ArOCH$_3$), 3.65 (s, 3 H, ArOCH$_3$), 3.57 (s, 3 H, ArOCH$_3$), 3.49 (d, 1 H, J=9.9 Hz, CHC≡N), 3.21 (dd, 1 H, J=14.6, 2.0 Hz, CH$_2$ArOH), 3.15–3.08 (m, 1 H, CHCHC≡N), 2.87 (dd, 1 H, J=13.9, 11.7 Hz, CH$_2$ArOTBS), 2.73 (m, 2 H, CH$_2$NCH$_2$), 2.58 (m, 2 H, CH$_2$NCH$_2$), 2.34 (dd, 1 H, J=14.4, 11.2 Hz, CH$_2$ArOH), 2.25 (s, 3 H, ArCH$_3$), 2.19 (s, 3 H, ArCH$_3$), 2.15 (dd (obsc), 1 H, CH$_2$ArOTBS), 0.96 (s, 9 H, SiC(CH$_3$)$_3$), 0.10 (s, 3 H, SiCH$_3$), 0.09 (s, 3 H, SiCH$_3$). $^{13}$C NMR (100 MHz, CDCl$_3$), δ 156.4, 151.3, 149.1, 148.6, 145.0 144.4, 144.2, 142.5, 141.3, 127.6, 127.0, 125.1, 125.0, 124.6, 122.4, 120.2, 119.9, 119.6, 114.7, 66.8, 66.7, 64.1, 60.7, 60.6, 60.4, 59.8, 56.6, 55.0, 50.3, 47.3, 28.9, 28.5, 25.7, 18.2, 9.8, 9.6, −4.6 FTIR (neat film), cm$^{-1}$ 3345 (w, br, OH/NH), 2934 (s), 2251 (w, C≡N), 1715 (s, C=O), 1471 (s). HRMS (ES) Calcd for C$_{50}$H$_{65}$N$_4$O$_9$Si (M+H)$^+$: 893.4521, Found: 893.4535.

(S)-Morpholino nitrile diastereomer, 7: $^1$H NMR (400 MHz, CDCl$_3$), δ 7.74 (d, 2 H, J=7.3 Hz, ArH), 7.48 (t, 2 H, J=8.0 Hz, ArH), 7.40–7.35 (m, 2 H, ArH), 7.32–7.24 (m, 2 H, ArH), 6.37 (s, 1 H, ArH), 6.29 (s, 1 H, ArOH), 5.78 (d, 1 H, J=7.2 Hz, NHFmoc), 4.72 (br s, ArCHN), 4.37–4.28 (m, 1 H (CHNHFmoc), 1 H (OCH$_2$CH)), 4.17–4.11 (m, 2 H, OCH$_2$CH), 3.78–3.74 (m, 4 H, CH$_2$OCH$_2$), 3.76 (s, 3 H, ArOCH$_3$), 3.67 (s, 6 H, 2×ArOCH$_3$), 3.63 (s, 3 H, ArOCH$_3$), 3.46 (d, 1 H, J=7.3 Hz, CHC□N), 3.24–3.18 (m, 1 H (CH$_2$ArOH), 1 H (CHCHC□N)), 2.99 (dd, 1 H, J=13.9, 10.6 Hz, CH$_2$ArOTBS), 2.75–2.71 (m, 2 H, CH$_2$NCH$_2$), 2.64–2.60 (m, 2 H, CH$_2$NCH$_2$), 2.37–2.28 (m, 1 H (dd, CH$_2$ArOTBS), 1 H (dd, CH$_2$ArOH)), 2.22 (s, 3 H,ArCH$_3$) 2.19 (s, 3 H, ArCH$_3$), 0.95 (s, 9 H, SiC(CH$_3$)$_3$), 0.10 (s, 3 H, SiCH$_3$), 0.09 (s, 3 H, SiCH$_3$). $^{13}$C NMR (100 MHz, CDCl$_3$), δ 156.5, 151.4, 148.7, 148.6, 144.9, 144.3, 144.1, 143.9, 142.5, 141.2, 127.6, 127.0, 126.8, 125.2, 125.1, 124.2, 122.4, 120.4, 119.9, 116.1, 66.9, 66.6, 65.3, 60.8, 60.6, 59.8, 57.1, 54.6, 51.3, 50.9, 47.2, 29.2, 27.8, 25.7, 18.2, 9.8, 9.5, −4.6. FTIR (neat film), cm$^{-1}$3360 (m, br, OH/NH), 2934 (s), 2249 (w, C≡N), 1715 (s, C=O), 1480 (s). HRMS (ES) Calcd for C$_{50}$H$_{65}$N$_4$O$_9$Si (M+H)$^+$: 893.4521, Found: 893.4545.

N-Methyl-7

Formalin (554 μL, 7.39 mmol, 2.0 equiv) and sodium triacetoxyborohydride (1.17 g, 5.52 mmol, 1.5 equiv) were added sequentially to a solution of amine 7 (3.30 g, 3.69 mmol, 1 equiv) in acetonitrile (25 mL) at 23° C. After 30 min, the cloudy mixture was diluted with ethyl acetate (75 mL) and was washed with two 50-mL portions of 1:1 saturated aqueous sodium chloride solution-saturated aqueous sodium bicarbonate solution. The organic layer was dried over sodium sulfate and was concentrated. The residue was purified by flash column chromatography (40% ethyl acetate-hexanes) to afford N-methyl-7 as a white solid (3.29 g, 98%).

(R)-Morpholino nitrile diastereomer, N-methyl-7: $^1$H NMR (400 MHz, toluene-d$_8$), ~10:1 mixture of atropisomers, major signals only, δ 7.50 (d, 2 H, J=7.0 Hz, ArH), 7.39 (d, 1 H, J=6.6 Hz, ArH), 7.31 (d, 1 H, J=7.0 Hz, ArH), 7.21–7.13 (m, 4 H, ArH), 7.03 (s, 1 H, ArH), 6.09 (br s, 1 H, ArOH), 5.46 (d, 1 H, J=8.8 Hz, NHFmoc), 4.39–4.32 (m, 1 H, CHNHFmoc), 4.25 (d, 1 H, J=8.0 Hz, ArCHN), 4.03–3.98 (m, 1 H, OCH$_2$CH), 3.91–3.84 (m, 2 H, OCH$_2$CH), 3.58 (s, 3 H, ArOCH$_3$), 3.54 (s, 3 H, ArOCH$_3$), 3.46–3.43 (m, 4 H (CH$_2$OCH$_2$), 1 H (CHCHC☐N)), 3.44 (s, 3 H, ArOCH$_3$), 3.35 (dd (obsc), 1 H, CH$_2$ArOTBS), 3.34 (s, 3 H, ArOCH$_3$), 3.16–3.10 (m, 1 H (d, CHC☐N), 1 H (dd, CH$_2$ArOTBS)), 3.00 (dd, 1 H, J=15.0, 12.4 Hz, CH$_2$ArOH), 2.43–2.35 (m, 2 H (CH$_2$CHCH≡N), 1 H (CH$_2$ArOH)), 2.41 (2 s, 3 H each, ArCH$_3$ and NCH$_3$), 2.28 (s, 3 H, ArCH$_3$), 2.24–2.21 (m, 2 H, CH$_2$NCH$_2$), 1.05 (s, 9 H, SiC(CH$_3$)$_3$), 0.26 (s, 3 H, SiCH$_3$), 0.24 (s, 3 H, SiCH$_3$). $^{13}$C NMR (100 MHz, CDCl$_3$), two atropisomers, δ 156.1, 151.5, 148.5, 148.3, 144.8, 144.1, 144.0, 143.9, 142.3, 141.1, 127.5, 127.0, 126.9, 126.7, 125.2, 125.0, 124.9, 123.5, 122.6, 120.4, 119.8, 116.0, 66.7, 66.6, 64.6, 63.5, 61.1, 61.0, 60.6, 59.7, 57.5, 52.0, 47.1, 31.1, 25.7, 24.4, 18.1, 9.9, 9.5, −4.6. FTIR (neat film), cm$^{-1}$ 3357 (m, OH/NH), 2936 (s), 2250 (w, C≡N), 1715 (s, C=O), 1480 (s). HRMS (ES) Calcd for C$_{51}$H$_{67}$N$_4$O$_9$Si (M+H)$^+$: 907.4677, Found: 907.4666.

(S)-Morpholino nitrile diastereomer, N-methyl-7: $^1$H NMR (400 MHz, toluene-d$_8$), ~7:1 mixture of atropisomers, major signals only, δ 7.49 (d, 2 H, J=6.9 Hz, ArH), 7.35 (d, 1 H, J=7.1 Hz, ArH), 7.28 (dd, 1 H, J=6.3, 2.8 Hz, ArH), 7.23–7.18 (m, 4 H, ArH), 6.88 (s, 1 H, ArH), 5.48 (s, 1 H, ArOH), 4.90 (d, 1 H, J=9.6 Hz, NHFmoc), 4.24–4.15 (m, 1 H, CHNHFmoc), 4.09 (d, 1 H, J=10.7 Hz, ArCHN), 3.92 (dd, 1 H, J=8.2, 5.5 Hz, OCH$_2$CH), 3.89–3.76 (m, 1 H (CH$_2$CHNHFmoc), 1 H (CHC≡N), 2 H (OCH$_2$CH)), 3.69 (s, 3 H, ArOCH$_3$), 3.55 (s, 3 H, ArOCH$_3$), 3.50–3.48 (m, 4 H, CH$_2$OCH$_2$), 3.43 (s, 3 H, ArOCH$_3$), 3.39 (dd, 1 H, J=15.4, 6.2 Hz, CH$_2$CHCHC≡N), 3.19 (s, 3 H, ArOCH$_3$), 2.76–2.67 (m, 1 H (CH$_2$CHCHC≡N), 1 H (CHCHC≡N)), 2.64 (s, 3 H, NCH$_3$), 2.61 (dd, 1 H, J=13.7, 9.8 Hz, CH$_2$CHNHFmoc), 2.42–2.32 (m, 4 H, CH$_2$NCH$_2$), 2.27 (s, 3 H, ArCH$_3$), 2.00 (s, 3 H, ArCH$_3$), 1.06 (s, 9 H, SiC(CH$_3$)$_3$), 0.23 (s, 3 H, SiCH$_3$), 0.22 (s, 3 H, SiCH$_3$). $^{13}$C NMR (100 MHz, CDCl$_3$), two atropisomers, δ 155.8, 151.6, 148.8, 148.6, 144.6, 144.1, 144.0, 143.7, 142.7, 141.1, 141.0, 127.6, 127.5, 127.0, 126.9, 126.6, 125.1, 123.3, 122.3, 121.3, 120.6, 119.8, 117.3, 66.8, 66.5, 63.6, 61.2, 61.0, 60.7, 60.0, 59.8, 54.9, 50.2, 49.0, 47.1, 33.5, 25.7, 23.6, 18.1, 9.9, 9.5, −4.6. FTIR (neat film), cm$^{-1}$ 3402 (w, br, OH/NH), 2952 (m), 2252 (w, C≡N), 1713 (s, C=O), 1480 (s). HRMS (ES) Calcd for C$_{51}$H$_{67}$N$_4$O$_9$Si (M+H)$^+$: 907.4677, Found: 907.4713.

Amine 8

Acetic acid (530 μL, 9.28 mmol, 2.4 equiv) and tetrabutylammonium fluoride (1.0 M in tetrahydrofuran, 4.24 mL, 4.24 mmol, 1.1 equiv) were added sequentially to a solution of N-methyl-7 (3.50 g, 3.86 mmol, 1 equiv) in tetrahydrofuran (7.7 mL) at 0° C. The solution was then warmed to 23° C. After 1.5 h, the solution was diluted with 25% saturated aqueous sodium bicarbonate solution (25 mL) and was extracted with ether (3×25 mL). The combined organic layers were dried over sodium sulfate and were concentrated to afford N-Fmoc-8 as a white foam (3.06 g, >99%). A portion of the residue (1.22 g, 1.54 mmol, 1 equiv) was dissolved in dichloromethane (4.4 mL), and the resulting solution was treated with 1,8-diazabicyclo[5.4.0]undec-7-ene (DBU, 300 μL, 2.01 mmol, 1.3 equiv) to cleave the N-Fmoc group. After 30 min, the reaction solution was loaded directly onto a flash chromatography column. Elution with 25:1 dichloromethane-methanol afforded amine 8 as a solid (845 mg, 96%).

(R)-Morpholino nitrile diastereomer, 8: $^1$H NMR (400 MHz, CDCl$_3$), δ 6.86 (s, 1 H, ArH), 3.84 (s, 3 H, ArOCH$_3$), 3.81–3.76 (m, 4 H, CH$_2$OCH$_2$), 3.76 (s, 3 H, ArOCH$_3$), 3.72 (d (obsc), 1 H, ArCHNCH$_3$), 3.70 (s, 3 H, ArOCH$_3$), 3.66 (d, 1 H, J=2.7 Hz, CHC≡N), 3.52 (dd, 1 H, J=13.2, 2.2 Hz, CH$_2$CHNH$_2$), 3.33 (dd, 1 H, J=14.7, 4.4 Hz, CH$_2$CHCHC≡N), 2.97–2.91 (m, 1 H, CHNH$_2$), 2.80–2.76 (m, 2 H, CH$_2$NCH$_2$), 2.74 (m, 1 H, CHCHC≡N), 2.67–2.60 (m, 2 H, CH$_2$NCH$_2$), 2.61 (dd (obsc), 1 H, CH$_2$CHNH$_2$), 2.60 (s, 3 H, NCH$_3$), 2.40 (dd, 1 H, J=14.7, 12.8 Hz, CH$_2$CHCHC≡N), 2.23 (s, 3 H, ArCH$_3$), 2.21 (s, 3 H, ArCH$_3$). $^{13}$C NMR (100 MHz, CDCl$_3$), δ 150.5, 148.2, 146.8, 145.6, 144.4, 143.9, 128.2, 124.5, 124.2, 123.4, 121.8, 116.4, 114.3, 67.2, 66.7, 64.8, 62.0, 61.2, 60.7, 60.5, 60.2, 52.2, 46.8, 33.6, 23.5, 9.9, 9.5. FTIR (neat film), cm$^{-1}$ 3364 (m, br, OH/NH), 2938 (s), 2250 (w, C≡N), 1455 (s). HRMS (ES) Calcd for C$_{30}$H$_{43}$N$_4$O$_7$ (M+H)$^+$: 571.3132, Found: 571.3106.

(S)-Morpholino nitrile diastereomer, 8: $^1$H NMR (400 MHz, CDCl$_3$), δ 6.68 (s, 1 H, ArH), 3.85 (s, 3 H, ArOCH$_3$), 3.84–3.73 (m, 4 H (CH$_2$OCH$_2$), 1 H (ArCHNCH$_3$)), 3.78 (s, 3 H, AROCH$_3$), 3.75 (s, 3 H, ArOCH$_3$), 3.69 (dd, 1 H, J=10.3, 3.0 Hz, CH$_2$CHNH$_2$), 3.64 (s, 3 H, ArOCH$_3$), 3.62 (d, 1 H, J=9.5 Hz, CHC≡N), 3.31 (dd, 1 H, J=15.6, 6.4 Hz, CH$_2$CHCHC≡N), 2.97–2.91 (m, 1 H, CHNH$_2$), 2.90–2.83 (m, 1 H, CHCHC≡N), 2.78–2.73 (m, 2 H, CH$_2$NCH$_2$), 2.64–2.59 (m, 2 H, CH$_2$NCH$_2$), 2.59 (s, 3 H, NCH$_3$), 2.35 (dd, 1 H, J=13.6, 10.6 Hz, CH$_2$CHNH$_2$), 2.24 (s, 3 H, ArCH$_3$), 2.22 (s, 3 H, ArCH$_3$), 2.10 (dd, 1 H, J=15.7, 11.6 Hz, CH$_2$CHCHC≡N). $^{13}$C NMR (100 MHz, CDCl$_3$), δ 150.4, 148.5, 146.1, 145.3, 144.6, 144.2, 128.4, 124.6, 124.2, 123.3, 121.1, 117.1, 114.4, 67.2, 66.8, 66.7, 61.2, 61.1, 60.7, 60.5, 60.4, 56.3, 50.5, 49.3, 35.0, 23.7, 9.9, 9.5. FTIR (neat film), cm$^{-1}$ 3360 (m, br, OH/NH), 2941 (m), 2251 (w, C≡N), 1455 (s). HRMS (ES) Calcd for C$_{30}$H$_{43}$N$_4$O$_7$ (M+H)$^+$: 571.3132, Found: 571.3146.

Tetrahydroisoquinoline 9

A deoxygenated (3 freeze-pump-thaw cycles) solution of N-Fmoc glycinal (190 mg, 0.675 mmol, 1.2 equiv) in dichloromethane (11.3 mL) was transferred by cannula to a solid mixture of amine 8 (322 mg, 0.564 mmol, 1 equiv) and sodium sulfate (1.20 g, 8.45 mmol, 15 equiv). The resulting suspension was stirred for 17.5 h at 23° C., then was filtered through a plug of cotton, rinsing with a 6-mL portion of dichloromethane. The filtrate was concentrated and the residue was purified by flash column chromatography (50→70% ethyl acetate-hexanes→ethyl acetate→200:1 ethyl acetate-methanol) to afford tetrahydroisoquinoline 9 as a solid (299 mg, 64%).

(R)-Morpholino nitrile diastereomer, 9: $^1$H NMR (400 MHz, CDCl$_3$), signals broadened due to atropisomerism, δ 7.76 (dd, 2 H, J=7.3, 3.5 Hz, ArH), 7.57 (t, 2 H, J=7.4 Hz, ArH), 7.31 (m, 2 H, ArH), 7.28 (m, 2 H, ArH), 5.38 (br s, 1 H, NHFmoc), 4.40–4.31 (m, 1 H (CHCH$_2$NHFmoc), 2 H (OCH$_2$CH)), 4.23 (m, 1 H, OCH$_2$CH), 3.90 (m, 1 H, CH$_2$NHFmoc), 3.84–3.65 (m, 1 H (CH$_3$NCHCHNH), 4 H (CH$_2$OCH$_2$)), 3.76 (s, 3 H, ArOCH$_3$), 3.74 (s, 3 H, ArOCH$_3$), 3.67 (s, 3 H, ArOCH$_3$), 3.65 (s, 3 H, ArOCH$_3$), 3.58–3.56 (m, 1 H (CHC≡N), 1 H (ArCH$_2$CHNH)), 3.43 (m, 1 H, CH$_2$NHFmoc), 3.28 (dd, 1 H, CH$_2$CHNCH$_3$), 2.86 (m, 1 H, CH$_2$CHNCH$_3$), 2.75–2.71 (m, 2 H, CH$_2$NCH$_2$), 2.68 (m, 1 H, ArCH$_2$CHNH), 2.62 (br s, 3 H, NCH$_3$), 2.60 (m, 2 H, CH$_2$NCH$_2$), 2.39 (m, 1 H (CH$_2$CHNCH$_3$), 1 H (ArCH$_2$CHNH)), 2.21 (s, 6 H, 2×ArCH$_3$). $^{13}$C NMR (100 MHz, CDCl$_3$), δ 157.1, 149.1, 148.4, 145.5, 144.0, 143.7, 143.3, 141.8, 141.2, 127.6, 127.0, 125.9, 125.1, 123.3, 122.7, 122.3, 120.4, 119.9, 116.0, 66.8, 66.6, 65.9, 65.0, 61.1, 60.7, 60.6, 60.5, 58.9, 52.4, 52.2, 51.8, 47.2, 46.4, 26.8, 24.0, 9.6, 9.5. FTIR (neat film), cm$^{-1}$ 3278 (m, OH/NH), 2940 (m), 2249 (w, C≡N), 1705 (s, C=O), 1450 (s). HRMS (ES) Calcd for C$_{47}$H$_{56}$N$_5$O$_9$ (M+H)$^+$: 834.4078, Found: 834.4106.

(S)-Morpholino nitrile diastereomer, 9: $^1$H NMR (500 MHz, CDCl$_3$), signals broadened due to atropisomerism, δ 7.76 (d, 2 H, J=7.0 Hz, ArH), 7.57 (d, 2 H, J=6.5 Hz, ArH), 7.39 (m, 2 H, ArH), 7.30 (m, 2 H, ArH), 5.44 (br s, 1 H, NHFmoc), 4.42 (dd, 1 H, OCH$_2$CH), 4.35 (m, 1 H CHCH$_2$NHFmoc), 4.28 (t, 1 H, OCH$_2$CH), 4.22 (dd, 1 H, OCH$_2$CH), 3.85–3.82 (m, 1 H (CH$_2$NHFmoc), 1 H (CH$_2$CHNCH$_3$)), 3.75–3.65 (m, 4 H (CH$_2$OCH$_2$), 1 H (CHC≡N), 3.74 (br s, 9 H, 3×ArOCH$_3$), 3.65 (s, 3 H, ArOCH$_3$), 3.37 (m, 1 H, CH$_2$NHFmoc), 3.32 (dd, 1 H, ArCH$_2$CHNH), 3.27 (m, 1 H, CH$_3$NCHCHNH), 2.87 (m, 1 H, CH$_2$CHNCH$_3$), 2.74 (m, 1 H, ArCH$_2$CHNH), 2.70 (m, 2 H, CH$_2$NCH$_2$), 2.59 (br s, 3 H, NCH$_3$), 2.53 (m, 2 H, CH$_2$NCH$_2$), 2.36 (dd, 1 H, CH$_2$CHNCH$_3$), 2.24 (s, 3 H, ArCH$_3$), 2.22 (s, 3 H, ArCH$_3$), 2.13 (dd, 1 H, ArCH$_2$CHNH). $^{13}$C NMR (125 MHz, CDCl$_3$), δ 157.0, 149.1, 148.6, 145.3, 144.1, 143.9, 143.7, 141.8, 141.2, 127.6, 127.0, 125.8, 125.1, 123.3, 122.9, 122.5, 121.9, 120.7, 119.9, 116.3, 66.8, 66.6, 66.1, 62.1, 61.1, 60.7, 60.5, 60.3, 57.0, 52.0, 50.5, 48.9, 47.2, 27.7, 24.0, 9.5, 6.0. FTIR (neat film), cm$^{-1}$ 3274 (m, OH/NH), 2939 (m), 2249 (w, C≡N), 1704 (s, C=O), 1451 (s). HRMS (ES) Calcd for C$_{47}$H$_{56}$N$_5$O$_9$ (M+H)$^+$: 834.4078, Found: 834.4103.

Pentacyclic Intermediate 2

A solution of anhydrous zinc chloride in tetrahydrofuran (0.50 M, 4.26 mL, 2.14 mmol, 3.0 equiv) and trimethylsilyl cyanide (190 μL, 1.42 mmol, 2.0 equiv) were added sequentially to a solution of morpholino nitrile 9 (595 mg, 0.713 mmol, 1 equiv) in 2,2,2-trifluoroethanol (8.5 mL) at 23° C. After 7 h, an aqueous solution of EDTA (20 mL, 0.20 M (ethylenedinitrilo)tetraacetic acid, disodium salt-0.40 M sodium hydroxide, pH 10) was added, and the resulting mixture was extracted with ethyl acetate (2×25 mL). The combined organic layers were washed with a 20-mL portion of 1:1 saturated aqueous sodium chloride solution-saturated aqueous sodium bicarbonate solution, then were dried over sodium sulfate and were concentrated. Purification of the residue by radial chromatography (40%→60% ethyl acetate-hexanes) furnished pentacyclic intermediate 2 as a white solid (464 mg, 87%). $^1$H NMR (500 MHz, CDCl$_3$), ~5:1 mixture of rotamers, major signals only, δ 7.75 (t, 2 H, J=7.9 Hz, ArH), 7.46–7.39 (m, 4 H, ArH), 7.30 (t, 2 H, J=7.4 Hz, ArH), 5.63 (s, 1 H, ArOH), 5.54 (s, 1 H, ArOH), 4.54 (t, 1 H, J=5.8 Hz, NHFmoc), 4.32 (dd, 1 H, J=10.8, 6.8 Hz, OCH$_2$CH), 4.22 (dd, 1 H, J=10.8, 6.3 Hz, OCH$_2$CH), 4.14 (br s, 1 H, ArCHNCH$_3$), 4.12 (app t, 1 H, J=4.4 Hz, CHCH$_2$NHFmoc), 4.06 (app t, 1 H, J=6.4 Hz, OCH$_2$CH), 3.73 (s, 3 H, ArOCH$_3$), 3.68 (br s, 1 H, CHC☐N), 3.60 (2 s, 3 H each, 2×ArOCH$_3$), 3.55 (s, 3 H, ArOCH$_3$), 3.28 (br d, 1 H, J=7.6 Hz, CHCHC≡N), 3.24–3.20 (m, 1 H (ArCHCHN), 1 H (ArCHCHCH$_2$), 1 H (CH$_2$NHFmoc)), 3.11–3.06 (m, 1 H, CH$_2$NHFmoc), 2.96 (dd, 1 H, J=18.5, 7.8 Hz, ArCH$_2$CHNCH$_3$), 2.33 (d, 1 H, J=18.5 Hz, ArCH$_2$CHNCH$_3$), 2.31 (s, 3 H, NCH$_3$), 2.18 (s, 3 H, ArCH$_3$), 2.11 (s, 3 H, ArCH$_3$), 1.88 (dd, 1 H, J=15.7, 12.5 Hz, ArCHCHCH$_2$). $^{13}$C NMR (100 MHz, CDCl$_3$), δ 156.0, 148.2, 144.0, 143.7, 143.6, 143.2, 141.6, 141.2, 127.6, 127.0, 125.0, 124.8, 123.8, 122.3, 122.1, 119.8, 119.7, 118.5, 118.1, 116.8, 65.9, 60.7, 60.6, 59.6, 57.1, 56.6, 56.5, 55.2, 47.2, 45.3, 41.7, 25.7, 21.2, 9.6. FTIR (neat film), cm$^{-1}$ 3395 (m, br, OH/NH), 2938 (m), 2250 (w, C≡N), 1714 (s, C=O), 1463 (s). HRMS (ES) Calcd for C$_{43}$H$_{47}$N$_4$O$_8$ (M+H)$^+$: 747.3394, Found: 747.3424.

N-Fmoc Cleavage of Pentacyclic Intermediate 2

1,8-Diazabicyclo[5.4.0]undec-7-ene (DBU, 140 μL, 0.936 mmol, 1.3 equiv) was added to a solution of pentacyclic intermediate 2 (538 mg, 0.720 mmol, 1 equiv) in dichloromethane (2.9 mL) at 23° C. After 30 min, the reaction solution was loaded directly onto a flash chromatography column. Elution with 25:1→20:1 dichloromethane-methanol afforded the deprotected product as a white solid (330 mg, 87%).

$^1$H NMR (500 MHz, CDCl$_3$), δ 4.16 (br s, 1 H, ArCHNCH$_3$), 4.03 (br d, 1 H, J=3.2 Hz, CHCH$_2$NH$_2$), 4.00 (d, 1 H, J=2.1 Hz, CHC≡N), 3.74 (2 s, 3 H each, 2×ArOCH$_3$), 3.68 (s, 3 H, ArOCH$_3$), 3.61 (s, 3 H, ArOCH$_3$), 3.39 (br d, 1 H, J=7.6 Hz, CHCHC≡N), 3.24 (app dd, 1 H, J =11.8, 2.4 Hz, ArCH$_2$CHCHAr), 3.20 (dd, 1 H, J=15.7, 2.1 Hz, ArCH$_2$CHCHAr), 3.07 (dd, 1 H, J=18.4, 8.0 Hz, CH$_2$CHCHC≡N), 2.84 (dd, 1 H, J=13.2, 1.8 Hz, CH$_2$NH$_2$), 2.60 (dd, 1 H, J =13.4, 5.9 Hz, CH$_2$NH$_2$), 2.43 (d, 1 H, J=18.4 Hz, CH$_2$CHCHC≡N), 2.32 (s, 3 H, NCH$_3$), 2.22 (s, 3 H, ArCH$_3$), 2.18 (s, 3 H, ArCH$_3$), 1.83 (dd, 1 H, J=15.3, 11.9 Hz, ArCH$_2$CHCHAr). $^{13}$C NMR (125 MHz, CDCl$_3$), δ 148.3, 148.0, 144.6, 143.3, 143.1, 142.6, 124.5, 123.8, 122.5, 122.0, 120.1, 118.2, 117.0, 60.7, 60.6, 60.5, 60.4, 59.9, 59.2, 56.5, 56.3, 55.1, 46.0, 41.7, 25.8, 21.5, 9.5 (2 C). FTIR (neat film), cm$^{-1}$ 3356 (w, br, OH/NH), 2936 (m), 2250 (w, C≡N), 1463 (s). HRMS (ES) Calcd for C$_{28}$H$_{37}$N$_4$O$_6$ (M+H)$^+$: 525.2713, Found: 525.2690.

Pyruvamide 11

N,N-Diethylaniline (34 μL, 0.21 mmol, 1.1 equiv) and pyruvoyl chloride (65 μL, 0.61 mmol, 3.0 equiv) were added sequentially to a solution of the primary amine (107 mg, 0.204 mmol, 1 equiv) in dichloromethane (4.1 mL) at 0° C. After 30 min, a 10-mL portion of half-saturated aqueous sodium bicarbonate solution was added, and the resulting mixture was extracted with ethyl acetate (10 mL). The organic layer was washed once each with 10-mL portions of half-saturated aqueous sodium bicarbonate solution and 1:1 saturated aqueous sodium chloride solution-saturated aqueous sodium bicarbonate solution, then was dried over sodium sulfate and was concentrated. Flash column chromatography (60% ethyl acetate-hexanes) afforded pyruvamide 11 as a white solid (105 mg, 87%).

$^1$H NMR (400 MHz, CDCl$_3$), δ 6.44 (t, 1 H, J=5.6 Hz, NHCO), 5.71 (s, 1 H, ArOH), 5.59 (s, 1 H, ArOH), 4.23 (br s, 1 H, CHCH$_2$NHCO), 4.15 (d, 1 H, J=2.1 Hz, ArCHNCH$_3$), 4.02 (d, 1 H, J=2.4 Hz, CHC≡N), 3.79 (s, 3 H, ArOCH$_3$), 3.73 (s, 3 H, ArOCH$_3$), 3.66 (app dt (obsc), 1 H, CH$_2$NHCO), 3.65 (s, 3 H, ArOCH$_3$), 3.58 (s, 3 H, ArOCH$_3$), 3.41 (br d, 1 H, J=7.9 Hz, CHCHC≡N), 3.29 (app dt, 1 H, J=13.6, 4.7 Hz, CH$_2$NHCO), 3.24–3.20 (m, 1 H (ArCHCHCH$_2$Ar), 1 H (ArCHCHCH$_2$Ar)), 3.05 (dd, 1 H, J=18.5, 8.1 Hz, CH$_2$CHCHC≡N), 2.48 (d, 1 H, J=18.5 Hz, CH$_2$CHCHC≡N), 2.30 (s, 3 H, NCH$_3$), 2.23 (s, 3 H, COCH₃), 2.18 (s, 3 H, ArCH₃), 2.16 (s, 3 H, ArCH₃), 1.92 (dd, 1 H, J=16.2, 12.1 Hz, ArCHCHCH₂). $^{13}$C NMR (125 MHz, CDCl₃), δ 196.1, 159.9, 148.4, 148.2, 143.5, 143.3 (2 C), 141.5, 125.0, 123.5, 122.4, 118.0, 117.5, 116.4, 60.8, 60.7, 60.4, 59.9, 59.6, 56.5 (2 C), 56.3, 55.0, 41.8, 41.5, 25.8, 24.3, 21.1, 9.6 (2 C). FTIR (neat film), cm$^{-1}$ 3378 (m, br, OH/NH), 2937 (m), 2251 (w, C≡N), 1720 (m, C=O), 1682 (s, C=O), 1463 (s). HRMS (ES) Calcd for C₃₁H₃₉N₄O₈ (M+H)⁺: 595.2768, Found: 595.2739.

(−)-Saframycin A (1)

Iodosobenzene (189 mg, 0.859 mmol, 2.5 equiv) was added to a solution of pyruvamide 11 (203 mg, 0.341 mmol, 1 equiv) in 50% acetonitrile-water (8.0 mL) at 0° C. After 1 h, the reaction mixture was loaded directly onto a C₁₈-silica flash chromatography column and was eluted with 50% acetonitrile-water to provide synthetic (−)-saframycin A (1) as a yellow solid (127 mg, 66%). Spectral data and chromatographic properties of synthetic 1 were identical to those of an authentic sample of natural saframycin A.

$^1$H NMR (500 MHz, CDCl₃), δ 6.67 (br dd, 1 H, J=8.1, 3.7 Hz, NHCO), 4.06 (br d, 1 H, J=2.0 Hz, CHN(CH₃) CHCHC≡N), 4.02 (2 s, 3 H, each, 2×OCH₃), 3.99 (d, 1 H, J=2.4 Hz, CHC≡N), 3.97 (m, 1 H, CHCH₂NH), 3.72 (ddd, 1 H, J=14.2, 8.8, 1.5 Hz, CH₂NH), 3.43 (br d, 1 H, J=7.6 Hz, CHCHC≡N), 3.26 (dt, 1 H, J=14.2, 4.2 Hz, CH₂NH), 3.13 (dt, 1 H, J=11.4, 2.9 Hz, CHNCHC≡N), 2.88 (dd, 1 H, J=17.7, 2.6 Hz, CH₂CHCHNCH₃), 2.82 (dd, 1 H, J=21.1, 7.6 Hz, CH₂CHCHC≡N), 2.31 (s, 3 H, NCH₃), 2.25 (s, 3 H, COCH₃), 2.24 (d, 1 H, J=21.0 Hz, CH₂CHCHC≡N), 1.98 (s, 3 H, CCH₃), 1.92 (s, 3 H, CCH₃), 1.28 (ddd, 1 H, J=17.7, 11.5, 2.7 Hz, CH₂CHNCHC≡N). $^{13}$C NMR (125 MHz, CDCl₃), δ 196.7, 186.6, 185.3, 182.4, 180.8, 160.2, 155.9, 155.6, 141.5, 141.2, 135.6, 135.5, 129.2, 128.3, 116.6, 61.1, 60.9, 58.2, 56.2, 54.5, 54.2, 53.9, 41.6, 40.6, 25.0, 24.2, 21.5, 8.7 (2 C). FTIR (neat film), cm$^{-1}$ 3407 (w, NH), 2944 (w), 2249 (w, C≡N), 1720 (w), 1682 (m, C=O), 1652 (s, C=O), 1615 (m, C=C), 1447 (m). HRMS (ES) Calcd for C₂₉H₃₁N₄O₈ (M+H)⁺: 563.2142, Found: 563.2169. $[α]_D^{23}$ (synthetic 1)=−4.6°. $[α]_D^{23}$ (natural 1)=−4.0°.

Figure 3:
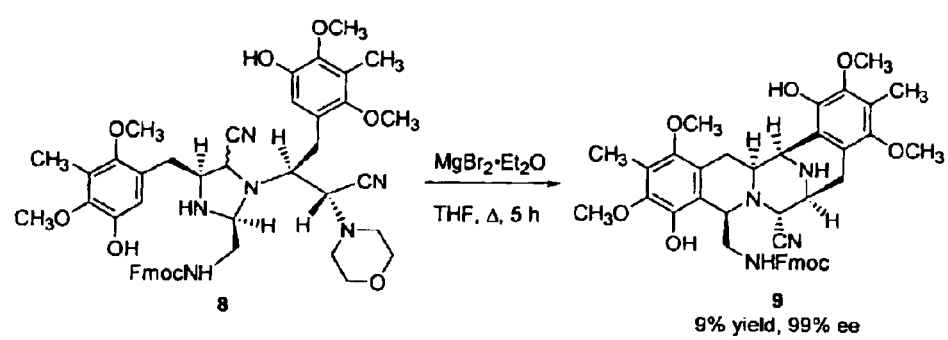
FIG. 3 depicts the synthesis of a precursor of saframycin A (9) from an N-linked trimeric α-amino aldehyde precursor.

B. In yet another embodiment of the present invention, the general methodology as described is exemplified by the one-step construction of the pentacyclic skeleton of saframycin A (9) from a trimeric α-amino aldehyde precursor (8), as depicted in FIG. 3. Specifically, recognizing that synthetic studies have shown that the potent antitumor alkaloid saframycin A can be assembled from glycine, alanine, and two molecules of tyrosine (Mikami et al. *J. Biol. Chem.* 1985, 260, 344; Arai et al. *Antimicrob. Agents Chemother.* 1985, 28, 5; Arai et al. In *The Alkaloids*; Brossi, A., Ed.; Academic Press: New York, 1983; Vol. 21, Chapter 3; Remers, W.A. In *The Chemistry of Antitumor Antibiotics*; Wiley-Interscience: New York, 1988; Vol. 2, Chapter 3.) As demonstrated above (in part A), an efficient synthesis for the generation of alkaloids via the directed condensation of α-amino aldehydes was achieved. Over the course of the five steps described above, the components were linked in a stepwise fashion in a sequence involving two Pictet-Spengler cyclization reactions and an intramolecular Strecker reaction, to form the pentacyclic saframycin A precursor 5 (same as (2) depicted in FIG. 1; see, Myers, A. G.; Kung, D. W. *J. Am. Chem. Soc.* 1999, 121, 10828). In yet another embodiment, as demonstrated herein, alkaloid skeletons, specifically the saframycin skeleton as demonstrated below, can be assembled in one remarkable transformation from an N-linked oligomer of three α-amino aldehyde components 2, 3 and 4, (FIG. 4) a reaction that suggests for the first time a viable pathway linking saframycin A (1) with an oligopeptide precursor and, therefore, a possible biosynthetic route.

Figure 5:
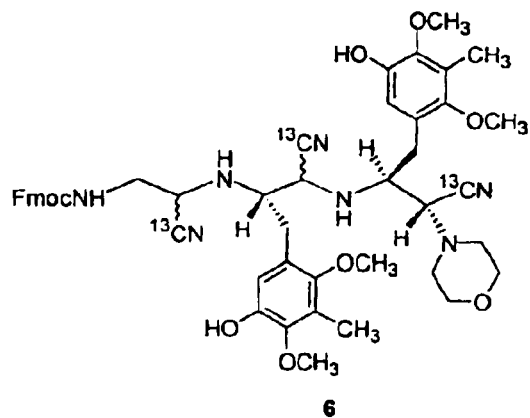
FIG. 5 depicts the synthesis of an N-linked trimeric α-amino aldehyde precursor (8).
Figure 5:
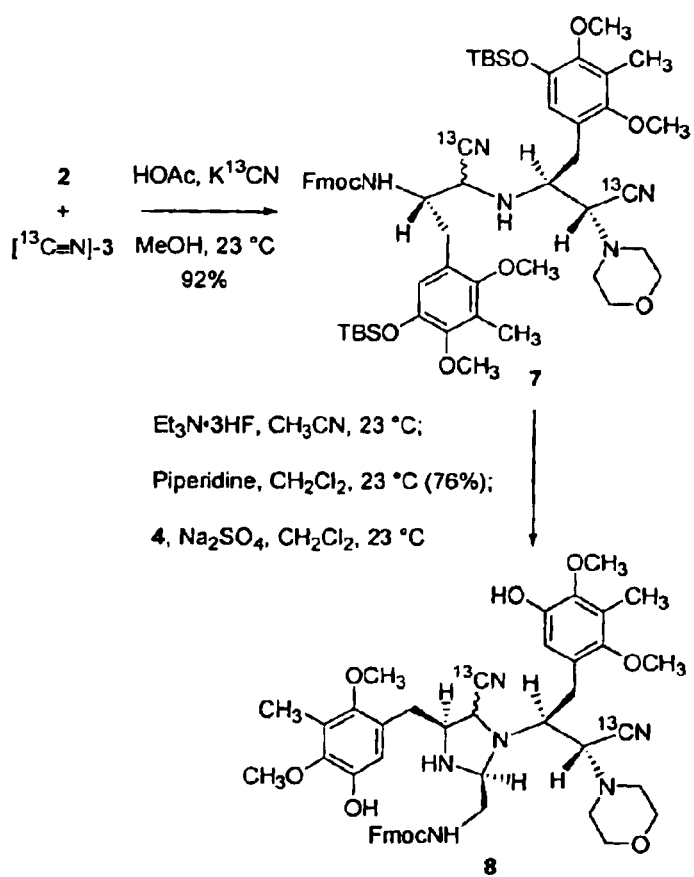

The specific oligomer that was targeted initially was the trimeric amino nitrile, 6, in which 2, 3, and 4 are linked by sequential Strecker reactions (see FIG. 5). The amino nitrile groups serve to covalently join the three α-amino aldehyde components and were proposed to function later as precursors to electrophilic imine or iminium intermediates that would mediate the three cyclization reactions leading to the saframycin skeleton (For selected examples of the use of amino nitrites as imine/iminium ion precursors in biomimetic systems, see (a) Overman, L. E.; Jacobsen, E. J. *Tetrahedron Lett.* 1982, 23, 2741 (b) Ksander et al. *Helv. Chim. Acta* 1987, 70, 1115; (c) Bonin et al. *Org. Synth.* 1992, 70, 54). Previously, it had been demonstrated that α-amino aldehydes can be coupled using the Strecker reaction without epimerization of the α-stereocenter (Myers et al. *J. Am. Chem. Soc.* 1999, 121, 8401). Because amino nitrile formation was anticipated to form two diastereomeric products in each case (of no consequence in later C—C bond forming reactions) $^{13}$C labeled cyanide was utilized in the synthesis to facilitate $^{13}$–C NMR analysis of the products. Also, the sequence was begun with a single diastereomer of the C-protected α-amino aldehyde component 3, bearing a $^{13}$C-label on the cyano group.

Figure 4:
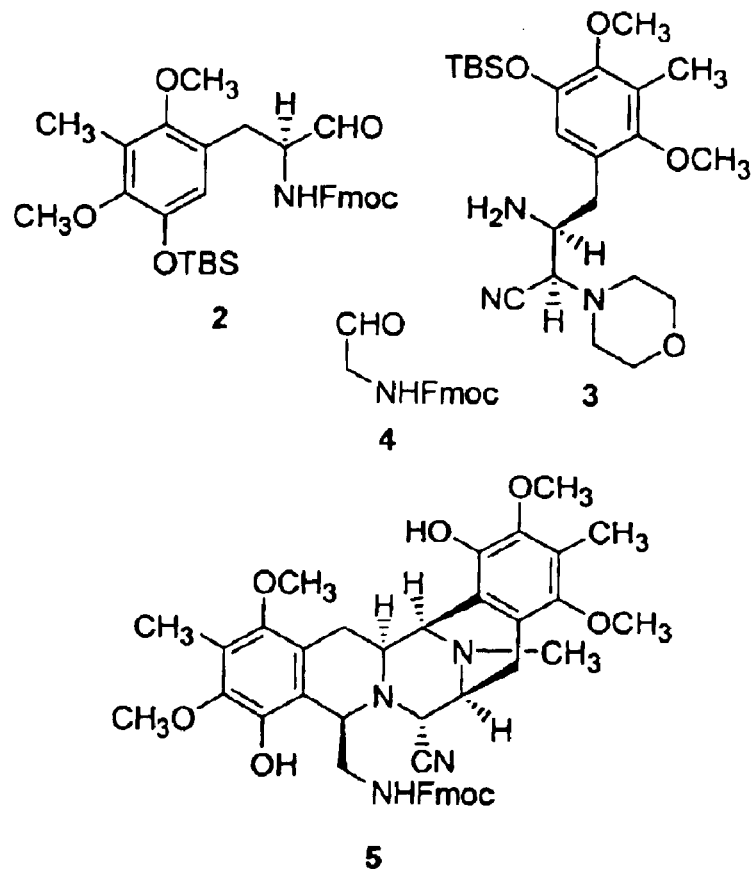
FIG. 4 depicts precursors in the synthesis of saframycin A.

The order of introduction of α-amino aldehyde components was 3+2, then 4, representing C- to N-terminus directionality in the synthesis. Mixing 3 (1 equiv, 93% ee, $^{13}$C-labeled cyano group) and its N-protected α-amino aldehyde counterpart 2 (1.05 equiv, 96% ee) in dichlorometane with suspended sodium sulfate led to formation of the corresponding imine, cleanly and without α-epimerization, as previously demonstrated above. In this instance, however, the imine was captured by Strecker reaction with hydrogen cyanide in methanol at 23° C. (1.6 equiv acetic acid, 1.5 equiv K$^{13}$CN, FIG. 5), whereas in the route described above, the imine was cyclized by warming (35° C.) in the presence of lithium bromide. The expected α-amino nitrites 7 (1.1:1 mixture of diastereomers) were obtained in 92% yield after isolation by flash column chromatograpy (FIG. 4). Sequential removal of the silyl ethers (triethylamine trihydrofluoride, 2.5 equiv, CH₃CN, 23° C.) and the N-Fmoc group (30% piperidine-CH₂Cl₂, 23° C., 76%, two steps) of 7 afforded the fully deprotected "dimer" for coupling with the third component, N-Fmoc glycinal (4). Attempted Strecker coupling of these components was complicated by internal cyclization of the glycinaldimine intermediate. Recognizing that such a process provided an aminal product that was functionally equivalent to the trimeric α-amino nitrile originally targeted, the condensation reaction was optimized to form this product (compound 8, FIG. 5). Thus, addition of 4 (1.1 equiv) to a solution of the deprotected dimeric α-amino aldehyde (1 equiv) in dichloromethane at 23° C. led to smooth condensation in the absence of hydrogen cyanide to afford a product formulated as the cyclic aminals 8. These products were not stable to chromatography on silica gel, but $^1$H- and $^{13}$C-NMR analysis showed that they had been formed cleanly (~90% combined yield). Only diastereomers were detected spectroscopically, and these were present in the same ratio as the starting material 7, suggesting that the cyclic aminal has been formed with a single stereochemistry, tentatively assigned as shown in FIG. 5.

Subsequently sequential treatment of 8 with the Lewis acids lithium bromide (dimethoxyethane, reflux) and then zinc chloride (trifluoroethanol-THF, 23° C.), and assisted by the fact that 8 was fortuitously well separated chromatographically from all other reaction products, it was possible to isolate the desired pentacyclic saframycin A precursor 9 from the reaction mixture in pure form (4%). With further experimentation, conditions were found to bring about the transformation of 8 to 9 in one step, and in higher yield (FIGS. 3 and 6); heating a solution of 8 in tetrahydrofuran at reflux in the presence of magnesium bromide etherate (20 equiv) afforded 9 in 8.4 and 9.0% yield in two separate experiments. Importantly, N-acylation of 9 with the enantiomeric Mosher acid chlroides followed by HPLC analysis of the amide products established that 9 had been formed without racemization (9 was 99% ee). N-Methylation of 9 with formalin and sodium triacetoxyborohydride in acetonitrile afforded the pentacyclic saframycin A precursor 5, (as depicted in FIG. 4) identical with an authentic sample prepared by the earlier synthetic route ($^1$H NMR, IR, TLC, and HPLC analysis), except for the anticipated spectroscopic differences attributed to the $^{13}$C label. Intermediate 5 can be transformed into saframycin A in three steps (50% yield) (see, for example, FIG. 2).

Figure 6:
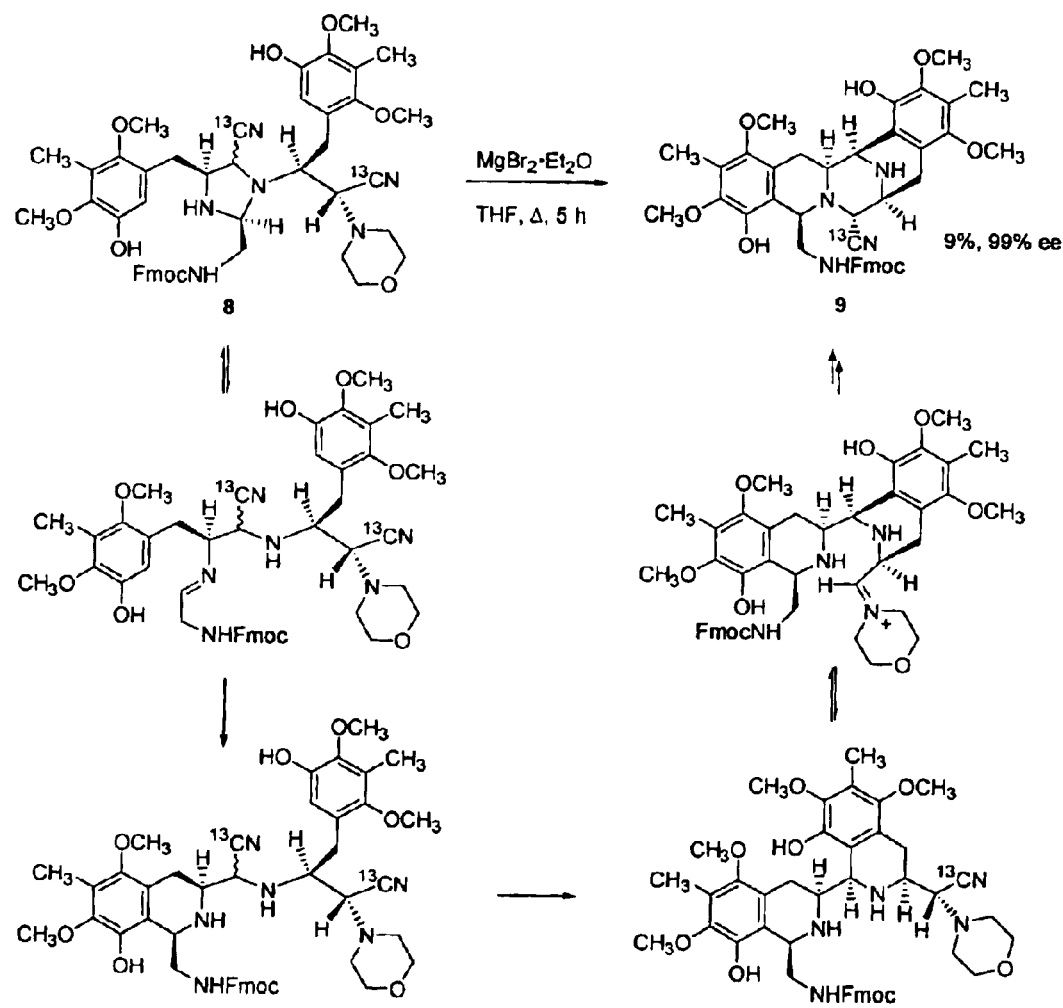
FIG. 6 depicts the synthesis of a precursor of saframycin A (9) from an N-linked trimeric α-amino aldehyde precursor (8).
Figure 7:
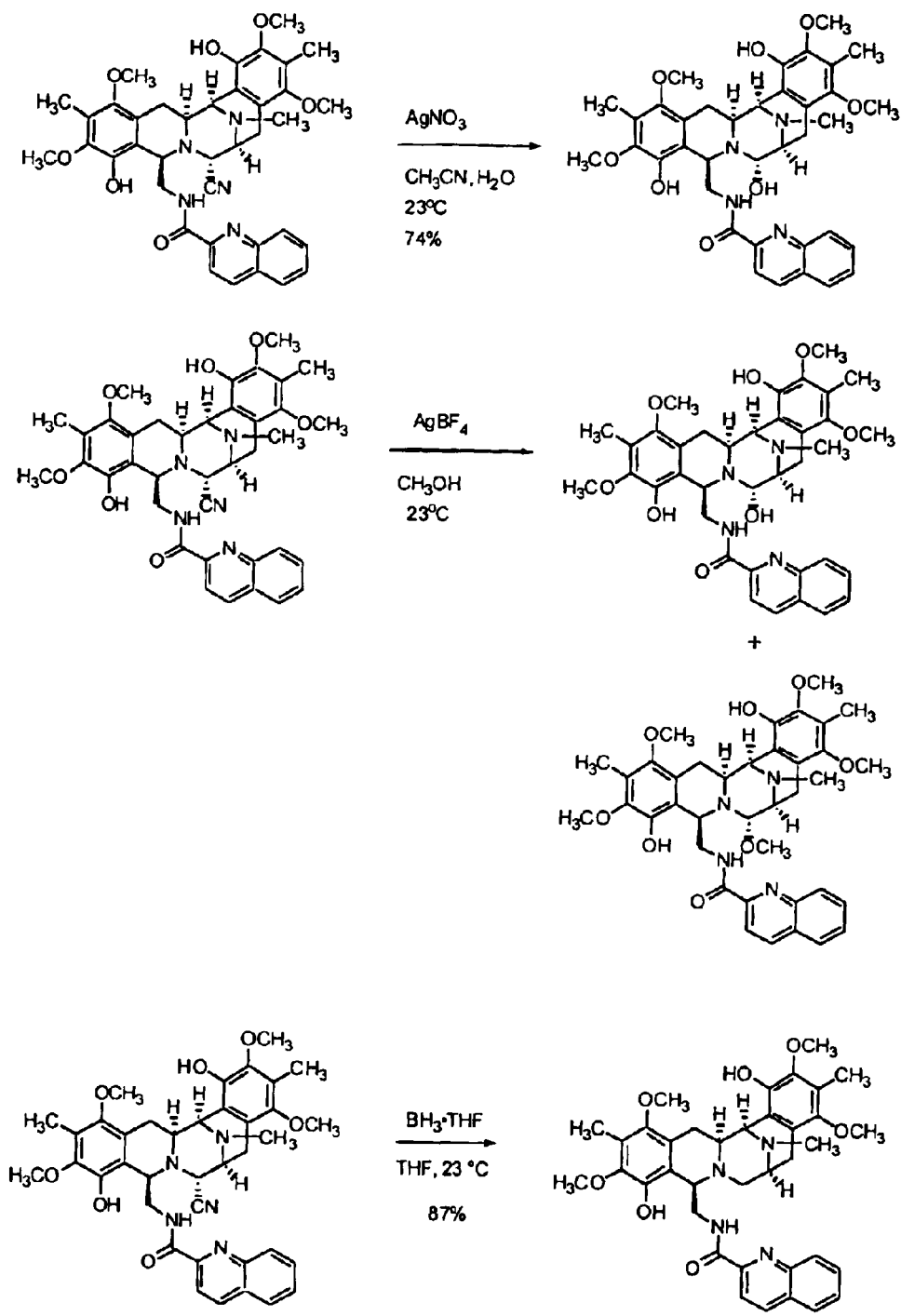
FIG. 7 depicts the synthesis of exemplary inventive analogues of saframycin.
Figure 8:
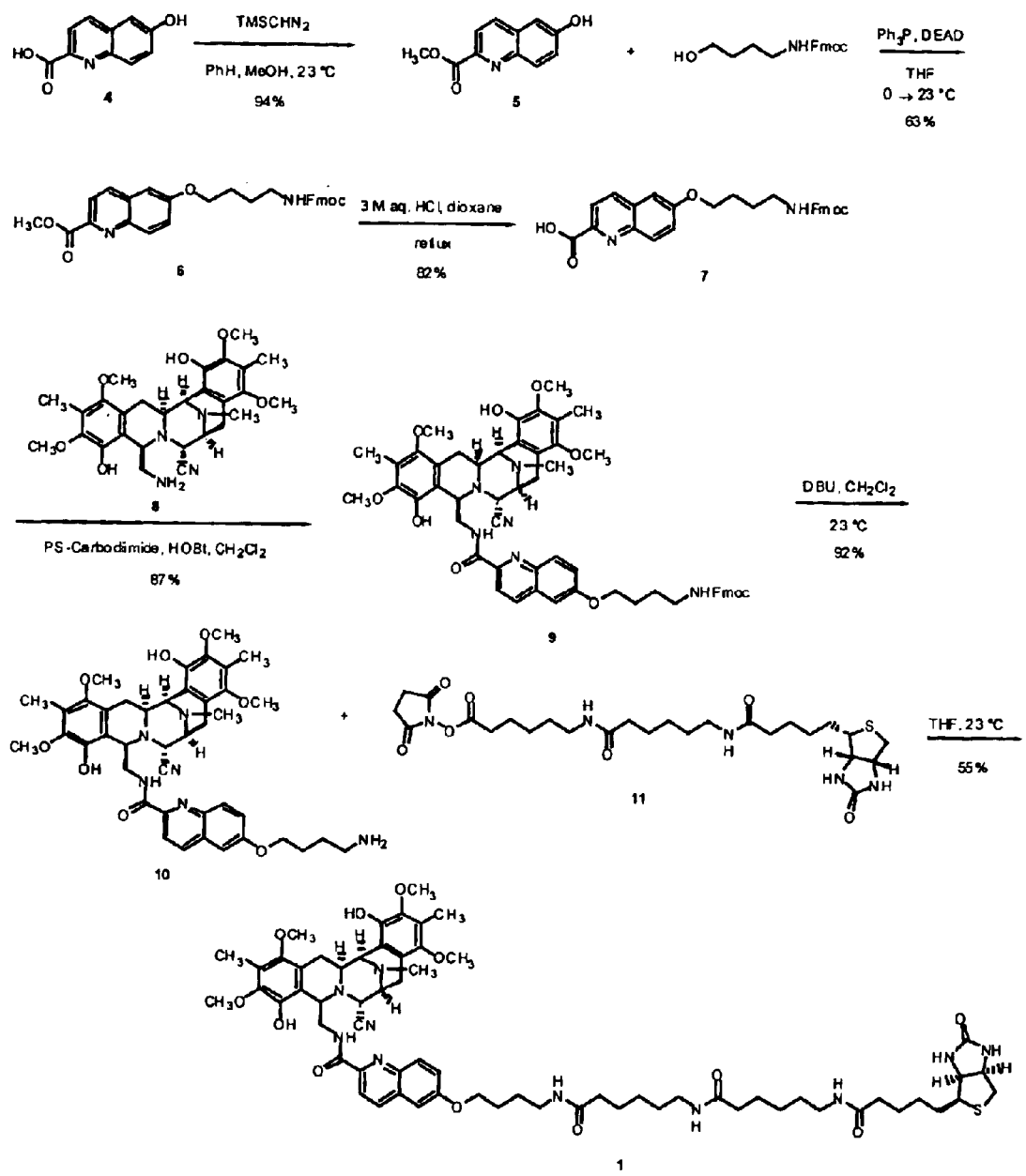
FIG. 8 depicts depicts the synthesis of exemplary inventive analogues of saframycin.
Figure 9:
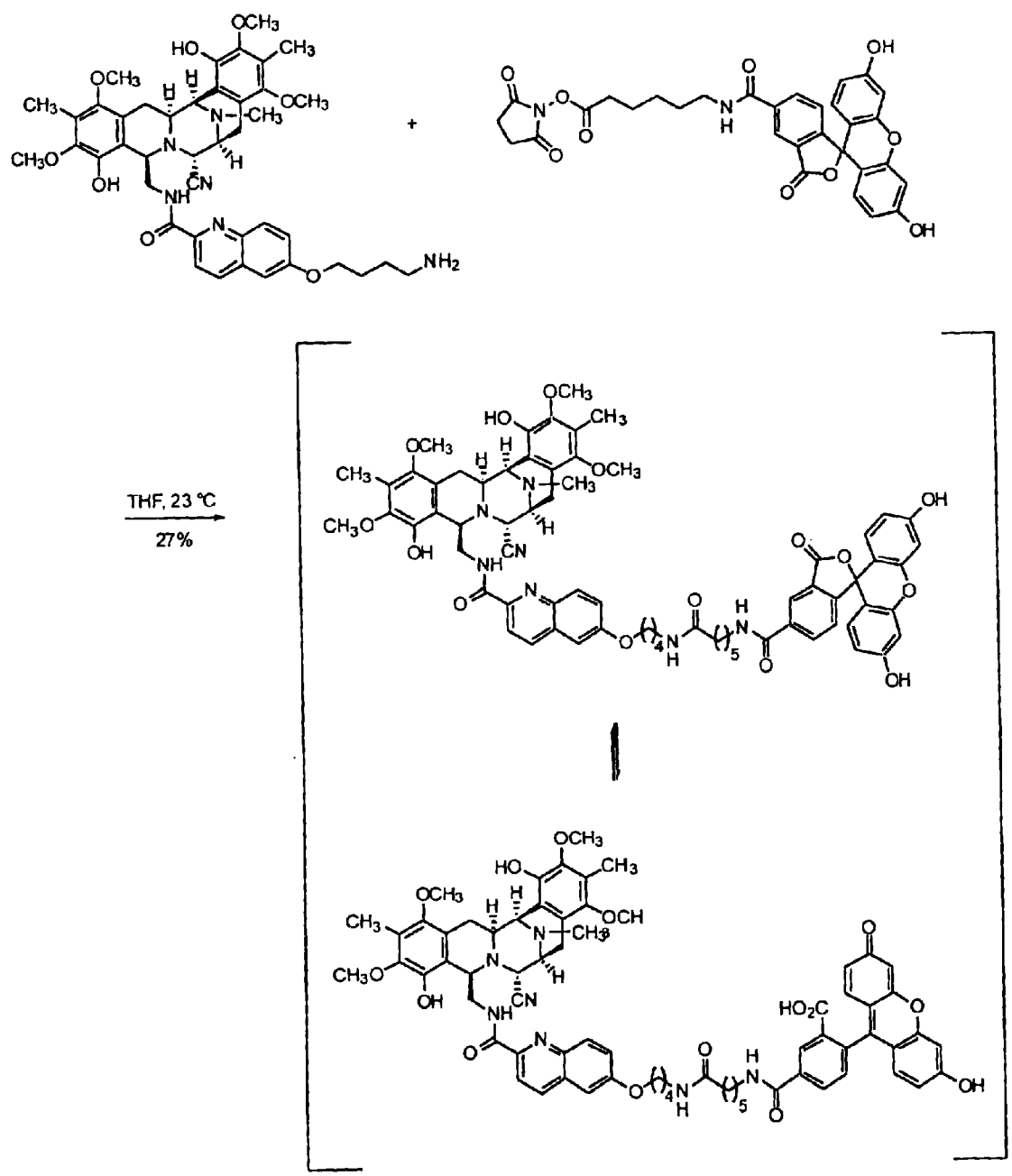
FIG. 9 depicts depicts the synthesis of exemplary inventive analogues of saframycin.

The one-step conversion of the N-linked oligomer 8 to the pentacyclic intermediate 9 involves an exceptional number of individual steps. Three cyclization reactions occur, and three of the five stereocenters of saframycin A are established in this step. In theory, each of the five stereogenic centers of the precursor 5 (shown in FIG. 4) is epimerizable under the reaction conditions. A single epimerization event may divert the course of reaction from 9. In that product which is formed, the α-amino aldehyde-derived centers are preserved. Many viable sequences can be envisioned to transform 8 into 9; the pathway shown in FIG. 6 is proposed as that which naturally occurs. In background studies, we have found that aminals have a greater propensity to form imine or iminium ion intermediates under mildly acidic conditions than secondary amino nitrites which, in turn, are more labile than tertiary amino nitrites (Myers et al. *J. Am. Chem. Soc.* 1999, 121, 8401). For this reason, without wishing to be bound by any a particular theory, it is proposed that cleavage of the aminal occurs first, followed by trapping of the resultant imine by Pictet-Spengler cyclization, as depicted in FIG. 6. Subsequent ionization of the secondary amino nitrile is proposed to initiate a second Pictet-Spengler cyclization. Finally, ionization of the tertiary amino nitrile group leads to internal Strecker reaction to form the pentacyclic product 9. It is interesting to note that the ordering of the two Pictet-Spengler reactions in this proposed sequence is opposite to that of our earlier stepwise condensation route. Both Pictet-Spengler cyclizations are believed to proceed with cis selectivity, as observed in the earlier stepwise route.

II. Synthesis of Analogues of Saframycins:

A) General Procedures: All reactions were performed in oven-dried or flame-dried round-bottomed flasks. The flasks were fitted with rubber septa or glass stoppers. Commercial reagents were used as received with the following exceptions: THF was distilled from sodium benzophenone ketyl at 760 Torr, methanol was distilled from magnesium methoxide at 760 Torr and dichloromethane was distilled from calcium hydride at 760 Torr. The spectroscopic and analytical data for all of the analogs is disclosed. All coupling constants are given in Hertz.

2) General Experimentals for Analogues:

It will be appreciated according to the novel methodology provided by the present invention that useful compounds can be obtained as described herein. In but one example, the methodology of the present invention enables the rapid production of hydroquinones as shown below bearing a protected amino functionality, which amino functionality can be deprotected and reacted with suitable reagents under suitable reaction conditions, certain examples of which are described below, to generate derivatives, as described in more detail herein.

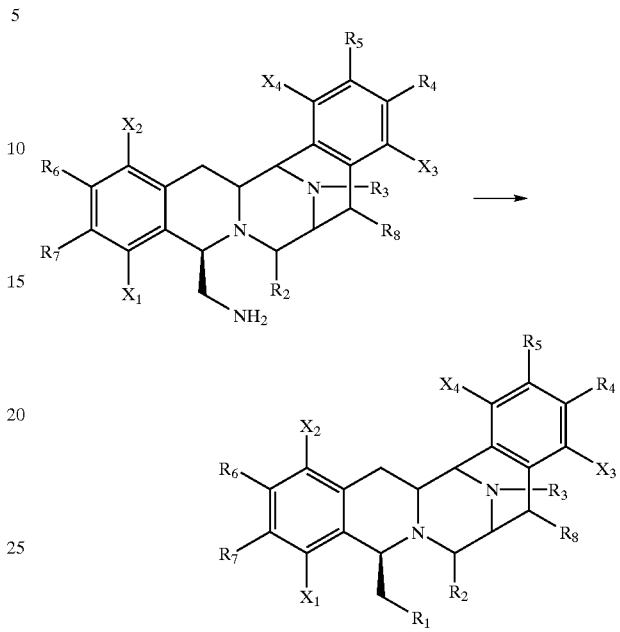

In certain embodiments of the present invention, acid chlorides bearing aryl, heteroaryl, aryloxy and alkyl functionalites are reacted with the amino compound presented above under suitable conditions with diethylaniline in methylene chloride to generate desired compounds.

In certain other embodiments of the present invention, aldehydes bearing heteroaryl and aryl functionalities are reacted with the amino compound presented above under suitable conditions with NaBH(OAc)$_3$ in acetonitrile to generate desired compounds.

In still other embodiments of the present invention, carboxylic acids bearing heteroaryl functionalities are reacted with the amino compound presented above under suitable conditions with EDC, HOBT, diethylaniline in tetrahydrofuran to generate desired compounds.

It will be appreciated by one of ordinary skill in the art that a variety of suitable reaction conditions can be utilized to functionalize the amino moiety of the compounds depicted above, and thus the generation of the analogues as described herein is not intended to be limited to the specific examples described herein.

In addition to the syntheses of exemplary analogues from the amino functionality as described generally and depicted above, it will be appreciated that the method of the invention provides for the synthesis of pentacyclic structures bearing (at R$_1$) O, S and C-containing functionalities, thus enabling access to a variety of analogues.

It will be appreciated that the compounds as described herein can be synthesized using traditional solution phase methods (as described generally above), or can be synthesized using solid-support techniques.

3. A Modular, Solid-supported Synthesis of a Library of (−)-Saframycin A Analogs As described herein, compounds as described generally above and herein can also be prepared using a modular solid-supported synthesis as described herein. Additionally, as described herein, the modular synthesis of the present invention permits extensive diversification of the core structure (e.g., $R_1$ moieties) as described herein. Furthermore, FIGS. 10–14B depict exemplary schemes and methods for the synthesis of inventive compounds using solid-supported techniques.

Note on Resin Handling:

All solid-supported reactions were followed calorimetrically or chromatographically by directly sampling resin beads from the reaction suspension via polypropylene syringe. The sampled beads were then washed on a polypropylene frit (Bio-Spin Disposable Chromatography Columns, P/N: 732–6008, Bio-Rad Laboratories, 2000 Alfred Nobel Drive, Hercules, Calif. 94547) and dried briefly in vacuo before being employed in calorimetric tests or exposed to cleavage cocktail (Kaiser, E., et. al. Anal. Biochem. 1976, 71, 261) (1° amine) and chloranil (Vojkovsky, T. Pept. Res., 1995, 8, 236) (2° amine)colorimetric assays were performed as reported (1999 Novabiochem Catalog & Peptide Synthesis Handbook, Calbiochem-Novabiochem Corporation, 10394 Pacific Center Court, San Diego, Calif. 92121, pp. S43).

The progress of solid-supported reactions was followed chromatographically by liberating product from the solid support by methanolysis of the siloxane linker: Washed resin samples (~5 mg) were suspended in a mixture of 100 μL dichloromethane, 20 μL methanol, and 10 μL concentrated hydrochloric acid in a polypropylene Eppendorf tube and allowed to stand for 10 min at 23° C. with occasional manual agitation (~every 3 min). The supernatant from this reaction mixture was analyzed by thin-layer chromatography, allowing semi-direct monitoring of the transformation of the previously solid-immobilized compounds.

Experimental Procedures:

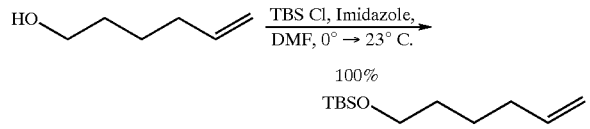

Imidazole (7.33 g, 107.7 mmol, 1.1 equiv) was added in one portion to a solution of 5-hexen-1-ol (9.81 g, 97.91 mmol, 1.0 equiv) in 98.0 mL N,N-dimethylformamide. The resulting clear solution was stirred for 10 min at 0° C. and t-butyldimethylsilyl chloride (16.2 g, 107.7 mmol, 1.1 equiv) was added. After stirring an additional 10 min at 0° C., the resulting reaction solution was allowed to warm to 23° C. and stirred for 1.5 hrs. Excess t-butyldimethylsilyl chloride was then quenched by the addition of 100 mL water, and the resulting aqueous solution extracted with 2×200 mL diethyl ether. The combined organic extracts were then washed with 2×400 mL water and 1×500 mL brine, dried over sodium sulfate, and concentrated in vacuo to afford spectroscopically pure siloxane product as a clear oil (22.28 g, 100%).

$^1$H NMR (500 MHz, CDCl$_3$), δ 5.85–5.77 (m, 1H, RCHCH$_2$), 5.00 (dq, 1H, J=17.5 Hz, RCHCH(Z)), 4.94 (dm, 1H, J=10.0 Hz, RCHCH (E)), 3.61 (t, 2H, J=6.5 Hz, CH$_2$OTBS), 2.06 (q, 2H, J=6.5 Hz, CH$_2$CHCH$_2$), 1.53 (m, 2H, J=6.0 Hz, CH$_2$CH$_2$OTBS), 1.42 (m, 2H, J=6.0 Hz, CH$_2$CH$_2$CHCH$_2$), 0.90 (s, 9H, SiC(CH$_3$)$_3$), 0.02 (s, 6H, Si(CH$_3$)$_2$). $^{13}$C NMR (100 MHz, CDCl$_3$), δ 139.2, 114.6, 63.3, 33.8, 32.5, 26.2, 25.4, 18.6, −5.1. FTIR (neat film), cm$^{-1}$ 3079 (w, CH), 2955 (s), 2930 (s), 2858 (s), 1472 (m), 1256 (s), 1103 (s), 960 (m), 836 (s), 775 (s). R$_f$ 0.70, 10% ethyl acetate-hexanes. HRMS (TOF-ES$^+$) Calcd for C$_{12}$H$_{27}$OSi (M+H)$^+$: 215.1831, Found.

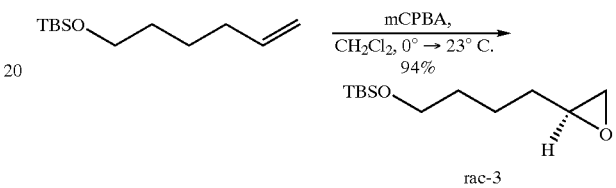

3-chloroperoxybenzoic acid (442.0 mg, 77%, 1.97 mmol, 1.2 equiv) was added in one portion to a solution of the siloxane substrate (352.2 mg, 1.64 mmol, 1.0 equiv) in 8.0 mL dichloromethane at 0° C. After 5 min, the reaction solution was allowed to warm to 23° C. and stir for 13 hr. The reaction solution was then diluted with 80 mL pentane and washed sequentially with 1×80 mL sat. aq. sodium bicarbonate, 1×80 mL sat. aq. sodium bisulfite, 1×80 mL sat. aq. sodium bicarbonate, and 1×80 mL brine. After drying over sodium sulfate, the organic layer was concentrated in vacuo and chromatographically purified (SiO$_2$, 7% ether-pentane→20% ether-pentane), providing the epoxide rac-3 as a clear oil (353.7 mg, 94%).

rac-3: $^1$H NMR (400 MHz, CDCl$_3$), δ 3.62 (t, 2H, J=6.0 Hz, CH$_2$OTBS), 2.91 (m, 1H, CH(O)CH$_2$), 2.75 (dd, 1H, J=4.0, 5.2 Hz, CH(O)CH$_2$ (Z)), 2.47 (dd, 1H, J=2.8, 5.2 Hz, CH(O)CH$_2$ (E)), 1.61–1.47 (m, 6H, CH$_2$CH$_2$CH$_2$CH$_2$OTBS), 0.98 (s, 9H, SiC(CH$_3$)$_3$), 0.05 (s, 6H, Si(CH$_3$)$_2$). $^{13}$C NMR (100 MHz, CDCl$_3$), δ 63.1, 52.5, 47.3, 32.8, 32.5, 26.2, 22.6, 18.6, −5.0. FTIR (neat film), cm$^{-1}$ 2951 (s), 2929 (s), 2856 (s), 1472 (s), 1255 (s), 1099 (s), 836 (s), 775 (s). R$_f$ 0.23, 5% ethyl acetate-hexanes. LRMS (TOF-ES$^+$) Calcd for C$_{12}$H$_{27}$O$_2$Si (M+H)$^+$: 231, Found: 231.

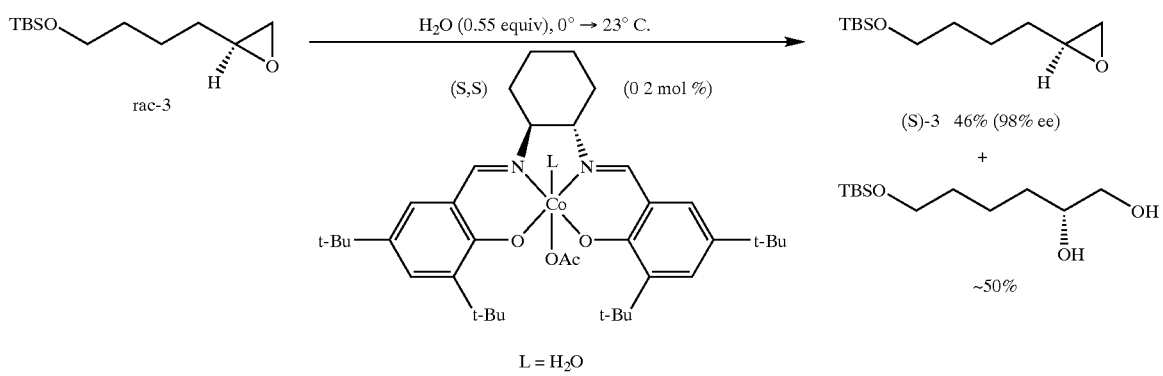

Glacial acetic acid (52.8 µL, 924.4 µmol, 10.2 equiv relative to catalyst) was added to a red-orange solution of (S,S)-(+)-N,N'-Bis(3,5-di-tert-butylsalicylidene)-1,2-cyclohexanediaminocobalt(II) (52.9 mg, 87.62 µmol, 0.2 mol %) in 1.1 mL toluene at 23° C. in a flask open to the air. The resulting solution was stirred for 30 min at 23° C. and was then concentrated in vacuo to provide a brown solid. Epoxide (rac-3) (11.39 g, 43.40 mmol, 1.0 equiv) was added to this catalyst, and the resulting brown-black solution stirred under argon at 0° C. for 10 min before adding water (430.2 µL, 23.87 mmol, 0.55 equiv) to the reaction solution. The resulting mixture was stirred for 5 min at 0° C. before removing the cooling bath. After 28 hr at 23° C., the enantioenriched epoxide (S)-3 was distilled directly from the reaction mixture (95–99° C., 0.5 mm Hg), affording epoxide (S)-3 as a clear oil (4.62 g, 46%) and the product diol as a red-brown oil (5.39 g, 50%, contaminated with catalyst and water). Both the epoxide and the diol were spectroscopically pure by $^1$H NMR. Epoxide (S)-3 was determined to be provided in >98% ee by Mosher ester analysis ($^{19}$F NMR) of the 2° azidoalcohol provided by reaction of the epoxide with sodium azide.

(S)-3: $^1$H NMR (400 MHz, CDCl$_3$), δ 3.62 (t, 2H, J=6.0 Hz, CH$_2$OTBS), 2.91 (m, 1H, CH(O)CH$_2$), 2.75 (dd, 1H, J=4.0, 5.2 Hz, CH(O)CH$_2$ (cis-)), 2.47 (dd, 1H, J=2.8, 5.2 Hz, CH(O)CH$_2$ (trans-)), 1.61–1.47 (m, 6H, CH$_2$CH$_2$CH$_2$CH$_2$OTBS), 0.98 (s, 9H, SiC(CH$_3$)$_3$), 0.05 (s, 6H, Si(CH$_3$)$_2$). $^{13}$C NMR (100 MHz, CDCl$_3$), δ 63.1, 52.5, 47.3, 32.8, 32.5, 26.2, 22.6, 18.6, −5.0. FTIR (neat film), cm$^{-1}$ 2951 (s), 2929 (s), 2856 (s), 1472 (s), 1255 (s), 1099 (s), 836 (s), 775 (s). R$_f$ 0.73, 50% ethyl acetate-hexanes. LRMS (TOF-ES$^+$) Calcd for C$_{12}$H$_{27}$O$_2$Si (M+H)$^+$: 231, Found: 231.

Diol: $^1$H NMR (400 MHz, CDCl$_3$), δ 3.72 (m, 1H, CH$_2$CH(OH)CH$_2$), 3.66 (ddd, 1H, J=3.2, 6.4, 10.8 Hz, CH$_2$OH), 3.63 (t, 2H, J=6.0 Hz, TBSOCH$_2$), 3.44 (ddd, 1H, J=4.8, 7.6 Hz, 12.4 Hz, CH$_2$OH), 2.11 (m, 1H, CH$_2$CH(OH)), 1.86 (m, 1H, CH$_2$CH(OH)), 1.51–1.58 (m, 2H, TBSOCH$_2$CH$_2$), 1.45–1.49 (m, 2H, CH$_2$CH$_2$CH(OH)), 0.89 (s, 9H, SiC(CH$_3$)), 0.05 (s, 6H, Si(CH$_3$)). $^{13}$C NMR (100 MHz, CDCl$_3$), δ 72.4, 67.0, 63.2, 33.1, 32.8, 26.2, 22.1, 18.6, −5.0. FTIR (neat film), cm$^{-1}$ 3372 (br, s, OH), 2935 (s, CH), 2857 (s, CH), 1472 (m), 1254 (m), 1102 (m), 836 (m), 775 (m). R$_f$ 0.21, 50% ethyl acetate-hexanes. HRMS (TOF-ES$^+$) Calcd for C$_{12}$H$_{29}$O$_3$Si (M+H)$^+$: 249.1886, Found: 249.1877.

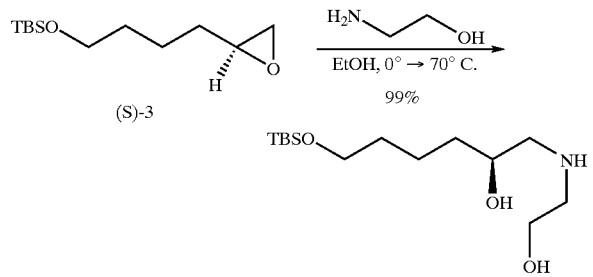

A solution of expoxide (S)-3 (4.78 g, 20.75 mmol, 1.0 equiv) in 207 mL abs. EtOH was stirred at 0° C. for 10 min. Ethanolamine (62.6 mL, 1.04 mol, 50.0 equiv), was then added gradually to the clear reaction solution over 10 min, providing a yellow solution which was allowed to warm to 23° C. This solution was at 70° C. for 1 hr. Ethanol was removed from the reaction solution in vacuo and the resulting yellow oil partitioned between 700 mL ethyl acetate and 700 mL water. The separated organic layer was then washed with 1×500 mL water and 1×500 mL brine, dried over potassium carbonate, and concentration in vacuo to provided analytically pure aminodiol as a yellowish transparent oil (5.99 g, 99%).

$^1$H NMR (400 MHz, CDCl$_3$), δ 3.68 (t, 2H, J=5.2 Hz, CH$_2$OH), 3.65 (m, 1H, CH(OH)), 3.62 (t, 2H, J=6.4 Hz, TBSOCH$_2$), 2.80 (q, 2H, J=5.6 Hz, CH$_2$CH$_2$OH), 2.74 (dd, 1H, J=3.2, 12.4 Hz, CH(OH)CH$_2$NH), 2.51 (dd, 1H, J=9.2, 12.0 Hz, CH(OH)CH$_2$NH), 1.50–1.58 (m, 2H, CH$_2$CH (OH)), 1.37–1.49 (m, 4H, TBSOCH$_2$CH$_2$CH$_2$), 0.89 (s, 9H, SiC(CH$_3$)$_3$), 0.05 (s, 6H, Si(CH$_3$)$_2$). $^{13}$C NMR (100 MHz, CDCl$_3$), δ 70.1, 63.3, 61.5, 55.2, 51.2, 35.0, 33.0, 26.2, 22.2, 18.6, −5.0. FTIR (neat film), cm$^{-1}$ 3304 (br, s, OH), 2929 (s), 2857 (s), 1471 (m), 1234 (m), 1098 (m). R$_f$ 0.35, 50% ethyl acetate-hexanes. HRMS (TOF-ES$^+$) Calcd for C$_{14}$H$_{34}$NO$_3$Si (M+H)$^+$: 292.2308, Found: 292.2297.

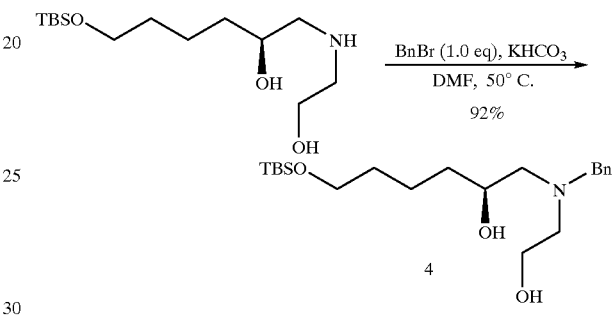

Potassium bicarbonate (6.93 g, 69.17 mmol, 2.0 equiv) was added to a solution of substrate aminodiol (10.08 g 34.58 mmol, 1.0 equiv) in 300 mL N,N-dimethylformamide. Benzyl bromide (4.20 mL, 34.58 mmol, 1.0 equiv) was then added to the vigorously stirred resulting white suspension, the reaction vessal wrapped in foil, and the reaction vessal heated at 50° C. for 2.3 hr. After cooling, the reaction mixture was partioned between 700 mL dichloromethane and 700 mL water and the organic layer was separated. The aqueous layer was sequentially extracted with 1×500 mL, 1×300 mL, and 1×200 mL dichloromethane. All the organic extracts were then combined, washed with 1×1.6 L water, and dried over sodium sulfate. Concentration of the dried extracts in vacuo provided benzyl amine 4 as a viscous yellow oil which did not require futher purification (12.60 g, 92%).

4: $^1$H NMR (400 MHz, CDCl$_3$), 1.3:1 mixture of rotamers, * indicates minor rotamer, δ 7.27–7.35 (m, 5H, C$_6$H$_5$), 3.868 (s, 1H*, CH$_2$*Ph), 3.83 (s, 1H, CH$_2$Ph), 3.64–3.71 (m, 2H, 2H*, CH$_2$OH, CH$_2$*OH), 3.59 (t, 2H, J=6.4 Hz, TBSOCH$_2$), 3.58 (s, 1H, CH$_2$Ph), 3.56 (s, 1H*, CH$_2$*Ph), 2.82 (dd, 1H*, CH$_2$*CH$_2$OH), 2.80 (dd, 1H, CH$_2$CH$_2$OH), 2.65 (t, 1H, CH$_2$CH$_2$OH), 2.61 (t, 1H*, CH$_2$*CH$_2$OH), 2.56 (dd, 1H, J=3.2, 13.2 Hz, CH(OH) CH$_2$N), 2.47 (dd, 1H, J=10.0, 12.8 Hz, CH(OH)CH$_2$N), 1.47–1.54 (m, 4H, TBSOCH$_2$CH$_2$CH$_2$CH$_2$), 1.34–1.42 (m, 2H, TBSOCH$_2$CH$_2$CH$_2$), 0.89 (s, 9H, SiC(CH$_3$)$_3$), 0.04 (s, 6H, Si(CH$_3$)$_2$). $^{13}$C NMR (100 MHz, CDCl$_3$), δ 138.6, 129.0, 128.6, 127.4, 68.2, 63.3, 61.0, 60.1, 59.8, 56.4, 34.8, 33.1, 26.3, 22.2, 18.7, −4.9. FTIR (neat film), cm$^{-1}$ 3362 (br, m, OH), 2924 (m), 2856 (m), 1460 (m), 1249 (m), 1092 (m), 834 (m). R$_f$ 0.34, 70% ethyl acetate-hexanes. HRMS (TOF-ES$^+$) Calcd for C$_{21}$H$_{40}$NO$_3$Si (M+H)$^+$: 382.2777, Found: 382.2760.

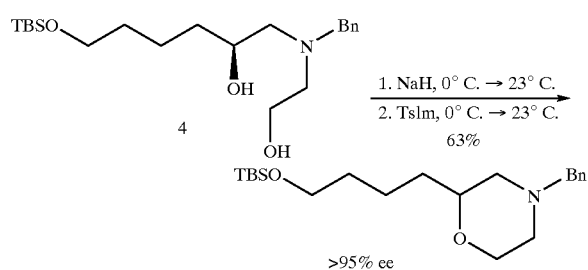

A solution of N-benzyl diol 4 (1.54 g, 4.02 mmol, 1.0 equiv) in 40.0 mL tetrahydrofuran was stirred at 0° C. for 10 min and was then added via cannula to sodium hydride (254.2 mg, 10.06 mmol, 2.5 equiv). The resulting white suspension was stirred vigorously at 0° C. for 5 min before removing the cooling bath. After 1 hr at 23° C., the reaction suspension was returned to a 0° C. bath for 10 min and N-tosylimidazole (894.5 mg, 4.02 mmol. 1.0 equiv) added in 3 portions over 12 min (gas evolution was observed subsequent to the addition of each portion). After stirring the resulting reaction solution for a further 10 min at 0° C., the cooling bath was again removed. After 1 hr at 23° C., excess sodium hydride was CAREFULLY quenched by the slow addition of 30 mL saturated aqueous ammonium chloride to the reaction suspension at 0° C. The reaction mixture was then partitioned between 340 mL ammounium chloride (sat., aq.) and 370 mL diethyl ether and the organic layer separated and washed further with 1×300 mL water and 1×200 mL brine. The aqueous washes were combined and extracted with 2×200 mL diethyl ether. All of the organic extracts were then combined and dried over sodium sulfate. Concentration of the extracts in vacuo provided a yellow oil, which was purified by flash column chromatography ($SiO_2$, 20% ethyl acetate-hexanes), affording the N-benzyl morpholine product as a yellow oil (926.6 mg, 63%).

$^1$H NMR (400 MHz, $CDCl_3$), 1:1 mix of rotamers, * indicates rotamer, δ 7.29–7.34 (m, 5H, $C_6H_5$), 3.83 (ddd, 1H, J=1.6, 2.8, 12.8 Hz, $CHOCH_2$), 3.64 (dt, 1H, J=2.0, 11.2 Hz, $CHOCH_2$), 3.58 (t, 2H, J=6.0 Hz, $TBSOCH_2$), 3.49 (s+m, 2H, $CH_2Ph$, CH(OR)CH), 3.48 (s, 1H*, $CH_2$*Ph), 2.72 (d, 1H, J=11.6 Hz, CH(OR)$CH_2$N), 2.65 (dd, 1H, J=1.6, 11.6 Hz, $OCH_2CH_2$N), 2.14 (dt, 1H, J=3.2, 11.6 Hz, $OCH_2CH_2$N), 1.84 (t, 1H, J=11.2 Hz, CH(OR)$CH_2$N), 1.41–1.54 (m, 4H, $TBSOCH_2CH_2CH_2CH_2$), 1.30–1.41 (m, 2H, $TBSOCH_2CH_2CH_2$), 0.88 (s, 9H, $SiC(CH_3)_3$), 0.03 (s, 6H, $Si(CH_3)_2$). $^{13}$C NMR (100 MHz, $CDCl_3$), δ 129.2, 128.3, 127.2, 75.8, 67.0, 63.5, 63.3, 58.9, 53.4, 33.7, 33.1, 26.2, 21.9, 18.7, −4.9. FTIR (neat film), cm$^{-1}$ 3372 (w), 2929 (s), 2856 (s), 1454 (m), 1255 (m), 1101 (s), 835 (s). $R_f$ 0.68, 70% ethyl acetate-hexanes. LRMS (TOF-ES$^+$) Calcd for $C_{21}H_{38}NO_2Si$ (M+H)$^+$: 364, Found: 364.

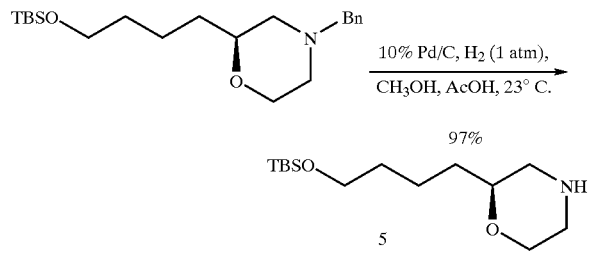

Glatial acetic acid (379.0 µL, 6.63 mmol, 2.6 equiv) was added to a solution of N-benzyl morpholine substrate (926.6 mg, 2.55 mmol, 1.0 equiv) in 30.0 mL methanol. 10% Palladium on activated carbon (271.2 mg, 254.8 µmol (Pd), 0.1 equiv), was then added to the clear solution. The resulting black suspension was cycled under a $H_2$ atmosphere (1 atm) by alternately evacuating the reaction vessal and refilling with $H_{2(g)}$ (5×). After stirring 2 hr under 1 atm hydrogen, the reaction suspension was filtered through Celite 545 (CAUTION: do not allow the catalyst to become dry—ignition hazard), the catalyst washed with 3×10 mL methanol, and the filtrate partioned between 100 mL diethyl ether and 100 mL sodium bicarbonate (sat., aq.). The organic layer was then washed with a further 1×80 mL brine and the combined aqueous washes extracted with 1×100 mL diethyl ether. All organic extracts were then combined, dried over potassium carbonate, and concentrated in vacuo to provide spectroscopically pure siloxymopholine 5 as an irridescent yellow-tinged oil (679.0 mg, 97%). Mosher amide analysis of siloxymorpoline 5 ($^1$H NMR) indicated that the product was provided in >95% ee.

5: $^1$H NMR (400 MHz, $CDCl_3$), δ 3.87 (dt, 1H, J=2.0, 11.6 Hz, $CHOCH_2$), 3.65 (ddd, 1H, J=7.2, 12.0, 14.0 Hz, $CHOCH_2$), 3.60 (t, 2H, J=6.4 Hz, $TBSOCH_2$), 3.47 (m, 1H, CH(OR)), 2.94 (dd, 1H, J=2.4, 12.4 Hz, CH(OR)$CH_2$), 2.88 (dd, 2H, J=2.8, 8.0 Hz, $OCH_2CH_2$N), 2.56 (dd, 1H, J=10.4, 12.4 Hz, CH(OR)$CH_2$N), 1.36–1.54 (m, 6H, $TBSOCH_2CH_2CH_2CH_2$), 0.88 (s, 9H, $SiC(CH_3)_3$), 0.04 (s, 6H, $Si(CH_3)_2$). $^{13}$C NMR (100 MHz, $CDCl_3$), δ 68.3, 63.2, 51.6, 46.2, 33.7, 33.0, 26.1, 21.7, 18.5, −5.1. FTIR (neat film), cm$^{-1}$ 3342 (w, NH), 2932 (s), 2856 (s), 1472 (m), 1461 (m), 1255 (m), 1094 (s), 835 (s). $R_f$ 0.43, 10% methanol-dichloromethane, triethylamine-dipped plate. HRMS (TOF-ES$^+$) Calcd for $C_{14}H_{32}NO_2Si$ (M+H)$^+$: 274.2202, Found: 274.2191.

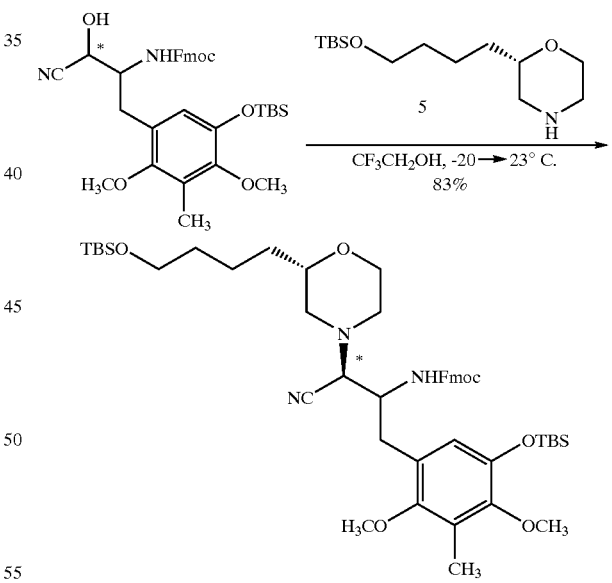

* 1:1.27 ratio diastereomers
(indicated is minor)

To a solution of siloxymorpholine 5 (606.6 mg, 2.22 mmol, 5.0 equiv) in 4.5 mL 2,2,2-trifluoroethanol was stirred over a −20° C. bath for 10 min and was then added by cannula to substrate cyanohydrin (Prepared as previously reported: Myers, A. G.; Kung, D. W.; Zhong, B.; Movassaghi, M.; and Kwon, S. *J. Am. Chem. Soc.* 1999, 121, 8401–8402; Myers, A. G.; Kung, D. W. *J. Am. Chem. Soc.* 1999, 121, 10828–10829) (273.4 mg, 453.56 µmol, 1.0 equiv) at −20° C. The resulting yellow solution was stirred for 5 min at −20° C., then allowed to warm to 23° C. After 3 hr at 23° C., the reaction solution was concentrated in vacuo, then from 1×5.0 mL benzene. Purification of the concentrate by flash column chromatography (SiO$_2$, 18% ethyl acetate-hexanes) afforded the syn-mopholinonitrile as a clear oil (149.6 mg, 38%) and the anti-mopholinonitrile as a clear oil (175.0 mg, 45%). Siloxymorpholine 5 was recovered from the column by elution with 10% methanol-dichloromethane+2% (v/v) triethylamine, affording recovered siloxymorpholine 5 as a yellow oil (493.9 mg, 100%).

syn-morpholinonitrile (minor): $^1$H NMR (400 MHz, CDCl$_3$), δ 7.76 (d, 2H, J=7.6 Hz, ArH), 7.54 (d, 2H, J=7.2 Hz, ArH), 7.40 (t, 2H, J=7.2 Hz, ArH), 7.30 (t, 2H, J=7.2 Hz, ArH), 6.54 (s, 1H, ArH), 5.29 (d, 1H, J=6.8 Hz, NHFmoc), 4.38 (app. t, 1H, J=7.6 Hz, CO$_2$CH$_2$), 4.27 (app. t, 1H, J=10.8 Hz, CO$_2$CH$_2$), 4.20 (t, 1H, J=6.8 Hz, CO$_2$CH$_2$CH), 4.18 (br s, 1H, OCHCH$_2$), 3.86 (d, 1H, J=11.6 Hz, OCH$_2$CH$_2$), 3.74 (s, 3H, ArOCH$_3$), 3.71 (s, 3H, ArOCH$_3$), 3.57 (t, 2H, TBSOCH$_2$), 3.50–3.40 (m, 2H, OCH$_2$CH$_2$, CHCN), 3.37 (m, 1H, CHNHFmoc), 3.10 (d, 1H, J=11.2 Hz, NCH$_2$), 2.94 (m, 1H, NCH$_2$), 2.86 (d, 1H, J=11.2 Hz, NCH$_2$), 2.52 (d, 1H, 9.6 Hz, CH$_2$Ar), 2.30 (t, 1H, J=10.4 Hz, CH$_2$Ar), 2.22 (s, 3H, ArCH$_3$), 1.52–1.26 (m, 6H, OCH$_2$CH$_2$CH$_2$CH$_2$), 0.99 (s, 9H, ArOSiC(CH$_3$)$_3$), 0.88 (s, 9H, ROSiC(CH$_3$)$_3$), 0.16, 0.15 (2s, 6H, ArOSi(CH$_3$)$_2$), 0.03 (s, 6H, ROSi(CH$_3$)$_2$). $^{13}$C NMR (100 MHz, CDCl$_3$), δ 151.5, 149.7, 145.4, 144.0, 141.5, 128.0, 127.3, 126.2, 125.4, 125.2, 123.7, 121.0, 120.3, 115.0, 75.8, 67.0, 66.7, 63.2, 61.9, 60.8, 60.1, 58.1, 50.9, 48.2, 47.3, 33.4, 33.0, 31.8, 26.2, 25.9, 21.7, 18.6, 18.4, 10.2, −4.3, −5.0. FTIR (neat film), cm$^{-1}$ 3352 (w, NH), 2931 (s), 2856 (s), 1727 (s, NCO$_2$), 1482 (m), 1255 (s), 1238 (s), 1103 (m), 1066 (s), 838 (s). R$_f$ 0.53, 30% ethyl acetate-hexanes. HRMS (TOF-ES$^+$) Calcd for C$_{48}$H$_{72}$N$_3$O$_7$Si$_2$ (M+H)$^+$: 858.4909, Found: 858.4890.

epi-syn-morpholinonitrile (trace): $^1$H NMR (400 MHz, CDCl$_3$), δ 7.75 (d, 2H, J=7.6 Hz, ArH), 7.57 (dd, 2H, J=2.8, 7.2 Hz, ArH), 7.39 (t, 2H, J=7.6 Hz, ArH), 7.30 (t, 2H, J=7.2 Hz, ArH), 6.49 (s, 1H, ArH), 5.39 (d, 1H, J=8.4 Hz, NHFmoc), 4.34–4.31 (m, 2H, CO$_2$CH$_2$), 4.20 (t, 1H, J=7.6 Hz, CO$_2$CH$_2$CH), 4.13 (m, 1H, OCHCH$_2$), 3.97 (d, 1H, J=10.8 Hz, ROCH$_2$CH$_2$), 3.72 (s, 3H, ArOCH$_3$), 3.67 (s, 4H, ArOCH1$_3$, CHCN), 3.61 (t, 3H, J=6.4 Hz, TBSOCH$_2$, ROCH$_2$CH$_2$), 3.53 (m, 1H, CHNHFmoc), 3.03 (dd, 1H, J=4.0, 14.0 Hz, NCH$_2$), 2.87 (dd, 1H, J=7.6, 13.6 Hz, NCH$_2$), 2.81 (d, 1H, J=11.6 Hz, NCH$_2$), 2.57 (d, 1H, J=10.0 Hz, CH$_2$Ar), 2.52 (dd, 1H, J=2.8, 11.2 Hz, NCH$_2$), 2.34 (t, 1H, J=10.4 Hz, CH$_2$Ar), 2.21 (s, 3H, ArCH$_3$), 1.58–1.34 (m, 6H, TBSOCH$_2$CH$_2$CH$_2$CH$_2$), 0.97 (s, 9H, ArOSiC(CH$_3$)$_3$), 0.89 (s, 9H, ROSiC(CH$_3$)$_3$), 0.12 (app. d, 6H, J=6.8 Hz, ArOSi(CH$_3$)$_2$), 0.05 (s, 6H, ROSi(CH$_3$)$_2$). FTIR (neat film), cm$^{-1}$ 3346 (w, NH), 2932 (s), 2856 (s), 1721 (s, NCO$_2$), 1481 (m), 1451 (m), 1253 (s), 1104 (s), 1066 (s), 1010 (m), 838 (s). R$_f$ 0.49, 30% ethyl acetate-hexanes. HRMS (TOF-ES$^+$) Calcd for C$_{48}$H$_{72}$N$_3$O$_7$Si$_2$ (M+H)$^+$: 858.4909, Found: 858.4890.

anti-morpholinonitrile (major): $^1$H NMR (400 MHz, CDCl$_3$), δ 7.76 (d, 2H, J=7.2 Hz, ArH), 7.60–7.52 (m, 2H, ArH), 7.40 (t, 2H, J=7.6 Hz, ArH), 7.30 (dt, 2H, J=1.2, 7.6 Hz, ArH), 6.50 (s, 2H, ArH), 5.44 (d, 1H, J=8.0 Hz, NHFmoc), 4.33 (d, 2H, J=7.6 Hz, CO$_2$CH$_2$), 4.21 (t, 1H, J=7.2 Hz, CO$_2$CH$_2$CH), 4.17 (m, 1H, OCHCH$_2$), 3.90 (d, 1H, J=10.0 Hz, OCH$_2$CH$_2$), 3.72 (s, 3H, ArOCH$_3$), 3.67 (s, 3H, ArOCH$_3$), 3.63 (d, 1H, CHCN), 3.61 (t, 2H, J=6.4 Hz, TBSOCH$_2$), 3.55 (t, 1H, J=6.4 Hz, OCH$_2$CH$_2$), 3.51 (s, 1H, CHNFmoc), 3.02 (dd, 1H, J=4.0, 13.6 Hz, NCH$_2$), 2.89 (dd, 1H, J=7.6, 14.0 Hz, NCH$_2$), 2.85 (d, 1H, J=10.0 Hz, NCH$_2$), 2.64 (dt, 1H, J=11.6 Hz, NCH$_2$), 2.52 (d, 1H, J=10.4 Hz, CH$_2$Ar), 2.25 (t, 1H, J=10.8 Hz, CH$_2$Ar), 2.21 (s, 3H, ArCH$_3$), 1.56–1.36 (m, 6H, OCH$_2$CH$_2$CH$_2$CH$_2$), 0.98–0.96 (m, 9H, ArOSiC(CH$_3$)$_3$), 0.89–0.86 (m, 9H, ROSiC(CH$_3$)$_3$), 0.15–0.12 (m, 6H, ArOSi(CH$_3$)$_2$), 0.05–0.02 (m, 6H, ROSi(CH$_3$)$_2$). $^{13}$C NMR (100 MHz, CDCl$_3$), δ 156.1, 151.4, 149.6, 145.3, 144.1, 141.4, 127.8, 127.2, 126.1, 125.3, 124.3, 120.9, 120.8, 120.1, 75.8, 71.3, 67.4, 66.7, 63.2, 60.6, 60.0, 53.1, 47.2, 33.6, 33.4, 33.0, 32.9, 31.7, 29.9, 26.1, 25.8(2), 21.8, 18.3, 10.1, −4.4(2), −5.1. FTIR (neat film), cm$^{-1}$ 3341 (w, NH), 2929 (s), 2857 (m), 1725 (s), 1481 (s), 1253 (s), 1237 (s), 1065 (s), 838 (s). R$_f$ 0.41, 30% ethyl acetate-hexanes. HRMS (TOF-ES$^+$) Calcd for C$_{48}$H$_{72}$N$_3$O$_7$Si$_2$ (M+H)$^+$: 858.4909, Found: 858.4873.

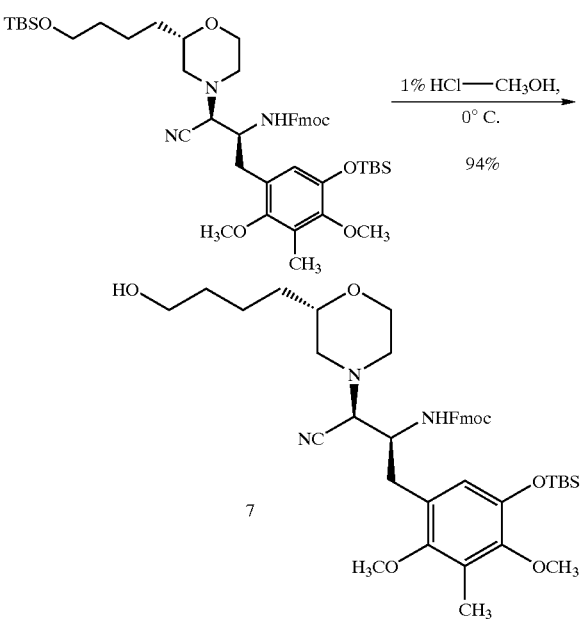

Concentrated hydrochloric acid (240.0 μL, 2.88 mmol, 1% v/v with methanol, ~6 equiv) was added to a solution of syn-aminonitrile substrate (406.2 mg, 473.3 μmol, 1.0 equiv) in 24.0 mL methanol that had been stirred at 0° C. for 10 min. After 5 min, the reaction solution was partitioned between 240 mL diethyl ether and 240 mL (3:1) water:sodium bicarbonate (sat, aq). The organic layer was isolated and washed with 1×150 mL brine. The combined aqueous layers were then further extracted with 1×250 mL diethyl ether and the combined organic extracts dried over sodium sulfate. Concentration in vacuo followed by column chromatography (SiO$_2$, 60% ethyl acetate-hexanes) provided alcohol 7 as a clear oil (330.5 mg, 94%).

7: $^1$H NMR (400 MHz, CDCl$_3$), δ 7.76 (d, 2H, J=8.0 Hz, ArH), 7.54 (d, 2H, J=7.6 Hz, ArH), 7.40 (t, 2H, J=8.0 Hz, ArH), 7.30 (t, 2H, J=7.6 Hz, ArH), 6.55 (s, 1H, ArH), 5.30 (app d, 1H, NHFmoc), 4.39 (m, 1H, OCH$_2$CH), 4.27 (m, 1H, OCH$_2$CH), 4.20 (t, 1H, J=6.4 Hz, OCH$_2$CH), 3.87 (d, 1H, J=10.8 Hz, CH$_2$CHO), 3.74 (s, 3H, ArOCH$_3$), 3.72 (s, 3H, ArOCH$_3$), 3.66 (d, 1H, J=6.8 Hz, CHCN), 3.61 (t, 2H, J=5.6 Hz, HOCH$_2$), 3.50 (d, 1H, J=11.2 Hz, ROCH$_2$CH$_2$), 3.44 (d, 1H, J=9.2 Hz, ROCH$_2$CH$_2$), 3.37 (m, 1H, CHNHFmoc), 3.09 (d, 1H, J=13.2 Hz, CH$_2$Ar), 2.93 (m, 1H, CH$_2$NCH$_2$), 2.87 (m, 1H, CH$_2$NCH$_2$), 2.52 (m, 1H, CH$_2$NCH$_2$), 2.42 (m, 1H, CH$_2$NCH$_2$), 2.32 (m, 1H, CH$_2$Ar), 2.22 (s, 3H, ArCH$_3$), 1.54–1.33 (m, 6H, HOCH$_2$CH$_2$CH$_2$), 0.99 (s, 9H, C(CH$_3$)$_3$), 0.15, 0.16 (app d, 6H, Si(CH$_3$)$_2$). $^{13}$C NMR (100 MHz, CDCl$_3$), δ 175.2, 156.2, 151.5, 149.7, 144.0, 141.5, 128.0, 127.2, 126.2, 125.2, 123.7, 120.9, 120.3, 115.9, 75.7, 67.1, 66.7, 62.9, 61.9, 60.8, 60.1, 58.0, 50.9, 48.2, 47.3, 33.2, 32.8, 31.8, 25.9, 21.7, 18.4, 10.2, −4.3. FTIR (neat film), cm$^{-1}$ 3348 (br s, OH), 2934 (s), 2858 (s), 1721 (s, NHCO$_2$), 1482 (m), 1238 (m), 1064 (m), 869 (m), 738 (m). R$_f$ 0.50, 70% ethyl acetate-hexanes. LRMS (TOF-ES$^+$) Calcd for C$_{36}$H$_{43}$N$_3$NaO$_7$ (M-TBS+Na)$^+$: 651, Found: 651.

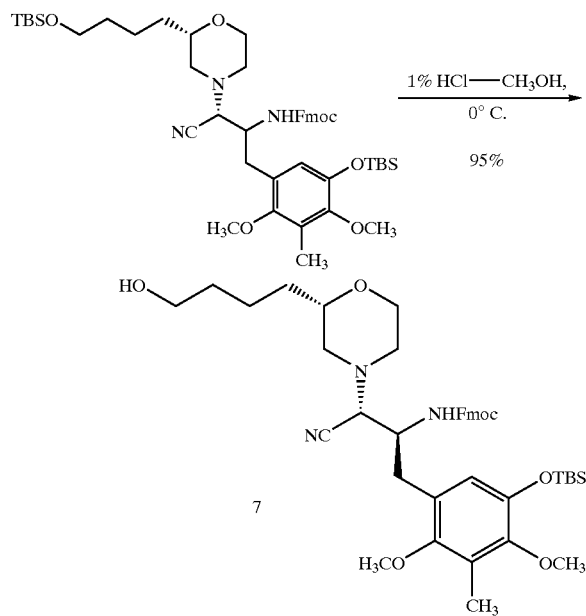

Concentrated hydrochloric acid (250.0 μL, 3.00 mmol, 1% v/v with methanol, ~3 equiv) was added to a solution of anti-aminonitrile substrate (916.2 mg, 1.07 mmol, 1.0 equiv) in 25.0 mL methanol that had been stirred at 0° C. for 10 min. After 5 min, the reaction solution was partitioned between 250 mL diethyl ether and 250 mL (3:1) water: sodium bicarbonate (sat, aq). The organic layer was isolated and washed with 1×150 mL brine. The combined aqueous layers were then further extracted with 2×250 mL diethyl ether and the combined organic extracts dried over sodium sulfate. Concentration in vacuo followed by column chromatography (SiO$_2$, 60% ethyl acetate-hexanes) provided alcohol epi-7 as a clear oil (756.5 mg, 95%).

epi7: $^1$H NMR (400 MHz, CDCl$_3$), δ 7.76 (d, 2H, J=7.2 Hz, ArH), 7.58 (dd, 2H, J=4.0, 7.2 Hz, ArH), 7.38 (t, 2H, J=7.6 Hz, ArH), 7.31 (dt, 2H, J=0.8, 7.2 Hz, ArH), 6.50 (s, 1H, ArH), 5.47 (d, 1H, J=8.8 Hz, NHFmoc), 4.33 (d, 2H, J=7.2 Hz, CO$_2$CH$_2$), 4.21 (t, 1H, J=7.2 Hz, CO$_2$CH$_2$CH), 4.18 (m, 1H, ROCH$_2$), 3.91 (d, 1H, J=9.6 Hz, OCHCH$_2$), 3.72 (s, 3H, ArOCH$_3$), 3.67 (s, 3H, ArOCH$_3$), 3.66–3.61 (m, 4H, HOCH$_2$, ROCH$_3$, CHCN), 3.51 (m, 1H, CHNHFmoc), 3.03 (dd, 1H, J=4.0, 14.0 Hz, NCH$_2$), 2.92–2.84 (m, 2H, NCH$_2$, CH$_2$Ar), 2.64 (dt, 1H, J=2.8, 10.8 Hz, NCH$_2$), 2.52 (d, 1H, J=10.8 Hz, NCH$_2$), 2.27 (d, 1H, J=10.4 Hz, CH$_2$Ar), 2.21 (s, 3H, ArCH$_3$), 1.61–1.36 (m, 6H, HOCH$_2$CH$_2$CH$_2$CH$_2$), 0.97 (s, 9H, SiC(CH$_3$)$_3$), 0.13 (app. d, 6H, J=4.4 Hz, Si(CH$_3$)$_2$). $^{13}$C NMR (100 MHz, CDCl$_3$), δ 156.2, 151.5, 149.7, 145.4, 144.2, 144.0, 141.5, 127.9, 127.3, 126.2, 125.5, 125.4, 124.4, 121.0, 120.2, 115.6, 75.9, 67.5, 66.8, 62.9, 61.9, 60.7, 60.1, 53.0, 52.7, 51.3, 47.3, 33.5, 32.8, 32.1, 25.9, 21.8, 18.4, 10.2, −4.3. FTIR (neat film), cm$^{-1}$ 3335 (m, NH/OH), 2933 (s), 2858 (m), 1714 (s, NCO$_2$), 1481 (s), 1451 (m), 1236 (s), 1117 (s), 1064 (m), 1012 (s), 867 (s), 739 (m). R$_f$ 0.46, 70% ethyl acetate-hexanes. HRMS (TOF-ES$^+$) Calcd for C$_{42}$H$_{58}$N$_3$O$_7$Si (M+H)$^+$: 744.4044, Found: 744.4060.

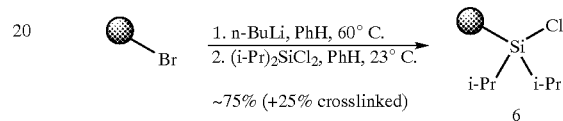

Polystyrene chlorodiisopropylsilane 6 was prepared by a modification of the procedure reported by Danishefsky (Randolph, J. T.; McClure, K. F.; Danishefsky, S. J. *J. Am. Chem. Soc.* 1995, 117, 5712–5719. Commercial 4-bromopolystyrene (Novabiochem, 4-bromo polystyrene HL (P/N: 01-64-0255), 50–100 mesh, Calbiochem-Novabiochem Corp., 10394 Pacific Center Court, San Diego, Calif. 92121) (3.65 g, 7.12 mmol, 1.95 mmol/g, 1.0 equiv) was washed with 2×35 mL benzene under an argon atmosphere in a modified round-bottomed flask bearing an integral glass vacuum frit and was then resuspended in 35 mL benzene. n-Butyl lithium (2.50 M in hexanes, 7.72 mL, 19.29 mmol, 2.71 equiv) was added to this suspension and the resulting mixture stirred at 60° C. for 3 hr. The cloudy white reaction supernatant was then removed by vacuum filtration and the resin washed with 1×35 mL benzene. The resin was then resuspended in 35 mL benzene and dichlorodiisopropylsilane (5.14 mL, 28.47 mmol, 4.0 equiv) added. The resulting suspension was stirred for 3 hr at 23° C. and the reaction supernatant again removed via filtration. The resin was then sequentially washed with 2×36 mL (5:1) benzene:acetonitrile, 1×35 mL benzene, 3×35 mL N,N-dimethylformamide, 2×35 mL tetrahydrofuran, and 2×35 mL dichloromethane and dried in vacuo for 8 hr to provide polystyrene chlorodiisopropylsilane 6 as a yellowish-white, free-flowing resin (3.98 g).

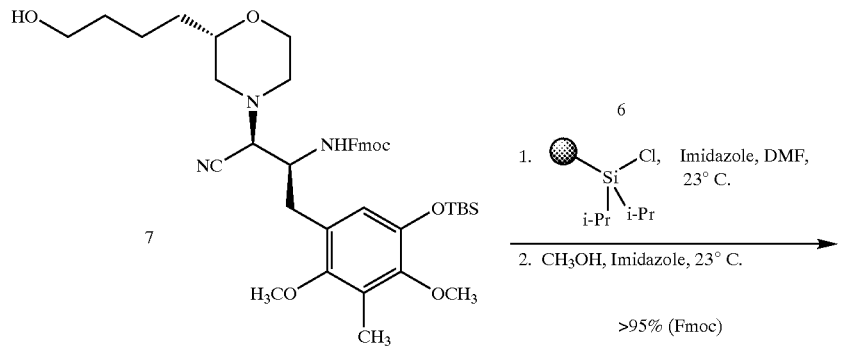

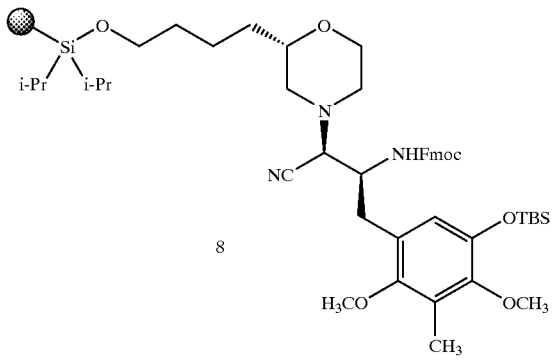

A solution of alcohol 7 (54.1 mg, 72.7 μmol, 1.0 equiv) in 3.6 mL N,N-dimethylformamide was added via cannula to a mixture of polystyrene chlorodiisopropylsilane 6 (412.3 mg, 566.1 μmol, 7.8 equiv, 1.373 mmol/g) and imidazole (44.6 mg, 654.4 μmol, 9.0 equiv) at 23° C. After 2 hrs, additional imidazole (89.1 mg, 1.31 mmol, 18.0 equiv) and methanol (117.8 μL, 2.91 μmol, 40.0 equiv) were added to the resulting clear suspension of yellowish resin and the resulting mixture stirred for 15 hr. The reaction supernatant was then removed by crimped cannula, and the product resin washed sequentially with 3×4 mL N,N-dimethylformamide, 3×4 mL tetrahydrofuran, and 2×4 mL dichloromethane, removing the wash solution via crimped cannula. Drying of the resin in vacuo for 5 hr provided a free-flowing yellowish-white resin. The yield of this transformation was determined by cleavage of the 9-fluorenylmethoxycarbonyl (Fmoc) protecting group (20% piperidine-N,N-dimethylformamide, 2 min) from a measured aliquot of resin followed by UV quantitation of the liberated dibenzofulvene chromophore ($A_{290}$) according to the established procedure (See, for example, 1999 Novabiochem Catalog & Peptide Synthesis Handbook, Calbiochem-Novabiochem Corporation, 10394 Pacific Center Court, San Diego, Calif. 92121, pp. S43). Averaging two replicate measurements gave a resin loading level of 0.1502 mmol/g (95%). (Note: trace Fmoc cleavage during the loading and capping reactions suggests >95% loading.) Chromatographic separation of material cleaved from the product resin by incubating ~5 mg samples of washed resin in a mixture of 100 μL $CH_2Cl_2$, 20 μL $CH_3OH$, and 10 μL conc. hydrochloric acid for 10 min indicated the solely the presence of substrate alcohol 7, confirming the clean formation of product resin 8.

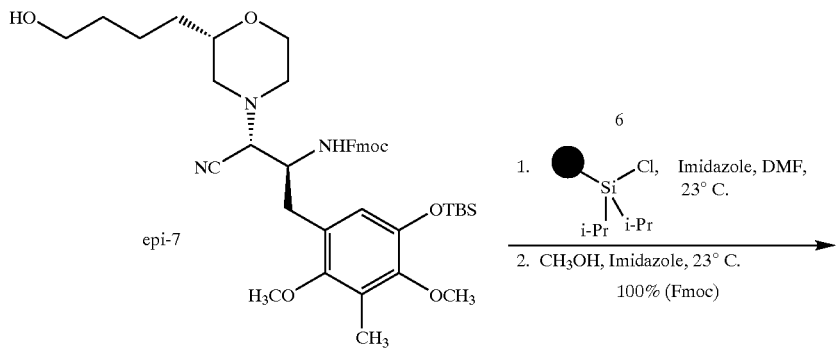

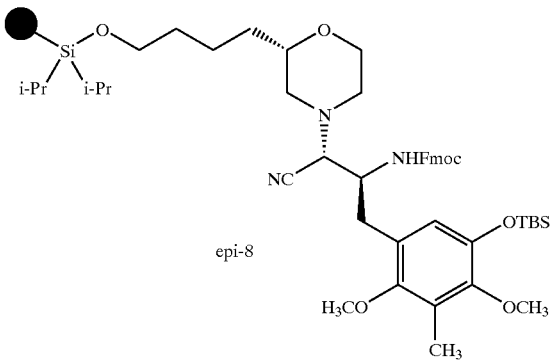

A solution of alcohol epi-7 (756.5 mg, 1.02 mmol, 1.0 equiv) in 40.0 mL N,N-dimethylformamide was added via cannula (along with 2×5.0 mL N,N-dimethylformamide washes) to a mixture of polystyrene chlorodiisopropylsilane 6 (3.98 g, 5.34 mmol, 5.24 equiv, 1.34 mmol/g) and imidazole (432.6 mg, 6.35 mmol, 6.25 equiv) at 23° C. After 5 hrs, additional imidazole (1.25 g, 18.3 mmol, 18.0 equiv) and methanol (1.65 mL, 40.7 mmol, 40.0 equiv) were added to the resulting clear suspension of yellowish resin and the resulting mixture stirred for 16 hr. The reaction supernatant was then removed by crimped cannula, and the product resin washed sequentially with 3×40 mL N,N-dimethylformamide, 3×40 mL tetrahydrofuran, and 2×40 mL dichloromethane, removing the wash solution via crimped cannula. Drying of the resin in vacuo for 5 hr provided a free-flowing yellowish-white resin. The yield of this transformation was determined by cleavage of the 9-fluorenylmethoxycarbonyl (Fmoc) protecting group (20% piperidine-N,N-dimethylformamide, 2 min) from a measured aliquot of resin followed by UV quantitation of the liberated dibenzofulvene chromophore ($A_{290}$) according to the established procedure.[7] Averaging two replicate measurements gave a resin loading level of 0.2345 mmol/g (100%). Chromatographic separation of material cleaved from the product resin by incubating ~5 mg samples of washed resin in a mixture of 100 μL $CH_2Cl_2$, 20 μL $CH_3OH$, and 10 μL conc. hydrochloric acid for 10 min indicated the solely the presence of substrate alcohol epi-7, confirming the clean formation of product resin epi-8.

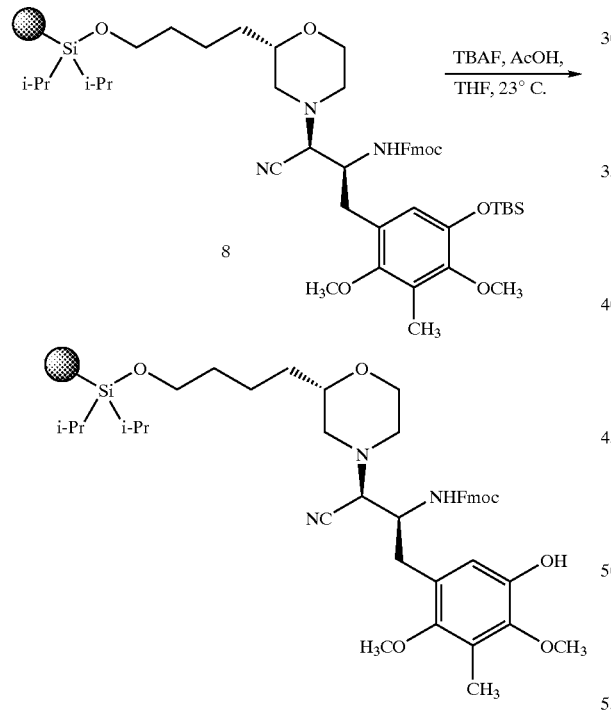

Acetic acid (253.8 μL, 4.44 mmol, 10.0 equiv) was added to a suspension of aminonitrile resin 8 (2.12 g, 444.2 μmol, 1.0 equiv, 0.1575 mmol/g) in 20.0 mL tetrahydrofuran. Tetra-n-butylammmonium fluoride (1.0 M in tetrahydrofuran, 2.22 mL, 2.22 mmol, 5.0 equiv) was then added to the reaction suspension and the resulting suspension stirred at 23° C. for 1.5 hr. The reaction supernatant was then removed via crimped cannula and the product resin washed sequentially with 3×20 mL N,N-dimethylformamide, 3×20 mL tetrahydrofuran, and 2×20 mL dichloromethane. The washed product resin was dried in vacuo overnight, affording a free-flowing yellow-orange resin. Photometric determination of the resin 9-fluorenylmethoxycarbonyl (Fmoc) loading level ($A_{290}$, 20% piperidine-N,N-dimethylformamide) gave a resin loading level of 0.09504 mmol/g, implying 45% Fmoc cleavage based on 100% yield for resin loading step. (TLC of the reaction supernatant confirms the formation of dibenzofulvene, indicating that Fmoc deprotection does occur under the reaction conditions.) Substrate was liberated from the product resin for solution-phase characterization by methanolysis of product resin aliquots (as described for 8 and epi-8 above), isolation of the supernatant solution (cannulation) followed by resin washing, aqueous workup of this substrate solution (sodium bicarbonate wash to neutralized hydrochloric acid), and chromatographic purification (90% ethyl acetate-hexanes).

$^1$H NMR (400 MHz, $CDCl_3$), δ 7.76 (d, 2H, J=7.6 Hz, ArH), 7.54 (d, 2H, J=7.2 Hz, ArH), 7.40 (t, 2H, J=7.6 Hz, ArH), 7.33 (t, 2H, J=6.0 Hz, ArH), 6.64 (s, 1H, ArH), 5.48 (s, 1H, ArOH), 5.32 (app d, 1H, J=6.4 Hz, NHFmoc), 4.32 (d, 2H, J=6.8 Hz, $CO_2CH_2$), 4.21 (t, 1H, J=6.8 Hz, $CO_2CH_2CH$), 4.16 (br s, 1H, $CHOCH_2$), 3.87 (d, 1H, J=10.8 Hz, $CHOCH_2$), 3.77 (s, 3H, $ArOCH_3$), 3.73 (s, 3H, $ArOCH_3$), 3.63 (m, 2H, $HOCH_2$), 3.53–3.44 (m, 2H, CHCN, $CHOCH_2$), 3.39 (m, 1H, CHNHFmoc), 3.06 (d, 1H, J=13.6 Hz, $OCH_2CH_2N$), 2.96 (m, 1H, $OCHCH_2N$), 2.87 (d, 1H, J=10.0 Hz, $OCH_2CH_2N$), 2.55 (t, 1H, J=11.2 Hz, $CH_2Ar$), 2.43 (t, 1H, J=10.4 Hz, $OCH_2CH_2N$), 2.30 (t, 1H, J=8.4 Hz, $CH_2Ar$), 2.26 (s, 3H, $ArCH_3$), 1.60–1.30 (m, 6H, $HOCH_2CH_2CH_2CH_2$). $^{13}$C NMR (100 MHz, $CDCl_3$), δ 156.2, 150.6, 145.6, 145.4, 144.1, 143.9, 141.5, 128.0, 127.3, 125.3, 125.1, 120.3, 116.0, 115.3, 75.7, 67.1, 66.6, 63.0, 61.8, 61.0, 60.9, 57.8, 51.1, 48.7, 47.3, 33.2, 32.7, 31.6, 21.7, 10.3. FTIR (neat film), $cm^{-1}$ 3347 (m, NH), 2939 (s), 2864 (m), 1712 (s, $NCO_2$), 1483 (s), 1450 (s), 1233 (s), 1111 (s), 1051 (s), 1008 (m), 738 (s). $R_f$ 0.14, 70% ethyl acetate-hexanes. HRMS (TOF-ES$^+$) Calcd for $C_{36}H_{44}N_3O_7$ $(M+H)^+$: 630.3179, Found: 630.3192.

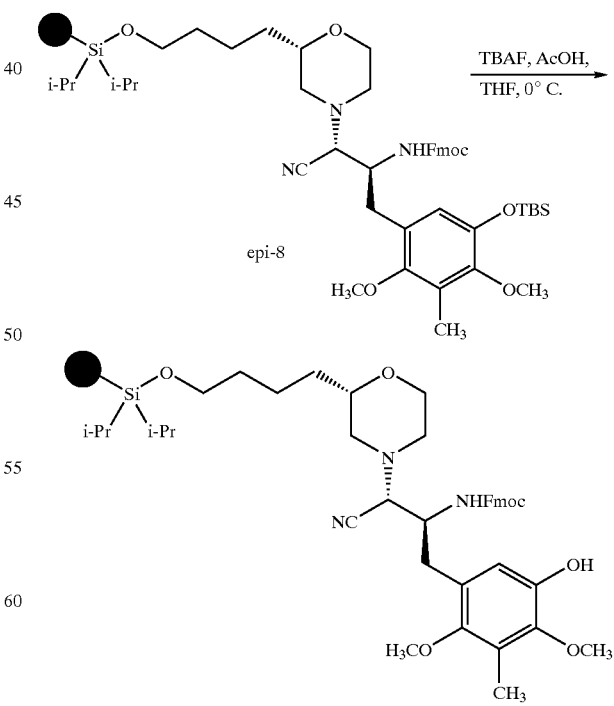

Acetic acid (9.0 μL, 156.8 μmol, 2.2 equiv) and tetra-n-butylammonium fluoride (1.0 M in tetrahydrofuran, 78.4 μL, 78.4 μmol, 1.1 equiv) were sequentially added to a suspension of siloxane resin epi-8 (328.0 mg, 71.27 μmol, 1.0 equiv) in 3.5 mL tetrahydrofuran that had been stirring at 0° C. for 10 min. After 4.5 hr, the reaction supernatant was removed via crimped cannula and the product resin washed with 2×4 mL N,N-dimethylformamide, 2×4 mL tetrahydrofuran, and 2×4 mL dichloromethane. The product resin was then dried in vacuo for 5 hr to provide a free-flowing, yellow resin. (Note: TLC of the reaction supernatant reveals the formation of dibenzofulvene, indicating that Fmoc deprotection occurs under the reaction conditions (see corresponding transformation of 8 above).)

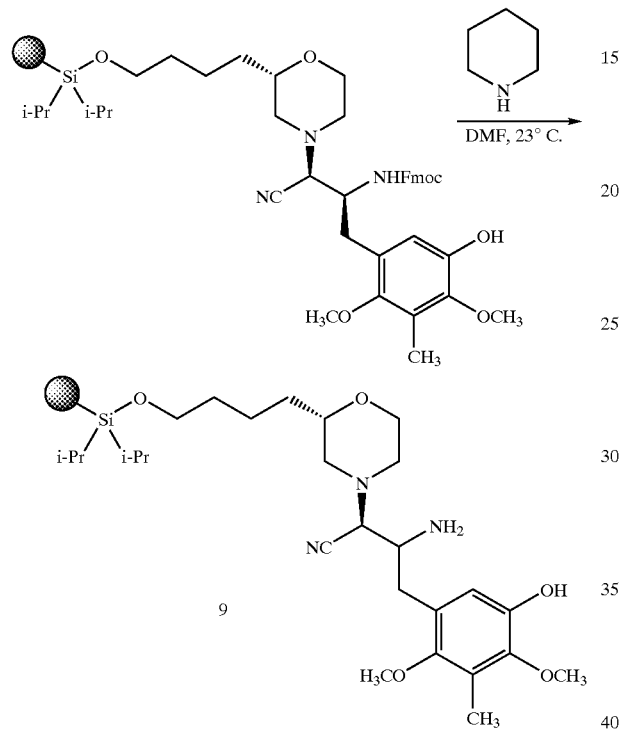

9

N-Fmoc-morpholinonitrile substrate resin (2.06 g, 443.5 μmol, 1.0 equiv, 0.2152 mmol/g) was suspended in 20.0 mL 20% (v/v) piperidine-N,N-dimethylformamide. The resulting suspension was stirred at 23° C. for 1.5 hr and the reaction supernatant then removed via crimped cannula. The product resin was then sequentially washed with 3×20 mL N,N-dimethylformamide, 3×20 mL tetrahydrofuran, and 2×20 mL dichloromethane and dried in vacuo to provide product resin 9 as a free-flowing tan solid. Methanolysis of aliquots of washed product resin indicated the sole presence of the expected siloxane cleavage product.

9: $^1$H NMR (400 MHz, CDCl$_3$), δ 6.68 (s, 1H, ArH), 3.93 (ddd, 1H, J=1.6, 3.6, 11.2 Hz, CHOCH$_2$), 3.78 (s, 3H, ArOCH$_3$), 3.70 (s, 3H, ArOCH$_3$), 3.64 (t, 2H, J=6.4 Hz, HOCH$_2$), 3.59 (dt, 1H, J=2.8, 11.6 Hz, CHOCH$_2$), 3.51 (m, 1H, CHNH$_2$), 3.38 (app dd, 1H, J=2.8, 8.4 Hz, CHOCH$_2$), 3.24 (d, 1H, J=10.0 Hz, CHCN), 3.07 (dd, 1H, J=3.2, 13.2 Hz, OCHCH$_2$N), 2.64 (d, 1H, J=11.2 Hz, OCH$_2$CH$_2$N), 2.56 (t, 1H, J 12.4 Hz, CH$_2$Ar), 2.53 (dd, 1H, J=6.4, 11.6 Hz, OCH$_2$CH$_2$N), 2.48 (dt, 1H, J=3.6, 11.6 Hz, OCH$_2$CH$_2$N), 2.41 (t, 1H, J=10.8 Hz, CH$_2$Ar), 2.24 (s, 1H, ArCH$_3$), 1.62–1.35 (m, 6H, HOCH$_2$CH$_2$CH$_2$CH$_2$). $^{13}$C NMR (100 MHz, CDCl$_3$), δ 150.7, 145.5, 145.2, 126.3, 125.2, 115.8, 114.8, 75.9, 66.5, 64.5, 62.9, 60.9 (2), 58.3, 50.3, 47.2, 34.9, 33.2, 32.8, 21.7, 10.2. FTIR (neat film), cm$^{-1}$ 3356 (br, m, NH, OH), 2940 (s, CH), 2862 (m), 1483 (m), 1458 (m), 1420 (m), 1113 (s), 1051 (m), 1010 (m), 911 (m), 732 (s). R$_f$ 0.28, 10% methanol-dichloromethane, triethylamine-dipped plate. HRMS (TOF-ES$^+$) Calcd for C$_{21}$H$_{34}$N$_3$O$_5$ (M+H)$^+$: 408.2498, Found: 408.2516.

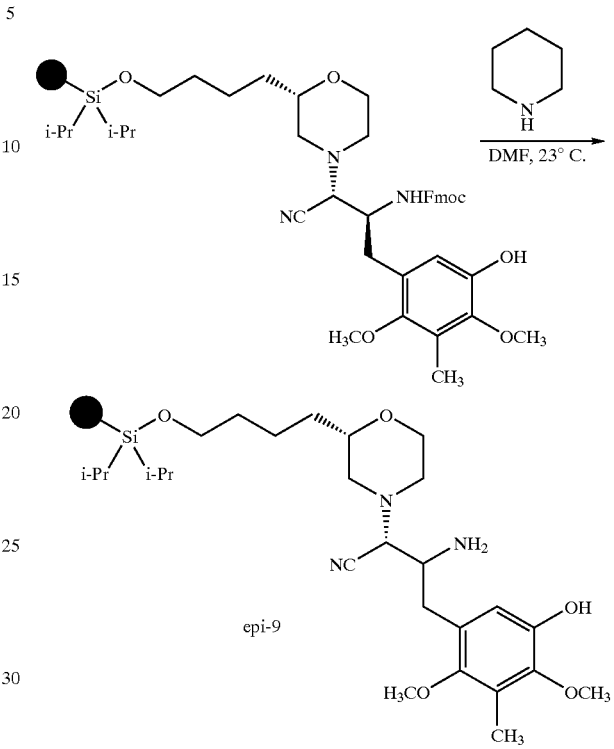

epi-9

N-Fmoc-morpholinonitrile substrate resin (315.0 mg, 70.19 μmol, 1.0 equiv, 0.2228 mmol/g) was suspended in 3.95 mL 20% (v/v) piperidine-N,N-dimethylformamide. The resulting suspension was stirred at 23° C. for 5 hr and the reaction supernatant then removed via crimped cannula. The product resin was then sequentially washed with 3×4 mL N,N-dimethylformamide, 3×4 mL tetrahydrofuran, and 2×4 mL dichloromethane and dried in vacuo to provide product resin epi-9 as a free-flowing cream-colored resin. Solid-immobilized substrate was liberated for characterization by a suspending a sample of the product resin (179.0 mg, 41.96 μmol, 1.0 equiv) in a mixture of dichloromethane (5.0 mL), methanol (170.0 μL, 4.2 mmol, 100.0 equiv), and concentrated hydrochloric acid (17.1 μL, 205.6 μmol, 4.9 equiv) at 23° C. over 22 hr. The reaction supernatant from this mixture was collected via crimped cannula along with 6×4 mL dichloromethane washes of the treated product resin sample and the combined filtrates partitioned between 30 mL sat. aqueous sodium bicarbonate and 30 mL dichlormethane. The organic layer was isolated and the aqueous layer extracted with a further 6×30 mL diethyl ether. The organic extracts were then combined, dried over sodium sulfate, and concentrated in vacuo. Chromatographic purification of the resulting orange oil (SiO$_2$, 3% methanol-dichlornethane on a column packed in eluent+5% triethylamine) provided the expected cleaved amine substrate as a yellow-tinged clear oil (5.2 mg, 28%).

epi-9: $^1$H NMR (400 MHz, CDCl$_3$), δ 6.61 (s, 1H, ArH), 3.91 (dm, 1H, J=11.6 Hz, ROCH$_2$), 3.79 (s, 3H, ArOCH$_3$), 3.72–3.67 (m, 3H, ROCH$_2$, OCHCH$_2$, CHCN), 3.66 (s, 3H, ArOCH$_3$), 3.52–3.44 (m, 2H, HOCH$_2$), 3.32 (dt, 1H, J=3.2, 8.4 Hz, CHNH$_2$), 3.16 (dd, 1H, J=3.2, 13.2 Hz, NCH$_2$), 2.81 (d, 1H, J=10.8 Hz, CH$_2$Ar), 2.65 (dt, 1H, J=3.6, 11.2, NCH$_2$), 2.54 (d, 1H, J=10.4 Hz, NCH$_2$), 2.37 (dd, 1H, J=8.4, 13.6 Hz, NCH$_2$), 2.24 (s, 3H, ArCH$_3$), 2.22–2.15 (m, 1H, CH$_2$Ar), 1.64–1.40 (m, 6H, HOCH$_2$CH$_2$CH$_2$CH$_2$),. $^{13}$C NMR (100 MHz, CDCl$_3$), δ 150.7, 145.5, 145.0, 127.2, 125.0, 116.4, 114.6, 75.7, 66.7, 65.9, 63.0, 60.9, 53.3, 52.8, 51.4, 35.2, 33.4, 32.8, 21.8, 17.4, 10.2. FTIR (neat film), cm$^{-1}$ 3358 (m, NH$_2$/OH), 2936 (s), 2864 (m), 1483 (m), 1452 (m), 1417 (m), 1232 (w), 1112 (s), 1050 (m), 1009 (m). R$_f$ 0.34, 10% methanol-dichloromethane, triethylamine-dipped plate. HRMS (TOF-ES$^+$) Calcd for C$_{21}$H$_{34}$N$_3$O$_5$ (M+H)$^+$: 408.2498, Found: 408.2480.

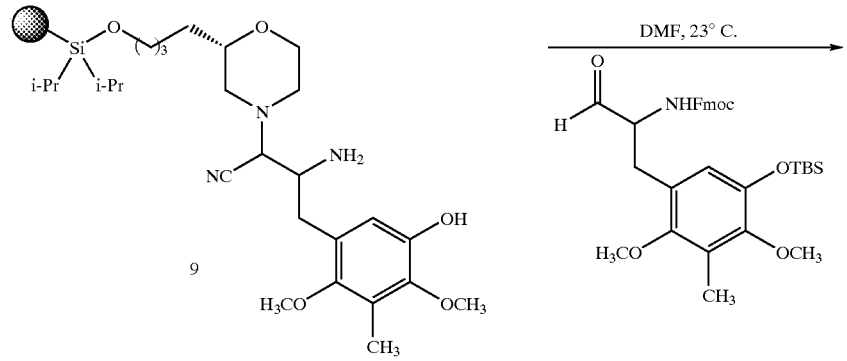

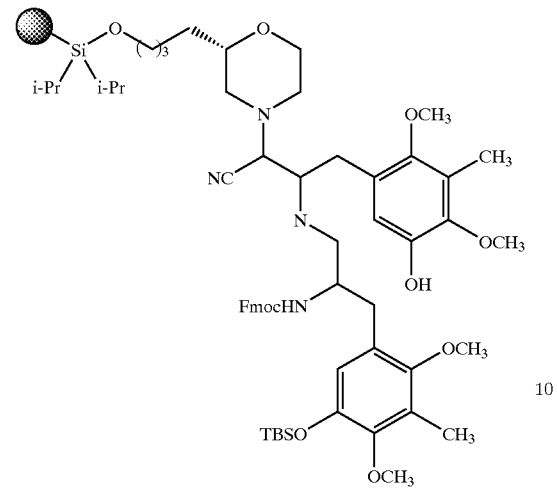

A solution of aldehyde Prepared as previously reported: (Myers, A. G.; Kung, D. W.; Zhong, B.; Movassaghi, M.; and Kwon, S. *J. Am. Chem. Soc.* 1999, 121, 8401–8402) (726.6 mg, 1.26 mmol, 2.84 equiv) in 15.0 mL N,N-dimethylformamide was added to amine resin 9 (1.96 g, 443.5 μmol, 1.0 equiv, 0.2261 mmol/g) via cannula using 2×5 mL N,N-dimethylformamide washes to quantitate the transfer. The resulting clear suspension of orangish resin was stirred at 23° C. in the dark for 5 hr before the reaction supernatant was removed via crimped cannula and the product resin washed sequentially with 2×20 mL N,N-dimethylformamide and 2×20 mL 1,2-dimethoxyethane. (Note: the reaction supernatant and N,N-dimethylformamide washes were collected to allow recovery of excess aldehyde (see below).) The resulting yellow resin (10) was employed directly in the synthesis of tetrahydroisoquinoline resin 11.

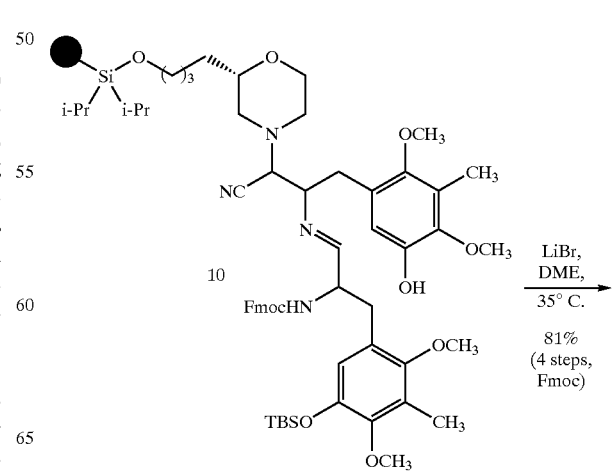

-continued

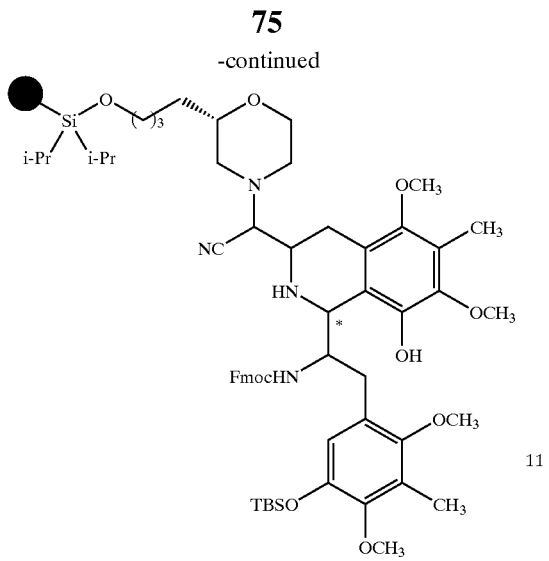

11

A solution of anhydrous lithium bromide (3.41 g, 39.30 mmol, 88 equiv) in 30.0 mL 1,2-dimethoxyethane (prepared with gentle heating) was added to imine resin 10 (2.21 mg, 443.5 μmol, 1.0 equiv, 0.2008 mmol/g) via a warm syringe and needle. The resulting clear suspension of yellow resin was placed on a 35° C. bath and stirred for 22 hr. The supernatant was then removed via crimped cannula and the product resin washed sequentially with 4×20 mL N,N-dimethylformamide, 3×20 mL tetrahydrofuran, and 2×20 mL dichloromethane and dried in vacuo to provide free-flowing orangish-white resin which gave a negative Kaiser test and positive chloranil test. Photometric determination of the product resin 9-fluorenylmethoxycarbonyl (Fmoc) loading level ($A_{290}$, 20% piperidine-N,N-dimethylformamide, duplicate measurements) established a resin loading level of 0.1698 mmol/g, consistent with an 81% yield of diastereomeric tetrahydroisoquinolines (average 95% yield/step, 4 steps). Liberation of substrate for characterization and establishment of diastereomeric ratio for the transformation was effected by incubating a suspension of product resin 11 (86.8 mg, 13.2 μmol (based on Fmoc loading level), 1.0 equiv) in 2.0 mL dichloromethane with methanol (53.5 μL, 1.32 mmol, 100.0 equiv) and concentrated hydrochloric acid (5.4 μL, 64.8 μmol, 4.9 equiv) at 23° C. After 1 hr, the reaction supernatant was collected via crimped cannula, along with 2×2 mL dichloromethane washes of the treated resin sample. This filtrates were partitioned between 30 mL dichloromethane and 30 mL sat. aq. sodium bicarbonate, the organic layer isolated, and the aqueous layer extracted with a further 2×30 mL diethyl ether. The combined organic extracts were then dried over sodium sulfate, concentrated in vacuo, and chromatographically purified ($SiO_2$, 70% ethyl acetate-hexanes→80% ethyl acetate-hexanes→100% ethyl acetate-hexanes), affording cis-11 (3.4 mg, 27%) and a mixture of trans-11 and epi-11 (epimeric at the aminonitrile methine and both centers in the tetrahydroisoquinoline ring) (0.8 mg, 6.3%, 1.8:1 trans- to epi-) as white foams (~6.7:1 diastereomeric ratio of cis- and trans-products).

cis-11: $^1$H NMR (500 MHz, $CDCl_3$), *denotes non-fused aromatic ring protons, δ 7.74 (d, 2H, J=8.0 Hz, ArH), 7.49 (d, 1H, J=7.0 Hz, ArH), 7.43 (d, 1H, J=7.5 Hz, ArH), 7.40–7.36 (m, 2H, ArH), 7.29–7.25 (m, 2H, ArH), 6.36 (s, 1H, ArH), 6.18 (s, 1H, ArOH), 5.68 (d, 1H, J=6.5 Hz, NHFmoc), 4.82 (s, 1H, NHCH), 4.57 (br s, 1H, NCHAr), 4.43 (dd, 1H, J=7.0, 10.5 Hz, $CO_2CH_2$), 4.16 (t, 1H, J=7.5 Hz, $CO_2CH_2CH$), 4.09 (app. t, 1H, J=10.0 Hz, $CO_2CH_2$), 3.93 (d, 1H, J=10.5 Hz, $ROCH_2CH_2$), 3.79 (s, 3H, ArOCH$_3$*), 3.69 (s, 3H, ArOCH$_3$*), 3.65 (s, 6H, 2×ArOCH$_3$), 3.61–3.58 (m, 1H, $ROCH_2CH_2$), 3.57 (app. s, 2H, HOCH$_2$), 3.47 (d, 1H, J=10.5 Hz, CHCN), 3.37 (br s, 1H, OCHCH$_2$), 3.20 (dd, 1H, J=1.5, 14.5 Hz, CH$_2$Ar), 3.11 (t, 1H, J=10.5 Hz, CH(CN)CH), 2.87 (t, 1H, J=13.5 Hz, CHNHFmoc), 2.65 (t, 2H, J=11.0 Hz, 2□NCH$_2$), 2.45 (t, 2H, J=11.0 Hz, 2×NCH$_2$), 2.33 (dd, 1H, J=11.0, 14.0 Hz, CH$_2$Ar), 2.25 (s, 3H, ArCH$_3$*), 2.19 (s, 3H, ArCH$_3$), 2.12 (t, 2H, J=13.0 Hz, CH$_2$Ar*), 1.64–1.40 (m, 6H, HOCH$_2$CH$_2$CH$_2$CH$_2$), 0.96 (s, 9H, SiC(CH$_3$)$_3$), 0.10 (2×s, 6H, Si(CH$_3$)$_2$). $^{13}$C NMR (100 MHz, $CDCl_3$), δ 156.7, 149.3, 148.8, 145.9, 145.3, 144.5, 144.1, 144.0, 142.8, 141.5, 140.1, 127.9, 127.3, 125.4, 124.8, 122.6, 120.3, 120.2, 119.8, 115.0, 75.8, 67.1, 66.5, 64.2, 63.0, 60.9, 60.1, 58.3, 56.8, 55.2, 52.2, 50.5, 47.4, 47.2, 33.3, 32.9, 29.9, 29.2, 28.6, 25.9, 21.8, 18.4, 10.1, 9.9, −4.4. FTIR (neat film), cm$^{-1}$ 3344 (m, NH), 2934 (s), 2857 (m), 1714 (s, NCO$_2$), 1463 (s), 1452 (s), 1238 (s), 1113 (s), 1060 (s), 869 (m), 783 (m). $R_f$ 0.48, 80% ethyl acetate-hexanes. HRMS (TOF-ES$^+$) Calcd for $C_{54}H_{73}N_4O_{10}Si$ (M+H)$^+$: 965.5096, Found: 965.5127.

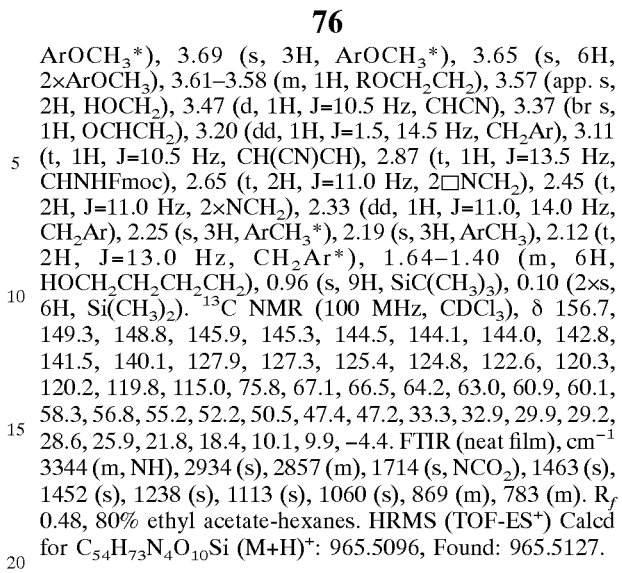

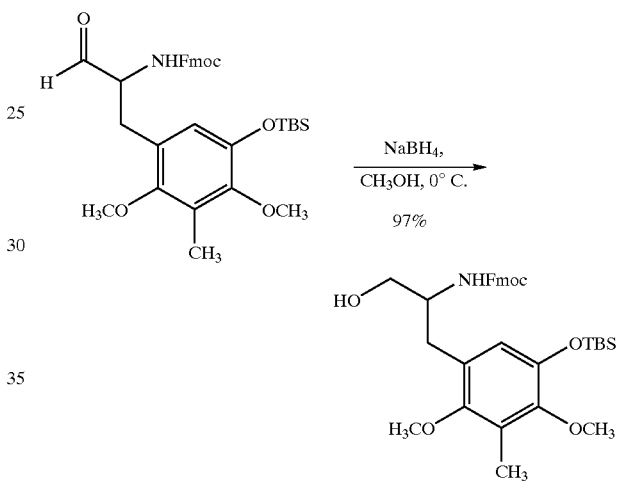

The N,N-dimethylformamide solution of substrate aldehyde isolated by filtration of resin 10 (see above) was partitioned between 250 mL diethyl ether and 250 mL water and the ether layer isolated. The aqueous layer was extracted further with 2×250 mL (1:1) hexanes-diethyl ether and all organic extracts combined, dried over sodium sulfate, and concentrated in vacuo (some N,N-dimethylformamide remained). The resulting oil (471.2 mg aldehyde (theoretical), 818.5 μmol, 1.0 equiv) was dissolved in 27.0 mL methanol and stirred at 0° C. for 10 min before adding sodium borohydride in one portion (15.5 mg, 409.2, mol, 0.5 equiv). After 25 min at 0° C., the reaction solution was diluted with 15 mL diethyl ether and excess sodium borohydride carefully quenched by the SLOW addition of 15 mL saturated aqueous ammonium chloride. The resulting solution was partitioned between 150 mL diethyl ether and 150 mL saturated aqueous ammonium chloride and the organic layer separated and washed with 1×100 mL sat. aq. ammonium chloride and 1×100 mL brine. All combined aqueous washes were then extracted 1×250 mL diethyl ether and all organic extracts were then combined, dried over sodium sulfate, and concentrated in vacuo. Chromatographic purification of the resulting product ($SiO_2$, 70% ethyl acetate-hexanes) provided the previously reported alcohol product (Myers, A. G.; Kung, D. W.; Zhong, B.; Movassaghi, M.; and Kwon, S. J. Am. Chem. Soc. 1999, 121, 8401–8402) as a clear oil (458.7 mg, 97%).

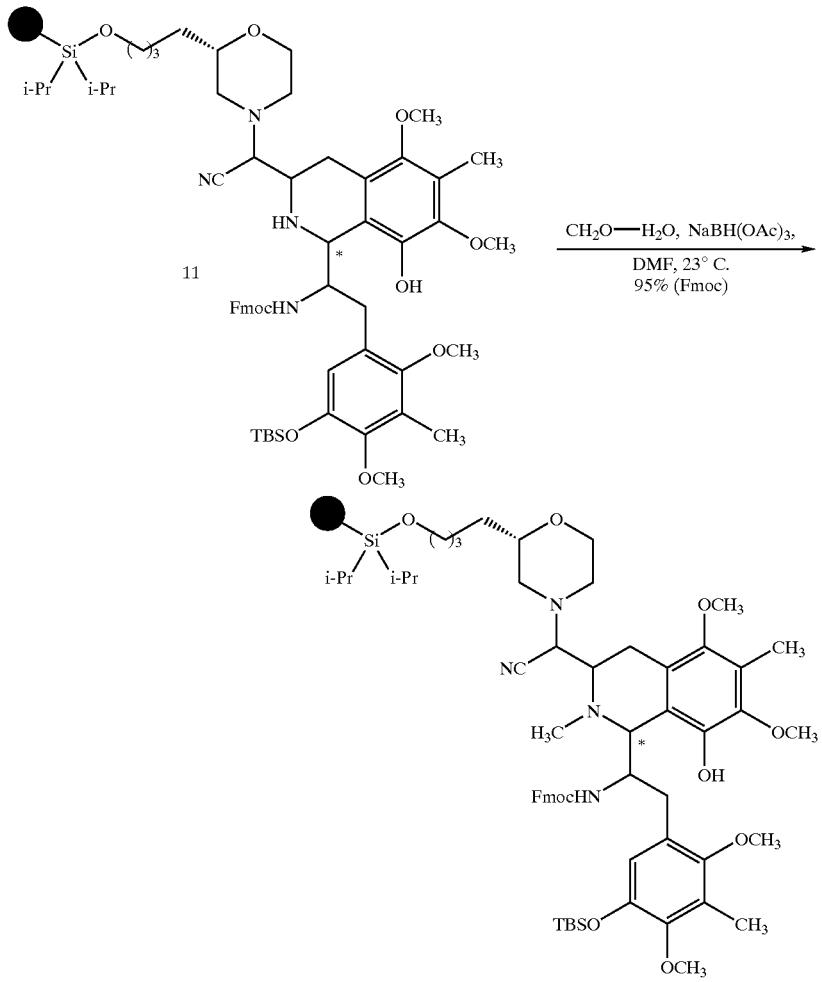

Formalin (660.5 µL, 8.87 mmol, 20.0 equiv) was added to a suspension of tetrahydroisoquinoline resin 11 (2.21 mg, 443.5 µmol, 1.0 equiv, 0.1762 mmol/g) and sodium triacetoxyborohydride (1.41 g, 6.65 mmol, 15.0 equiv) in 40.0 mL N,N-dimethylformamide. The resulting clear suspension of orangish resin was stirred for 3.5 hr before removing the reaction supernatant via crimped cannula and washing the resin sequentially with 5×30 mL N,N-dimethylformamide, 5×30 mL tetrahydrofuran, and 2×30 mL dichloromethane. Drying the product resin in vacuo provided a free-flowing, light orange resin than gave a negative chloranil test. Photometric determination of the product resin 9-fluorenylmethoxycarbonyl (Fmoc) loading level ($A_{290}$, 20% piperidine-N,N-dimethylformamide, duplicate measurements) established a resin loading level of 0.1571 mmol/g indicating a 95% yield for this transformation given chromatographic and colorimetric evidence for the completion of this reaction. Substrate cleavage for characterization was effected by incubating product resin (95.5 mg, 16.8 µmol, 1.0 equiv) in 2.7 mL dichloromethane with methanol (68.9 µL, 1.70 mmol, 100.0 equiv) and concentrated hydrochloric acid (7.0 µL, 83.3 µmol, 4.9 equiv) for 18 hr at 23° C. The reaction supernatant was then removed by crimped cannula and collected along with 5×2.5 mL dichloromethane washes of the treated resin. These filtrates were partitioned between 30 mL dichloromethane and 30 mL sat. aq. sodium bicarbonate and the organic layer was isolated. After further extraction of the aqueous layer (2×30 mL diethyl ether), all organic extracts were combined, dried over sodium sulfate, and concentrated in vacuo. Chromatographic purification of the resulting oil (prep TLC, $SiO_2$, 5% methanol-dichloromethane) provided the cis-tetrahydroisoquinoline product (10.2 mg, 62%) and trans-tetrahydroisoquinoline product (1.5 mg, 9%) as white solids (6.8:1 diastereomeric ratio).

cis-amine: $^1$H NMR (500 MHz, $CDCl_3$), * denotes non-fused aromatic ring protons, δ 7.72 (dd, 2H, J=4.0, 7.5 Hz, ArH), 7.41 (t, 2H, J=7.5 Hz, ArH), 7.36 (t, 2H, J=7.5 Hz, ArH), 7.26 (m, 2H, ArH), 6.52 (s, 1H, ArH), 6.17 (br s, 1H, ArOH), 5.50 (d, 1H, J=8.5 Hz, NHFmoc), 4.17–4.14 (m, 1H, $CO_2CH_2$), 4.00 (t, 1H, J=7.5 Hz, $CO_2CH_2CH$), 3.98–3.94 (m, 1H, $CO_2CH_2$), 3.93 (br s, 1H, NCHAr), 3.75 (d, 1H, J=8.0 Hz, $ROCH_2CH_2$), 3.68 (2×s, 6H, 2×$ArOCH_3$*), 3.66 (s, 3H, $ArOCH_3$), 3.65 (s, 3H, $ArOCH_3$), 3.60 (s, 2H, $HOCH_2$), 3.54 (m, 1H, $ROCH_2CH_2$), 3.48 (dt, 1H, J=2.0, 6.5 Hz, $OCHCH_2$), 3.43 (s, 1H, CHCN), 3.31 (d, 1H, J=11.0 Hz, $CH_2Ar$), 2.96–2.93 (m, 1H, $CHNCH_3$), 2.93–2.88 (m, 1H, CHNHFmoc), 2.75–2.67 (m, 3H, 2□$NCH_2$, $CH_2Ar$), 2.59 (s, 3H, $NCH_3$), 2.52 (app. dt, 2H, J=2.5, 11.0 Hz, $NCH_2$, $CH_2Ar$*), 2.26–2.19 (m, 2H, $NCH_2$, $CH_2Ar$*), 2.19 (s, 3H, $ArCH_3$*), 2.17 (s, 3H, $ArCH_3$), 1.61–1.49 (m, 4H, $HOCH_2CH_2CH_2CH_2$), 1.45–1.35 (m, 2H, $HOCH_2CH_2CH_2$), 0.95 (s, 9H, $SiC(CH_3)_3$), 0.11 (app. d, 6H, J=5.5 Hz, $Si(CH_3)_2$). $^{13}$C NMR (100 MHz, $CDCl_3$), δ

156.4, 151.6, 148.7, 148.5, 145.1, 144.3 (2), 144.1, 142.6, 141.3 (2), 127.8, 127.2 (2), 126.9, 125.4, 125.3, 125.2, 123.7, 122.9, 120.6, 120.1, 120.0, 116.3, 75.8, 66.9, 66.6, 64.7, 63.9, 63.7, 63.0, 61.4, 61.2, 60.8, 60.0, 58.4, 57.9, 50.5, 47.4, 33.3, 32.8, 31.2, 29.9, 25.9, 24.7, 21.8, 18.4, 10.1, 9.8, −4.4. FTIR (neat film), cm$^{-1}$ 3390 (m, NH), 2932 (s), 2857 (m), 1708 (s, NCO$_2$), 1480 (m), 1450 (m), 1416 (m), 1237 (m), 1115 (m), 1061 (s), 1009 (m), 870 (m), 741 (m). R$_f$ 0.42, 5% methanol-dichloromethane. HRMS (TOF-ES$^+$) Calcd for C$_{55}$H$_{75}$N$_4$O$_{10}$Si (M+H)$^+$: 979.5252, Found: 979.5210.

layer was separated and the aqueous layer extracted with 2×30 mL diethyl ether. All organic extracts were combined, dried over sodium sulfate, concentrated in vacuo, and chromatographically purified (prep TLC, 7% methanol-dichloromethane) to provide the expected siloxane cleavage products, the cis-tetrahydroisoquinoline (4.5 mg, 1.3%), and presumed trans-tetrahydroisoquinoline (0.5 mg, ~0.14%), as white solids. Photometric determination of the untreated product resin 9-fluorenylmethoxycarbonyl (Fmoc) loading level (A$_{290}$, 20% piperidine-N,N-dimethylformamide,

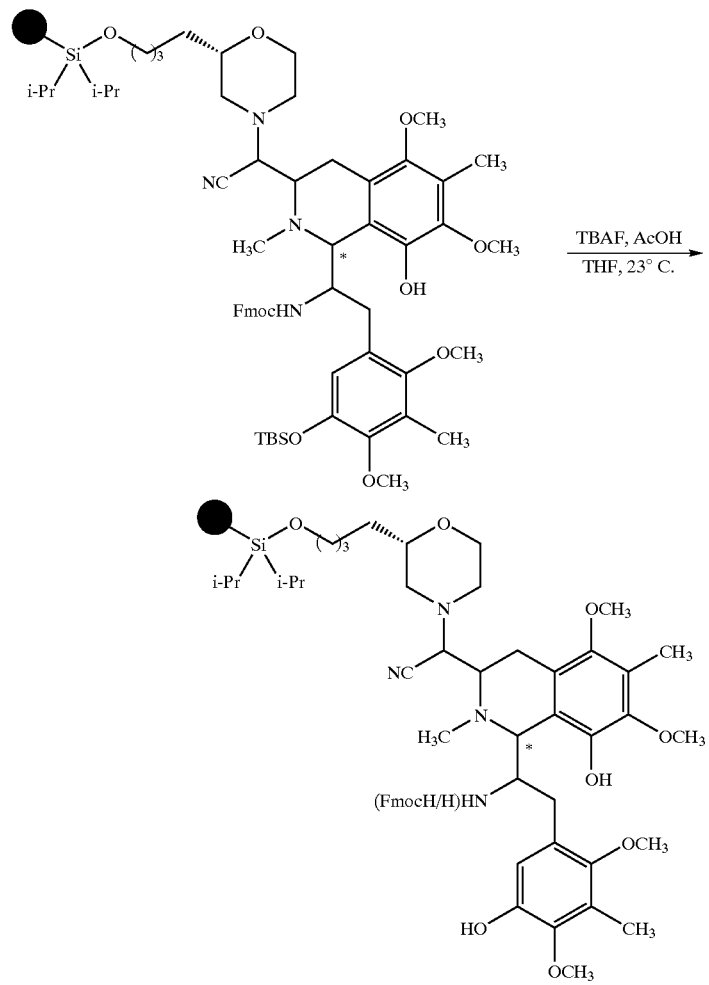

Tetra-n-butylammonium fluoride (1.0 M in tetrahydrofuran, 2.03 mL, 2.03 mmol, 5.0 equiv) was added to a suspension of N-methylated amine resin (2.42 g, 405.4, μmol, 1.0 equiv, 0.1678 mmol/g) and glatial acetic acid (231.7 μL, 4.05 mmol, 10.0 equiv) in 20.0 mL tetrahydrofuran at 23° C. The resulting suspension was stirred for 2.5 hr before the reaction supernatant was removed via crimped cannula. The product resin was washed sequentially with 2×20 mL N,N-dimethylformamide, 3×20 mL tetrahydrofuran, and 2×20 mL dichloromethane and dried in vacuo to provide a free-flowing yellow-orange resin. Cleaved substrate was recovered from the isolated reaction supernatant and N,N-dimethylforrnamide washes to determine the extent of siloxane cleavage through this procedure. The washes and supernatant were concentrated in vacuo to ~3 mL then partitioned between 30 mL diethyl ether and 30 mL (3:1) water-sodium bicarbonate (sat., aq.). The organic duplicate measurements) established a resin loading level of 0.07732 mmol/g, suggesting that ~58% of the resin-bound product had lost its Fmoc protecting group in this transformation (assuming a 98% yield for the phenolic siloxane deprotection (based on substrate resin-cleavage yields)). This deprotection of resin-bound product was confirmed by the isolation of dibenzofulvene (13.2 mg, 33%) from the reaction supernatant along with the diastereomeric tetrahydroisoquinolines described above.

cis-tetrahydroisoguinoline: $^1$H NMR (500 MHz, CDCl$_3$), * denotes non-fused aromatic ring protons, δ 7.72 (d, 2H, J=7.2 Hz, ArH), 7.43 (d, 2H, J=8.0 Hz, ArH), 7.36 (q, 2H, J=7.2 Hz, ArH), 7.26 (app. q, 2H, ArH), 6.64 (s, 1H, ArH), 6.21 (br s, 1H, ArOH), 5.63 (d, 1H, J=8.4 Hz, NHFmoc), 5.34 (br s, 1H, ArOH*), 4.24 (dd, 1H, J=6.8, 10.4 Hz, CO$_2$CH$_2$), 4.16 (d, 1H, J=6.0 Hz, CO$_2$CH$_2$), 4.03 (t, 1H, J=7.2 Hz, CO$_2$CH$_2$CH), 3.98–3.89 (m, 2H, NCHAr, ROCH$_2$CH$_2$), 3.74 (d, 1H, J=4.8 Hz, ROCH$_2$CH$_2$), 3.70 (s, 3H, ArOCH$_3$*), 3.69 (s, 3H, ArOCH$_3$*), 3.68 (s, 3H, ArOCH$_3$), 3.66 (s, 3H, ArOCH$_3$), 3.62 (m, 1H, OCHCH$_2$), 3.54 (br s, 2H, HOCH$_2$), 3.48 (m, 1H, CHCN), 3.31 (d, 1H, J=11.6 Hz, CH$_2$Ar), 3.03 (dd, 1H, J=10.8, 13.6 Hz, CHNCH$_2$), 2.93 (d, 1H, J=12.0 Hz, CHNHFmoc), 2.83 (dd, 1H, J=11.2 Hz, CH$_2$Ar), 2.75–2.66 (m,, 2H, 2×NCH$_2$), 2.59 (s, 3H, NCH$_3$), 2.53 (dt, 2H, J=2.8, 12.4 Hz, NCH$_2$, CH$_2$Ar*), 2.26–2.18 (m, 2H, NCH$_2$, CH$_2$Ar*), 2.23 (s, 3H, ArCH$_2$*), 2.18 (s, 3H, ArCH$_3$), 1.62–1.38 (m, 6H, HOCH$_2$CH$_2$CH$_2$CH$_2$). $^{13}$C NMR (100 MHz, CDCl$_3$), δ 156.5, 150.7, 148.5, 145.3, 144.5, 144.3, 144.1, 142.6, 141.4, 128.1, 127.8, 127.2 (2), 125.5, 125.3, 124.2, 123.6, 123.0, 120.5, 120.1, 116.4, 114.5, 75.8, 66.9, 66.6, 64.5, 63.6, 63.0, 61.4, 61.1, 61.0, 60.9 (2), 58.4, 58.2, 50.6, 47.4, 47.3, 33.3, 32.8, 31.3, 29.9, 24.7, 21.7, 10.2, 9.8. FTIR (neat film), cm$^{-1}$ 3392 (m, NH), 2939 (s), 2861 (m), 1702 (s, NCO$_2$), 1451 (m), 1416 (m), 1233 (m), 1112 (m), 1052 (s), 1009 (m), 910 (m), 733 (s). R$_f$ 0.25, 90% ethyl acetate-hexanes. HRMS (TOF-ES$^+$) Calcd for C$_{49}$H$_{61}$N$_4$O$_{10}$ (M+H)$^+$: 865.4387, Found: 865.4390.

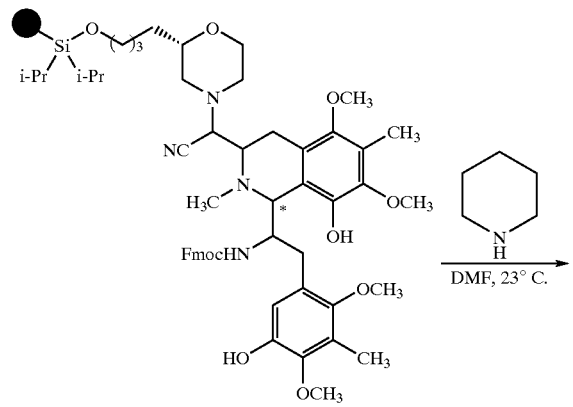

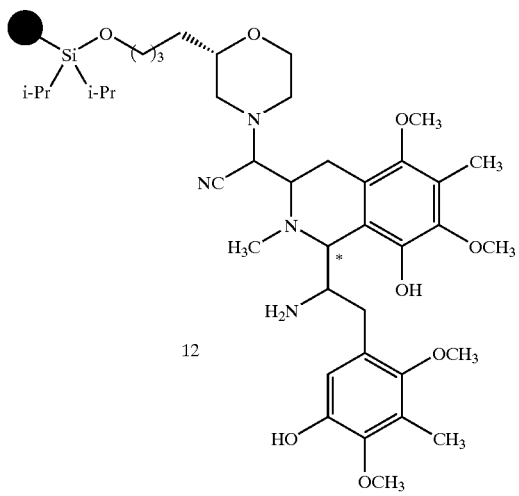

12

Substrate phenol resin (2.19 g, 355.5 μmol, 1.0 equiv, 0.1681 mmol/g) was suspended in 20.0 mL 20% (v/v) piperidine-N,N-dimethylformamide. The resulting clear suspension of orange resin was stirred for 1.5 hr at 23° C. before removing the reaction supernatant via crimped cannula. The product resin was sequentially washed with 3×20 mL N,N-dimethylformamide, 3×20 mL tetrahydrofuran, and 2×20 mL dichloromethane and dried in vacuo to provide a free-flowing orange resin. Soluble substrate was isolated for characterization by incubating a sample of product resin 12 (74.3 mg, 12.53 μmol, 1.0 equiv) in 2.0 mL dichloromethane with methanol (50.8 μL, 1.25 mmol, 100.0 equiv) and concentrated hydrochloric acid (5.1 μL, 61.42 μmol, 4.9 equiv) for 18.5 hr at 23° C. The reaction supernatant from this mixture was then collected via crimped cannula along with 6×2 mL dichloromethane washes of the treated resin. The combined washes and supernatant were partitioned between 30 mL dichloromethane and 30 mL sat. aq. sodium bicarbonate and the organic layer isolated. After further extraction of the aqueous layer (2×20 mL diethyl ether), all organic extracts were combined, dried over sodium sulfate, and concentrated in vacuo. Chromatographic purification of the resulting oil (SiO$_2$, 2% methanol-dichloromethane, column packed with eluent+1% triethylamine) afforded the expected cis-tetrahydroisoquinoline product as a white solid (1.6 mg, 20%).

cis-12: $^1$H NMR (400 MHz, CDCl$_3$), * denotes non-fused aromatic ring protons, δ 6.78 (s, 1H,ArH), 6.66 (s, 1H, ArOH), 5.60 (s, 1H, ArOH*), 3.98 (br s, 1H, NCHAr), 3.94 (d, 1H, J=10.8 Hz, ROCH$_2$CH$_2$), 3.82 (s, 3H, ArOCH$_3$*), 3.77 (s, 3H, ArOCH$_3$*), 3.73 (m, 1H, ROCH$_2$CH$_2$), 3.68 (s, 3H, ArOCH$_3$), 3.66 (s, 3H, ArOCH$_3$), 3.64 (t, 2H, J=6.0 Hz, HOCH$_2$), 3.54 (m, 2H, OCHCH$_2$, CHCN), 3.32 (dd, 1H, J=4.4, 15.2 Hz, CH$_2$Ar), 3.17 (m, 1H, NCH$_2$), 2.92 (d, 1H, J=10.8 Hz, NCH$_2$), 2.79–2.71 (m, 3H, CHNCH$_3$, CHNH$_2$, NCH$_2$), 2.62 (s, 3H, NCH$_3$), 2.52 (dt, 1H, J=2.8, 10.8 Hz, NCH$_2$), 2.41 (dd, 1H, J=13.2, 15.2 Hz, CH$_2$Ar), 2.24–2.20 (m, 2H, 2×CH$_2$Ar*), 2.22 (s, 3H, ArCH$_3$*), 2.21 (s, 3H, ArCH$_3$), 1.60–1.38 (m, 6H, HOCH$_2$CH$_2$CH$_2$CH$_2$). $^{13}$C NMR (100 MHz, CDCl$_3$), δ 150.4, 148.7, 146.4, 145.9, 145.0, 143.7, 124.8, 124.1, 123.4, 122.3, 116.6, 114.8, 75.7, 66.5, 64.9, 62.9, 61.7, 61.4, 61.1, 60.9, 60.8, 59.9, 59.7, 59.1, 58.2, 50.7, 47.3, 33.2, 32.7, 23.9, 21.7, 10.2, 9.8. FTIR (neat film), cm$^{-1}$ 3354 (w, OH/NH), 2936 (m), 2859 (w), 1455 (m), 1416 (m), 1112 (s), 1053 (m), 1005 (m). R$_f$ 0.49, 10% methanol-dichloromethane, triethylamine-dipped plate. HRMS (TOF-ES$^+$) Calcd for C$_{34}$H$_{51}$N$_4$O$_8$ (M+H)$^+$: 643.3707, Found: 643.3713.

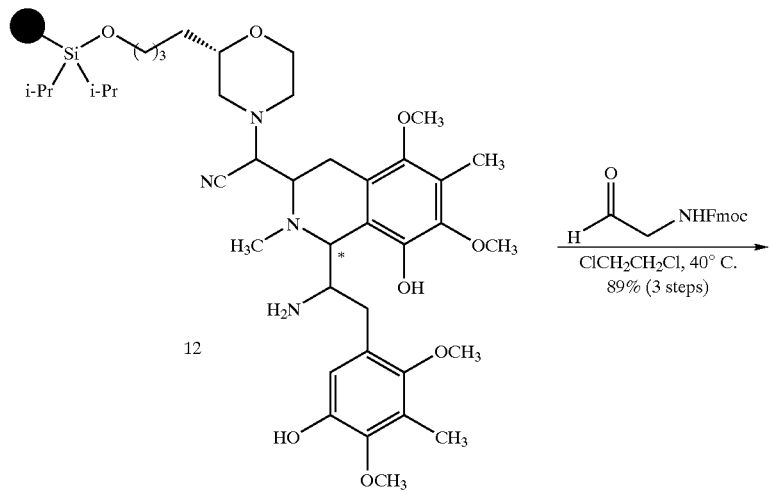

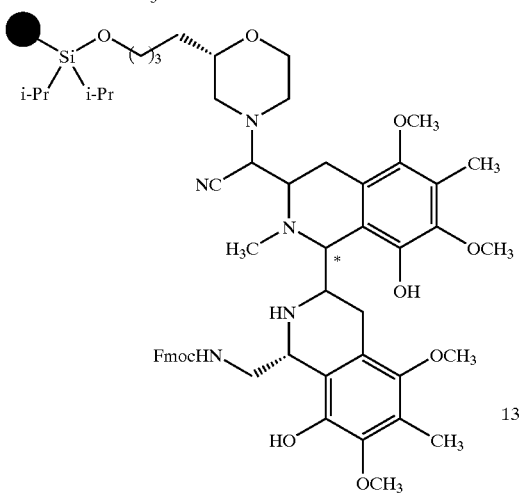

A solution of N-(9-fluorenylmethoxycarbonyl)-glycinal (Prepared as reported in Myers, A. G.; Kung, D. W. *J. Am. Chem. Soc.* 1999, 121, 10828–10829) (25.8 mg, 91.50 μmol, 3.0 equiv) in 3.1 mL dichloroethane was freeze-pump-thaw deoxygenated (3 cycles) and added via cannula to amine resin 12 (180.8 mg, 30.50 μmol, 1.0 equiv). The resulting resin suspension was stirred at 40° C. for 20 hr before removing the reaction supernatant via crimped cannula. The product resin was then washed with 6×3 mL tetrahydrofuran and 3×3 mL dichloromethane and dried in vacuo, yielding a free-flowing orange resin. Photometric determination of the product resin 9-fluorenylmethoxycarbonyl (Fmoc) loading level ($A_{290}$, 20% piperidine-N,N-dimethylformamide, duplicate measurements) established an Fmoc-loading level of 0.2076 mmol/g, consistent with a yield of >100% for this transformation, suggesting that product resin 13 has the ability to bind extra equivalents of aldehyde. An isolated yield for this transformation was obtained by incubating product resin 13 (88.58 mg, 14.31 μmol, 1.0 equiv) in 2.3 mL dichloromethane with methanol (57.9 μL, 1.43 mmol, 100.0 equiv) and concentrated hydrochloric acid (4.8 μL, 57.2 μmol, 4.9 equiv) for 19 hr at 23° C. The reaction supernatant was then collected via crimped cannula along with 6×2 mL dichloromethane washes of the treated resin and the combined filtrates partitioned between 30 mL dichloromethane and 30 mL sat. aq. sodium bicarbonate. The organic layer was isolated and the aqueous layer further extracted with 2×30 mL diethyl ether. All organic extracts were then combined, dried over sodium sulfate, and concentrated in vacuo to provide an orange oil. Chromatographic purification of this oil (prep TLC, $SiO_2$, 10% methanol-dichloromethane) afforded the expected cis-/cis-bis-tetrahydroisoquinoline cleavage product (5.7 mg, 44%, 3 steps) as a yellow-orange solid along with several diastereomeric products (various centers, 5.8 mg, 45%, 3 steps) that were not cleanly separated by prep TLC. The combined 89% isolated yield over three steps corresponds to an average yield per step of ~96%.

cis-13: $^1$H NMR (500 MHz, $CDCl_3$), * denotes unmethylated tetrahydroisoquinoline ring system, δ 7.76 (dd, 2H, J=3.5, 8.0 Hz, ArH), 7.59–7.54 (m, 2H, ArH), 7.41–7.38 (m, 2H, ArH), 7.30 (q, 2H, J=7.0 Hz, ArH), 5.72 (br s, 1H, ArOH), 5.37 (br s, 1H, NHFmoc), 4.37 (d, 2H, J=7.5 Hz, $CO_2CH_2$, NCHAr), 4.34 (d, 1H, $CO_2CH_2$), 4.21 (t, 1H, J=6.5 Hz, $CO_2CH_2CH$), 3.91 (d, 2H, J=11.5 Hz, $ROCH_2CH_2$, NCHAr*), 3.76 (s, 3H, $ArOCH_3$*), 3.74 (s, 3H, $ArOCH_3$), 3.71 (m, 1H, $ROCH_2CH_2$), 3.68 (m, 1H, $OCHCH_2$), 3.66 (2×s, 6H, 2×$ArOCH_3$), 3.64 (s, 1H, CHCN), 3.49 (m, 4H, $HOCH_2$, $CH_2NHFmoc$), 3.27 (d, 1H, J=11.5 Hz, $CH_2Ar$), 2.84 (d, 2H, J=11.0 Hz, $NCH_2$, $CH_2Ar$*), 2.71–2.68 (br s, 3H, $NCH_3$), 2.67–2.56 (m, 2H, $CHNCH_3$, CHNH), 2.48 (dt, 2H, J=3.5, 11.0 Hz, 2×$NCH_2$), 2.42 (m, 1H, $CH_2Ar$), 2.24–2.21 (m, 2H, $NCH_2$, $CH_2Ar$*), 2.22 (s, 3H, $ArCH_3$*), 2.21 (s, 3H, $ArCH_3$), 1.61–1.54 (m, 2H, HOCH$_2$CH$_2$), 1.54–1.46 (m, 2H, HOCH$_2$CH$_2$CH$_2$CH$_2$), 1.46–1.34 (m, 2H, HOCH$_2$CH$_2$CH$_2$). $^{13}$C NMR (100 MHz, CDCl$_3$), δ 157.5, 149.4, 148.7, 145.7, 144.3, 143.9, 143.7, 142.0, 141.5, 131.1, 130.8, 128.6, 127.9, 127.3, 126.2, 125.4, 123.7, 122.6, 120.2, 116.3, 75.8, 67.1, 66.5, 64.9, 63.0, 61.4, 61.1, 61.0, 60.7, 59.1, 58.3, 52.8, 49.9, 47.4, 47.0, 46.6, 33.3, 32.8, 29.9, 27.2, 24.2, 21.8, 9.9, 9.8. FTIR (neat film), cm$^{-1}$ 3390 (m, NH/OH), 2936 (s), 2863 (m), 1713 (m, NCO$_2$), 1451 (s), 1413 (m), 1258 (m), 1112 (s), 1057 (s), 1006 (m), 734 (s). R$_f$ 0.34, 10% methanol-dichloromethane. HRMS (TOF-ES$^+$) Calcd for C$_{51}$H$_{64}$N$_5$O$_{10}$ (M+H)$^+$: 906.4653, Found: 906.4688.

and washed with 1×10 mL brine and the aqueous layers then combined and extracted with a further 2×15 mL ethyl acetate. The combined organic extracts were then dried over sodium sulfate and concentrated in vacuo. Chromatographic purification of the resulting red oil (prep TLC, SiO$_2$, 5% methanol-dichloromethane) afforded pentacyclic product 2a as a white solid (2.0 mg, 41%) along with small amounts of the product aminonitrile hydrolysis product (0.4 mg, 8%).

2a: $^1$H NMR (400 MHz, CDCl$_3$), δ 7.76 (t, 2H, J=6.8 Hz, ArH), 7.47–7.39 (m, 2H, ArH), 7.30 (t, 2H, J=7.2 Hz, ArH), 5.57 (br s, 1H, ArOH), 5.51 (br s, 1H, ArOH), 4.53 (t, 1H,

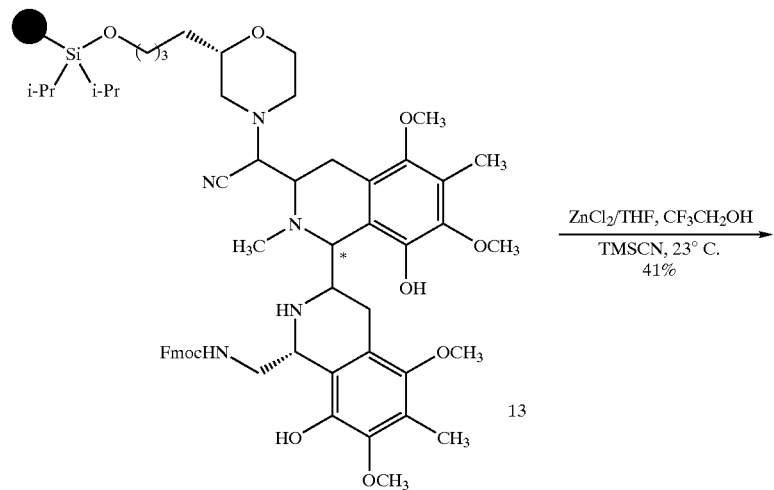

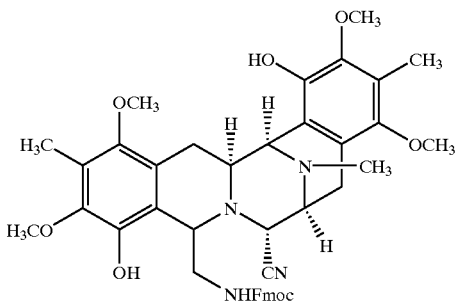

2a 2,2,2-trifluoroethanol (35.2 μL, 483.10 μmol, 68.6 equiv), zinc chloride (0.5 M in tetrahydrofuran, 70.4 μL, 35.21 μmol, 5.0 equiv), and trimethylsilylcyanide (3.8 μL, 28.17 μmol, 4.0 equiv) were sequentially added to a suspension of resin 13 (43.6 mg, 7.04 μmol, 1.0 equiv) in 105.6 μL tetrahydrofuran at 23° C. The resulting yellow suspension was stirred for 16 hr at 23° C. before diluting the reaction mixture with 1.5 mL tetrahydrofuran. The reaction supernatant was then collected via crimped cannula along with 5×2 mL tetrahydrofuran washes of the treated resin. The collected filtrates were partitioned between 5 mL ethyl acetate and 15 mL of an aqueous solution of 0.2 N ethylenediaminetetraacetic acid disodium salt dihydrate and 0.4 N sodium hydroxide (pH 10). The organic layer was isolated J=6.0 Hz, NHFmoc), 4.32 (dd, 1H, J=6.8, 10.8 Hz, CO$_2$CH$_2$), 4.22 (dd, 1H, J=6.0, 10.8 Hz, CO$_2$CH$_2$), 4.14 (br s, 1H, ArCHNCH$_3$), 4.11 (t, 1H, J=4.4 Hz, ArCHCH$_2$NHFmoc), 4.06 (t, 1H, J=6.4 Hz, CO$_2$CH$_2$CH), 3.74 (s, 3H, ArOCH$_3$), 3.60 (s, 6H, 2×ArOCH$_3$), 3.55 (s, 3H, ArOCH$_3$), 3.29 (d, 1H, J=7.2, ArCH$_2$CHNCH$_3$), 3.24–3.19 (m, 3H, ArCH$_2$CHNC(CN), ArCH$_2$CHNC(CN), CH$_2$NHFmoc), 3.11–3.04 (m, 1H, CH$_2$NHFmoc), 2.96 (dd, 1H, J=8.0, 18.8 Hz, ArCH$_2$CHNCH$_3$), 2.33 (d, 1H, J=11.6 Hz, ArCH$_2$CHNCH$_3$), 2.31 (s, 3H, NCH$_3$), 2.19 (s, 3H, ArCH$_3$), 2.11 (s, 3H, ArCH$_3$), 1.88 (dd, 1H, J=11.6, 16.4 Hz, ArCH$_2$CHNC(CN)). R$_f$ 0.38, 5% methanol-dichloromethane. LRMS (TOF-ES$^+$) Calcd for C$_{43}$H$_{47}$N$_4$O$_8$ (M+H)$^+$: 747, Found: 747.-

Exemplary Solid-supported Syntheses of Compounds Having Alternate Pentacyclic Core Structures:

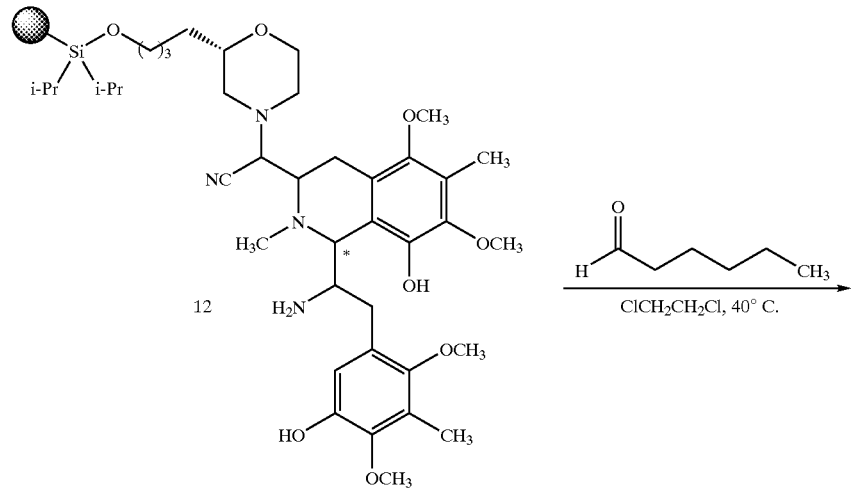

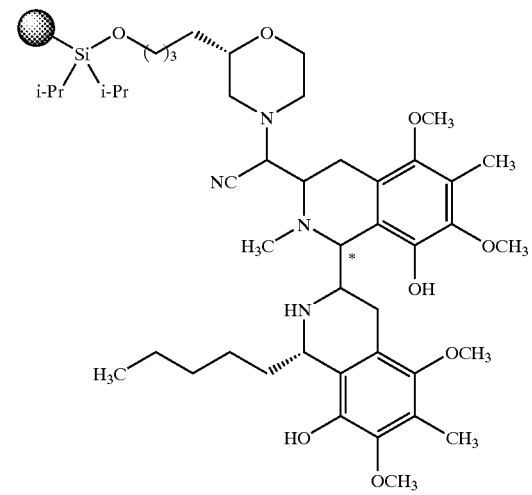

A solution of hexanal (7.8 μL, 64.70 μmol, 5.0 equiv) in 1.3 mL dichloroethane was freeze-pump-thaw deoxygenated (3 cycles) and added via cannula to amine resin 12 (76.7 mg, 12.94 μmol, 1.0 equiv). The resulting resin suspension was stirred in the dark at 40° C. for 20.5 hr before removing the reaction supernatant via crimped cannula. The product resin was then washed with 6×3 mL tetrahydrofuran and 3×3 mL dichloromethane and dried in vacuo, yielding a free-flowing orange resin. The product resin was directly employed in subsequent reactions.

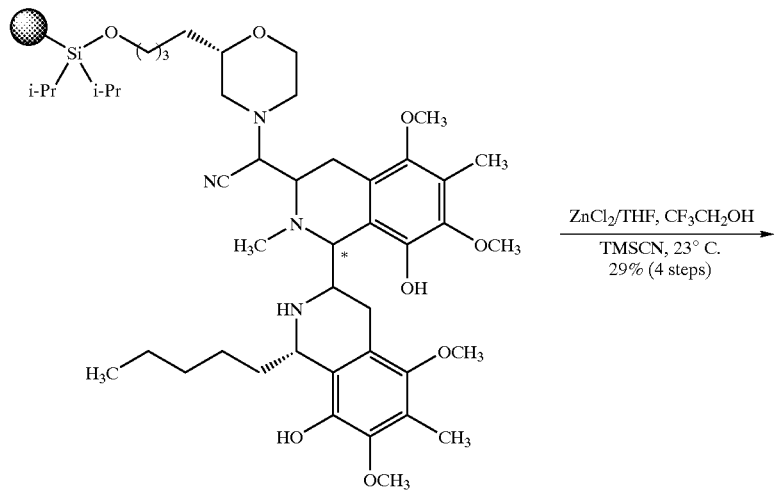

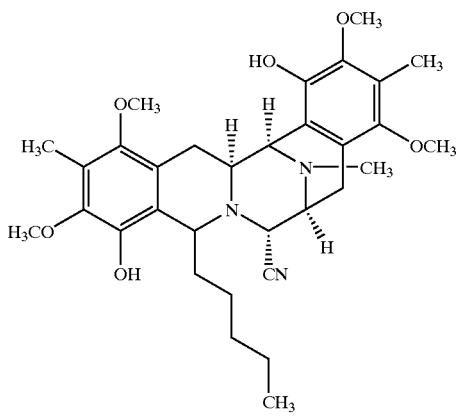

Zinc chloride (0.5 M in tetrahydrofuran, 2.3 mL, 1.16 mmol, 100.0 equiv) and trimethylsilylcyanide (151.8 μL, 1.14 mmol, 99.0 equiv) were sequentially added to a suspension of substrate resin (69.8 mg, 11.61 μmol, 1.0 equiv) in 460.0 μL 2,2,2-trifluoroethanol at 23° C. The resulting yellow suspension was stirred for 15.5 hr at 23° C. before removing and collecting the reaction supernatant via crimped cannula along with 5×3 mL tetrahydrofuran washes of the treated resin. The collected filtrates were partitioned between 10 mL ethyl acetate and 20 mL of an aqueous solution of 0.2 N ethylenediaminetetraacetic acid disodium salt dihydrate and 0.4 N sodium hydroxide (pH 10). The organic layer was isolated and washed with 1×15 mL brine and the aqueous layers then combined and extracted with a further 2×15 mL ethyl acetate. The combined organic extracts were then dried over sodium sulfate and concentrated in vacuo. Chromatographic purification of the resulting red oil ($SiO_2$, 40% ethyl acetate-hexanes) afforded the pentacyclic product as a white solid (1.9 mg, 29%, 4 steps).

$^1$H NMR (500 MHz, $C_6D_6$), ~2:1 mixture of rotamers, * denotes minor rotamer signals, δ 5.75 (s, 1H, ArOH), 5.18 (s, 1H, ArOH*), 5.17 (s, 1H, ArOH), 4.20 (m, 1H, ArCHNCH$_3$), 4.16 (d, 1H, J=2.0 Hz, ArCHNCH$_3$*), 3.93 (m, 1H, ArCHNC(CN)*), 3.90 (m, 1H, ArCHNC(CN)), 3.83 (d, 1H, J=3.2 Hz, CHCN), 3.73 (d, 1H, CHCN*), 3.53 (s, 3H, ArOCH$_3$*), 3.38 (s, 3H, ArOCH$_3$), 3.31 (s, 3H, ArOCH$_3$), 3.22 (s, 3H, ArOCH$_3$*), 3.14 (s, 3H, ArOCH$_3$*), 3.08 (s, 3H, ArOCH$_3$), 3.02 (s, 3H, ArOCH$_3$), 3.00 (s, 3H, ArOCH$_3$*), 2.98 (m, 1H, ArCH$_2$CHNCH$_3$), 2.80 (d, 1H, J=13.4 Hz, ArCH$_2$CHNC(CN)), 2.66 (dd, 1H, J=8.0, 18.8 Hz, ArCH$_2$CHNC(CN)), 2.58 (dt, 1H, J=4.4, 12.8 Hz, ArCH$_2$CHNCH$_3$), 2.23 (dt, 1H, 4.4, 18.0 Hz, ArCH$_2$CHNCH$_3$), 2.15 (s, 3H, NCH$_3$), 2.13 (m, 1H, ArCH$_2$CHNC(CN)), 2.12 (s, 3H, ArCH$_3$*), 2.11 (s, 3H, ArCH$_3$), 2.05 (s, 3H, ArCH$_3$), 2.04 (m, 1H, ArCHCH$_2$), 1.95 (d, 1H, J=18.8 Hz, ArCHCH$_2$), 1.62 (dt, 2H, J=4.8, 13.2 Hz, ArCHCH$_2$CH$_2$), 0.90–0.78 (m, 4H, CH$_2$CH$_2$CH$_2$CH$_3$), 0.65 (t, 3H, J=7.2 Hz, CH$_2$CH$_3$). FTIR (neat film), cm$^{-1}$ 2934 (m), 2859 (w), 1462 (s), 1414 (s), 1280 (m), 1109 (m), 1063 (m), 1005 (m). R$_f$ 0.32, 5% methanol-dichloromethane.

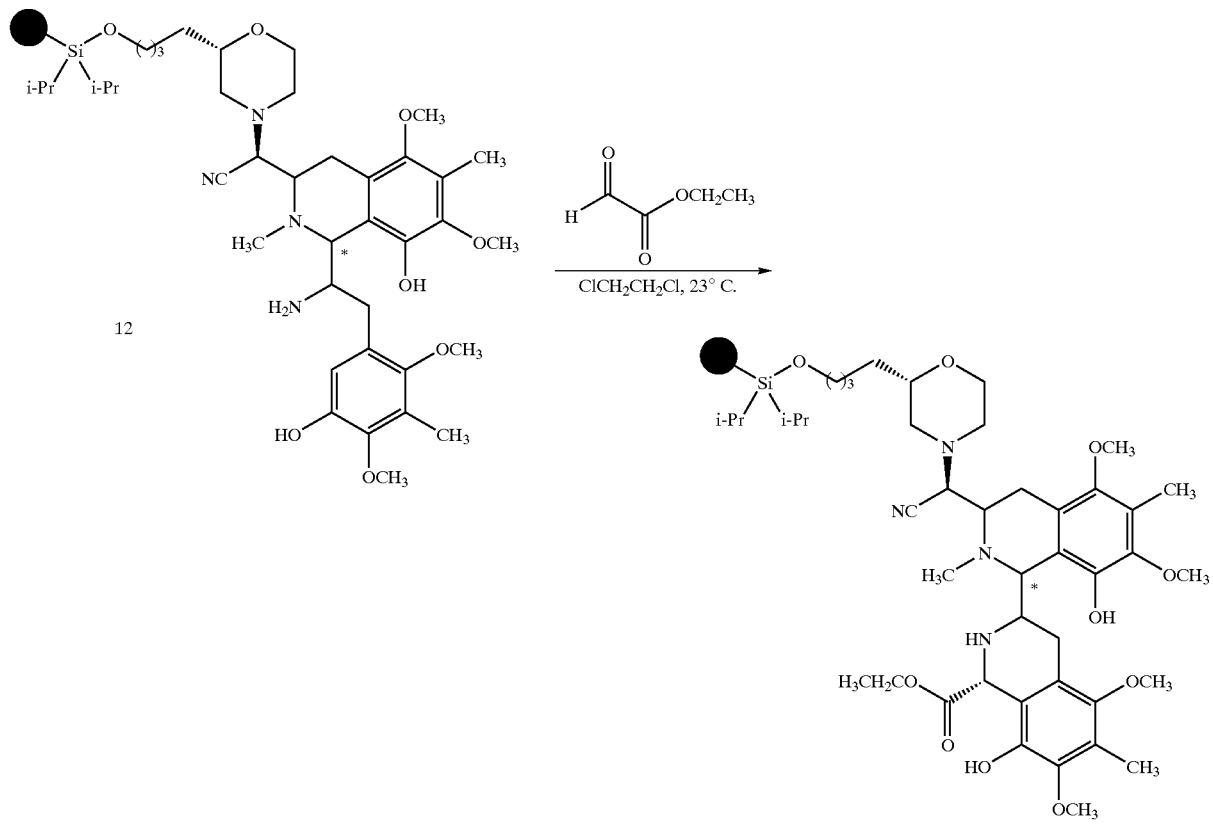

A solution of ethyl glyoxylate (50% w/w in toluene, 13.0 μL, 65.79 μmol, 5.0 equiv) in 1.3 mL dichloroethane was freeze-pump-thaw deoxygenated (3 cycles) and added via cannula to amine resin 12 (78.0 mg, 13.16 μmol, 1.0 equiv). The resulting resin suspension was stirred in the dark at 23° C. for 22 hr before removing the reaction supernatant via crimped cannula. The product resin was then washed with 2×3 N,N-dimethylformamide, 4×3 mL tetrahydrofuran, and 2×2 mL dichloromethane and dried in vacuo, yielding a free-flowing orange resin. The product resin was directly employed in subsequent reactions.

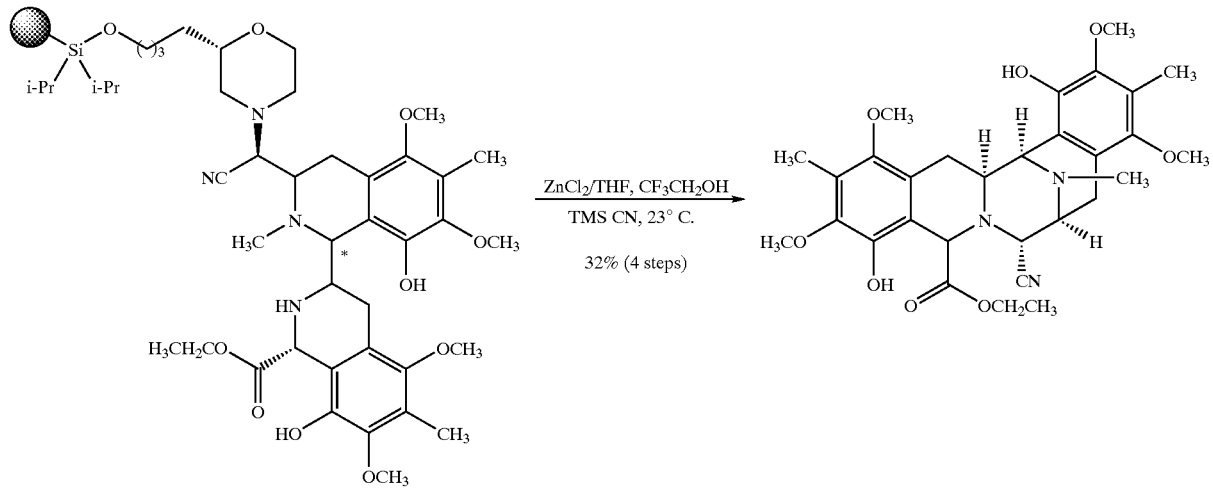

2,2,2-trifluoroethanol (61.6 μL, 845.4 μmol, 68.6 equiv), zinc chloride (0.5 M in tetrahydrofuran, 123.3 μL, 61.64 μmol, 5.0 equiv), and trimethylsilylcyanide (6.6 μL, 49.31 μmol, 4.0 equiv) were sequentially added to a suspension of substrate resin (74.1 mg, 12.33 μmol, 1.0 equiv) in 185.0 μL tetrahydrofuran at 23° C. The resulting yellow suspension was stirred for 7 hr at 23° C. before diluting the reaction mixture with 1.5 mL tetrahydrofuran. The reaction supernatant was then collected via crimped cannula along with 5×2 mL tetrahydrofuran washes of the treated resin. The collected filtrates were partitioned between 5 mL ethyl acetate and 15 mL of an aqueous solution of 0.2 N ethylenediaminetetraacetic acid disodium salt dihydrate and 0.4 N sodium hydroxide (pH 10). The organic layer was isolated and washed with 1×10 mL brine and the aqueous layers then combined and extracted with a further 2×15 mL ethyl acetate. The combined organic extracts were then dried over sodium sulfate and concentrated in vacuo. Chromatographic purification of the resulting orange oil (prep TLC, $SiO_2$, 5% methanol-dichloromethane) afforded the pentacyclic product as a yellowish-white solid (2.2 mg, 31.5%, 4 steps)

$^1$H NMR (400 MHz, $CDCl_3$), δ 5.56 (s, 1H, ArOH), 5.51 (s, 1H, ArOH), 4.57 (s, 1H, ArCHCO$_2$), 4.35 (d, 1H, J=2.4 Hz, CHCN), 4.17 (dd, 1H, J=1.2, 2.8 Hz, ArCHNCH$_3$), 4.04–3.97 (m, 1H, CO$_2$CH$_2$), 3.95–3.85 (m, 1H, CO$_2$CH$_2$), 3.75 (s, 3H, ArOCH$_3$), 3.74 (s, 3H, ArOCH$_3$), 3.65 (s, 3H, ArOCH$_3$), 3.63 (s, 3H, ArOCH$_3$), 3.39 (d, 1H, J=8.0 Hz, ArCH$_2$CHC(CN)), 3.26 (dt, 1H, J=2.4, 11.2 Hz, ArCH$_2$CHNC(CN)), 3.22 (dd, 1H, J=2.8, 15.6 Hz, ArCH$_2$CHNC(CN)), 3.03 (dd, 1H, J=8.0, 18 Hz, ArCH$_2$CHNCH$_3$), 2.41 (d, 1H, J=18.4 Hz, ArCH$_2$CHNCH$_3$), 2.30 (s, 3H, NCH$_3$), 2.21 (s, 3H, ArCH$_3$), 2.20 (s, 3H, ArCH$_3$), 2.03 (dd, 1H, J=11.6, 15.2 Hz, ArCH$_2$CHNC(CN)), 1.01 (t, 3H, J=7.2 Hz, CO$_2$CH$_2$CH$_3$). FTIR (neat film), cm$^{-1}$ 3422 (m, OH), 2936 (m), 2829 (w), 1728 (m, CO$_2$), 1464 (s), 1414 (s), 1276 (m), 1152 (m), 1061 (s), 1027 (m), 1004 (m). $R_f$ 0.39, 5% methanol-dichloromethane. HRMS (TOF-ES$^+$) Calcd for $C_{30}H_{38}N_3O_8$ (M+H)$^+$: 568.2658, Found: 568.2677.

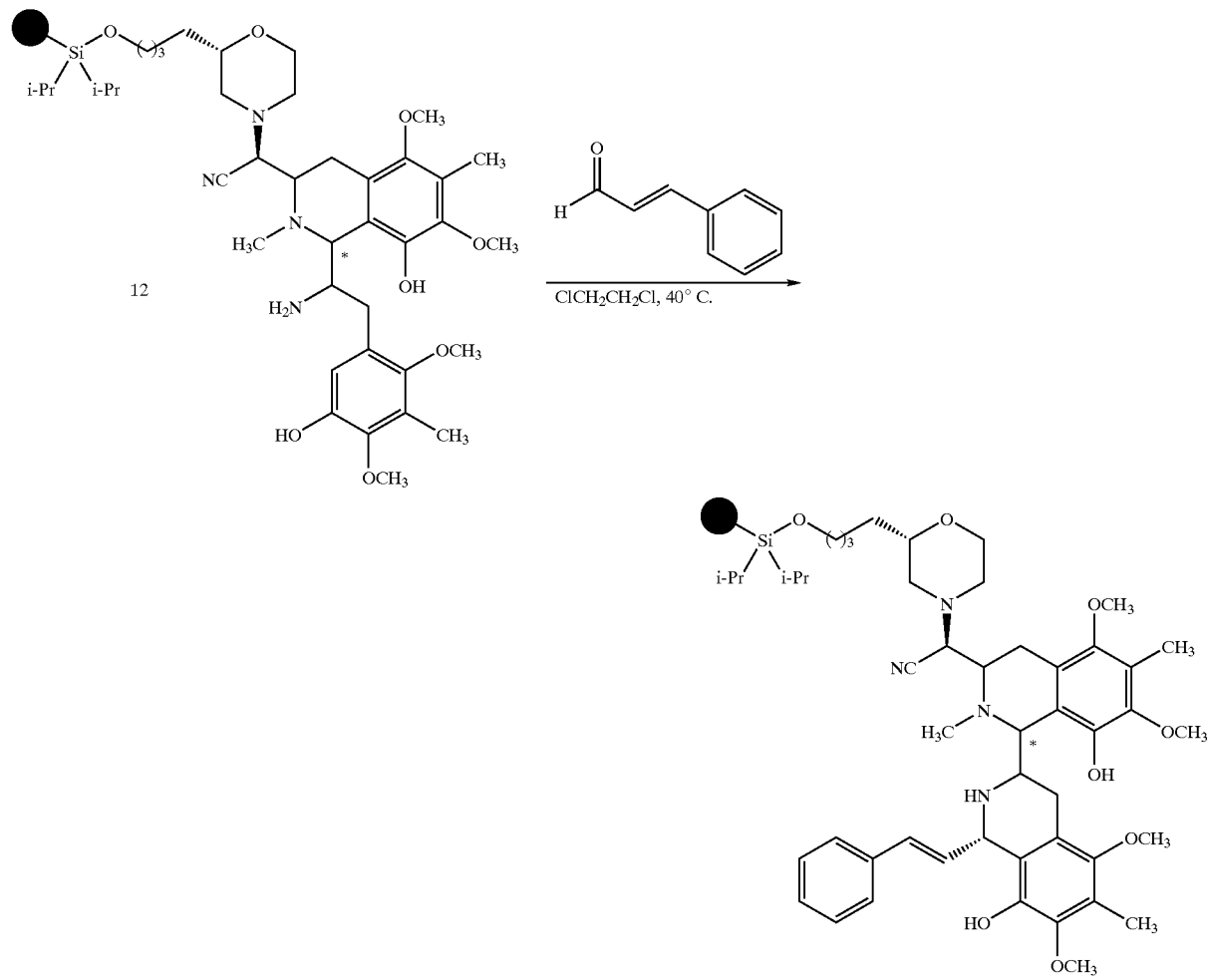

A solution of trans-cinnamaldehyde (8.8 μL, 69.42 μmol, 5.0 equiv) in 1.35 mL dichloroethane was freeze-pump-thaw deoxygenated (3 cycles) and added via cannula to amine resin 12 (82.3 mg, 13.88 μmol, 1.0 equiv). The resulting resin suspension was stirred in the dark at 40° C. for 21 hr before removing the reaction supernatant via crimped cannula. The product resin was then washed with 2×3 N,N-dimethylformamide, 4×3 mL tetrahydrofuran, and 2×2 mL dichloromethane and dried in vacuo, yielding a free-flowing orange resin. The product resin was directly employed in subsequent reactions.

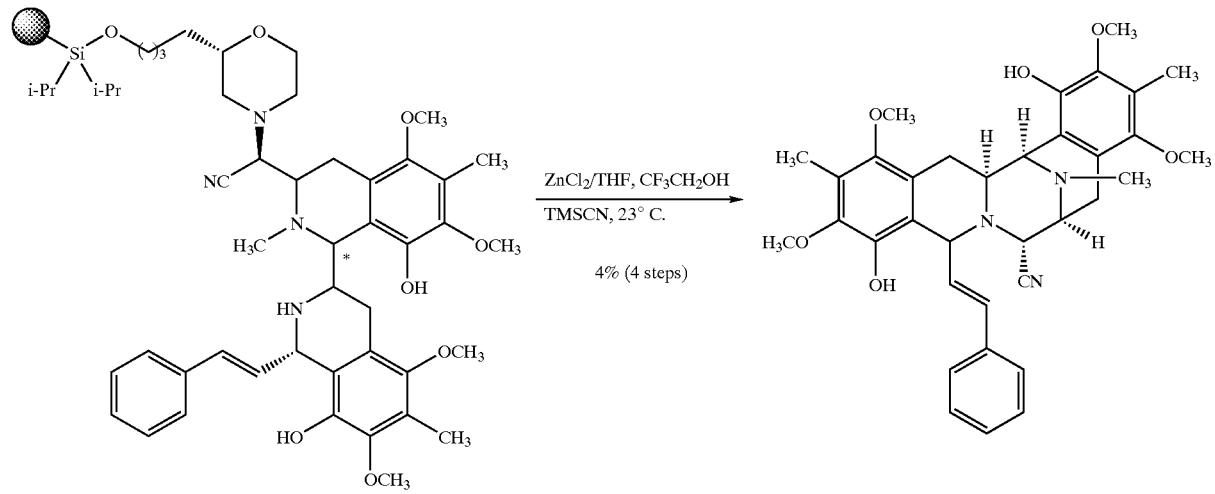

2,2,2-trifluoroethanol (65.0 μL, 892.1 μmol, 68.3 equiv), zinc chloride (0.5 M in tetrahydrofuran, 130.6 μL, 65.29 μmol, 5.0 equiv), and trimethylsilylcyanide (7.0 μL, 52.23 μmol, 4.0 equiv) were sequentially added to a suspension of substrate resin (78.9 mg, 13.06 μmol, 1.0 equiv) in 196.0 μL tetrahydrofuran at 23° C. The resulting yellow suspension was stirred for 5.5 hr at 23° C. before diluting the reaction mixture with 1.5 mL tetrahydrofuran. The reaction supernatant was then collected via crimped cannula along with 5×2 mL tetrahydrofuran washes of the treated resin. The collected filtrates were partitioned between 5 mL ethyl acetate and 15 mL of an aqueous solution of 0.2 N ethylenediaminetetraacetic acid disodium salt dihydrate and 0.4 N sodium hydroxide (pH 10). The organic layer was isolated and washed with 1×10 mL brine and the aqueous layers then combined and extracted with a further 2×15 mL ethyl acetate. The combined organic extracts were then dried over sodium sulfate and concentrated in vacuo. Chromatographic purification of the resulting yellow-brown oil (prep TLC, $SiO_2$, 5% methanol-dichloromethane) afforded the pentacyclic product as a white solid (0.3 mg, 4%, 4 steps)

$^1$H NMR (400 MHz, $CDCl_3$), δ 7.21–7.12 (m, 5H, ArH), 6.42 (d, 1H, J=15.2 Hz, CHCHAr), 6.03 (dd, 1H, J=5.6, 15.6 Hz, CHCHAr), 5.56 (s, 1H, ArOH), 5.49 (s, 1H, ArOH), 4.59 (d, 1H, J=6.0 Hz, ArCHCHCHAr), 4.21 (d, 1H, J=2.4 Hz, CHCN), 4.02 (d, 1H, J=2.8 Hz, ArCHNCH$_3$), 3.78 (s, 3H, ArOCH$_3$), 3.73 (s, 3H, ArOCH$_3$), 3.61 (s, 3H, ArOCH$_3$), 3.60 (s, 3H, ArOCH$_3$), 3.39 (d, 1H, J=6.4 Hz, ArCH$_2$CHC(CN)), 3.32 (dt, 1H, J=12.0 Hz, ArCH$_2$CHNC(CN)), 3.26 (dd, 1H, J=2.4, 15.6 Hz, ArCH$_2$CHNC(CN)), 3.04 (dd, 1H, J=8.0, 18.4 Hz, ArCH$_2$CHNCH$_3$), 2.48 (d, 1H, J=18.8 Hz, ArCH$_2$CHNCH$_3$), 2.35 (s, 3H, NCH$_3$), 2.28 (s, 3H, ArCH$_3$), 2.18 (s, 3H, ArCH$_3$), 2.00 (dd, 1H, J=12.8, 14.0 Hz, ArCH$_2$CHNC(CN)). FTIR (neat film), cm$^{-1}$ 3357 (w, OH), 2918 (m), 2849 (w), 1463 (s), 1415 (s), 1109 (s), 1060 (s), 1002 (s), 744 (m). R$_f$ 0.37, 5% methanol-dichloromethane. HRMS (ApCI$^+$) Calcd for $C_{34}H_{39}N_2O_6$ (M-CN)$^+$: 571, Found: 571.

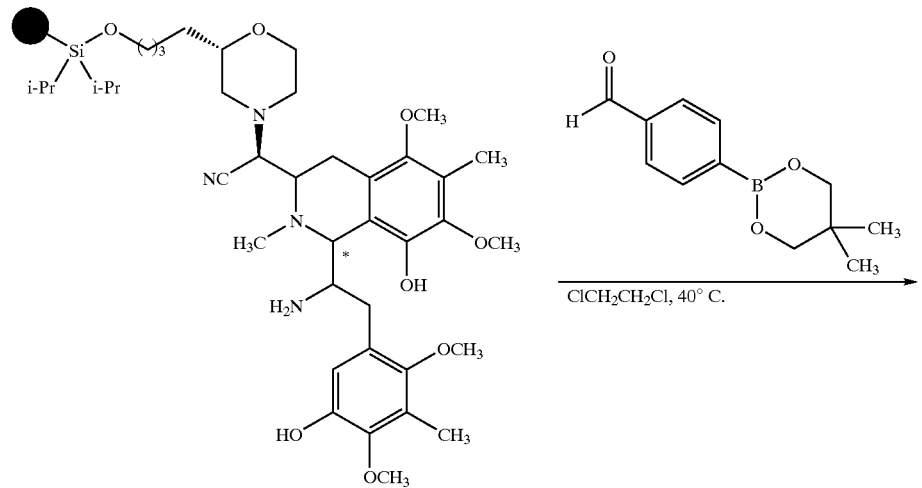

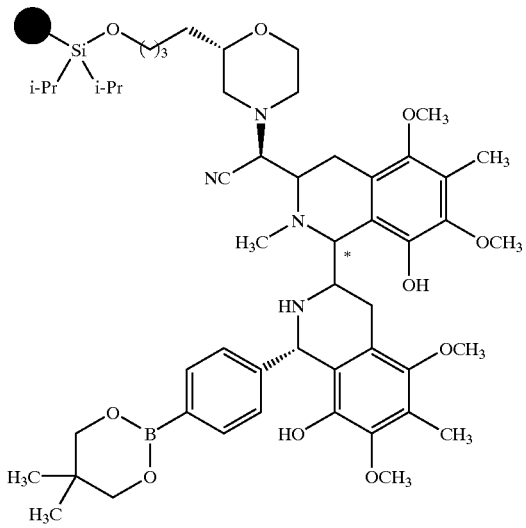

A solution of benzaldehyde boronate ester (5.2 mg, 23.87 μmol, 5.0 equiv) in 600 μL 1,2-dichloroethane was freeze-pump-thaw deoxygenated (3 cycles) and then added via cannula to the amine resin (28.3 mg, 4.77 μmol, 0.1687 mmol/g, 1.0 equiv). The resulting suspension was stirred at 75° C. for 31 h and the supernatant was then removed via cannula. The product resin was washed with 4×1 mL N,N-dimethylformamide, 6×1 mL tetrahydrofuran, and 2×1 mL diethyl ether and then dried in vacuo to provide 26.2 mg free-flowing orange resin.

$R_f$ 0.48 (methanolysis product, decomposes), 10% methanol-dichloromethane.

superntant and washes were partitioned between 15 mL dichloromethane and 15 mL aqueous phosphate buffer solution (0.05 M sodium phosphate monobasic, 0.05 M potassium phosphate dibasic, pH 7) and the organic layer isolated. The organic layer was then washed with an additional 8 mL phosphate buffer solution, dried over sodium sulfate, and concentrated in vacuo to provide an orangish-brown oil. Lyophilization of this oil from 300 μL benzene afforded the heptacyclic product as a tan solid (2.2 mg, 57.7% yield (9 steps)).

$^1$H NMR (600 MHz, CDCl$_3$), δ 7.53 (d, 2H, J=7.8 Hz, ArH), 7.16 (d, 2H, J=7.8 Hz, ArH), 5.58 (s, 1H, ArOH), 5.30

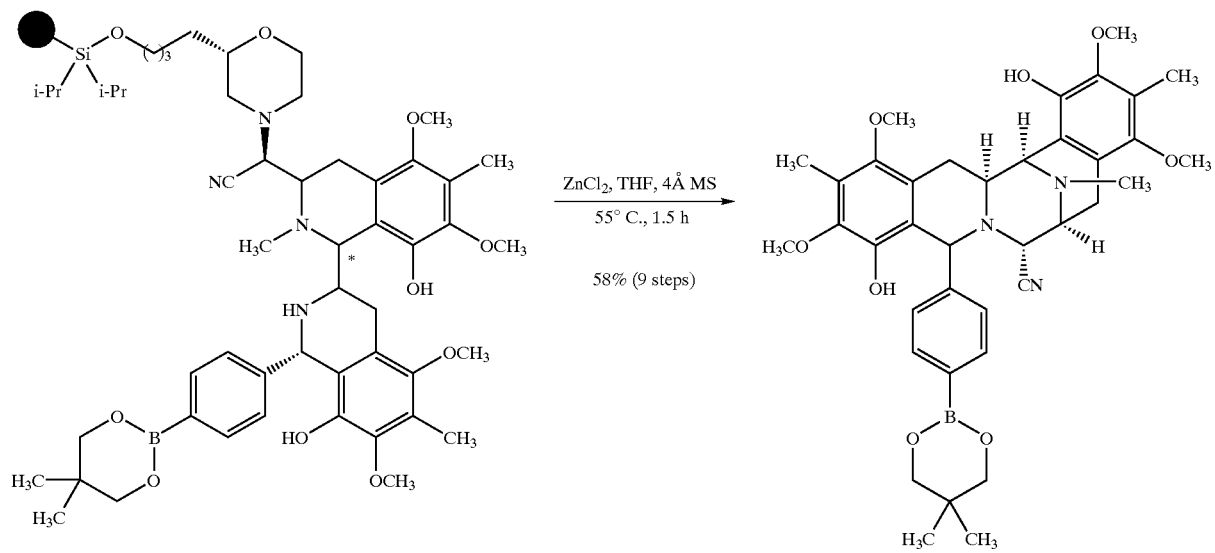

Zinc chloride (25.7 μL, 0.5 M in tetrahydrofuran, 12.83 μmol, 3.0 equiv) was added to a mixture of boronate resin (26.2 mg, 4.28 μmol, 0.1632 mmol/g, 1.0 equiv) and 4 Å molecular sieves (2.5 mg) suspended in 160.0 μL tetrahydrofuran. The resulting suspension was stirred at 55° C. for 1.5 h. The reaction supernatant was then removed via crimped cannula and collected along with 5×1.5 mL dichloromethane washes of the product resin. The combined (s, 1H, ArOH), 4.89 (s, 1H, CHAr$_1$Ar$_2$), 4.23 (d, 1H, J=3.0 Hz, N(CH$_3$)CH), 3.80 (s, 3H, ArOCH$_3$), 3.73 (s (obsc.), 1H, CHCN), 3.71 (s, 6H, 2×ArOCH$_3$), 3.64 (s, 2H, BOCH$_2$), 3.63 (s, 2H, BOCH$_2$), 3.47 (s, 3H, ArOCH$_3$), 3.39 (dt, 1H, J=10.8 Hz, N(CH$_3$)CHCH), 3.31 (dd, 1H, J=2.4, 16.2 Hz, N(CH$_3$)CHCHCH$_2$), 3.25 (d, 1H, J=8.4 Hz, NCH(CN)CH), 2.83 (dd, 1H, J=8.4, 18.0 Hz, NCH(CN)CHCH$_2$), 2.26 (s, 3H, NCH$_3$), 2.25 (s, 3H, ArCH$_3$), 2.18 (dd, 1H, J=5.4, 15.6

Hz, N(CH$_3$)CHCHCH$_2$), 2.15 (s, 3H, ArCH$_3$), 1.84 (d, 1H, J=18.0 Hz, NCH(CN)CHCH$_2$), 0.98 (s, 6H, C(CH$_2$)$_2$). R$_f$ 0.27 (decomposes), 5% methanol-dichloromethane. HRMS (TOF-ES$^+$) Calcd for C$_{38}$H$_{47}$BN$_3$O$_8{}^+$ (M+H)$^+$: 684.3456, Found: 684.3487.

Exemplary Alternate N-alkylation Reaction:

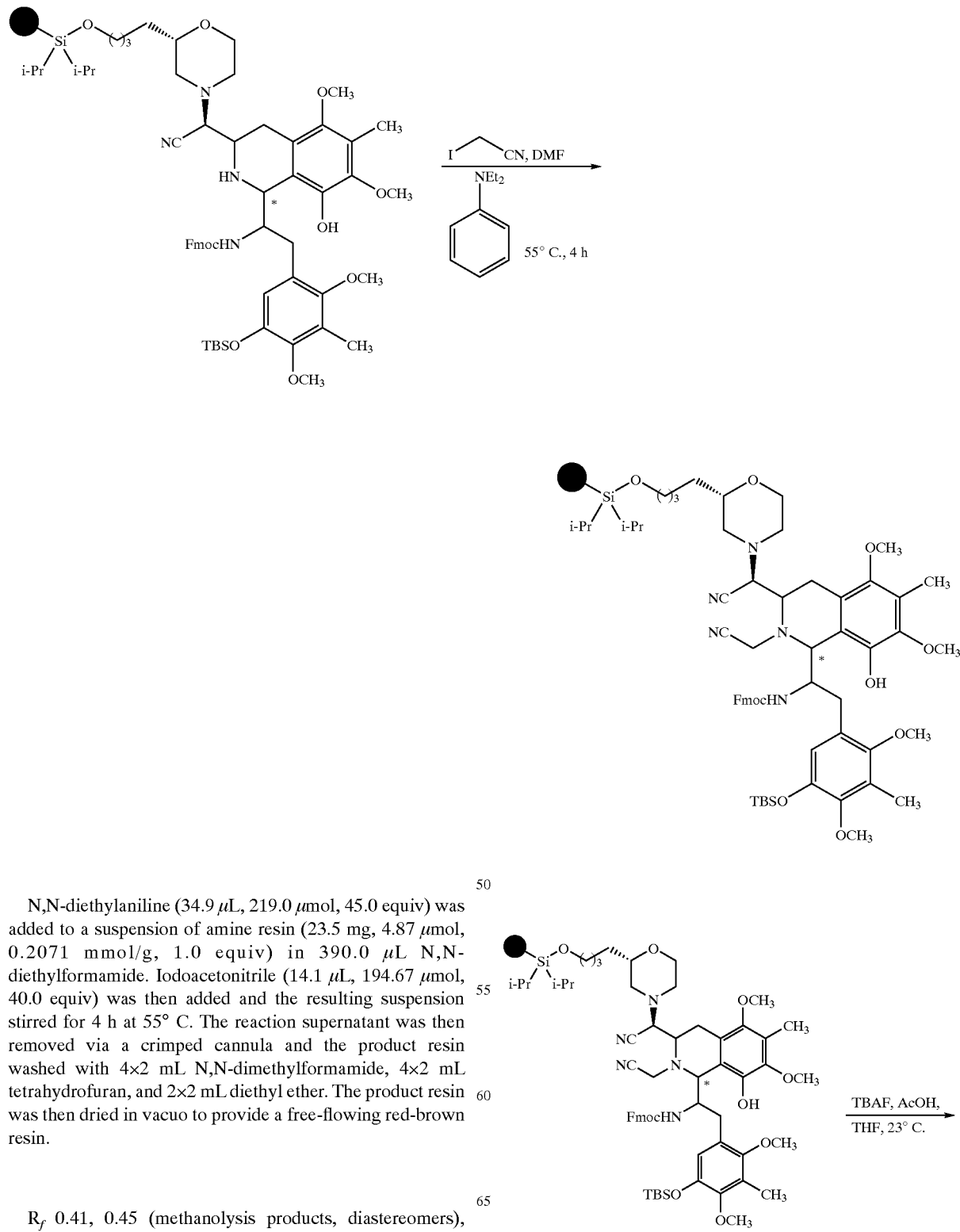

N,N-diethylaniline (34.9 μL, 219.0 μmol, 45.0 equiv) was added to a suspension of amine resin (23.5 mg, 4.87 μmol, 0.2071 mmol/g, 1.0 equiv) in 390.0 μL N,N-diethylformamide. Iodoacetonitrile (14.1 μL, 194.67 μmol, 40.0 equiv) was then added and the resulting suspension stirred for 4 h at 55° C. The reaction supernatant was then removed via a crimped cannula and the product resin washed with 4×2 mL N,N-dimethylformamide, 4×2 mL tetrahydrofuran, and 2×2 mL diethyl ether. The product resin was then dried in vacuo to provide a free-flowing red-brown resin.

R$_f$ 0.41, 0.45 (methanolysis products, diastereomers), 10% methanol-dichloromethane.

101

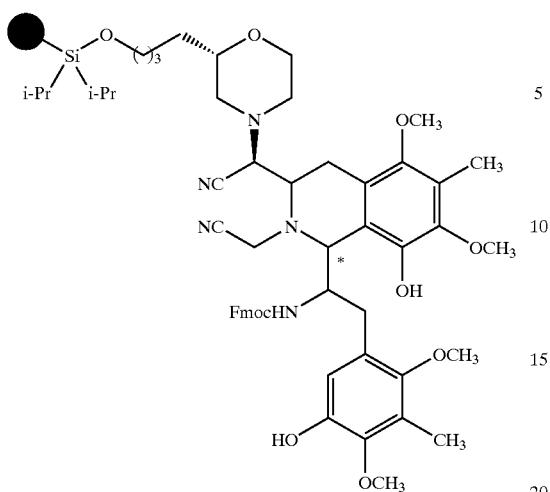

102

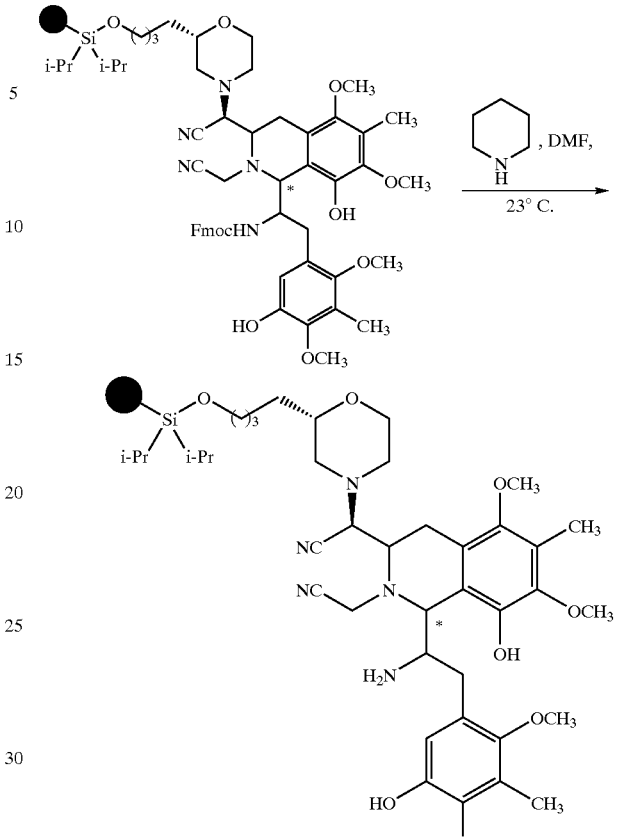

Acetic acid (1.1 µL, 18.65 µmol, 4.0 equiv) and tetrabutylammonium fluoride (1.0 M in tetrahydrofuran, 9.3 µL, 9.30 µmol, 2.0 equiv) were sequentially added to a suspension of silylphenol resin (22.7 mg, 4.66 µmol, 0.2054 mmol/g, 1.0 equiv) in 230 µL tetrahydrofuran. The resulting suspension was stirred at 23° C. for 2.5 h before removal of the superntant solution via crimped cannula. Washing of the product resin with with 4×1 mL N,N-dimethylfornamide, 4×1 mL tetrahydrofuran, and 2×1 mL diethyl ether and drying in vacuo afforded the phenol resin as a free-flowing brown-orange resin.

Piperidine (60.0 µL, 620.57 µmol, 133 equiv) was added to a suspension of phenol resin (22.2 µγ, 4.66 µmol, 1.0 equiv) in 240 µL N,N-diethylformamide and the resulting suspension was stirred for 3.5 h at 23° C. The superntant solution was then removed via crimped cannula and the product resin washed with 4×1 mL N,N-dimethylformamide, 6×1 mL tetrahydrofuran, and 2×1 mL diethyl ether. Drying of the washed resin in vacuo provided the immbolized aminophenol as a free-flowing orange resin.

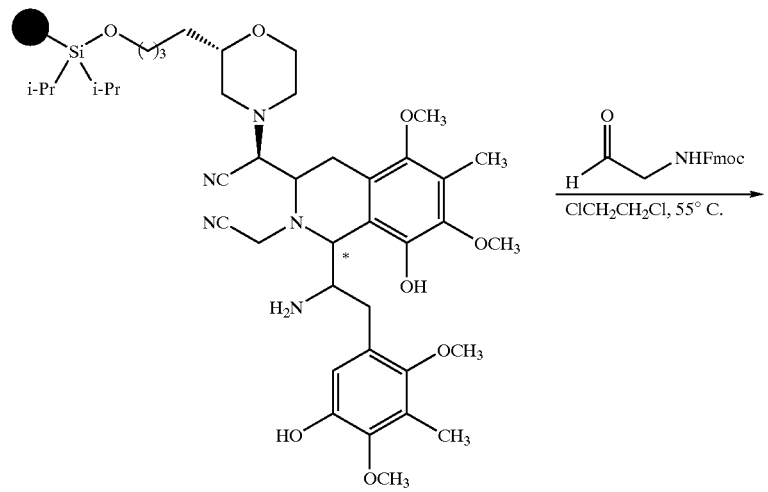

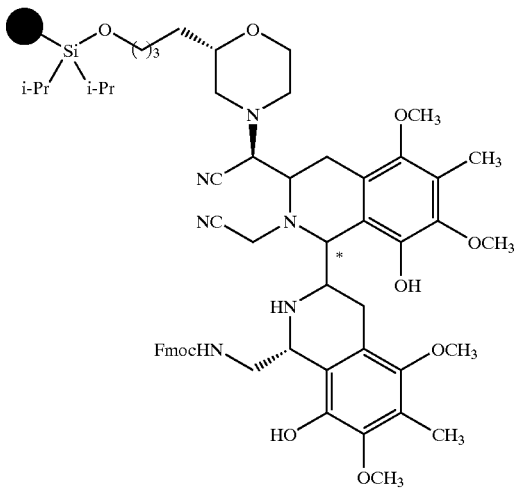

A solution of N-Fmoc glycinal (3.9 mg, 13.98 µmol, 3.0 equiv) in 350 µL 1,2-dichloroethane was freeze-pump-thaw deoxygenated (3 cycles) and then added via cannula to the aminophenol resin (21.2 mg, 4.66 µmol, 1.0 equiv). The resulting suspension was stirred at 55° C. for 17 h before the supernatant solution was removed via crimped cannula. The product resin was then washed with 3×1 mL N,N-dimethylformamide, 5×1 L tetrahydrofuran, and 2×1 mL diethyl ether and dried in vacuo to afford the immbolilized bistetrahydroisoquinoline as a free-flowing brown-orange resin.

$R_f$ 0.47 (methanolysis product), 10% methanol dichloromethane.

vacuo to afford the product bis-aminonitrile as an off-white solid (0.8 mg, 21.4% yield (9 steps)).

$^1$H NMR (600 MHz, CDCl$_3$), δ 7.78 (m, 2H, J=7.8 Hz, ArH), 7.60 (d, 1H, J=7.8 Hz, ArH), 7.49 (m, 1H, ArH), 7.41 (m, 2H, ArH), 7.32 (m, 2H, ArH), 5.56 (s, 1H, ArOH), 5.54 (s, 1H, ArOH), 4.47 (t, 1H, NHFmoc), 4.31 (t, 1H, J=6.0 Hz, CO$_2$CH$_2$), 4.29 (s, 1H, N(CH$_2$CN)CHAr), 4.24 (t, 1H, J=7.8 Hz, CO$_2$CH$_2$), 4.11 (t, 1H, J=4.2 Hz, NCHCH$_2$NHFmoc), 4.07 (t, 1H, CO$_2$CH$_2$CH$_2$), 3.75 (s, 3H, ArOCH$_3$), 3.73 (s, 3H, ArOCH$_3$), 3.63 (s, 1H, NCH(CN)CH), 3.61 (s, 3H, ArOCH$_3$), 3.48 (s, 3H, ArOCH$_3$), 3.40 (d, 1H, J=16.8 Hz, NCH$_2$CN), 3.34 (d, 1H, J=16.8 Hz, NCH$_2$CN), 3.28–3.17

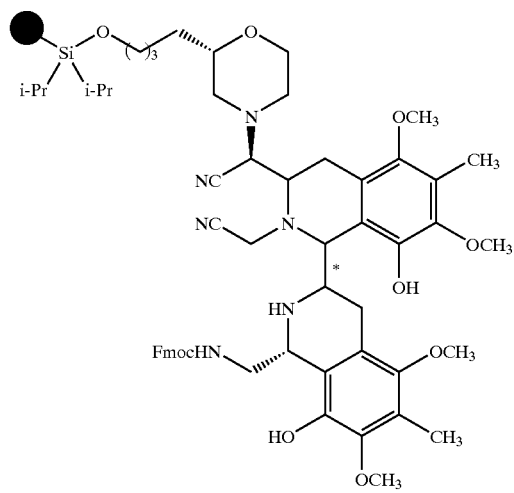
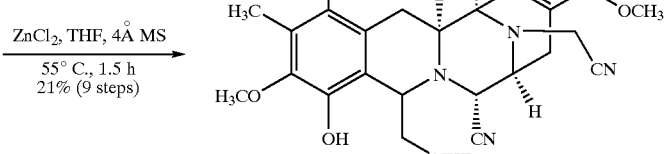

Zinc chloride (29.0 µL, 0.5 M in tetrahydrofuran, 14.51 µmol, 3.0 equiv) was added to a mixture of N-Fmoc resin (23.2 mg, 4.84 µmol, 0.2085 mmol/g, 1.0 equiv) and 4 Å molecular sieves (2.5 mg) suspended in 180.0 µL tetrahydrofuran. The resulting suspension was stirred at 55° C. for 1.5 h before being diluted with 650 µL dichloromethane. The resulting suspension was loaded onto a short silica gel plug and eluted with 4 plug-volumes of 10% tetrahydrofuran-dichloromethane. The eluted solvent was concentrated in (m, 3H, CH$_2$NHFmoc, N(CH$_2$CN)CHCH, N(CH$_2$CN)CHCHCH$_2$), 2.93–2.85 (m, 2H, CH$_2$NHFmoc, NCH(CN)CHCH$_2$), 2.36 (d, 1H, J=19.2 Hz, NCH(CN)CHCH$_2$), 2.19 (s, 3H, ArCH$_3$), 2.17 (s, 3H, ArCH$_3$), 1.85 (m, 1H, N(CH$_2$CN)CHCHCH$_2$). FTIR (neat film), cm$^{-1}$ 3350 (m, OH), 2925 (m), 1714 (s), 1455 (m), 1415 (m), 1109 (s), 1059 (s), 760 (m). $R_f$ 0.50, 5% methanol-dichloromethane. HRMS (TOF-ES$^+$) Calcd for C$_{44}$H$_{46}$N$_5$O$_8$$^+$ (M+H)$^+$: 772.3346, Found: 772.3369.

4) Synthesis and Characterization of Certain Exemplary Analogues:

It will be appreciated that although the synthesis of certain of the compounds are described using traditional solution phase techniques (for example as described in section 1 and 2 above) and the synthesis of certain of the compounds are described using solid-supported techniques (for example, as described in section 3 above), each of the compounds described below can be prepared using either traditional solution phase techniques or solid-supported techniques.

EXAMPLE 1 bis-2-Pyridyl Derivative

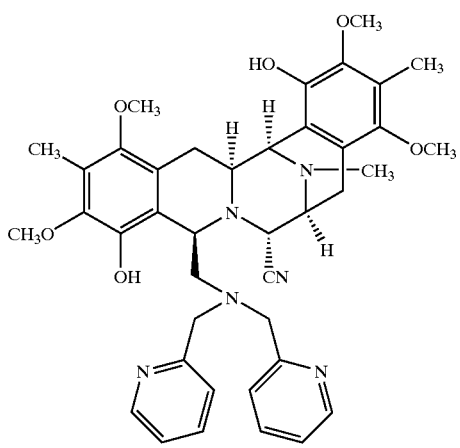

Pyridine 2-carboxaldehyde (0.29 μL, 3.0 μmol, 2.0 equiv) and sodium triacetoxy-borohydride (0.48 mg, 2.3 μmol, 1.5 equiv) were added sequentially, each in one portion, to a stirred solution of the amine (0.8 mg, 1.5 μmol, 1 equiv) in acetonitrile (0.1 mL) at 24° C. under an argon atmosphere. The mixture was stirred for 1 h and then a second portion of pyridine 2-carboxaldehyde (0.29 μL, 3.0 μmol, 2.0 equiv) and sodium triacetoxyborohydride (0.48 mg, 2.3 μmol, 1.5 equiv) were added sequentially, each in one portion. The mixture was stirred for a further 30 min, then was diluted with ethyl acetate (10 mL) and washed with a 1:1 mixture of brine solution and saturated aqueous sodium hydrogen carbonate solution (2×3 mL). The organic layer was dried over sodium sulfate and concentrated in vacuo to leave a colorless oil. Purification by flash column chromatography (ethyl acetate→80% ethyl acetate-methanol) gave the bis-2-pyridyl derivative (0.8 mg, 85%) as a white solid.

$^1$H NMR (500 MHz, CDCl$_3$), δ 10.47 (br. s, 1H, NH), 8.51 (d, 1H, J=4.9, ArH), 7.64 (ddd, 1H, J=9.4, 7.8, 1.7, ArH), 7.37 (d, 1H, J=7.8, ArH), 7.19 (m, 1H, ArH), 5.48 (s, 1H, ArOH), 4.27 (d, 1H, J=2.5, CHC≡N), 4.10 (br. d, 1H, J=~1.5, ArCHNCH$_3$), 4.00 (dd, 1H, J=9.3, 2.5, ArCHCH$_2$NH), 3.82 (s, 3H, ArOCH$_3$), 3.81 (s, 4H, NCH$_2$Ar), 3.75 (s, 3H, ArOCH$_3$), 3.62 (s, 3H, ArOCH$_3$), 3.58 (s, 3H, ArOCH$_3$), 3.38 (br. d, 1H, J=~9.8, CHCHC≡N), 3.19–3.12 (m, 2H, ArCHCHCH$_2$Ar, ArCHCHCH$_2$Ar), 3.05 (dd, 1H, J=18.1, 8.3, CH$_2$CHCHCE≡N), 2.88 (dd, 1H, J=13.7, 2.4, ArCHCH$_2$N), 2.62 (dd, 1H, J=13.7, 9.3, ArCHCH$_2$N), 2.45 (d, 1H, J=18.1, CH$_2$CHCHC≡N), 2.28 (s, 3H, NCH$_3$), 2.23 (s, 3H, ArCH$_3$), 2.18 (s, 3H, ArCH$_3$), 1.73 (dd, 1H, J=14.9, 11.0, ArCHCHCH$_2$). FTIR (neat film), cm$^{-1}$ 3354, 2923, 2687, 2226, 1456. HRMS (ES) Calcd for C$_{40}$H$_{47}$N$_6$O$_6$ (MH)$^+$: 707.3557, Found: 707.3580.

EXAMPLE 2

2-Furylmethyl Derivative

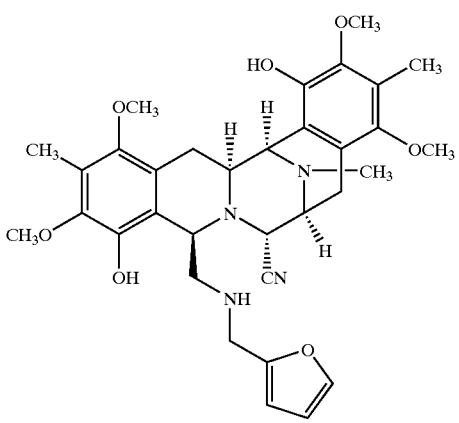

Furaldehyde (0.32 μL, 3.8 μmol, 2.0 equiv) and sodium triacetoxyborohydride (0.61 mg, 2.9 μmol, 1.5 equiv) were added sequentially, each in one portion, to a stirred solution of the amine (1.0 mg, 1.9 μmol, 1 equiv) in acetonitrile (0.1 mL) at 24° C. under an argon atmosphere. The mixture was stirred for 50 min, then was diluted with ethyl acetate (10 mL) and washed with a 1:1 mixture of brine solution and saturated aqueous sodium hydrogen carbonate solution (2×3 mL). The organic layer was dried over sodium sulfate and concentrated in vacuo to leave a brown oil. Purification by flash column chromatography (80% ethyl acetate-hexanes) gave the 2-furylmethyl derivative (1.1 mg, 95%) as a white solid.

$^1$H NMR (500 MHz, CDCl$_3$), δ 7.34 (dd, 1H, J=1.0, 0.9, ArH), 6.30 (dd, 1H, J=3.2, 1.7, ArH), 6.10 (app. d, 1H, J=~2.4, ArH), 5.52 (s, 1H, ArOH), 4.15 (dd, 1H, J=2.9, 1.0, ArCHNCH$_3$), 4.00 (dd, 1H, J=7.9, 3.0, ArCHCH$_2$NH), 3.98 (d, 1H, J=2.5, CHC≡N), 3.79 (s, 3H, ArOCH$_3$), 3.76 (s, 3H, ArOCH$_3$), 3.72 (qu, 2H, AB system, ArCH$_2$NH), 3.61 (s, 3H, ArOCH$_3$), 3.60 (s, 3H, ArOCH$_3$), 3.38 (br. d, 1H, J=~9.8, CHCHC≡N), 3.25–3.21 (m, 2H, ArCHCHCH$_2$Ar, ArCHCHCH$_2$Ar), 3.05 (dd, 1H, J=18.5, 8.0, CH$_2$CHCHC≡N), 2.66 (dd, 1H, J=13.2, 3.4, ArCHCH$_2$NH), 2.60 (dd, 1H, J=13.2, 8.1, ArCHCH$_2$NH), 2.36 (d, 1H, J=18.5, CH$_2$CHCHC≡N), 2.31 (s, 3H, NCH$_3$), 2.22 (s, 3H, ArCH$_3$), 2.19 (s, 3H, ArCH$_3$), 1.82 (dd, 1H, J=15.6, 12.2, ArCHCHCH$_2$Ar). FTIR (neat film), cm$^{-1}$ 3395, 3313, 2933, 2226, 1462. HRMS (ES) Calcd for C$_{33}$H$_{41}$N$_4$O$_7$ (MH)$^+$: 605.2975, Found: 605.2956.

EXAMPLE 3

L-Tryptophan Derivative

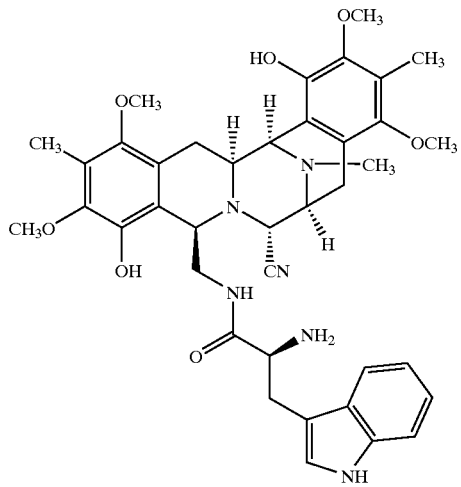

Palladium on carbon (10 wt %, 0.18 mg, 0.17 μmol, 0.1 equiv) was added in one portion to the carbobenzyloxy-protected tryptophan derivative (1.5 mg, 1.7 μmol, 1 equiv) in methanol (0.5 mL) at 23° C. A hydrogen atmosphere was introduced by alternatively evacuating the reaction flask and flushing with hydrogen. The reaction mixture was stirred for 3 h 20 min, then was filtered through a short pad of Celite. Concentration in vacuo left a white solid, which was purified by flash column chromatography (ethyl acetate→10:1 ethyl acetate-methanol) to give the L-tryptophan derivative (0.5 mg, 42%) as a white solid along with recovered starting material (0.5 mg, 33%).

$^1$H NMR (500 MHz, CDCl$_3$), δ 8.17 (br. s, 1H, ArNH), 7.56 (d, 1H, J=7.8, ArH), 7.37 (d, 1H, J=8.3, ArH), 7.20 (m, 1H, ArH), 7.11 (m, 1H, ArH), 6.84 (t, 1H, J=5.6, NHCO), 6.69 (d, 1H, J=2.4, ArH), 5.40 (s, 1H, ArOH), 5.31 (s, 1H, ArOH), 4.14–4.10 (m, 2H, CHCH$_2$NHCO, ArCHNCH$_3$), 3.85 (d, 1H, J=2.4, CHC≡N), 3.76 (s, 3H, ArOCH$_3$), 3.70 (s, 3H, ArOCH$_3$), 3.61 (s, 3H, ArOCH$_3$), 3.66 (ddd, 1H, J=13.6, 6.8, 3.3, CH$_2$NHCO), 3.49 (s, 3H, ArOCH$_3$), 3.34–3.27 (m, 1H (CHCHC≡N), 1H (CH$_2$NHCO), 1H (NHCOCHNH$_2$)), 3.23 (ddd, 1H, J=11.7, 2.4, 2.4, ArCHCHCH$_2$Ar), 3.16 (dd, 1H, J=9.0, 2.4, ArCHCHCH$_2$Ar), 3.02 (dd, 1H, J=14.6, 4.8, NHCOCHCH$_2$), 2.95 (dd, 1H, J=18.6, 7.9, CH$_2$CHCHC≡N), 2.69 (dd, 1H, J=14.6, 7.3, NHCOCHCH$_2$), 2.41 (d, 1H, J=18.6, CH$_2$CHCHC≡N), 2.28 (s, 3H, NCH$_3$), 2.21 (s, 3H, ArCH$_3$), 2.08 (s, 3H, ArCH$_3$), 1.89 (dd, 1H, J=15.0, 10.7, ArCHCHCH$_2$). FTIR (neat film), cm$^{-1}$ 3354, 2913, 2226, 1651, 1262. HRMS (ES) Calcd for C$_{39}$H$_{46}$N$_6$O$_7$ (MH)$^+$: 711.3506, Found: 711.3488.

EXAMPLE 4

Benzyl Derivative

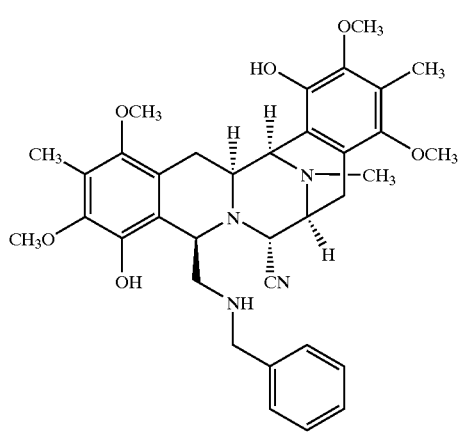

Benzaldehyde (0.43 μL, 4.2 μmol, 2.0 equiv) and sodium triacetoxyborohydride (0.67 mg, 3.1 μmol, 1.5 equiv) were added sequentially, each in one portion, to a stirred solution of the amine (1.0 mg, 1.9 μmol, 1 equiv) in acetonitrile (0.1 mL) at 23° C. under an argon atmosphere. The mixture was stirred for 45 min, then was diluted with ethyl acetate (10 mL) and washed with a 1:1 mixture of brine solution and saturated aqueous sodium hydrogen carbonate solution (2×3 mL). The organic layer was dried over sodium sulfate and concentrated in vacuo to leave a colorless oil. Purification by flash column chromatography (ethyl acetate) gave the benzyl derivative (1.2 mg, 93%) as a white solid.

$^1$H NMR (500 MHz, CDCl$_3$), δ 7.33–7.28 (m, 3H, ArH), 7.19–7.17 (m, 2H, ArH), 5.52 (s, 1H, ArOH), 5.31 (s, 1H, ArOH), 4.14 (dd, 1H, J=2.9, 1.0, ArCHNCH$_3$), 4.01 (t, 1H, J=5.6 ArCHCH$_2$NH), 3.86 (d, 1H, J=2.4, CHC≡N), 3.80 (s, 3H, ArOCH$_3$), 3.75 (s, 3H, ArOCH$_3$), 3.73 (d, 2H, J=3.0, ArCH$_2$NH), 3.61 (s, 3H, ArOCH$_3$), 3.56 (s, 3H, ArOCH$_3$), 3.35 (br.d, 1H, J=~7.8, CHCHC≡N), 3.25–3.21 (m, 2H, ArCHCHCH$_2$Ar, ArCHCHCH$_2$Ar), 3.02 (dd, 1H, J=18.6, 7.8, CH$_2$CHCHC≡N), 2.66 (d, 1H, J=5.3, ArCHCH$_2$NH), 2.33 (d, 1H, J=18.6, CH$_2$CHCHC≡N), 2.30 (s, 3H, NCH$_3$), 2.20 (s, 6H, 2∞ArCH$_3$), 1.83 (dd, 1H, J=15.8, 12.0, ArCHCHCH$_2$Ar). FTIR (neat film), cm$^{-1}$ 3395, 2923, 2574, 2226, 1456, 1108. HRMS (ES) Calcd for C$_{35}$H$_{43}$N$_4$O$_6$ (MH)$^+$: 615.3182, Found: 615.3176.

EXAMPLE 5

2-Pyridyl Derivative

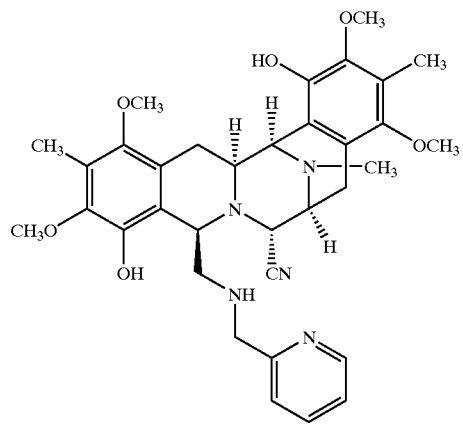

Pyridine 2-carboxaldehyde (0.36 μL, 3.8 μmol, 2.0 equiv) and sodium triacetoxy-borohydride (0.61 mg, 2.9 μmol, 1.5 equiv) were added sequentially, each in one portion, to a stirred solution of the amine (1.0 mg, 1.9 μmol, 1 equiv) in acetonitrile (0.15 mL) at 24° C. under an argon atmosphere. The mixture was stirred for 40 min, then was diluted with ethyl acetate (10 mL) and washed with a 1:1 mixture of brine solution and saturated aqueous sodium hydrogen carbonate solution (2×3 mL). The organic layer was dried over sodium sulfate and concentrated in vacuo to leave a white solid. Purification by flash column chromatography (ethyl acetate→90% ethyl acetate-methanol) gave the 2-pyridyl derivative (0.6 mg, 51%) as a white solid.

$^1$H NMR (500 MHz, CDCl$_3$), δ 8.53–8.52 (m, 1H, ArH), 7.63 (ddd, 1H, J=7.8, 7.8, 2.0, ArH), 7.19 (ddd, 1H, J=7.8, 5.8, 1.0, ArH), 7.14 (d, 1H, J=7.8, ArH), 5.51 (s, 1H, ArOH), 4.15 (dd, 1H, J=2.5, 1.0, ArCHNCH$_3$), 4.07 (d, 1H, J=2.4, CHC≡N), 4.05 (dd, 1H, J=8.3, 2.5, ArCHCH$_2$NH), 3.86 (q, 2H, AB system, ArCH$_2$NH), 3.78 (s, 3H, ArOCH$_3$), 3.75 (s, 3H, ArOCH$_3$), 3.61 (s, 3H, ArOCH$_3$), 3.52 (s, 3H, ArOCH$_3$), 3.39 (br. d, 1H, J=~8.8, CHCHC≡N), 3.26–3.21 (m, 2H, ArCHCH$_2$Ar, ArCHCHCH$_2$Ar), 3.03 (dd, 1H, J=18.1, 7.6, CH$_2$CHCHC≡N), 2.75 (dd, 1H, J=12.7, 2.6, ArCHCH$_2$NH), 2.62 (dd, 1H, J=12.7, 8.5, ArCHCH$_2$NH), 2.35 (d, 1H, J=18.1, CH$_2$CHCHC≡N), 2.31 (s, 3H, NCH$_3$), 2.19 (s, 3H, ArCH$_3$), 2.19 (s, 3H, ArCH$_3$), 1.83 (dd, 1H, J=15.6, 12.2, ArCHCHCH$_2$Ar). FTIR (neat film), cm$^{-1}$ 3303, 2923, 2226, 1456, 1108. HRMS (ES) Calcd for C$_{34}$H$_{42}$N$_5$O$_6$ (MH)$^+$: 616.3135, Found: 616.3156.

EXAMPLE 6

N-Carbobenzyloxy-L-tryptophan Derivative

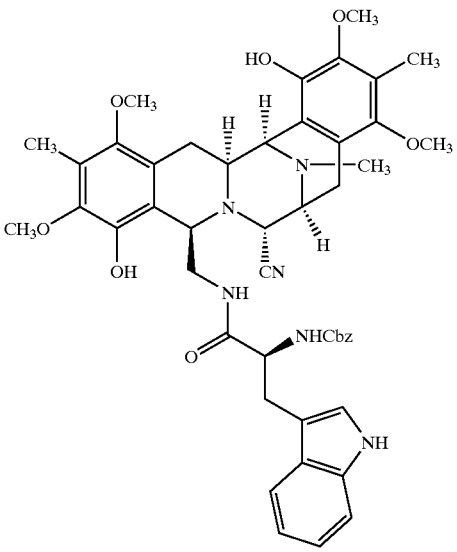

Diethylaniline (0.60 μL, 3.8 μmol, 1.1 equiv) was added in one portion to a stirred solution of the amine (1.8 mg, 3.4 μmol, 1 equiv) in THF (0.3 mL) at 0° C. under an argon atmosphere and the solution was stirred for 5 min. N-Carbobenzyloxy-L-tryptophan (1.5 mg, 4.5 μmol, 1.3 equiv), 1-[3-(dimethylamino)propyl]-3-ethylcarbodiimide hydro-chloride (0.85 mg, 4.5 μmol, 1.3 equiv) and 1-hydroxybenzotriazole (0.56 mg, 4.1 μmol, 1.2 equiv) were then added separately, each in one portion, to the above solution at 0° C. The reaction mixture was warmed to 23° C. over 13 h 55 min, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a white solid, which was purified by flash column chromatography (65% ethyl acetate-hexanes) to give the N-carbobenzyloxy-L-tryptophan derivative (2.6 mg, 90%) as a white solid.

$^1$H NMR (500 MHz, CDCl$_3$), δ 8.20 (br. s, 1H, IndNH), 7.73 (d, 1H, J=7.8, ArH), 7.41 (d, 1H, J=7.8, ArH), 7.35 (br. s, 3H, ArH), 7.23 (m, 2H, ArH), 7.17 (t, 1H, J=7.3, ArH), 7.02 (d, 1H, J=2.4, ArH), 5.71 (br. s, 1H, NHCO), 5.58 (s, 1H, ArOH), 5.51 (s, 1H, ArOH), 5.42 (d, 1H, J=7.8, CbzNH), 5.11 (s, 2H, ArCH$_2$O), 4.36–4.32 (br. m, 1H), 4.04 (d, 1H, J=1.5, CHC≡N), 3.84–3.81 (br. m, 1H), 3.74 (s, 3H, ArOCH$_3$), 3.70 (s, 6H, 2×ArOCH$_3$), 3.57 (s, 3H, ArOCH$_3$), 3.24–3.21 (br. m, 2H), 3.16 (dd, 1H, J=15.6, 2.4, ArCHCH$_2$Ar), 3.09–3.04 (m, 3H), 2.83–2.80 (br. m, 1H), 2.68–2.61 (br. m, 2H), 2.24 (s, 3H, NCH$_3$), 2.19 (s, 3H, ArCH$_3$), 2.17 (s, 3H, ArCH$_3$), 1.97 (d, 1H, J=18.6, CH$_2$CHCHC≡N), 1.74 (dd, 1H, J=15.6, 12.2, ArCHCHCH$_2$). FTIR (neat film), cm$^{-1}$ 3344, 2923, 1708, 1672, 1456. HRMS (ES) Calcd for C$_{47}$H$_{53}$N$_6$O$_9$ (MH)$^+$: 845.3874, Found: 845.3910.

EXAMPLE 7

Indole-4-carboxylic Acid Amide Derivative

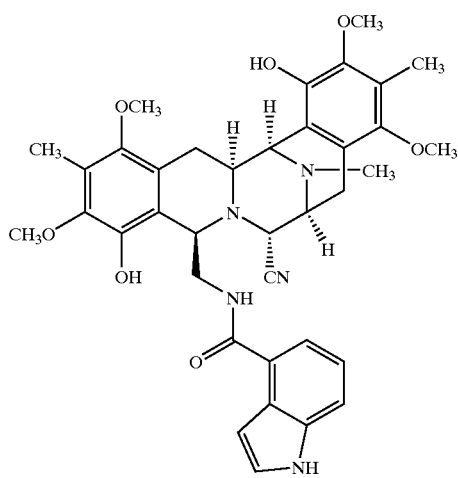

Indole-4-carboxylic acid (0.51 mg, 3.2 μmol, 1.5 equiv), was added in one portion to a stirred solution of the amine (1.1 mg, 2.1 μmol, 1 equiv) in dichloromethane (0.15 mL) at 23° C. under an argon atmosphere and the solution was stirred for 10 min. N-Cyclohexylcarbodiimide-N'-propyloxymethyl polystyrene (Argonaut Technologies, 1.13 mmol/g, 3.7 mg, 4.2 μmol, 2.0 equiv) was then added, in one portion, to the above solution at 23° C. The reaction mixture was stirred gently at 23° C. for 18 h 20 min, then was purified by flash column chromatography (80% ethyl acetate-hexanes) to give the indole-4-carboxylic acid amide derivative (0.8 mg, 60%) as a white solid.

$^1$H NMR (500 MHz, CDCl$_3$), δ 8.19 (s, 1H, ArNH), 7.40 (d, 1H, J=7.8, ArH), 7.16 (t, 1H, J=3.0, ArH), 6.97 (t, 1H, J=7.8, ArH), 6.69 (bt, 1H, J=~2.0, ArH), 6.52 (d, 1H, J=7.3, ArH), 6.00 (d, 1H, J=6.3, NH), 5.71 (s, 1H, ArOH), 5.59 (s, 1H, ArOH), 4.34 (br. s, 1H, CHCH$_2$NHCO), 4.28 (ddd, 1H, J=13.7, 8.3, 2.0, CH$_2$NHCO), 4.22 (bd, 1H, J=~2.0, ArCHNCH$_3$), 4.15 (d, 1H, J=2.9, CHC≡N), 3.75 (s, 3H, ArOCH$_3$), 3.74 (s, 3H, ArOCH$_3$), 3.45 (br. d, 1H, J=~7.3, CHCHC≡N), 3.40 (s, 3H, ArOCH$_3$), 3.38–3.33 (m, 1H (CH$_2$NHCO), 1H (ArCHCHCH$_2$Ar)), 3.29 (s, 3H, ArOCH$_3$), 3.28 (app. dd (obsc.), 1H, J=~16.1, 2.9, ArCHCHCH$_2$Ar), 3.08 (dd, 1H, J=18.6, 8.0, CH$_2$CHCHC≡N), 2.43 (d, 1H, J=18.6, CH$_2$CHCHC≡N), 2.31 (s, 3H, NCH$_3$), 2.15 (s, 3H, ArCH$_3$), 2.08 (dd, 1H, J=16.1, 11.7, ArCHCHCH$_2$Ar), 2.01 (s, 3H, ArCH$_3$). FTIR (neat film), cm$^{-1}$ 3393, 2926, 2227, 1641. HRMS (ES) Calcd for C$_{37}$H$_{41}$N$_5$O$_7$ (MH)$^+$: 668.3084, Found: 668.3062.

EXAMPLE 8

Indole-3-carboxylic Acid Amide Derivative

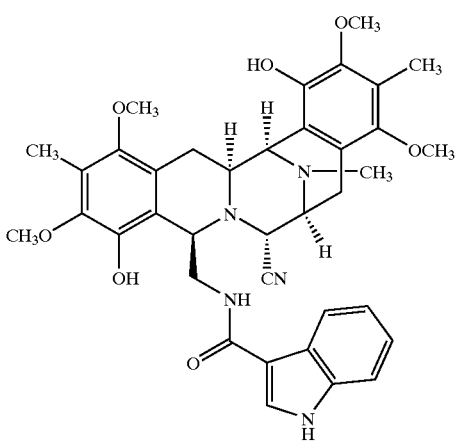

Indole-3-carboxylic acid (0.55 mg, 3.4 μmol, 1.5 equiv), was added in one portion to a stirred solution of the amine (1.2 mg, 2.2 μmol, 1 equiv) in dichloromethane (0.2 mL) at 23° C. under an argon atmosphere and the solution was stirred for 10 min. N-Cyclohexylcarbodiimide-N'-propyloxymethyl polystyrene (Argonaut Technologies, 1.13 mmol/g, 8.0 mg, 9.2 μmol, 4.0 equiv) was then added, in one portion, to the above solution at 23° C. The reaction mixture was stirred gently at 23° C. for 16 h 45 min, then was purified by flash column chromatography (85% ethyl acetate-hexanes) to give the indole-3-carboxylic acid amide derivative (1.2 mg, 86%) as a white solid.

$^1$H NMR (500 MHz, CDCl$_3$), δ 8.20 (br. s, 1H, ArNH), 7.80 (d, 1H, J=8.3, ArH), 7.32 (app. d, 1H, J=7.4, ArH), 7.18 (td, 1H, J=7.4, 1.3, ArH), 7.08 (td, 1H, J=~7.4, 1.0, ArH), 6.55 (d, 1H, J=2.9, ArH), 5.75 (s, 1H, ArOH), 5.67 (br. d, 1H, J=~5.9, NH), 5.61 (s, 1H, ArOCH), 4.31 (br. s, 1H, CHCH$_2$NHCO), 4.23 (dd, 1H, J=3.0, 1.0, ArCHNCH$_3$), 4.16–4.12 (m, 2H, CHC≡N, CH$_2$NHCO), 3.81 (s, 3H, ArOCH$_3$), 3.74 (s, 3H, ArOCH$_3$), 3.45 (br. s, 4H ArOCH$_3$, CHCHC≡N), 3.37 (ddd, 1H, J=12.0, 2.6, 2.6, ArCHCHCH$_2$Ar), 3.34 (s, 3H, ArOCH$_3$), 3.30 (ddd, 1H, J=13.7, 3.9, 2.7, CH$_2$NHCO), 3.26 (dd, 1H, J=15.8, 2.6, ArCHCHCH$_2$Ar), 3.10 (dd, 1H, J=18.5, 7.8, CH$_2$CHCHC≡N), 2.49 (d, 1H, J=18.5, CH$_2$CHCHC≡N), 2.34 (s, 3H, NCH$_3$), 2.14 (s, 3H, ArCH$_3$), 2.06 (s, 3H, ArCH$_3$), 2.02 (dd, 1H, J=15.8, 11.7, ArCHCHCH$_2$Ar). FTIR (neat film), cm$^{-1}$ 3388, 2925, 2225, 1620. HRMS (ES) Calcd for C$_{37}$H$_{41}$N$_5$O$_7$ (MH)$^+$: 668.3084, Found: 668.3062.

EXAMPLE 9

Propionamide Derivative

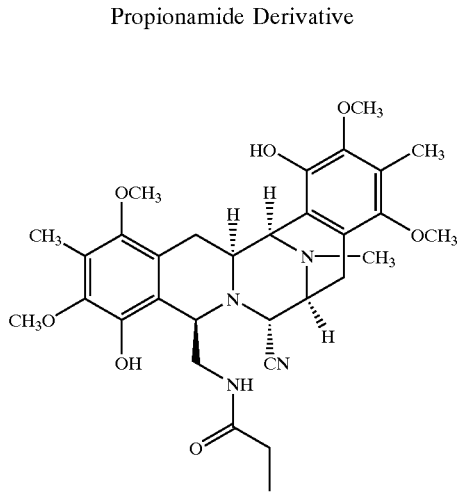

Diethylaniline (0.60 µL, 4.0 µmol, 1.1 equiv) and propionyl chloride (1.0 mg, 1.0 µL, 10.9 µmol, 3.0 equiv) were added separately, each in one portion, to a stirred solution of the amine (1.9 mg, 3.6 µmol, 1 equiv) in dichloromethane (0.2 mL) at 0° C. under an argon atmosphere. The reaction mixture was stirred at 0° C. for 30 min, then was quenched by the addition of a 1:1 mixture of water and saturated aqueous sodium hydrogen carbonate solution (4 mL). The mixture was extracted with ethyl acetate (2×15 mL) and the combined organic layer was washed with a 1:1 mixture of brine solution and saturated aqueous sodium hydrogen carbonate solution (5 mL). The organic layer was dried over sodium sulfate and concentrated in vacuo to leave a colorless oil. Purification by flash column chromatography (ethyl acetate→90% ethyl acetate-methanol) gave the propionamide derivative (1.9 mg, 90%) as a white solid.

$^1$H NMR (500 MHz, CDCl$_3$), δ 5.63 (s, 1H, ArOH), 5.60 (s, 1H, ArOH), 5.21 (d, 1H, J=5.9, NH), 4.20 (d, 1H, J=2.0, ArCHNCH$_3$), 4.17 (bd, 1H, J=2.9, CHCH$_2$NHCO), 4.03 (d, 1H, J=2.4, CHC≡N), 3.84 (ddd, 1H, J=13.4, 8.3, 1.9, CH$_2$NHCO), 3.78 (s, 3H, ArOCH$_3$), 3.75 (s, 3H, ArOCH$_3$), 3.71 (s, 3H, ArOCH$_3$), 3.60 (s, 3H, ArOCH$_3$), 3.43 (br. d, 1H, J=~7.8, CHCHC≡N), 3.32 (ddd, 1H, J=11.9, 2.7, 2.7, ArCHCHCH$_2$Ar), 3.24 (dd, 1H, J=15.8, 2.7, ArCHCHCH$_2$Ar), 3.12–3.07 (m, 2H, CH$_2$CHCHC≡N, CH$_2$NHCO), 2.50 (d, 1H, J=18.5, CH$_2$CHCHC≡N), 2.35 (s, 3H, NCH$_3$), 2.25 (s, 3H, ArCH$_3$), 2.19 (s, 3H, ArCH$_3$), 1.90 (dd, 1H, J=15.8, 12.0, ArCHCHCH$_2$Ar), 1.56 (q, 2H, J=7.8, CH$_3$CH$_2$CO), 0.74 (t, 3H, J=7.8, CH$_3$CH$_2$CO). FTIR (neat film), cm$^{-1}$ 3385, 2923, 2226, 1657. HRMS (ES) Calcd for C$_{31}$H$_{40}$N$_4$O$_7$ (MH)$^+$: 581.2975, Found: 581.2948.

EXAMPLE 10

Naphthalene-1-carboxylic Acid Amide Derivative

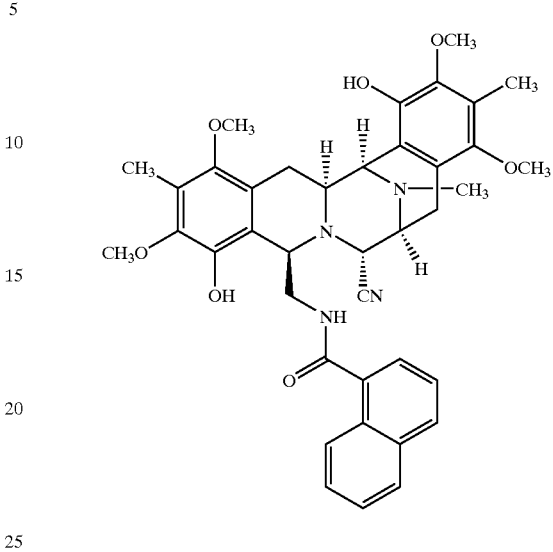

Diethylaniline (0.27 µL, 1.7 µmol, 1.1 equiv) was added in one portion to a stirred solution of the amine (0.8 mg, 1.5 µmol, 1 equiv) in THF (0.2 mL) at 0° C. under an argon atmosphere and the solution was stirred for 5 min. 1-Naphthoic acid (0.34 mg, 2.0 µmol, 1.3 equiv), 1-[3-(dimethylamino)propyl]-3-ethylcarbodiimide hydrochloride (0.38 mg, 2.0 µmol, 1.3 equiv) and 1-hydroxybenzotriazole (0.25 mg, 1.8 µmol, 1.2 equiv) were then added separately, each in one portion, to the above solution at 0° C. The reaction mixture was warmed to 23° C. over 14 h 45 min, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a white solid, which was purified by flash column chromatography (80% ethyl acetate-hexanes) to give the naphthalene-1-carboxylic acid amide derivative (0.7 mg, 68%) as a white solid.

$^1$H NMR (500 MHz, CDCl$_3$), δ 7.79–7.75 (m, 3H, ArH), 7.45–7.42 (m, 1H, ArH), 7.36 (ddd, 1H, J=7.3, 6.8, 1.2, ArH), 7.19 (dd, 1H, J=7.8, 6.8, ArH), 6.76 (app. d, 1H, J=~6.8, ArH), 5.71 (s, 1H, ArOH), 5.67 (d, 1H, J=4.9, NH), 5.49 (s, 1H, ArOH), 4.37–4.33 (m, 2H CH$_2$NHCO, CHCH$_2$NHCO), 4.17 (d, 1H, J=1.4, ArCHNCH$_3$), 4.16 (d, 1H, J=2.9, CHC≡N), 3.77 (s, 3H, ArOCH$_3$), 3.55 (s, 3H, ArOCH$_3$), 3.45–3.39 (m, 5H, CHCHC≡N, ArOCH$_3$, CH$_2$NHCO), 3.34 (ddd, 1H, J=12.0, 2.7, 2.7, ArCHCHCH$_2$Ar), 3.28 (s, 3H, ArOCH$_3$), 3.24 (dd, 1H, J=16.1, 2.5, ArCHCHCH$_2$Ar), 3.05 (dd, 1H, J=18.6, 8.0, CH$_2$CHCHC≡N), 2.43 (d, 1H, J=18.6, CH$_2$CHCHC≡N), 2.29 (s, 3H, NCH$_3$), 2.20 (s, 3H, ArCH$_3$), 1.95 (dd, 1H, J=16.1, 11.7, ArCHCHCH$_2$Ar), 1.88 (s, 3H, ArCH$_3$). FTIR (neat film), cm$^{-1}$ 3395, 2923, 2226, 1651. HRMS (ES) Calcd for C$_{39}$H$_{42}$N$_4$O$_7$ (MH)$^+$: 679.3132, Found: 679.3106.

EXAMPLE 11

Phenylurea Derivative

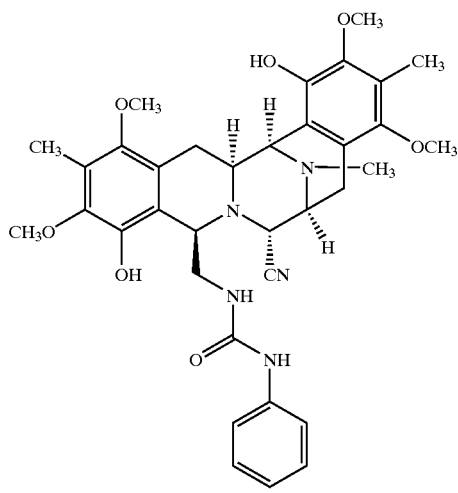

Diethylaniline (0.33 μL, 2.1 μmol, 1.1 equiv) and phenyl isocyanate (0.25 μL, 2.3 μmol, 1.2 equiv) were added separately, each in one portion, to a stirred solution of the amine (1.0 mg, 1.9 μmol, 1 equiv) in dichloromethane (0.2 mL) at 0° C. under an argon atmosphere. The reaction mixture was stirred at 0° C. for 25 min, then was quenched by the addition of a 1:1 mixture of water and saturated aqueous sodium hydrogen carbonate solution (4 mL). The mixture was extracted with dichloromethane (2×10 mL) and the organic layer was dried over sodium sulfate and concentrated in vacuo to leave a white solid. Purification by flash column chromatography (70% ethyl acetate) gave the phenylurea derivative (0.9 mg, 74%) as a white solid.

$^1$H NMR (500 MHz, CDCl$_3$), δ 7.27–7.23 (m, 4H, ArH), 7.01–6.98 (m, 1H, ArH), 6.26 (s, 1H, NH), 5.66 (s, 1H, ArOH), 5.53 (s, 1H, ArOH), 4.36 (t, 1H, J=5.8, NH), 4.23–4.21 (m, 2H, CHCH$_2$NHCO, ArCHNCH$_3$), 4.03 (d, 1H, J=2.4, CHC≡N), 3.81 (s, 6H, 2×ArOCH$_3$) 3.74 (s, 3H, ArOCH$_3$), 3.59 (s, 3H, ArOCH$_3$), 3.44 (ddd, 1H, J13.7, 5.4, 5.4, CH$_2$NHCO), 3.38 (br. d, 1H, J=7.3, CHCHC≡N), 3.31 (ddd, 1H, J=12.7, 2.4, 2.4, ArCHCHCH$_2$Ar), 3.21 (dd, 1H, J=15.6, 2.9, ArCHCHCH$_2$Ar), 3.10 (dd, 1H, J=18.5, 7.3, CH$_2$CHCHC≡N), 2.75–2.69 (m, 2H, CH$_2$NHCO, CH$_2$CHCHC≡N), 2.43 (s, 3H, NCH$_3$), 2.26 (s, 3H, ArCH$_3$), 2.19 (s, 3H, ArCH$_3$), 1.82 (dd, 1H, J=15.6, 12.5, ArCHCHCH$_2$Ar). FTIR (neat film), cm$^{-1}$ 3374, 2923, 2226, 1672. HRMS (ES) Calcd for C$_{35}$H$_{41}$N$_5$O$_7$ (MH)$^+$: 644.3084, Found: 644.3110.

EXAMPLE 12

Biphenyl-2-carboxylic Acid Amide Derivative

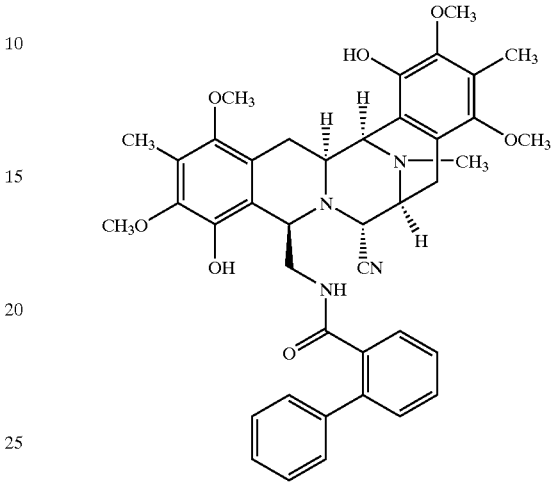

2-Biphenylcarboxylic acid (0.51 mg, 2.6 μmol, 1.5 equiv) was added in one portion to a stirred solution of the amine (0.9 mg, 1.7 μmol, 1 equiv) in dichloromethane (0.2 mL) at 23° C. under an argon atmosphere and the solution was stirred for 10 min. N-Cyclohexylcarbodiimide-N'-propyloxymethyl polystyrene (Argonaut Technologies, 1.13 mmol/g, 3.0 mg, 3.4 μmol, 2.0 equiv) was then added, in one portion, to the above solution at 23° C. The reaction mixture was stirred gently at 23° C. for 19 h 30 min, then was purified by flash column chromatography (70% ethyl acetate-hexanes) to give the biphenyl-2-carboxylic acid amide derivative (0.9 mg, 75%) as a white solid.

$^1$H NMR (500 MHz, CDCl$_3$), δ 7.40 (td, 1H, J=7.3, 1.4, ArH), 7.33–7.29 (m, 4H, ArH), 7.24–7.22 (m, 2H, ArH), 7.20 (td, 1H, J=7.3, 1.4, ArH), 6.96 (dd, 1H, J=5.8, 1.0, ArH), 5.55 (s, 1H, ArOH), 5.53 (s, 1H, ArOH), 5.52 (t, 1H, J=5.8, NH), 4.13 (d, 1H, J=2.5, CHC≡N), 4.03 (t, 1H, J=3.9, CHCH$_2$NHCO), 3.77 (d, 1H, J=2.5, ArCHNCH$_3$), 3.73 (s, 3H, ArOCH$_3$), 3.72 (s, 3H, ArOCH$_3$), 3.58 (s, 3H, ArOCH$_3$), 3.45 (s, 3H, ArOCH$_3$), 3.45–3.40 (m, 1H, CH$_2$NHCO), 3.36–3.31 (m, 2H, CH$_2$NHCO, CHCHC≡N), 3.22–3.18 (m, 2H, ArCHCHCH$_2$Ar, ArCHCHCH$_2$Ar), 3.03–2.98 (dd, 1H, J=18.6, 8.3, CH$_2$CHCHC≡N), 2.39 (d, 1H, J=18.6, CH$_2$CHCHC≡N), 2.27 (s, 3H, NCH$_3$), 2.20 (s, 3H, ArCH$_3$), 2.12 (s, 3H, ArCH$_3$), 1.86 (dd, 1H, J=16.2, 12.2, ArCHCHCH$_2$Ar). FTIR (neat film), cm$^{-1}$ 3402, 2930, 2231, 1654. HRMS (ES) Calcd for C$_{41}$H$_{44}$N$_4$O$_7$ (MH)$^+$: 705.3288, Found: 705.3317.

EXAMPLE 13

Phenyl Acetyl Derivative

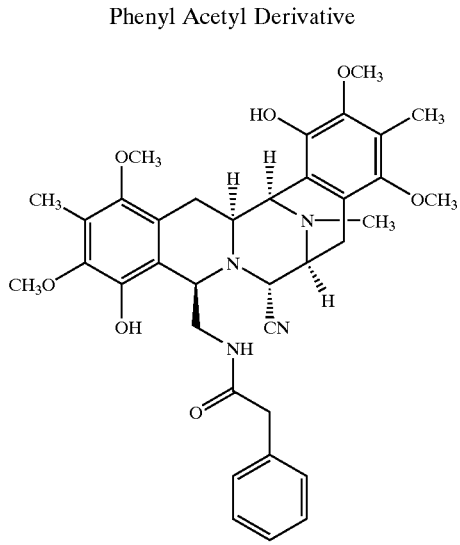

Diethylaniline (0.50 µL, 2.9 µmol, 1.1 equiv) and phenyl acetyl chloride (1.1 µL, 8.0 µmol, 3.0 equiv) were added separately, each in one portion, to a stirred solution of the amine (1.4 mg, 2.7 µmol, 1 equiv) in dichloromethane (0.15 mL) at 0° C. under an argon atmosphere. The reaction mixture was stirred at 0° C. for 30 min, then was quenched by the addition of a 1:1 mixture of water and saturated aqueous sodium hydrogen carbonate solution (4 mL). The mixture was extracted with ethyl acetate (2×15 mL) and the combined organic layer was washed with a 1:1 mixture of brine solution and saturated aqueous sodium hydrogen carbonate solution (5 mL). The organic layer was dried over sodium sulfate and concentrated in vacuo to leave a light yellow oil. Purification by flash column chromatography (80% ethyl acetate-hexanes) gave the phenyl acetyl derivative (1.7 mg, 99%) as a white solid.

$^1$H NMR (500 MHz, CDCl$_3$), δ 7.21–7.17 (m, 3H, ArH), 6.90–6.89 (m, 2H, ArH), 5.59 (s, 1H, ArOH), 5.41 (t, 1H, J=5.1, NHCO), 5.39 (s, 1H, ArOH), 4.17 (d, 1H, J=1.9, ArCHNCH$_3$), 4.09 (dd, 1H, J=5.4, 2.4, CHCH$_2$NHCO), 4.02 (d, 1H, J=2.5, CHC≡N), 3.75 (s, 3H, ArOCH$_3$), 3.74 (s, 3H, ArOCH$_3$), 3.71 (s, 3H, ArOCH$_3$), 3.66 (app. ddd (obsc), 1H, CH$_2$NHCO), 3.56 (s, 3H, ArOCH$_3$), 3.39 (br. d, 1H, J=~8.8, CHCHC≡N), 3.23 (ddd, 1H, J=11.7, 2.4, 2.4, ArCHCHCH$_2$Ar), 3.20–3.15 (m, 2H, CH$_2$NHCO, ArCHCHCH$_2$Ar)), 3.15 (d, 1H, J=15.1, NHCOCH$_2$Ar), 3.06 (dd, 1H, J=18.6, 8.3, CH$_2$CHCHC≡N), 2.96 (d, 1H, J=15.1, NHCOCH$_2$Ar), 2.51 (d, 1H, J=18.6, CH$_2$CHCHC≡N), 2.32 (s, 3H, NCH$_3$), 2.24 (s, 3H, ArCH$_3$), 2.18 (s, 3H, ArCH$_3$), 1.81 (dd, 1H, J=16.4, 12.0, ArCHCHCH$_2$Ar). FTIR (neat film), cm$^{-1}$ 3385, 2923, 2226, 1667, 1462. HRMS (ES) Calcd for C$_{36}$H$_{43}$N$_4$O$_7$ (MH)$^+$: 643.3132, Found: 643.3130.

EXAMPLE 14

2-Hydroxy-naphthalene-1-carboxylic Acid Amide Derivative

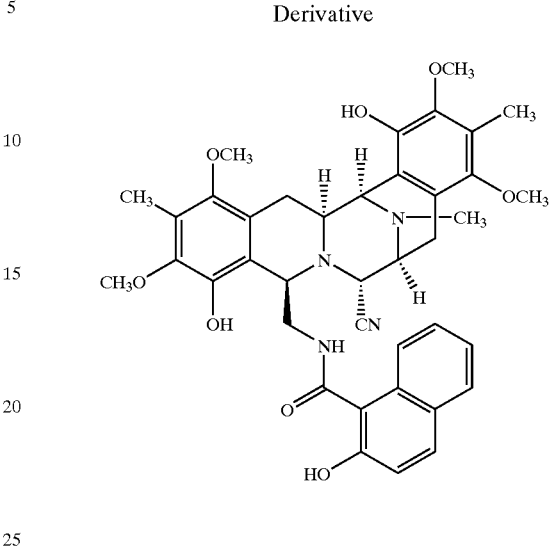

Diethylaniline (0.27 µL, 1.7 µmol, 1.1 equiv) was added in one portion to a stirred solution of the amine (0.8 mg, 1.5 µmol, 1 equiv) in THF (0.2 mL) at 0° C. under an argon atmosphere and the solution was stirred for 5 min. 2-Hydroxy-1-naphthoic acid (0.37 mg, 2.0 µmol, 1.3 equiv), 1-[3-(dimethylamino)propyl]-3-ethylcarbodiimide hydrochloride (0.38 mg, 2.0 µmol, 1.3 equiv) and 1-hydroxybenzotriazole (0.25 mg, 1.8 µmol, 1.2 equiv) were then added separately, each in one portion, to the above solution at 0° C. The reaction mixture was warmed to 23° C. over 13 h 20 min, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a white solid, which was purified by flash column chromatography (85% ethyl acetate-hexanes) to give the 2-hydroxy-naphthalene-1-carboxylic acid amide derivative (1.1 mg, 100%) as a white solid.

$^1$H NMR (500 MHz, CDCl$_3$), 67 11.22 (s, 1H, NaphOH), 7.70 (d, 1H, J=8.8, ArH), 7.66 (d, 1H, J=7.8, ArH), 7.28 (d (obsc.), 1H, ArH), 7.23 (t, 1H, J=7.8, ArH), 7.11 (t, 1H, J=7.8, ArH), 7.04 (d, 1H, J=8.8, ArH), 6.10 (br. s, 1H, NH), 5.71 (s, 1H, ArOH), 5.46 (s, 1H, ArOH), 4.40 (br. s, 1H, CHCH$_2$NHCO), 4.27 (app. dd, 1H, J=~13.8, 6.1, CH$_2$NHCO), 4.17–4.15 (m, 2H, ArCHNCH$_3$, CHC≡N), 3.75 (s, 3H, ArOCH$_3$), 3.68 (s, 3H, ArOCH$_3$), 3.54 (ddd, 1H, J=14.2, 3.9, 3.9, ArCHCHCH$_2$Ar), 3.48 (s, 3H, ArOCH$_3$), 3.42 (br. d, 1H, J=~7.9, CHCHC≡N), 3.38–3.33 (m, 1H, CH$_2$NHCO), 3.28 (dd, 1H, J=16.2, 2.8, ArCHCHCH$_2$Ar), 3.15 (s, 3H, ArOCH$_3$), 2.99 (dd, 1H, J=18.1, 8.3, CH$_2$CHCHC≡N), 2.32 (d, 1H, J=18.1, CH$_2$CHCHC≡N), 2.25 (s, 3H, NCH$_3$), 2.24 (s, 3H, ArCH$_3$), 2.12 (dd, 1H, J=16.2, 11.8, ArCHCHCH$_2$), 1.78 (s, 3H, ArCH$_3$). FTIR (neat film), cm$^{-1}$ 3395, 2923, 2226, 1626. HRMS (ES) Calcd for C$_{39}$H$_{42}$N$_4$O$_8$ (MH)$^+$: 695.3081, Found: 695.3096.

EXAMPLE 15

2-Furoic Acid Amide Derivative

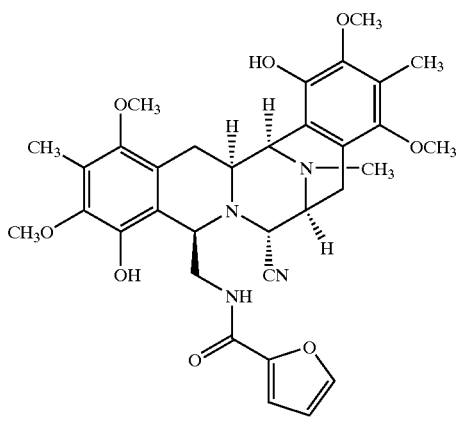

Diethylaniline (0.33 μL, 2.1 μmol, 1.1 equiv) was added in one portion to a stirred solution of the amine (1.0 mg, 1.9 μmol, 1 equiv) in THF (0.15 mL) at 0° C. under an argon atmosphere and the solution was stirred for 10 min. 2-Furoic acid (0.28 mg, 2.5 μmol, 1.3 equiv), 1-[3-(dimethylamino)propyl]-3-ethylcarbodiimide hydrochloride (0.48 mg, 2.5 μmol, 1.3 equiv) and 1-hydroxybenzotriazole (0.31 mg, 2.3 μmol, 1.2 equiv) were then added separately, each in one portion, to the above solution at 0° C. The reaction mixture was warmed to 23° C. over 19 h, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layers were dried over sodium sulfate. Concentration in vacuo left a yellow oil, which was purified by flash column chromatography (70% ethyl acetate-hexanes) to give the 2-furoic acid amide derivative (1.0 mg, 85%) as a white solid.

$^1$H NMR (500 MHz, CDCl$_3$), δ 7.18–7.17 (m, 1H, ArH), 6.70 (dd, 1H, J=3.4, 1.0, ArH), 6.31 (dd, 1H, J=3.4, 2.0, ArH), 6.07 (d, 1H, J=6.9, NH), 5.63 (s, 1H, ArOH), 5.60 (s, 1H, ArOH), 4.28 (br. d, 1H, J=~2.0, ArCHCH$_2$NH), 4.22 (d, 1H, J=1.5, ArCHNCH$_3$), 4.10–4.05 (m, 2H, CHC≡N, ArCHCH$_2$NH), 3.83 (s, 3H, ArOCH$_3$), 3.74 (s, 3H, ArOCH$_3$), 3.54 (s, 3H, ArOCH$_3$), 3.45 (br. d, 1H, J=~7.8, CHCHC≡N), 3.42 (s, 3H, ArOCH$_3$), 3.32 (ddd, 1H, J=12.0, 2.7, 2.7, ArCHCHCH$_2$Ar), 3.23 (dd, 1H, J=16.1, 2.4, ArCHCHCH$_2$Ar), 3.23–3.19 (1H, m, ArCHCH$_2$NH), 3.12 (dd, 1H, J=18.6, 8.3, CH$_2$CHCHC≡N), 2.48 (d, 1H, J=18.6, CH$_2$CHCHC≡N), 2.35 (s, 3H, NCH$_3$), 2.16 (s, 3H, ArCH$_3$), 2.15 (s, 3H, ArCH$_3$), 2.04 (dd, 1H, J=16.1, 11.7, ArCHCHCH$_2$Ar). FTIR (neat film), cm$^{-1}$ 3385, 2933, 2226, 1651, 1462. HRMS (ES) Calcd for C$_{33}$H$_{39}$N$_4$O$_8$ (MH)$^+$: 619.2768, Found: 619.2790.

EXAMPLE 16

Indole-3-glyoxamide Derivative

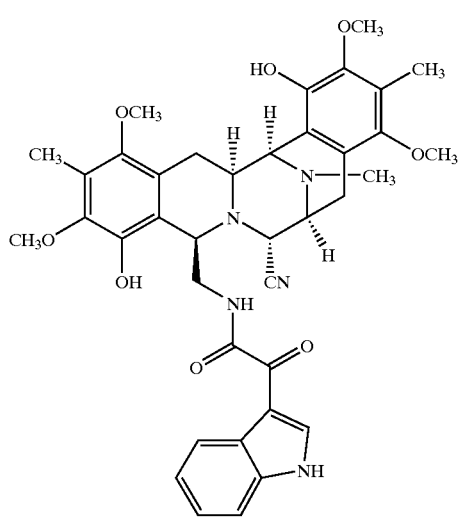

Indole-3-glyoxylic acid (0.55 mg, 2.9 μmol, 1.5 equiv) was added in one portion to a stirred solution of the amine (1.0 mg, 1.9 μmol, 1 equiv) in dichloromethane (0.15 mL) at 23° C. under an argon atmosphere and the solution was stirred for 10 min. N-Cyclohexylcarbodiimide-N'-propyloxymethyl polystyrene (Argonaut Technologies, 1.13 mmol/g, 3.4 mg, 3.8 μmol, 2.0 equiv) was then added, in one portion, to the above solution at 23° C. The reaction mixture was stirred gently at 23° C. for 15 h 20 min, then was purified by flash column chromatography (70% ethyl acetate-hexanes) to give the indole-3-glyoxamide derivative (0.9 mg, 60%) as a white solid.

$^1$H NMR (500 MHz, CDCl$_3$), δ 8.85 (d, 1H, J=3.4, ArH), 8.65 (br. s, 1H, ArNH), 8.20 (dd, 1H, J=7.1, 2.1, ArH), 7.42 (dd, 1H, J=6.6, 1.7, ArH), 7.32–7.28 (m, 2H, ArH), 7.01 (t, 1H, J=5.7, NH), 5.67 (s, 1H, ArOH), 5.55 (s, 1H, ArOH), 4.31 (br. t, 1H, CHCH$_2$NHCO), 4.19 (d, 1H, J=2.0, ArCHNCH$_3$), 4.10 (d, 1H, J=2.4, CHC≡N), 3.76 (s, 3H, ArOCH$_3$), 3.75–3.71 (m, 4H, ArOCH$_3$, CH$_2$NHCO), 3.61 (s, 3H, ArOCH$_3$), 3.57 (s, 3H, ArOCH$_3$), 3.45–3.39 (m, 2H, CHCHC≡N, CH$_2$NHCO), 3.29–3.25 (m, 2H, ArCHCHCH$_2$Ar, ArCHCHCH$_2$Ar), 3.09 (dd, 1H, J=18.4, 8.0, CH$_2$CHCHC≡N), 2.58 (d, 1H, J=18.4, CH$_2$CHCHC≡N), 2.33 (s, 3H, NCH$_3$), 2.18 (s, 3H, ArCH$_3$), 2.10 (dd, 1H, J=16.4, 12.0, ArCHCHCH$_2$Ar), 1.95 (s, 3H, ArCH$_3$). FTIR (neat film), cm$^{-1}$ 3370, 2926, 2227, 1675, 1625. HRMS (ES) Calcd for C$_{38}$H$_{41}$N$_5$O$_8$ (MH)$^+$: 696.3033, Found: 696.3002.

EXAMPLE 17

Pyrazine-2-carboxylic Acid Amide Derivative

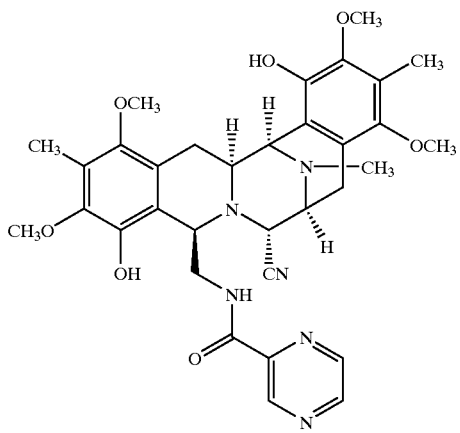

Diethylaniline (0.33 μL, 2.1 μmol, 1.1 equiv) was added in one portion to a stirred solution of the amine (1.0 mg, 1.9 μmol, 1 equiv) in THF (0.2 mL) at 0° C. under an argon atmosphere and the solution was stirred for 5 min. 2-Pyrazinecarboxylic acid (0.31 mg, 2.5 μmol, 1.3 equiv), 1-[3-(dimethylamino)propyl]-3-ethylcarbodiimide hydrochloride (0.48 mg, 2.5 μmol, 1.3 equiv) and 1-hydroxybenzotriazole (0.31 mg, 2.3 μmol, 1.2 equiv) were then added separately, each in one portion, to the above solution at 0° C. The reaction mixture was warmed to 23° C. over 17 h 40 min, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a white solid, which was purified by flash column chromatography (80% ethyl acetate-hexanes) to give the pyrazine-2-carboxylic acid amide derivative (1.1 mg, 92%) as a white solid.

$^1$H NMR (500 MHz, CDCl$_3$), δ 9.10 (d, 1H, J=1.5, ArH), 8.60 (d, 1H, J=2.4, ArH), 8.17 (app. t, 1H, J=~2.0, ArH), 7.33 (t, 1H, J=5.4, NH), 5.65 (s, 1H, ArOH), 5.52 (s, 1H, ArOH), 4.33 (br. s, 1H, CHCH$_2$NHCO), 4.18 (br. s, 1H, ArCHNCH$_3$), 4.11 (d, 1H, J=2.4, CHC≡N), 3.93 (ddd, 1H, J=13.4, 6.7, 2.0, CH$_2$NHCO), 3.75 (s, 3H, ArOCH$_3$), 3.74 (s, 3H, ArOCH$_3$), 3.57 (s, 3H, ArOCH$_3$), 3.49 (ddd, 1H, J=13.4, 4.4, 4.4, CH$_2$NHCO), 3.45 (obsc. d, 1H, CHCHC≡N), 3.44 (s, 3H, ArOCH$_3$), 3.29 (br. d, 1H, J=11.7, ArCHCHCH$_2$Ar), 3.20 (dd, 1H, J=16.1, 2.4, ArCHCHCH$_2$Ar), 3.07 (dd, 1H, J=18.5, 8.3, CH$_2$CHCHC≡N), 2.55 (d, 1H, J=18.5, CH$_2$CHCHC≡N), 2.32 (s, 3H, NCH$_3$), 2.16 (s, 3H, ArCH$_3$), 2.08 (dd, 1H, J=16.1, 12.2, ArCHCHCH$_2$Ar), 2.08 (s, 3H, ArCH$_3$). FTIR (neat film), cm$^{-1}$ 3372, 2922, 2231, 1728, 1676. HRMS (ES) Calcd for C$_{33}$H$_{38}$N$_6$O$_7$ (MH)$^+$: 631.2880, Found: 631.2853.

EXAMPLE 18

Pyruvamide Derivative

Diethylaniline (0.37 μL, 2.3 μmol, 1.1 equiv) was added in one portion to a stirred solution of the amine (1.1 mg, 2.1 μmol, 1 equiv) in THF (0.15 mL) at 0° C. under an argon atmosphere and the solution was stirred for 5 min. Pyruvic acid (0.18 μL, 2.7 μmol, 1.3 equiv), 1-[3-(dimethylamino) propyl]-3-ethylcarbodiimide hydrochloride (0.52 mg, 2.7 μmol, 1.3 equiv) and 1-hydroxybenzotriazole (0.34 mg, 2.5 μmol, 1.2 equiv) were then added separately, each in one portion, to the above solution at 0° C. The reaction mixture was warmed to 23° C. over 14 h 15 min, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a white solid, which was purified by flash column chromatography (70% ethyl acetate-hexanes) to give the pyruvamide derivative (1.2 mg, 96%) as a white solid.

$^1$H NMR (500 MHz, CDCl$_3$), δ 6.45 (t, 1H, J=5.6, NHCO), 5.62 (s, 1H, ArOH), 5.56 (s, 1H, ArOH), 4.24 (dd, 1H, J=4.1, 1.9, CHCH$_2$NHCO), 4.17 (dd, 1H, J=3.1, 1.2, ArCHNCH$_3$), 4.03 (d, 1H, J=2.9, CHC≡N), 3.81 (s, 3H, ArOCH$_3$), 3.76 (s, 3H, ArOCH$_3$), 3.67 (s, 3H, ArOCH$_3$), 3.66 (app. ddd (obsc), 1H, CH$_2$NHCO), 3.60 (s, 3H, ArOCH$_3$), 3.42 (br. d, 1H, J=~8.8, CHCHC≡N), 3.31 (ddd, 1H, J=13.6, 5.6, 4.1, CH$_2$NHCO), 3.26–3.21 (m, 2H, ArCHCHCH$_2$Ar, ArCHCHCH$_2$Ar), 3.07 (dd, 1H, J=18.6, 8.3, CH$_2$CHCHC≡N), 2.49 (d, 1H, J=18.6, CH$_2$CHCHC≡N), 2.32 (s, 3H, NCH$_3$), 2.24 (s, 3H, COCH$_3$), 2.20 (s, 3H, ArCH$_3$), 2.17 (s, 3H, ArCH$_3$), 1.93 (dd, 1H, J=16.4, 12.0, ArCHCHCH$_2$Ar). FTIR (neat film), cm$^{-1}$ 3378, 2937, 2251, 1720, 1682, 1463. HRMS (ES) Calcd for C$_{31}$H$_{39}$N$_4$O$_8$ (MH)$^+$: 595.2768, Found: 595.2787.

EXAMPLE 19

Benzamide Derivative

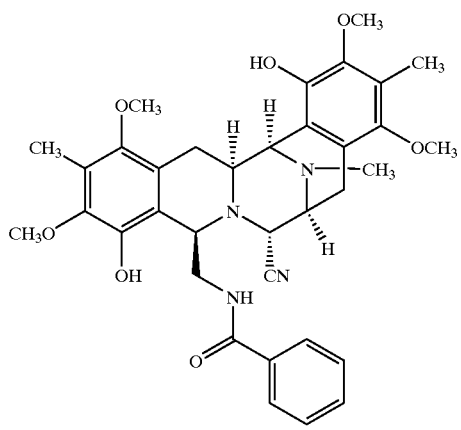

Diethylaniline (0.33 μL, 2.1 μmol, 1.1 equiv) and benzoyl chloride (0.66 μL, 5.7 μmol, 3.0 equiv) were added separately, each in one portion, to a stirred solution of the amine (1.0 mg, 1.9 μmol, 1 equiv) in dichloromethane (0.15 mL) at 0° C. under an argon atmosphere. The reaction mixture was stirred at 0° C. for 30 min, then was quenched by the addition of a 1:1 mixture of water and saturated aqueous sodium hydrogen carbonate solution (4 mL). The mixture was extracted with ethyl acetate (2×15 mL) and the combined organic layer was washed with a 1:1 mixture of brine solution and saturated aqueous sodium hydrogen carbonate solution (4 mL). The organic layer was dried over sodium sulfate and concentrated in vacuo to leave a white solid. Purification by flash column chromatography (70% ethyl acetate-hexanes) gave the benzamide derivative (1.1 mg, 92%) as a white solid.

$^1$H NMR (500 MHz, CDCl$_3$), δ 7.39–7.36 (m, 1H, ArH), 7.23–7.20 (m, 2H, ArH), 7.06–7.04 (m, 2H, ArH), 5.99 (br. d, 1H, J=~6.3, NHCO), 5.67 (s, 1H, ArOH), 5.65 (s, 1H, ArOH), 4.31 (br. d, 1H, J=~2.4, CHCH$_2$NHCO), 4.24 (dd, 1H, J=2.9, 1.5, ArCHNCH$_3$), 4.20 (ddd, 1H, J=13.7, 8.3, 2.0, CH$_2$NHCO), 4.10 (d, 1H, J=2.9, CHC≡N), 3.82 (s, 3H, ArOCH$_3$), 3.74 (s, 3H, ArOCH$_3$), 3.45 (br. d, 1H, J=~8.8, CHCHC≡N), 3.44 (s, 3H, ArOCH$_3$), 3.38 (s, 3H, ArOCH$_3$), 3.36 (app. ddd (obsc), 1H, ArCHCH$_2$Ar), 3.32–3.27 (m, 2H, CH$_2$NHCO, ArCHCH$_2$Ar), 3.11 (dd, 1H, J=18.5, 7.8, CH$_2$CHCHC≡N), 2.43 (d, 1H, J=18.5, CH$_2$CHCHC≡N), 2.33 (s, 3H, NCH$_3$), 2.16 (s, 3H, ArCH$_3$), 2.07 (s, 3H, ArCH$_3$), 2.03 (dd, 1H, J=15.9, 12.0, ArCHCHCH$_2$Ar). FTIR (neat film), cm$^{-1}$ 3395, 2933, 2226, 1656, 1462, 1056. HRMS (ES) Calcd for C$_{35}$H$_{41}$N$_4$O$_7$ (MH)$^+$: 629.2975, Found: 629.3002.

EXAMPLE 20

Carbamic Acid Benzyl Ester Derivative

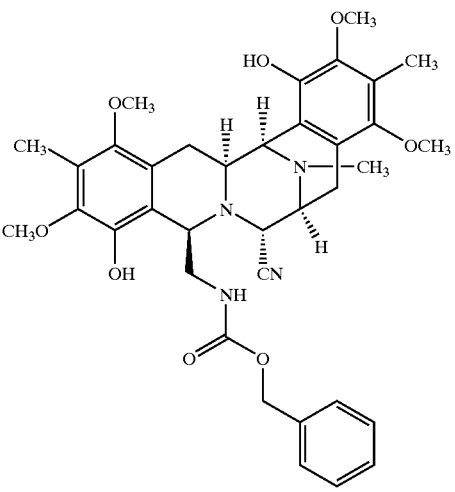

Diethylaniline (0.27 μL, 1.7 μmol, 1.1 equiv) and benzyl chloroformate (0.65 μL, 4.6 μmol, 3.0 equiv) were added separately, each in one portion, to a stirred solution of the amine (0.8 mg, 1.5 μmol, 1 equiv) in dichloromethane (0.1 mL) at 0° C. under an argon atmosphere. The reaction mixture was stirred at 0° C. for 30 min, then was quenched by the addition of a 1:1 mixture of water and saturated aqueous sodium hydrogen carbonate solution (3 mL). The mixture was extracted with ethyl acetate (2×10 mL) and the combined organic layer was washed with a 1:1 mixture of brine solution and saturated aqueous sodium hydrogen carbonate solution (5 mL). The organic layer was dried over sodium sulfate and concentrated in vacuo to leave a light yellow oil. Purification by flash column chromatography (60% ethyl acetate-hexanes) gave the carbamic acid benzyl ester derivative (1.0 mg, 99%) as a white solid.

$^1$H NMR (500 MHz, CDCl$_3$), δ 7.30–7.27 (m, 3H, ArH), 7.14–7.12 (m, 2H, ArH), 5.58 (s, 1H, ArOH), 5.52 (s, 1H, ArOH), 4.80 (s, 2H, OCH$_2$Ar), 4.42 (br. d, 1H, J=~5.4, NHCO), 4.17–4.15 (m, 2H, ArCHNCH$_3$, CHCH$_2$NHCO), 3.99 (d, 1H, J=2.0, CHC≡N), 3.74 (s, 3H, ArOCH$_3$), 3.64 (s, 3H, ArOCH$_3$), 3.60 (s, 3H, ArOCH$_3$), 3.58 (app. ddd (obsc), 1H, CH$_2$NHCO), 3.58 (s, 3H, ArOCH$_3$), 3.38 (br. d, 1H, J=~7.3, CHCHC≡N), 3.28 (ddd, 1H, J=12.0, 2.7, ArCHCHCH$_2$Ar), 3.20 (dd, 1H, J=15.8, 2.4, ArCHCHCH$_2$Ar), 3.14 (ddd, 1H, J=13.4, 3.9, 3.9, CH$_2$NHCO), 3.07 (dd, 1H, J=18.6, 7.8, CH$_2$CHCHC≡N), 2.47 (d, 1H, J=18.6, CH$_2$CHCHC≡N), 2.33 (s, 3H, NCH$_3$), 2.20 (s, 3H, ArCH$_3$), 2.10 (s, 3H, ArCH$_3$), 1.90 (dd, 1H, J=15.8, 12.0, ArCHCHCH$_2$Ar). FTIR (neat film), cm$^{-1}$ 3405, 2923, 2226, 1713, 1462. HRMS (ES) Calcd for C$_{36}$H$_{43}$N$_4$O$_8$ (MH)$^+$: 659.3081, Found: 659.3110.

EXAMPLE 21

Carbamic Acid 4-methoxy-phenyl Ester Derivative

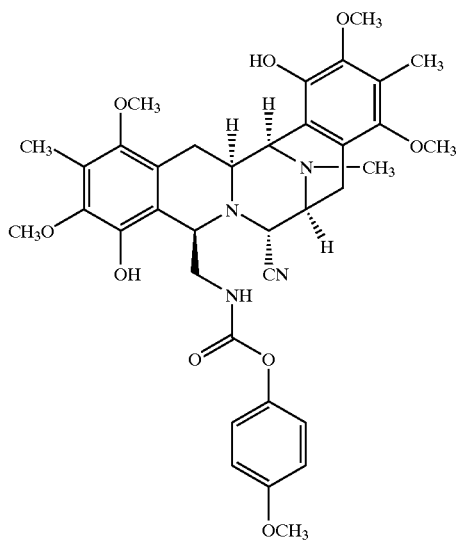

Diethylaniline (0.33 µL, 2.1 µmol, 1.1 equiv) and 4-methoxyphenyl chloroformate (0.85 µL, 5.7 µmol, 3.0 equiv) were added separately, each in one portion, to a stirred solution of the amine (1.0 mg, 1.9 µmol, 1 equiv) in dichloromethane (0.15 mL) at 0° C. under an argon atmosphere. The reaction mixture was stirred at 0° C. for 40 min, then was quenched by the addition of a 1:1 mixture of water and saturated aqueous sodium hydrogen carbonate solution (3 mL). The mixture was extracted with ethyl acetate (2×10 mL) and the combined organic layer was washed with a 1:1 mixture of brine solution and saturated aqueous sodium hydrogen carbonate solution (5 mL). The organic layer was dried over sodium sulfate and concentrated in vacuo to leave a colorless oil. Purification by flash column chromatography (50% 70→% ethyl acetate-hexanes) gave the carbamic acid 4-methoxyphenyl ester derivative (0.9 mg, 70%) as a white solid.

$^1$H NMR (500 MHz, CDCl$_3$), δ 6.75 (d, 1H, J=9.3, ArH), 6.67 (d, 1H, J=8.8, ArH), 5.61 (s, 1H, ArOH), 5.57 (s, 1H, ArOH), 4.67 (app. d, 1H, J=6.8, NHCO), 4.21 (d, 1H, J=1.9, ArCHNCH$_3$), 4.19 (br. d, 1H, J=~12.5, CHCH$_2$NHCO), 4.05 (d, 1H, J=2.4, CHC≡N), 3.75 (s, 3H, ArOCH$_3$), 3.74 (s, 3H, ArOCH$_3$), 3.71 (s, 3H, ArOCH$_3$), 3.67 (app. ddd (obsc), 1H, CH$_2$NHCO), 3.63 (s, 3H, ArOCH$_3$), 3.62 (s, 3H, ArOCH$_3$), 3.43 (br. d, 1H, J=~7.8, CHCHC≡N), 3.34 (ddd, 1H, J=12.0, 2.5, 2.5, ArCHCHCH$_2$Ar), 3.26 (dd, 1H, J=15.8, 2.8, ArCHCHCH$_2$Ar), 3.16–3.10 (m, 2H, CH$_2$NHCO, CH$_2$CHCHC≡N), 2.51 (d, 1H, J=18.6, CH$_2$CHCHC≡N), 2.37 (s, 3H, NCH$_3$), 2.22 (s, 3H, ArCH$_3$), 2.17 (s, 3H, ArCH$_3$), 2.01 (dd. 1H, J=15.8, 12.0, ArCHCHCH$_2$Ar). FTIR (neat film), cm$^{-1}$ 3508, 3385, 2923, 2226, 1733, 1195. HRMS (ES) Calcd for C$_{36}$H$_{43}$N$_4$O$_9$ (MH)$^+$: 675.3030, Found: 675.3019.

Example 22

Pyridine-2-carboxylic Acid Amide Derivative

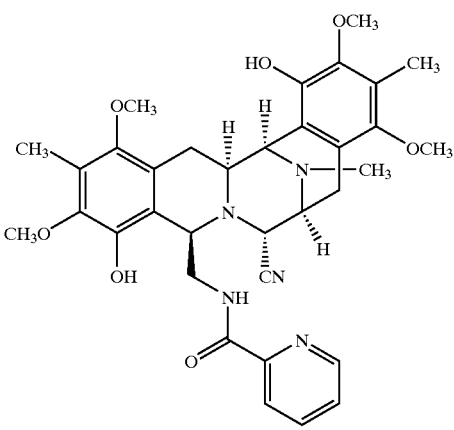

Diethylaniline (0.27 µL, 1.7 µmol, 1.1 equiv) was added in one portion to a stirred solution of the amine (0.8 mg, 1.5 µmol, 1 equiv) in THF (0.15 mL) at 0° C. under an argon atmosphere and the solution was stirred for 10 min. Picolinic acid (0.24 mg, 2.0 µmol, 1.3 equiv), 1-[3-(dimethylamino) propyl]-3-ethylcarbodiimide hydrochloride (0.38 mg, 2.0 µmol, 1.3 equiv) and 1-hydroxybenzotriazole (0.25 mg, 1.8 µmol, 1.2 equiv) were then added separately, each in one portion, to the above solution at 0° C. The reaction mixture was warmed to 23° C. over 17 h 45 min, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a yellow oil, which was purified by flash column chromatography (70% ethyl acetate-hexanes) to give the pyridine-2-carboxylic acid amide derivative (1.0 mg, 100%) as a white solid.

$^1$H NMR (500 MHz, CDCl$_3$), δ 8.20–8.19 (m, 1H, ArH), 7.92 (dd, 1H, J=7.8, 1.0, ArH), 7.71 (ddd, 1H, J=7.6, 7.6, 1.5, ArH), 7.68 (t, 1H, J=5.6, NH), 7.30 (m, 1H, ArH), 5.65 (s, 1H, ArOH), 5.52 (s, 1H, ArOH), 4.28 (t, 1H, J=3.2, ArCHCH$_2$NH), 4.22 (dd, 1H, J=3.0, 1.0, ArCHNCH$_3$), 4.13 (d, 1H, J=2.5, CHC≡N), 3.85 (ddd, 1H, J=13.2, 6.6, 3.0, ArCHCH$_2$NH), 3.75 (s, 3H, ArOCH$_3$), 3.73 (s, 3H, ArOCH$_3$), 3.55 (s, 3H, ArOCH$_3$), 3.51–3.45 (m, 1H, ArCHCH$_2$NH), 3.44 (s, 3H, ArOCH$_3$), 3.44 (br. d, 1H, J=~7.8, CHCHC≡N), 3.28 (ddd, 1H, J=12.0, 3.0, 3.0, ArCHCHCH$_2$Ar), 3.22 (dd, 1H, J=15.7, 2.4, ArCHCHCH$_2$Ar), 3.08 (dd, 1H, J=18.6, 8.1, CH$_2$CHCHC≡N), 2.58 (d, 1H, J=18.6, CH$_2$CHCHC≡N), 2.31 (s, 3H, NCH$_3$), 2.16 (s, 3H, ArCH$_3$), 2.16 (dd, 1H (obsc), ArCHCHCH$_2$Ar), 2.09 (s, 3H, ArCH$_3$). HRMS (ES) Calcd for C$_{34}$H$_{40}$N$_5$O$_7$ (MH)$^+$: 630.2927, Found: 630.2904.

EXAMPLE 23

Indole-2-carboxylic Acid Amide Derivative

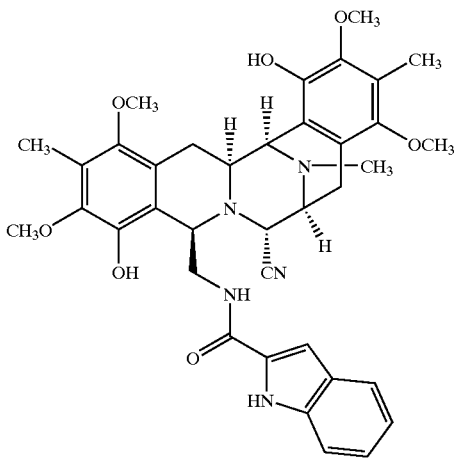

Diethylaniline (0.33 µL, 2.1 µmol, 1.1 equiv) was added in one portion to a stirred solution of the amine (1.0 mg, 1.9 µmol, 1 equiv) in THF (0.15 mL) at 0° C. under an argon atmosphere and the solution was stirred for 5 min. Indole-2-carboxylic acid (0.40 mg, 2.5 µmol, 1.3 equiv), 1-[3-(dimethylamino)propyl]-3-ethylcarbodiimide hydrochloride (0.48 mg, 2.5 µmol, 1.3 equiv) and 1-hydroxybenzotriazole (0.31 mg, 2.3 µmol, 1.2 equiv) were then added separately, each in one portion, to the above solution at 0° C. The reaction mixture was warmed to 23° C. over 15 h 30 min, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a white solid, which was purified by flash column chromatography (60% ethyl acetate-hexanes) to give the indole-2-carboxylic acid amide derivative (1.1 mg, 87%) as a white solid.

$^1$H NMR (500 MHz, CDCl$_3$), δ 8.80 (s, 1H, ArNH), 7.65 (d, 1H, J=8.7, ArH), 7.31 (d, 1H, J=8.3, ArH), 7.23 (ddd, 1H, J=6.9, 6.9, 1.0, ArH), 7.12 (ddd, 1H, J=6.9, 6.9, 1.0, ArH), 5.89 (dd, 1H, J=8.3, 2.5, NH), 5.69 (s, 1H, ArOH), 5.68 (s, 1H, ArOH), 5.58 (d, 1H, J=1.5, ArH), 4.31 (br. s, 1H, ArCHCH$_2$NH), 4.26 (dd, 11H, J=3.0, 1.0, ArCHNCH$_3$), 4.16 (ddd, 1H, J=13.6, 8.5, 2.4, ArCHCH$_2$NH), 4.10 (d, 1H, J=2.5, CHC≡N), 3.80 (s, 3H, ArOCH$_3$), 3.74 (s, 3H, ArOCH$_3$), 3.56 (s, 3H, ArOCH$_3$), 3.48 (br. d, 1H, J=~8.5, CHCHC≡N), 3.37–3.33 (m, 2H, ArCHCH$_2$NH, ArCHCHCH$_2$Ar), 3.32 (s, 3H, ArOCH$_3$), 3.25 (dd, 1H, J=16.1, 2.9, ArCHCHCH$_2$Ar), 3.14 (dd, 1H, J=18.5, 8.3, CH$_2$CHCHC≡N), 2.55 (d, 1H, J=18.5, CH$_2$CHCHC≡N), 2.35 (s, 3H, NCH$_3$), 2.15 (s, 3H, ArCH$_3$), 2.13 (s, 3H, ArCH$_3$), 2.01 (dd, 1H, J=16.1, 12.2, ArCHCHCH$_2$Ar). FTIR (neat film), cm$^{-1}$ 3405, 3292, 2923, 2226, 1646, 1544, 1056. HRMS (ES) Calcd for C$_{37}$H$_{42}$N$_5$O$_7$ (MH)$^+$: 668.3084, Found: 668.3112.

EXAMPLE 24

Isoguinoline-1-carboxylic Acid Amide Derivative

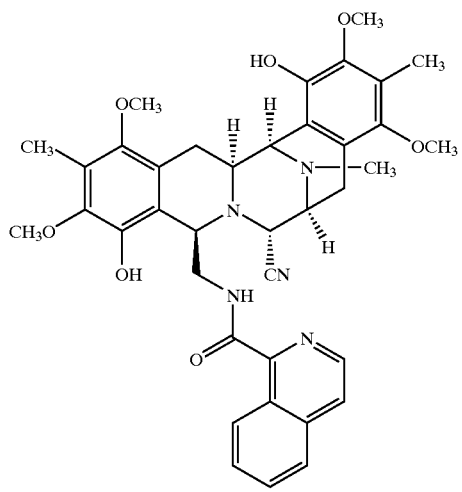

1-Isoquinolinecarboxylic acid (0.59 mg, 3.4 µmol, 1.5 equiv) was added in one portion to a stirred solution of the amine (1.2 mg, 2.3 µmol, 1 equiv) in dichloromethane (0.15 mL) at 23° C. under an argon atmosphere and the solution was stirred for 10 min. N-Cyclohexylcarbodiimide-N'-propyloxymethyl polystyrene (Argonaut Technologies, 1.13 mmol/g, 4.0 mg, 4.6, µmol, 2.0 equiv) was then added, in one portion, to the above solution at 23° C. The reaction mixture was stirred gently at 23° C. for 21 h, then was purified by flash column chromatography (85% ethyl acetate-hexanes) to give the isoquinoline-1-carboxylic acid amide derivative (1.1 mg, 71%) as a white solid.

$^1$H NMR (500 MHz, CDCl$_3$), δ 9.30 (d, 1H, J=8.8, ArH), 8.09 (d, 1H, J=5.4, ArH), 7.77 (d, 1H, J=8.3, ArH), 7.76 (t, 1H, J=6.4, NH), 7.68–7.65 (m, 2H, ArH), 7.60–7.56 (m, 1H, ArH), 5.71 (s, 1H, ArOH), 5.55 (s, 1H, ArOH), 4.37 (t, 1H, J=3.3, CHCH$_2$NHCO), 4.20 (app. d, 1H, J=~2.0, ArCHNCH$_3$), 4.16 (d, 1H, J=2.5, CHC≡N), 3.92 (ddd, 1H, J=13.6, 7.1, 3.2 CH$_2$NHCO), 3.75 (s, 3H, ArOCH$_3$), 3.71 (s, 3H, ArOCH$_3$), 3.51 (ddd, 1H, J=13.6, 4.4, 4.4, CH$_2$NHCO), 3.44 (s, 4H, ArOCH$_3$, CHCHC≡N), 3.40 (s, 3H, ArOCH$_3$), 3.31 (ddd, 1H, J=11.8, 2.7, 2.7, ArCHCH$_2$Ar), 3.24 (dd, 1H, J=15.6, 2.4, ArCHCH$_2$Ar), 3.07 (dd, 1H, J=18.4, 7.6, CH$_2$CHCHC≡N), 2.61 (d, 1H, J=18.4, CH$_2$CHCHC≡N), 2.31 (s, 3H, NCH$_3$), 2.28 (dd, 2.28 (dd, 1H, J=15.6, 11.7, ArCHCH$_2$Ar), 2.14 (s, 3H, ArCH$_3$), 1.89 (s, 3H, ArCH$_3$). FTIR (neat film), cm$^{-1}$ 3376, 2926, 2230, 1665. HRMS (ES) Calcd for C$_{38}$H$_{41}$N$_5$O$_7$ (MH)$^+$: 680.3084, Found: 680.3112.

129
EXAMPLE 25

5-Fluoro-indole-2-carboxylic Acid Amide Derivative

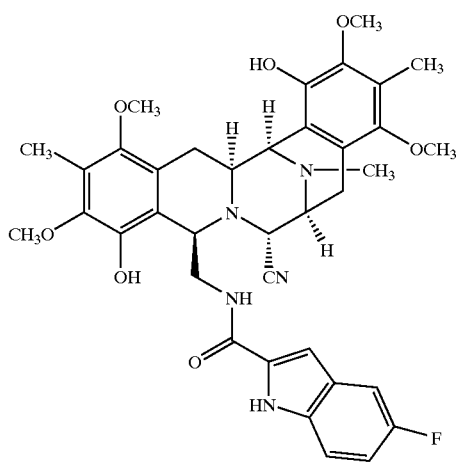

5-Fluoro-2-indolecarboxylic acid (0.51 mg, 2.9 μmol, 1.5 equiv) was added in one portion to a stirred solution of the amine (1.0 mg, 1.9 μmol, 1 equiv) in dichloromethane (0.2 mL) at 23° C. under an argon atmosphere and the solution was stirred for 10 min. N-Cyclohexylcarbodiimide-N'-propyloxymethyl polystyrene (Argonaut Technologies, 1.13 mmol/g, 3.4 mg, 3.8 μmol, 2.0 equiv) was then added, in one portion, to the above solution at 23° C. The reaction mixture was stirred gently at 23° C. for 16 h 40 min, then was purified by flash column chromatography (80% ethyl acetate-hexanes) to give the 5-fluoro-indole-2-carboxylic acid amide derivative (1.1 mg, 85%) as a white solid.

$^1$H NMR (500 MHz, CDCl$_3$), δ 8.85 (br. s, 1H, ArNH), 7.32 (dd, 1H, J=9.2, 2.4, ArH), 7.22 (dd, 1H, J=10.8, 4.4, ArH), 6.98 (td, 1H, J=8.8, 2.4, ArH), 5.87 (br. d, 1H, J=~6.9, NH), 5.72 (s, 1H, ArOH), 5.69 (s, 1H, ArOH), 5.43 (br. d, 1H, J=~2.0, ArH), 4.30 (br. s, 1H, CHCH$_2$NHCO), 4.25 (br. d, 1H, J=~2.9, ArCHNCH$_3$), 4.20 (ddd, 1H, J=13.4, 8.8, 2.0, CH$_2$NHCO), 4.09 (d, 1H, J=2.5, CHC≡N), 3.84 (s, 3H, ArOCH$_3$), 3.73 (s, 3H, ArOCH$_3$), 3.55 (s, 3H, ArOCH$_3$), 3.47 (br. d, 1H, J=~8.8, CHCHC≡N), 3.35 (ddd, 1H, J=11.7, 2.7, 2.7, ArCHCHCH$_2$Ar), 3.28 (obsc. ddd, 1H, CH$_2$NHCO), 3.27 (s, 3H, ArOCH$_3$), 3.24 (dd, 1H, J=16.1, 2.5, ArCHCHCH$_2$Ar), 3.13 (dd, 1H, J=18.6, 8.3, CH$_2$CHCHC≡N), 2.53 (d, 1H, J=18.6, CH$_2$CHCHC≡N), 2.35 (s, 3H, NCH$_3$), 2.15 (s, 3H, ArCH$_3$), 2.11 (s, 3H, ArCH$_3$), 1.98 (dd, 1H, J=16.1, 12.0, ArCHCHCH$_2$Ar). FTIR (neat film), cm$^{-1}$ 3398, 2925, 2225, 1645. HRMS (ES) Calcd for C$_{37}$H$_{40}$N$_5$O$_7$F (MH)$^+$: 686.2990, Found: 686.3020.

130
EXAMPLE 26

Phenylpyruvamide Derivative

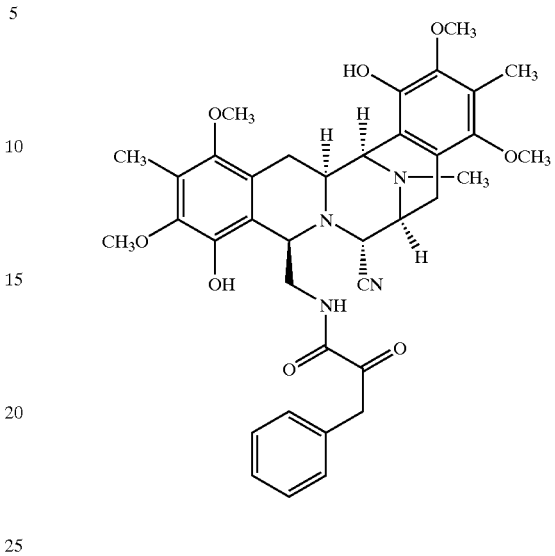

Diethylaniline (0.43 μL, 2.7 μmol, 1.1 equiv) was added in one portion to a stirred solution of the amine (1.3 mg, 2.5 μmol, 1 equiv) in THF (0.25 mL) at 0° C. under an argon atmosphere and the solution was stirred for 5 min. Phenylpyruvic acid (0.53 mg, 3.2 μmol, 1.3 equiv), 1-[3-(dimethylamino)propyl]-3-ethylcarbodiimide hydrochloride (0.62 mg, 3.2 μmol, 1.3 equiv) and 1-hydroxybenzotriazole (0.40 mg, 3.0 μmol, 1.2 equiv) were then added separately, each in one portion, to the above solution at 0° C. The reaction mixture was warmed to 23° C. over 13 h 40 min, then was quenched with saturated aqueous ammonium chloride solution (3 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a white solid, which was purified by flash column chromatography (70% ethyl acetate-hexanes) to give the phenylpyruvamide derivative (1.4 mg, 84%) as a white solid.

$^1$H NMR (500 MHz, CDCl$_3$), δ 7.27–7.23 (m, 3H, ArH), 7.04–7.02 (m, 2H, ArH), 6.56 (br. d, 1H, J=~4.9, NH), 5.61 (s, 1H, ArOH), 5.54 (s, 1H, ArOH), 4.25 (br. d, 1H, J=~2.0, CHCH$_2$NHCO), 4.17 (br. d, 1H, J=~2.4, ArCHNCH$_3$), 4.00 (d, 1H, J=2.4, CHC≡N), 3.90 (AB system, 2H, ArCH$_2$COCONH), 3.84 (obsc. ddd, 1H, J=13.7, 8.5, 1.9, CH$_2$NHCO), 3.74 (s, 3H, ArOCH$_3$), 3.60 (s, 3H, ArOCH$_3$), 3.54 (s, 3H, ArOCH$_3$), 3.52 (s, 3H, ArOCH$_3$), 3.41 (br. d, 1H, J=~7.8, CHCHC≡N), 3.27 (ddd, 1H, J=11.7, 2.5, 2.5, ArCHCHCH$_2$Ar), 3.21 (dd, 1H, J=16.1, 2.4, ArCHCHCH$_2$Ar), 3.17 (ddd, 1H, J=13.7, 3.9, 3.9, CH$_2$NHCO), 3.07 (dd, 1H, J=18.6, 8.3, CH$_2$CHCHC≡N), 2.42 (d, 1H, J=18.6, CH$_2$CHCHC≡N), 2.32 (s, 3H, NCH$_3$), 2.18 (s, 3H, ArCH$_3$), 2.11 (s, 3H, ArCH$_3$), 1.94 (dd, 1H, J=16.1, 12.0, ArCHCHCH$_2$Ar). FTIR (neat film), cm$^{-1}$ 3367, 2929, 2229, 1723, 1681. HRMS (ES) Calcd for C$_{37}$H$_{42}$N$_4$O$_8$ (MH)$^+$: 671.3081, Found: 671.3112.

EXAMPLE 27

2-Fluorobenzamide Derivative

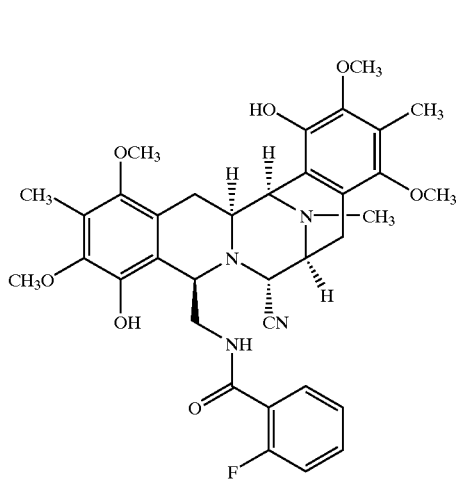

2-Fluorobenzoic acid (0.36 mg, 2.6 μmol, 1.5 equiv) was added in one portion to a stirred solution of the amine (0.9 mg, 1.7 μmol, 1 equiv) in dichloromethane (0.2 mL) at 23° C. under an argon atmosphere and the solution was stirred for 10 min. N-Cyclohexylcarbodiimide-N'-propyloxymethyl polystyrene (Argonaut Technologies, 1.13 mmol/g, 3.0 mg, 3.4 μmol, 2.0 equiv) was then added, in one portion, to the above solution at 23° C. The reaction mixture was stirred gently at 23° C. for 13 h, then was purified by flash column chromatography (70% ethyl acetate-hexanes) to give the 2-fluorobenzamide derivative (1.1 mg, 99%) as a white solid.

$^1$H NMR (500 MHz, CDCl$_3$), δ 7.78 (td, 1H, J=7.8, 1.9, ArH), 7.38–7.34 (m, 1H, ArH), 7.13 (td, 1H, J=7.8, 1.0, ArH), 6.85–6.81 (m, 1H, ArH), 6.35 (br. s, 1H, NH), 5.68 (s, 1H, ArOH), 5.56 (s, 1H, ArOH), 4.32 (br. d, 1H, J=~1.9, CHCH$_2$NHCO), 4.20 (dd, 1H, J=12.9, 1.0, ArCHNCH$_3$), 4.12 (d, 1H, J=2.5, CHC≡N), 4.09–4.05 (m, 1H, CH$_2$NHCO), 3.75 (s, 6H, 2×ArOCH$_3$), 3.59 (s, 3H, ArOCH$_3$), 3.46 (obsc. ddd, 1H, J=~14.2, 3.7, 3.7, CH$_2$NHCO), 3.44 (br. d, 1H, J=~8.8, CHCHC≡EN), 3.37 (s, 3H, ArOCH$_3$), 3.30 (br. d, 1H, J=~11.7, ArCHCHCH$_2$Ar), 3.26 (dd, 1H, J=15.6, 2.7, ArCHCHCH$_2$Ar), 3.06 (dd, 1H, J=18.5, 8.0, CH$_2$CHCHC≡N), 2.43 (d, 1H, J=18.5, CH$_2$CHCHC≡N), 2.30 (s, 3H, NCH$_3$), 2.19 (s, 3H, ArCH$_3$), 2.11 (dd, 1H, J=15.6, 11.7, ArCHCHCH$_2$Ar), 2.00 (s, 3H, ArCH$_3$). FTIR (neat film), cm$^{-1}$ 3403, 2932, 2231, 1649. HRMS (ES) Calcd for C$_{35}$H$_{39}$N$_4$O$_7$F (MH)$^+$: 647.2881, Found: 647.2903.

EXAMPLE 28

Quinoline-2-carboxylic Acid Amide Derivative

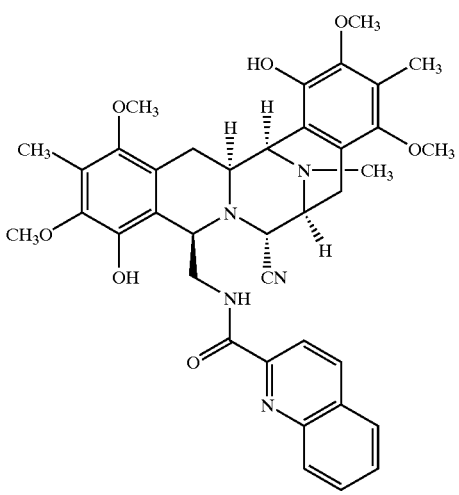

Quinaldic acid (0.50 mg, 2.9 μmol, 1.5 equiv) was added in one portion to a stirred solution of the amine (1.0 mg, 1.9 μmol, 1 equiv) in dichloromethane (0.2 mL) at 23° C. under an argon atmosphere and the solution was stirred for 10 min. N-Cyclohexylcarbodiimide-N'-propyloxymethyl polystyrene (Argonaut Technologies, 1.13 mmol/g, 3.4 mg, 3.8 μmol, 2.0 equiv) was then added, in one portion, to the above solution at 23° C. The reaction mixture was stirred gently at 23° C. for 16 h 50 min, then was purified by flash column chromatography (70% ethyl acetate-hexanes) to give the quinoline-2-carboxylic acid amide derivative (1.1 mg, 85%) as a white solid.

$^1$H NMR (500 MHz, CDCl$_3$), δ 8.23 (d, 1H, J=8.3, ArH), 8.13 (d, 1H, J=8.3, ArH), 7.95 (t, 1H, J=5.6, NH), 7.84 (d, 1H, J=8.1, ArH), 7.81 (d, 1H, J=8.1, ArH), 7.72 (ddd, 1H, J=8.3, 6.8, 1.4, ArH), 7.59 (ddd, 1H, J=8.3, 6.8, 1.0, ArH), 5.71 (br. s, 1H, ArOH), 5.44 (s, 1H, ArOH), 4.39 (t, 1H, J=3.9, CHCH$_2$NHCO), 4.19 (d, 1H, J=2.4, CHC≡N), 4.17 (d, 1H, J=1.5, ArCHNCH$_3$), 3.81–3.77 (m, 4H, CH$_2$NHCO, ArOCH$_3$), 3.61–3.57 (s, 7H, CH$_2$NHCO, 2×ArOCH$_3$), 3.42 (br. d, 1H, CHCHC≡N), 3.38 (s, 3H, ArOCH$_3$), 3.31–3.26 (m, 2H, ArCHCHCH$_2$Ar, CH$_2$CHCHC≡N), 3.08 (dd, 1H, J=18.6, 8.3, CH$_2$CHCHC≡N), 2.74 (d, 1H, J=18.6, CH$_2$CHCHC≡N), 2.27 (s, 3H, NCH$_3$), 2.21 (s, 3H, ArCH$_3$), 2.16 (dd, 1H, J=16.1, 12.2, ArCHCHCH$_2$Ar), 1.94 (s, 3H, ArCH$_3$). FTIR (neat film), cm$^{-1}$ 3385, 2933, 2226, 1667. HRMS (ES) Calcd for C$_{38}$H$_{41}$N$_5$O$_7$ (MH)$^+$: 680.3084, Found: 680.3094.

EXAMPLE 29

4-Methylphenyl Sulfonamide Derivative

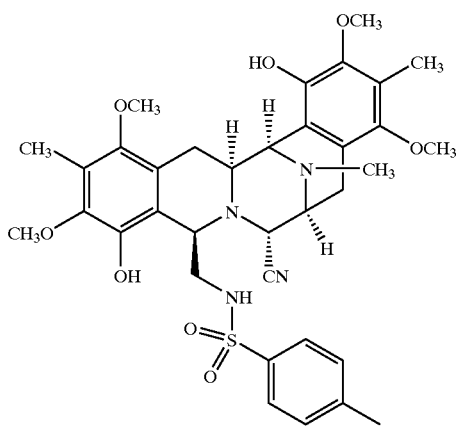

Diethylaniline (0.33 μL, 2.1 μmol, 1.1 equiv) was added in one portion to a stirred solution of the amine (1.0 mg, 1.9 μmol, 1 equiv) in THF (0.1 mL) at 0° C. under an argon atmosphere and the solution was stirred for 5 nin. p-Toluenesulfonyl chloride (0.73 mg, 3.8 mol, 2.0 equiv) was then added in one portion to the above solution at 0° C. The reaction mixture was stirred at 0° C. for 1 hr and then quenched with a 1:1 mixture of saturated aqueous sodium hydrogen carbonate solution and water (4 mL). The mixture was diluted with ethyl acetate (10 mL) and the layers were separated. The aqueous layer was extracted with ethyl acetate (10 mL) and the combined organic layer was dried over sodium sulfate. Concentration in vacuo left a yellow oil, which was purified by flash column chromatography (60% ethyl acetate-hexanes) to give the 4-methylphenyl sulfonamide derivative (1.2 mg, 93%) as a white solid.

EXAMPLE 30

7-Methylquinoline-2-carboxylic Acid Amide Derivative

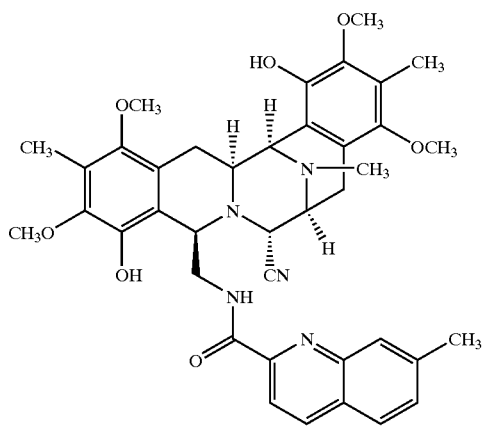

A solution of the amine 4 (1.0 mg, 1.9 μmol, 1.0 equiv) in dichloromethane (0.1 mL) was added to 7-methylquinoline-2-carboxylic acid (2.8 μmol, 1.5 equiv) and 1-hydroxybenzotriazole (0.44 mg, 3.2 μmol, 1.7 equiv) in a vial at 23° C. The solution was stirred for 5 min, then N-cyclohexylcarbodiimide-N'-propyloxymethyl polystyrene (Argonaut Technologies, 1.13 mmol/g, 3.4 mg, 3.8 μmol, 2.0 equiv) was added in one portion at 23° C. The reaction mixture was stirred gently at 23° C. under an argon atmosphere for 16 h. PS-Trisamine (Argonaut Technologies, 4.71 mmol/g, 2.0 mg, 9.5 μmol, 5.0 equiv) was then added in one portion and the reaction mixture was stirred for a further 2 h. The mixture was filtered through Celite (0.5 cm) and concentrated in vacuo to give the 7-methylquinoline-2-carboxylic acid amide derivative (1.2 mg, 95%) as an off-white solid.

$^1$H NMR (500 MHz, CDCl$_3$), δ 8.18 (d, 1H, J=8.8, ArH), 8.07 (d, 1H, J=8.3, ArH), 7.93 (br t, 1H, J=5.8, NH), 7.73 (d, 1H, J=8.3, ArH), 7.62 (s, 1H, ArH), 7.43 (dd, 1H, J=8.3, 1.5, ArH), 5.72 (br s, 1H, ArOH), 5.42 (br s, 1H, ArOH), 4.39 (t, 1H, J=3.9, CHCH$_2$NHCO), 4.19 (d, 1H, J=2.9, CHC≡N), 4.16 (d, 1H, J=1.5, ArCHNCH$_3$), 3.81–3.77 (m, 4H, CH$_2$NHCO, ArOCH$_3$), 3.64 (s, 3H, ArOCH$_3$), 3.58 (s, 3H, ArOCH$_3$), 3.51 (ddd, 1H, J=13.2, 4.4, 4.4, CH$_2$NHCO), 3.42 (br d, 1H, J=8.8, CHCHC≡N), 3.36 (s, 3H, ArOCH$_3$), 3.32–3.25 (m, 2H, ArCHCHCH$_2$Ar, ArCHCHCH$_2$Ar), 3.07 (dd, 1H, J=18.1, 8.3, CH$_2$CHCHC≡N), 2.75 (d, 1H, J=18.1, CH$_2$CHCHC≡N), 2.59 (s, 3H, ArCH$_3$), 2.28 (s, 3H, NCH$_3$), 2.23 (s, 3H, ArCH$_3$), 2.14 (dd, 1H, J=15.4, 11.5, ArCHCHCH$_2$Ar), 1.92 (s, 3H, ArCH$_3$); FTIR (neat film, cm$^{-1}$) 3383 (m, br, OH/NH), 2934 (m), 2228 (w, C≡N), 1668 (s, C=O), 1463 (s); HRMS (ES) Calcd for C$_{39}$H$_{43}$N$_5$O$_7$ (MH)$^+$: 694.3240, found: 694.3219.

EXAMPLE 31

Quinoxaline-2-carboxylic Acid Amide Derivative

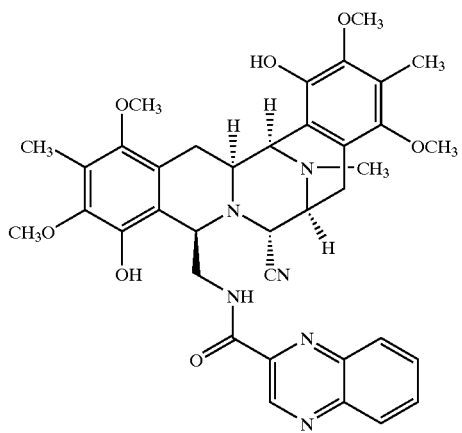

$^1$H NMR (500 MHz, CDCl$_3$), δ 9.47 (s, 1H, ArH), 8.14 (d, 1H, J=8.3, ArH), 7.85–7.82 (m, 1H, ArH), 7.79–7.76 (m, 2H, ArH), 7.53 (dd, 1H, J=6.6, 4.6, NH), 5.69 (s, 1H, ArOH), 5.35 (s, 1H, ArOH), 4.39 (t, 1H, J=3.2, CHCH$_2$NHCO), 4.18 (d, 1H, J=2.4, CHC≡N), 4.13 (d, 1H, J=1.9, ArCHNCH$_3$), 3.88 (ddd, 1H, J=13.7, 7.6, 4.6, CH$_2$NHCO), 3.79 (s, 3H, ArOCH$_3$), 3.64 (1H, ddd, J=13.7, 4.3, 3.0, CH$_2$NHCO), 3.61 (3H, s, ArOCH$_3$), 3.60 (3H, s, ArOCH$_3$), 3.44 (br d, 1H, J=8.6, CHCHC≡N), 3.29–3.25 (m, 2H, ArCHCHCH$_2$Ar, ArCHCHCH$_2$Ar), 3.25 (s, 3H, ArOCH$_3$), 3.04 (dd, 1H, J=18.5, 8.3, CH$_2$CHCHC≡N), 2.70 (d, 1H, J=18.5, CH$_2$CHCHC≡N), 2.25 (s, 3H, NCH$_3$), 2.23 (s, 3H, ArCH$_3$), 2.12 (dd, 1H, J=16.1, 12.2, ArCHCHCH$_2$Ar), 1.88 (s, 3H, ArCH$_3$); FTIR (neat film, cm$^{-1}$) 3383 (m, br, OH/NH), 2933 (m), 2228 (w, C≡N), 1673 (s, C=O), 1463 (s); HRMS (ES) Calcd for C$_{37}$H$_{40}$N$_6$O$_7$ (MH)$^+$: 681.3036, found: 681.3062.

EXAMPLE 32

6-Chloroquinoline-2-carboxylic Acid Amide Derivative

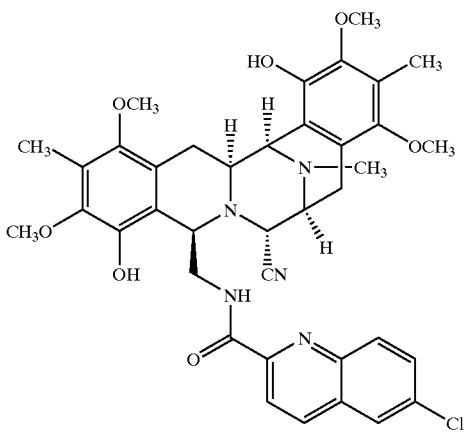

$^1$H NMR (500 MHz, CDCl$_3$), δ 8.14 (s, 2H, ArH), 7.85 (t, 1H, J=5.6, NH), 7.82 (d, 1H, J=2.0, ArH), 7.74 (d, 1H, J=9.2, ArH), 7.67 (dd, 1H, J=9.3, 2.4, ArH), 5.69 (s, 1H, ArOH), 5.45 (s, 1H, ArOH), 4.39 (t, 1H, J=3.7, CHCH$_2$NHCO), 4.17 (br s, 2H, CHC≡N, ArCHNCH$_3$), 3.76 (s, 3H, ArOCH$_3$), 3.72 (ddd, 1H, J=13.7, 6.3, 4.4, CH$_2$NHCO), 3.64 (ddd, 1H, J=13.7, 5.3, 3.9, CH$_2$NHCO), 3.56 (s, 3H, ArOCH$_3$), 3.54 (s, 3H, ArOCH$_3$), 3.49 (s, 3H, ArOCH$_3$), 3.43 (br d, 1H, J=8.3, CHCHC≡N), 3.30–3.27 (m, 2H, ArCHCHCH$_2$Ar, ArCHCHCH$_2$Ar), 3.07 (dd, 1H, J=18.3, 8.3, CH$_2$CHCHC≡N), 2.69 (d, 1H, J=18.3, CH$_2$CHCHC≡N), 2.28 (s, 3H, NCH$_3$), 2.20 (s, 3H, ArCH$_3$), 2.16 (obs dd, 1H, J=16.2, 11.7, ArCHCHCH$_2$Ar), 1.95 (s, 3H, ArCH$_3$); FTIR (neat film, cm$^{-1}$) 3383 (m, br, OH/NH), 2923 (s), 2228 (w, C≡N), 1668 (s, C=O), 1458 (s); HRMS (ES) Calcd for C$_{38}$H$_{40}$N$_5$O$_7$Cl (MH)$^+$: 714.2694, found: 714.2721.

EXAMPLE 33

Pentafluorobenzamide Derivative

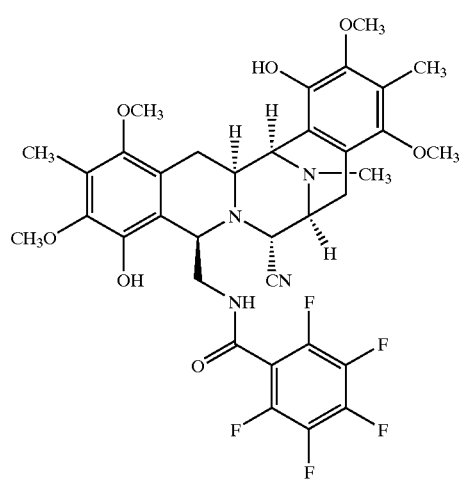

$^1$H NMR (500 MHz, CDCl$_3$), δ 5.66–5.65 (br m, 2H, ArOH, NH), 5.57 (s, 1H, ArOH), 4.27 (br m, 1H, CHCH$_2$NHCO), 4.17 (d, 1H, J=1.5, ArCHNCH$_3$), 4.05–4.01 (m, 2H, CHC≡N, CH$_2$NHCO), 3.76 (s, 3H, ArOCH$_3$), 3.74 (s, 3H, ArOCH$_3$), 3.64 (s, 3H, ArOCH$_3$), 3.57 (s, 3H, ArOCH$_3$), 3.44 (br d, 1H, J=8.3, CHCHC≡N), 3.34–3.30 (m, 2H, ArCHCHCH$_2$Ar, CH$_2$NHCO), 3.25 (dd, 1H, J=16.2, 2.9, ArCHCHCH$_2$Ar), 3.05 (dd, 1H, J=18.5, 7.8, CH$_2$CHCHC≡N), 2.43 (d, 1H, J=18.5, CH$_2$CHCHC≡N), 2.32 (s, 3H, NCH$_3$), 2.21 (s, 3H, ArCH$_3$), 2.04 (s, 3H, ArCH$_3$), 1.95 (dd, 1H, J=16.2, 12.2, ArCHCHCH$_2$Ar); FTIR (neat film, cm$^{-1}$) 3363 (m, br, OH/NH), 2933 (m), 2228 (w, C≡N), 1678 (s, C=O), 1502 (s); HRMS (ES) Calcd for C$_{35}$H$_{35}$N$_4$O$_7$F$_5$ (MH)$^+$: 719.2504, found: 719.2479.

EXAMPLE 34

3-Methoxybenzamide Derivative

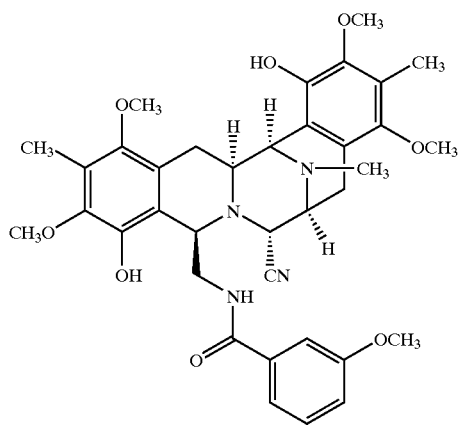

$^1$H NMR (500 MHz, CDCl$_3$), δ 7.10 (br s, 1H, ArH), 7.07 (t, 1H, J=7.8, ArH), 6.91 (dd, 1H, J=8.3, 1.9, ArH), 6.19 (d, 1H, J=7.8, ArH), 6.00 (d, 1H, J=5.9, NH), 5.69 (br s, 1H, ArOH), 5.64 (s, 1H, ArOH), 4.31 (br d, 1H, J=2.4, CHCH$_2$NHCO), 4.23 (d, 1H, J=2.0, ArCHNCH$_3$), 4.13 (obs ddd, 1H, J=13.7, 8.3, 2.0, CH$_2$NHCO), 4.10 (d, 1H, J=2.4, CHC≡N), 3.79 (s, 3H, ArOCH$_3$), 3.75 (s, 3H, ArOCH$_3$), 3.74 (s, 3H, ArOCH$_3$), 3.48 (s, 3H, ArOCH$_3$), 3.45 (br d, 1H, J=8.8, CHCHC≡N), 3.42 (s, 3H, ArOCH$_3$), 3.36–3.27 (m, 3H, ArCHCHCH$_2$Ar, CH$_2$NHCO (1H), ArCHCHCH$_2$Ar (1H)), 3.10 (dd, 1H, J=18.6, 8.3, CH$_2$CHCHC≡N), 2.43 (d, 1H, J=18.6, CH$_2$CHCHC≡N), 2.32 (s, 3H, NCH$_3$), 2.16 (s, 3H, ArCH$_3$), 2.08 (s, 3H, ArCH$_3$), 2.03 (dd, 1H, J=16.1, 11.7, ArCHCHCH$_2$Ar); FTIR (neat film, cm$^{-1}$) 3395 (m, br, OH/NH), 2933 (m), 2226 (w, C≡N), 1651 (m, C=O), 1462 (s); HRMS (ES) Calcd for C$_{36}$H$_{42}$N$_4$O$_8$ (MH)$^+$: 659.3081, found: 659.3081.

EXAMPLE 35

Hemiaminal Derivative

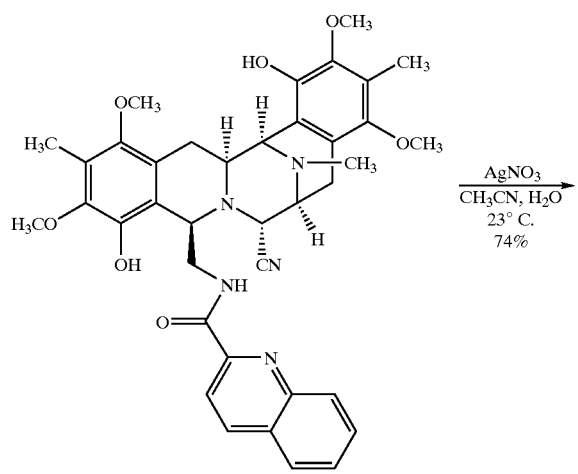

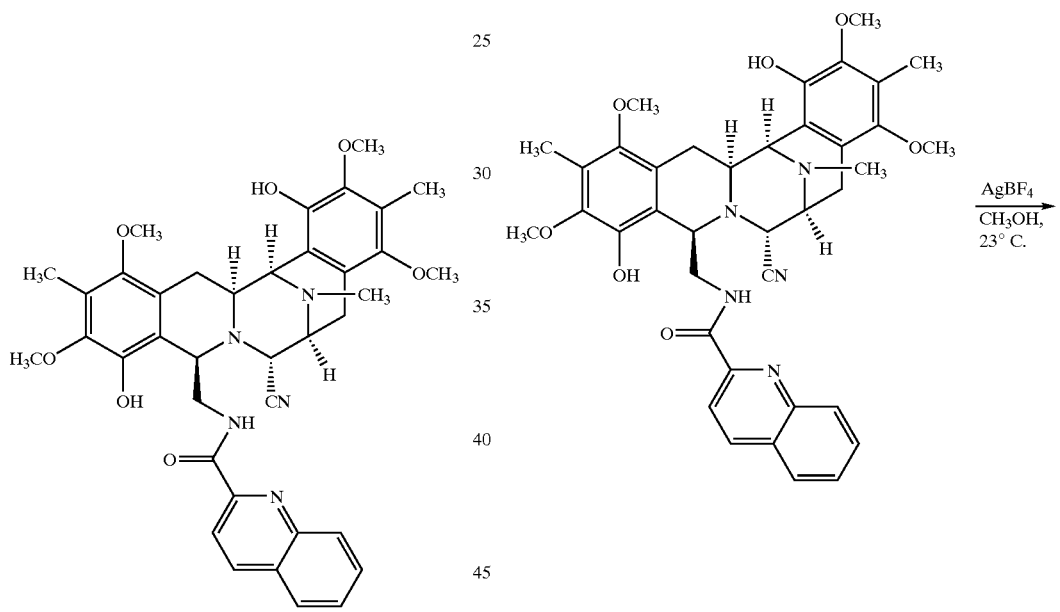

A solution of silver nitrate (15.9 mg, 93.6 µmol, 58.5 equiv) in a mixture of water and acetonitrile (3:2, 500 µl) was added to the quinoline-2-carboxylic acid amide derivative (1.1 mg, 1.6 µmol, 1 equiv). The reaction mixture was stirred at 23° C. in the dark for 4 h. A 1:1 mixture of saturated aqueous sodium bicarbonate and saturated aqueous sodium chloride solution (2 mL, freshly prepared) was added and the mixture was stirred for 5 min. A further 1:1 mixture of saturated aqueous sodium bicarbonate and saturated aqueous sodium chloride solution (20 mL, freshly prepared) was then added. The mixture was extracted with methylene chloride (5×10 ml). The combined organic extract was dried over sodium sulfate and was then concentrated to leave a solid residue. The solid residue was purified by flash column chromatography (4% methanol-methylene chloride) to provide the hemiaminal (0.8 mg, 74%) as a white solid.

$^1$H NMR (500 MHz, CDCl$_3$), δ 8.22 (d, 1H, J=8.5, ArH), 8.12 (d, 1H, J=8.5, ArH), 8.04 (t, 1H, J=5.5, NH), 7.82 (d, 1H, J=8.5, ArH), 7.72 (m, 2H, ArH), 7.59 (ddd, 1H, J=8.5, 4.5, 1.5, ArH), 5.72 (br s, 1H, ArOH), 5.54 (s, 1H, ArOH), 4.84 (t, 1H, J=4.0, CHCH$_2$NHCO), 4.60 (d, 1H, J=2.0, CHOH), 4.12 (dd, 1H, J=3.5, 1.5, CHCHOH), 3.78–3.68 (m, 4H, CH$_2$NHCO, ArOCH$_3$), 3.63 (1s, 3H, ArOCH$_3$), 3.47 (1s, 3H, ArOCH$_3$), 3.45 (1s, 3H, ArOCH$_3$). 3.38 (m, 1H, CH$_2$NHCO), 3.27 (m, 2H, ArCHCHCH$_2$Ar, ArCHCHCH$_2$Ar), 3.01 (dd, 1H, J=16.5, 8.0, ArCHCHCH$_2$Ar), 2.60 (d, 2H, J=17, CH$_2$CHCHOH), 2.27 (s, 3H, NCH$_3$), 2.21 (dd, 1H, J=16.5, 11.5, ArCHCHCH$_2$Ar), 2.17 (1s, 3H, ArCH$_3$), 1.92 (1s, 3H, ArCH$_3$). FTIR (neat film), cm$^{-1}$ 3360, 2936, 1667, 1415. HRMS (ES) Calcd for C$_{37}$H$_{43}$N$_4$O$_8$ (MH)$^+$: 671.3081, Found: 671.3083.

EXAMPLE 36

Methoxy Derivative

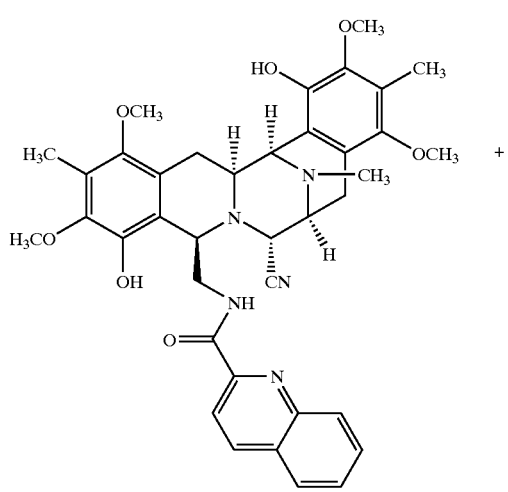

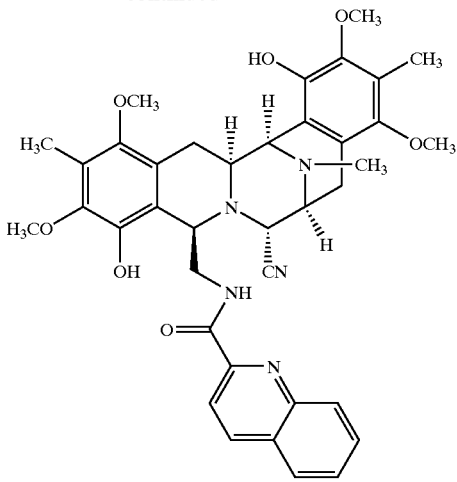

EXAMPLE 37

Reduced Quinalascidin Analog

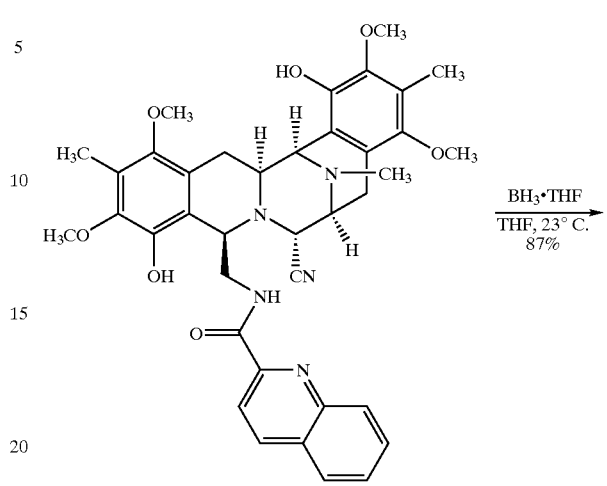

A solution of the quinoline-2-carboxylic acid amide derivative (0.8 mg, 1.2 μmol, 1 equiv) in methanol (0.5 mL) was added, via cannula, to silver tetrafluoroborate (22 mg, 113 μmol, 96 equiv) in an oven-dried glass vial. The reaction mixture was stirred at 23° C. in the dark for 24 h. A 1:1 mixture of saturated aqueous sodium bicarbonate and saturated aqueous sodium chloride solution (1 mL, freshly prepared) was added and the mixture was stirred for 5 min. A further 1:1 mixture of saturated aqueous sodium bicarbonate and saturated aqueous sodium chloride solution (10 mL, freshly prepared) was then added. The mixture was extracted with methylene chloride (4×10 mL). The combined organic extract was dried over sodium sulfate and was concentrated. The solid residue was purified by flash column chromatography (4% methanol-methylene chloride) to provide the hemiaminal (0.45 mg, 57%) as a white solid and the methoxy derivative (0.16 mg, 19.8%) as a white solid.

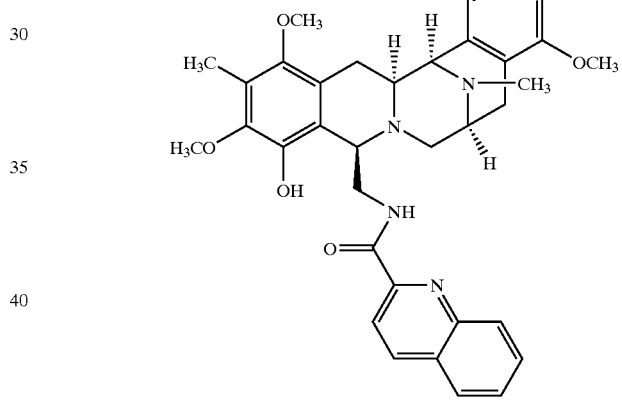

$^1$H NMR of the methoxy derivative (500 MHz, CDCl$_3$), δ 8.19 (d, 1H, J=8.0, ArH), 8.07 (d, 1H, J=8.0, ArH), 7.83 (m, 2H, NH, ArH), 7.76 (t, 1H, J=7.0, ArH), 7.62 (t, 1H, J=7.0, ArH), 7.53 (d, 1H, J=8.0, ArH), 5.60 (br s, 1H, ArOH), 5.33 (s, 1H, ArOH), 4.64 (s, 1H, CHCH$_2$NHCO), 4.59 (d, 1H, J=3.0, CHOCH$_3$), 4.18 (d, 1H, J=3.5, 1.5, CH$_2$NHCO), 4.06 (dd, 1H, J=14, 7.5, CHCHOH), 3.78 (1s, 3H, ArOCH$_3$), 3.69 (1s, 3H, ArOCH$_3$), 3.59 (m, 1H, CH$_2$NHCO), 3.37 (m, 1H, ArCHCHCH$_2$Ar), 3.29 (m, 1H, ArCHCHCH$_2$Ar), 3.16 (1s, 3H, ArOCH$_3$), 3.05 (1s, 3H, ArOCH$_3$), 2.99 (dd, 1H, J=18.5, 9, CH$_2$CHCHOCH$_3$), 2.88 (d, 1H, J=9, CH$_2$CHCHOCH$_3$), 2.52 (s, 3H, CHOCH$_3$), 2.36 (d, J=18.5, ArCHCHCH$_2$Ar), 2.27 (s, 3H, NCH$_3$), 1.96 (ddd, J=18.5, 11, 2.5, ArCHCHCH$_2$Ar), 1.76 (1s, 3H, ArCH$_3$), 1.74 (1s, 3H, ArCH$_3$). HRMS (ES) Calcd for C$_{38}$H$_{45}$N$_4$O$_8$ (MH)$^+$: 685.3237, Found: 685.3259.

A solution of borane tetrahydrofuran complex in tetrahydrofuran (1.0 M, 9.0 μL, 9 μmol, 5.0 equiv) was added to a solution of the quinoline-2-carboxylic acid amide derivative (1.2 mg, 1.8 μmol, 1 equiv) in tetrahydrofuran (0.2 mL). The resulting colorless solution was stirred at 23° C. for 2.5 h. 1,4-Diazabicyclo[2.2.2]octane (DABCO, 6.1 mg, 0.054 mmol, 30 equiv) and water (0.2 mL) were added to the reaction mixture in sequence. The resulting colorless solution was stirred at 23° C. for 20 h. The solution was diluted with dichloromethane (5 mL) and the resulting mixture was dried over sodium sulfate and was concentrated. Purification of the white solid residue by flash chromatography (10% methanol-distilled ethyl acetate) afforded the reduced derivative (1.0 mg, 87%) as a white solid: R$_f$ 0.16, 10% methanolethyl acetate; $^1$H NMR (500 MHz, CD$_3$OD) δ 8.17 (d, 1H, J=8.5 Hz, CHCHCCONH), 8.08 (d, 1H, J=8.5 Hz, CHCHCCONH), 8.05 (br t, 1H, CONH), 7.80 (d, 1H, J=8.5 Hz, NCCH), 7.73 (ddd, 1H, J=7.5, 6.8, 1.5 Hz, NCCHCH), 7.70 (d, 1H, J=8.0 Hz, NCCHCHCHCH), 7.57 (ddd, 1H, J=8.0, 7.0, 1.5 Hz, NCCHCHCH), 5.75 (br s, 1H, ArOH), 5.55 (s, 1H, ArOH), 4.20 (br s, 1H, ArCHNCH$_3$), 4.02 (br t, 1H, CHCH$_2$NHCO), 3.85 (br m, 1H, CHCH$_2$NHCO), 3.73

(s, 3H, ArOH), 3.67 (dt, 1H, J=13.0, 4.5 Hz, CHCH₂NHCO), 3.60 (s, 3H, ArOH), 3.44 (s, 3H, ArOH), 3.43 (s, 3H, ArOH), 3.18–3.23 (m, 3H, ArCHCHCH₂Ar, ArCH₂CHCH₂N, ArCH₂CHCH₂N), 3.05 (dd, 1H, J=18.0, 7.5 Hz, ArCH₂CHCH₂N), 2.90–3.00 (m, 2H, ArCHCHCH₂Ar, ArCH₂CHCH₂N), 2.71 (d, 1H, J=20.0 Hz, ArCH₂CHCH₂N), 2.29 (s, 3H, NCH₃), 2.23 (dd, 1H, J=15.5, 12.0 Hz, ArCHCHCH₂Ar), 2.13 (s, 3H, ArCH₃), 1.92 (s, 3H, ArCH₃); FTIR (neat film), cm⁻¹ 3364 (br, NH, OH), 1668 (s, C=O); HRMS (TOF MS ES+) m/z calcd for C₃₇H₄₃N₄O₇ (M+H)⁺ 655.3132, found 655.3123.

EXAMPLE 38

Synthesis of Labeled Analogs

As described generally above, certain of the inventive compounds can also be modified to permit attachment of labeling reagents. For example, certain aryl and heteroaryl groups (and other groups) as defined generically herein, can be modified (by attachment of a linker structure, generally an aliphatic, heteroaliphatic, aryl, or heteroaryl moiety (or any combination thereof) which moiety is substituted or unsubstituted, cyclic or acyclic, branched or unbranched.

Methyl ester 5:

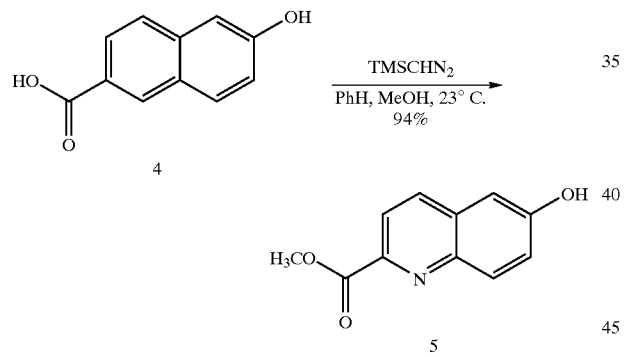

A solution of trimethylsilyldiazomethane in hexanes (2.0 M, 0.241 mL, 0.484 mmol, 2.1 equiv) was added dropwise via syringe to a suspension of acid 4 (52.0 mg, 0.231 mmol, 1 equiv) in a mixture of benzene (3.5 mL) and methanol (1.0 mL). The resulting red solution was stirred at 23° C. for 35 min. The solution was concentrated and the residual red oil was purified by flash column chromatography (25→35% ethyl acetate-hexanes). Methyl ester 5 was obtained as a white solid (44.5 mg, 94%); a bis-methylated biproduct (3.2 mg, 6%) was also isolated. Methyl ester 5: R_f 0.39, ethyl acetate; ¹H NMR (400 MHz, CDCl₃) δ 8.22 (d, 1H, J=8.2 Hz, CHCHCOH), 8.16 (d, 1H, J=8.4 Hz, CHCHCO₂CH₃), 8.13 (d, 1H, J=9.2 Hz, CHCHCO₂CH₃), 7.40 (dd, 1H, J=9.2, 2.8 Hz CHCHCOH), 7.17 (d, 1H, J=3.2 Hz, CHCOH), 5.66 (br s, 1H, OH), 4.07 (s, 3H, OCH₃); ¹³C NMR (100 MHz, CD₃OD) δ 166.9, 159.3, 145. 143.8, 137.0, 132.8, 132.1, 124.6, 122.1, 109.1, 53.2; FTIR (neat film), cm⁻¹ 3106 (br, OH), 1726 (m, C=O), 1228 (s, Ar—OH); HMRS (CI) m/z calcd for C₁₁H₁₀NO₃ (M+H)⁺ 204.0661, found 204.0665.

Ether 6:

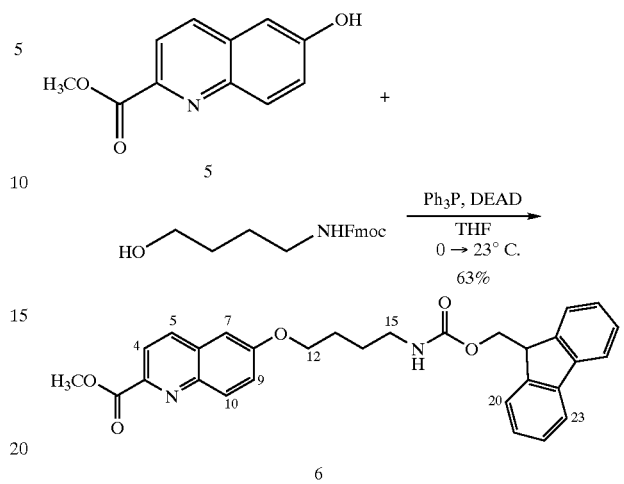

Diethyl azodicarboxylate (0.255 mL, 1.62 mmol, 4.0 equiv) was added dropwise via syringe to an ice-cold solution of phenol 5 (82.2 mg, 0.405 mmol, 1 equiv), N-Fmoc-1-amino-4-butanol (0.504 g, 1.62 mmol, 4.0 equiv), and triphenylphosphine (0.424 g, 1.62 mmol, 4.0 equiv) in tetrahydrofuran (2.7 mL). The resulting yellow solution was allowed to warm to 23° C. and was stirred for 19 h. The solution was concentrated. Purification of the residual yellow oil by flash column chromatography (50% ether-pentane→70% ether-pentane) afforded ether 6 as a white solid (126.8 mg, 63%): R_f 0.23, 50% ethyl acetate-hexanes; ¹H NMR (data given for major rotamer, 500 MHz, CDCl₃) δ 8.19 (d, 1H, J=9.0 Hz, C₁₀H), 8.13–8.16 (m, 2H, C₄H, C₅H), 7.76 (d, 2H, J=7.5 Hz, C₂₃H), 7.59 (d, 2H, J=7.5 Hz, C₂₀H), 7.38–7.43 (m, 3H, C₂₂H), C₉H), 7.30 (t, 2H, J=7.5 Hz, C₂₁H), 7.09 (d, 1H, J=2.0 Hz, C₇H), 4.86 (br m, 1H, CONH), 4.43 (d, 2H, J=7.0 Hz, CO₂CH₂), 4.21 (t, 1H, J=6.5 Hz, CO₂CH₂CH), 4.13 (t, 2H, J=5.8 Hz, C₁₂H₂), 4.07 (s, 3H, OCH₃), 3.31 (q, 2H, J=6.3 Hz, C₁₅H₂), 1.91 (quint, 2H, J=7.0 Hz, C₁₃H₂), 1.76 (quint, 2H, J=7.5 Hz, C₁₄H₂); ¹³C NMR (100 MHz, CDCl₃) δ 166.1, 158.7, 156.5, 145.3, 143.9, 143.6 141.3, 135.6, 132.1, 130.8, 127.6, 127.0, 124.9, 123.6, 121.4, 119.9, 105.2, 67.8, 66.5, 47.2, 40.5, 29.7, 26.7, 26.2; FTIR (neat film), cm⁻¹ 3334 (br, NH), 1720 (br s, OC=O, NHC=O), 1227 (s, Ar—OCH₂).

Carboxylic Acid 7:

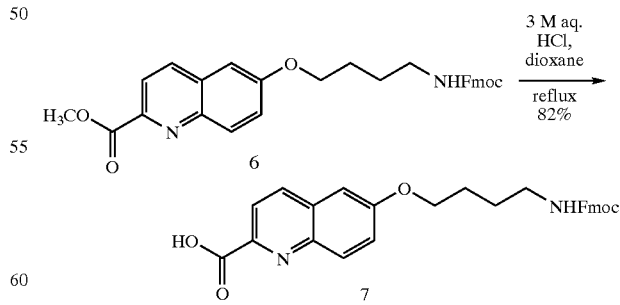

A solution of methyl ester 6 (123 mg, 0.247 mmol) in a mixture of 3 M aq. HCl (0.5 mL) and p-dioxane (2.5 mL) was heated at reflux for 9 h. The solution was allowed to cool to 23° C., and was concentrated. The residual yellow solid was recrystallized from ethanol:water (2:1, 30 mL).

Upon cooling to −20° C., a white amorphous solid precipitated. The solid was collected by vacuum filtration and was washed with water (2 mL), yielding acid 7 (106 mg, 82%) as a white powder: $R_f$ 0.0, 50% ethyl acetate-hexanes; $^1$H NMR (500 MHz, CD$_3$OD) δ 8.36 (d, 1H, J=9.0 Hz, C$_4$H), 8.09–8.13 (m, 2H, C$_3$H, C$_9$H), 7.77 (d, 2H, J=7.5 Hz, C$_{22}$H), 7.62 (d, 2H, J=7.5 Hz, C$_{20}$H), 7.49 (dd, 1H, J=9.5, 2.5 Hz, C$_8$H), 7.34–7.38 (m, 3H, C$_{21}$H, C$_6$H), 7.27 (t, 2H, J=7.3 Hz, C$_{20}$H), 4.34 (d, 2H, J=6.5 Hz, CO$_2$CH$_2$), 4.18 (t, 2H, J=6.0 Hz, ArOCH$_2$), 4.16 (t, 1H, J=6.5 Hz, CO$_2$CH$_2$CH), 3.21 (t, 2H, J=6.5 Hz, CH$_2$NHCO$_2$), 1.88 (quint, 2H, J=7.0 Hz, ArOCH$_2$CH$_2$), 1.72 (quint, 2H, J=7.3 Hz, CH$_2$CH$_2$NHCO$_2$); $^{13}$C NMR (100 MHz, CD$_3$OD) δ 165.7, 159.5, 157.0, 146.1, 145.2, 143.3, 142.1, 136.8, 131.9, 131.7, 128.1, 127.6, 125.5, 124.2, 121.4, 120.6, 106.4, 68.6, 48.2, 40.9, 30.3, 27.3, 26.9; FTIR (neat film), cm$^{-1}$ 3326 (br, CO$_2$H, NH), 1714 (s, HOC=O, NHCO$_2$), 1227 (s, Ar—OCH$_2$); HRMS (TOF MS ES+) m/z calcd for C$_{29}$H$_{27}$N$_2$O$_5$ (M+H)$^+$ 483.1920, found 483.1924.

Amide 9:

was stirred gently at 23° C. for 19 h. The reaction mixture was directly purified by chromatography on a pipette column of silica gel (2% methanol-dichloromethane). Amide 9 was obtained as a colorless oil (22.2 mg, 87%): $R_f$ 0.59, 10% methanol-dichloromethane; $^1$H NMR (500 MHz, CDCl$_3$) δ 8.06 (m, 2H, CHCHCCONH, CHCHCCONH), 7.90 (t, 1H, J=6.0 Hz, CONH), 7.77 (d, 2H, J=7.5 Hz, ArH), 7.69 (d, 1H, J=9.5 Hz, CHCHCOCH$_2$), 7.60 (d, 2H, J=7.5 Hz, ArH), 7.40 (t, 2H, J=7.3 Hz, ArH), 7.35 (dd, 1H, J=9.5, 2.5 Hz, CHCHCOCH$_2$), 7.31 (t, 2H, J=7.5 Hz, ArH), 7.04 (d, 1H, J=2.5 Hz, CHCOCH$_2$), 5.71 (s, 1H, ArOH), 5.45 (s, 1H, ArOH), 4.85 (br m, 1H, OCONH), 4.44 (d, 2H, J=7.0 Hz, CO$_2$CH$_2$), 4.37 (t, 1H, J=3.8 Hz, CHCH$_2$NHCO), 4.22 (t, 1H, J=7.0 Hz, CO$_2$CH$_2$CH), 4.17–4.20 (m, 2H, CHC≡N, ArCHNCH$_3$), 4.14–4.18 (m, 2H, ArOCH$_2$), 3.75 (s, 3H, ArOCH$_3$), 3.69–3.75 (m, 1H, CH$_2$NHCO), 3.57 (s, 3H, ArOCH$_3$), 3.53 (s, 3H, ArOH$_3$), 3.52–3.57 (m, 1H, CH$_2$NHCO), 3.45 (s, 3H, ArOCH$_3$), 3.41 (d of m, 1H, J=7.0 Hz, CHCHC≡N), 3.32 (q, 2H, J=6.7 Hz, CH$_2$NHCO$_2$), 3.24–3.30 (m, 2H, ArCHCHCH$_2$Ar, ArCHCHCH$_2$Ar), 3.07

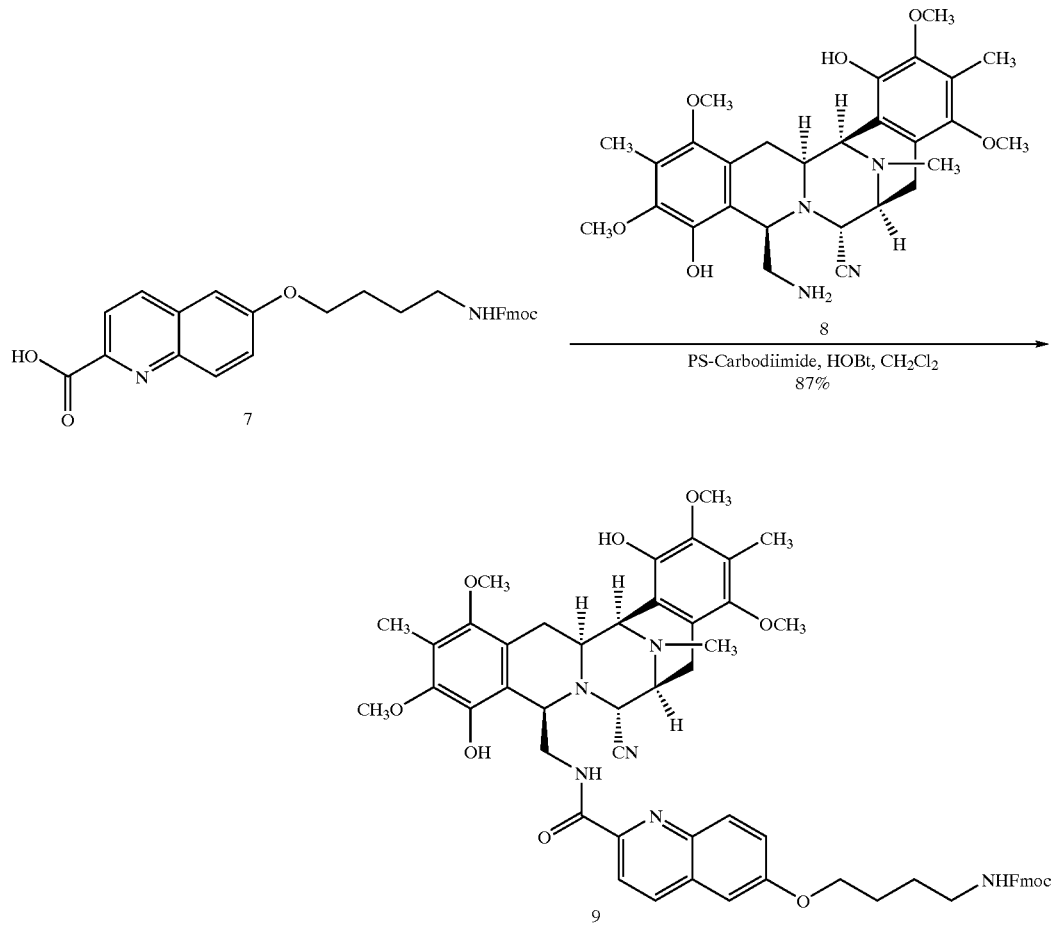

A solution of primary amine 8 (13.8 mg, 26.3 μmol, 1.02 equiv) in dichloromethane (0.75 mL) was added via cannula to a mixture of acid 7 (12.5 mg, 25.9, μmol, 1 equiv) and 1-hydroxybenzotriazole (5.9 mg, 43.7 μmol, 1.7 equiv) in an oven-dried glass vial. To the resulting suspension was added PS-carbodiimide (Argonaut Technologies, 1.39 mmol/g, 37.3 mg, 51.8 μmol, 2.0 equiv). The resulting suspension (dd, 1H, J=18.5, 8.0 Hz, CH$_2$CHCHC≡N), 2.74 (d, 1H, J=18.5 Hz, CH$_2$CHCHC≡N), 2.27 (s, 3H, NCH$_3$), 2.19 (s, 3H, ArCH$_3$), 2.12 (dd, 1H, J=16.3, 12.3 Hz, ArCHCHCH$_2$Ar), 1.99 (s, 3H, ArCH$_3$), 1.88–1.94 (m, 2H, CH$_2$CH$_2$OAr), 1.76–1.80 (m, 2H, CH$_2$CH$_2$NHCO$_2$); FTIR (neat film), cm$^{-1}$ 3378 (br, NH, OH), 2233 (w, C≡N), 1714

(m, NHCO$_2$), 1668 (m, NHC=O); HRMS (TOF MS ES+) m/z calcd for C$_{57}$H$_{16}$N$_6$O$_{10}$ (M+H)$^+$: 989.4449, found 989.4404.

Primary Amine 10:

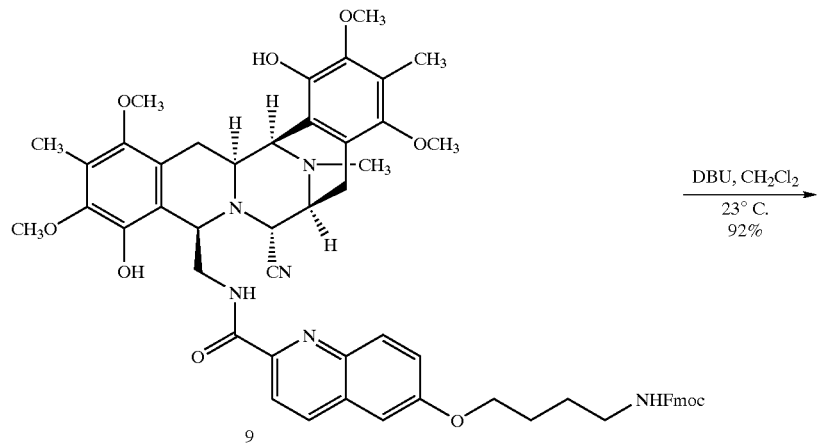

1,8-Diazabicyclo[5.4.0]undec-7-ene (DBU, 0.5 μL, 3.6 μmol, 1.5 equiv) was added to a solution of carbamate 9 (2.4 mg, 2.4 μmol, 1 equiv) in dichloromethane (0.1 mL). The resulting solution was stirred for 30 min. Purification of the crude reaction mixture by column chromatography on a pipette column (4% methanol-dichloromethane→10% methanol-dichloromethane→10% methanol in 98:2 dichloromethane:ammonium hydroxide), furnished primary amine 10 as a white solid (1.7 mg, 92%): R$_f$ 0.03, 10% methanol-dichloromethane; $^1$H NMR (400 MHz, CDCl$_3$) δ 8.06 (m, 2H, CHCHCCONH, CHCHCCONH), 7.90 (t, 1H, J=5.2 Hz, CONH), 7.69 (d, 1H, J=9.2 Hz, CHCHCOCH$_2$), 7.35 (dd, 1H, J=9.2, 2.8 Hz, CHCHCOCH$_2$), 7.03 (d, 1H, J=2.8 Hz, CHCOCH$_2$), 4.37 (t, 1H, J=3.6 Hz, CHCH$_2$NHCO), 4.15–4.18 (m, 2H, CHCE≡N, ArCHNCH$_3$), 4.11 (t, 1H, J=6.4 Hz, ArOCH$_2$), 4.11 (t, 1H, J=6.4 Hz, ArOCH$_2$), 3.75 (s, 3H, ArOCH$_3$), 3.69–3.75 (m, 1H, CH$_2$NHCO), 3.58 (s, 3H, ArOCH$_3$), 3.53–3.58 (m, 1H, CH$_2$NHCO), 3.53 (s, 3H, ArOCH$_3$), 3.46 (s, 3H, ArOCH$_3$), 3.40–3.43 (m, 1H, CHCHC≡N), 3.23–3.30 (m, 2H, ArCHCHCH$_2$Ar, ArCHCHCH$_2$Ar), 3.08 (dd, 1H, J=18.4, 8.4 Hz, CH$_2$CHCHC≡N), 2.83 (br m, 2H, CH$_2$NH$_2$), 2.74 (d, 1H, J=18.4 Hz, CH$_2$CHCHC≡N), 2.27 (s, 3H, NCH$_3$), 2.19 (s, 3H, ArCH$_3$), 2.12 (dd, 1H, J=16.2, 11.8 Hz, ArCHCHCH$_2$Ar), 1.99 (s, 3H, ArCH$_3$), 1.88–1.96 (m, 2H, CH$_2$CH$_2$OAr), 1.65–1.74 (m, 2H, CH$_2$CH$_2$NH$_2$); FTIR (neat film), cm$^{-1}$ 3378 (br, NH, OH), 2248 (w, C≡N), 1668 (m, NHC=O); HRMS (TOF MS ES+) m/z calcd for C$_{42}$H$_{51}$N$_6$O$_8$ (M+H)$^+$: 767.3768, found: 767.3759.

Biotinylated Quinalascidin Analog 1:

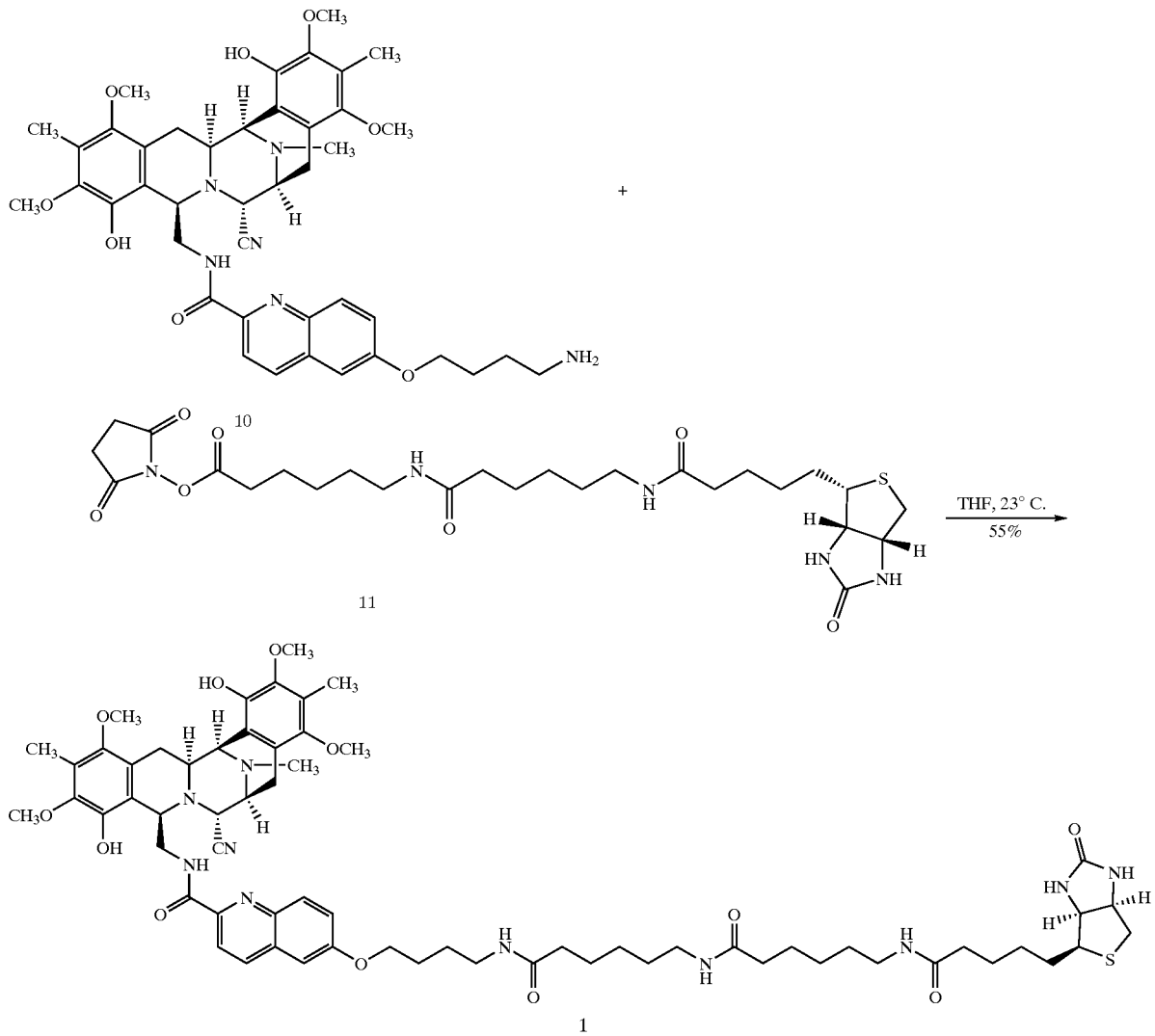

A suspension of primary amine 10 (0.8 mg, 1.0 μmol, 1 equiv) and N-hydroxy-succinimidyl ester 11 (Molecular Probes, 0.71 mg, 1.3 μmol, 1.3 equiv) in tetrahydrofuran (0.1 mL) in a glass vial was stirred at 23° C. for 14 h. The mixture was concentrated and the residual white solid was purified by column chromatography on a pipette column (5% methanol-dichloromethane→10% methanol-dichloromethane→10% methanol in 98:2 dichloromethane:ammonium hydroxide). Fractions containing the biotinylated product 1 were contaminated by remaining starting amine 10. Further purification by chromatography on Sephadex LH-20 (11 cm×1.3 cm, methanol, gravity) yielded 1 as a colorless oil (0.67 mg, 55%). Material used in isolation of quinalascidin-binding proteins by affinity precipitation was further purified by HPLC (Beckman Ultrasphere ODS reverse phase column, 10 mm×25 mm, flow rate 2.0 mL/min, isocratic elution with 40% acetonitrile-water, retention time 29 min): $R_f$ 0.45, 20% methanol-dichloromethane; $^1$H NMR (600 MHz, CD$_3$OD) δ 8.18 (d, 1H, J=8.4 Hz, CHCHCCONH), 7.85 (d, 1H, J=9.0 Hz, CHCHCCONH), 7.56 (d, 1H, J=9.0 Hz, CHCHCOCH$_2$), 7.40 (dd, 1H, J=9.0, 2.4 Hz, CHCHCOCH$_2$), 7.23 (d, 1H, J=2.4 Hz, CHCOCH$_2$), 4.44–4.48 (m, 2H, CHC≡N, SCH$_2$CHNH), 4.38 (br t, 1H, CHCH$_2$NHCO), 4.27 (dd, 1H, J=7.8, 4.0 Hz, SCHCHNH), 4.21 (br d, 1H, ArCRNCH$_3$), 4.13–4.17 (m, 2H, ArOCH$_2$), 3.94 (dd, 1H, J=13.8, 3.0 Hz, CHCH$_2$NHCO), 3.65 (s, 3H, ArOCH$_3$), 3.60–3.66 (m, 1H, CHCH$_2$NHCO), 3.43 (s, 3H, ArOCH$_3$), 3.41–3.46 (m, 1H, CHCHC≡N), 3.39 (s, 3H, ArOCH$_3$), 3.38 (s, 3H, ArOCH$_3$), 3.28–3.32 (obscured by solvent peak, 1H, ArCHCHCH$_2$Ar), 3.27 (t, 2H, J=7.2 Hz, ArOCH$_2$CH$_2$CH$_2$CH$_2$NHCO), 3.14 (t, 4H, J=7.2 Hz, CH$_2$CH$_2$NHCO, CH$_2$CH$_2$NHCO), 3.13–3.18 (obscured m, SCH), 3.10 (d of m, 1H, J=11.4 Hz, ArCHCHCH$_2$Ar), 3.03 (dd, 1H, J=18.6, 8.4 Hz, CH$_2$CHCHC≡N), 2.89 (dd, 1H, J=12.9, 5.1 Hz, SCH$_2$), 2.68 (d, 1H, J=12.6 Hz, SCH$_2$), 2.61 (d, 1H, J=18.6 Hz, CH$_2$CHCHC≡N), 2.27 (dd, 1H, J=15.9, 11.7 Hz, ArCHCHCH$_2$Ar), 2.22 (s, 3H, NCH$_3$), 2.14–2.22 (m, 6H, CH$_2$CO, CH$_2$CO, CH$_2$CO), 2.11 (s, 3H, ArCH$_3$), 1.86–1.92 (m, 2H, CH$_2$CH$_2$OAr), 1.85 (s, 3H, ArCH$_3$), 1.70–1.76 (m, 2H, ArOCH$_2$CH$_2$CH$_2$), 1.26–1.70 (m, 18 H, COCH$_2$CH$_2$CH$_2$CH$_2$NH (booth), CH$_2$CH$_2$CH$_2$CHS); LRMS (TOF MS ES+) m/z calcd for $C_{65}H_{91}N_{10}O_{12}S$ (M+H)$^+$ 1220, found 1220.

Fluorescein-labelled Quinalascidin Analog 2:

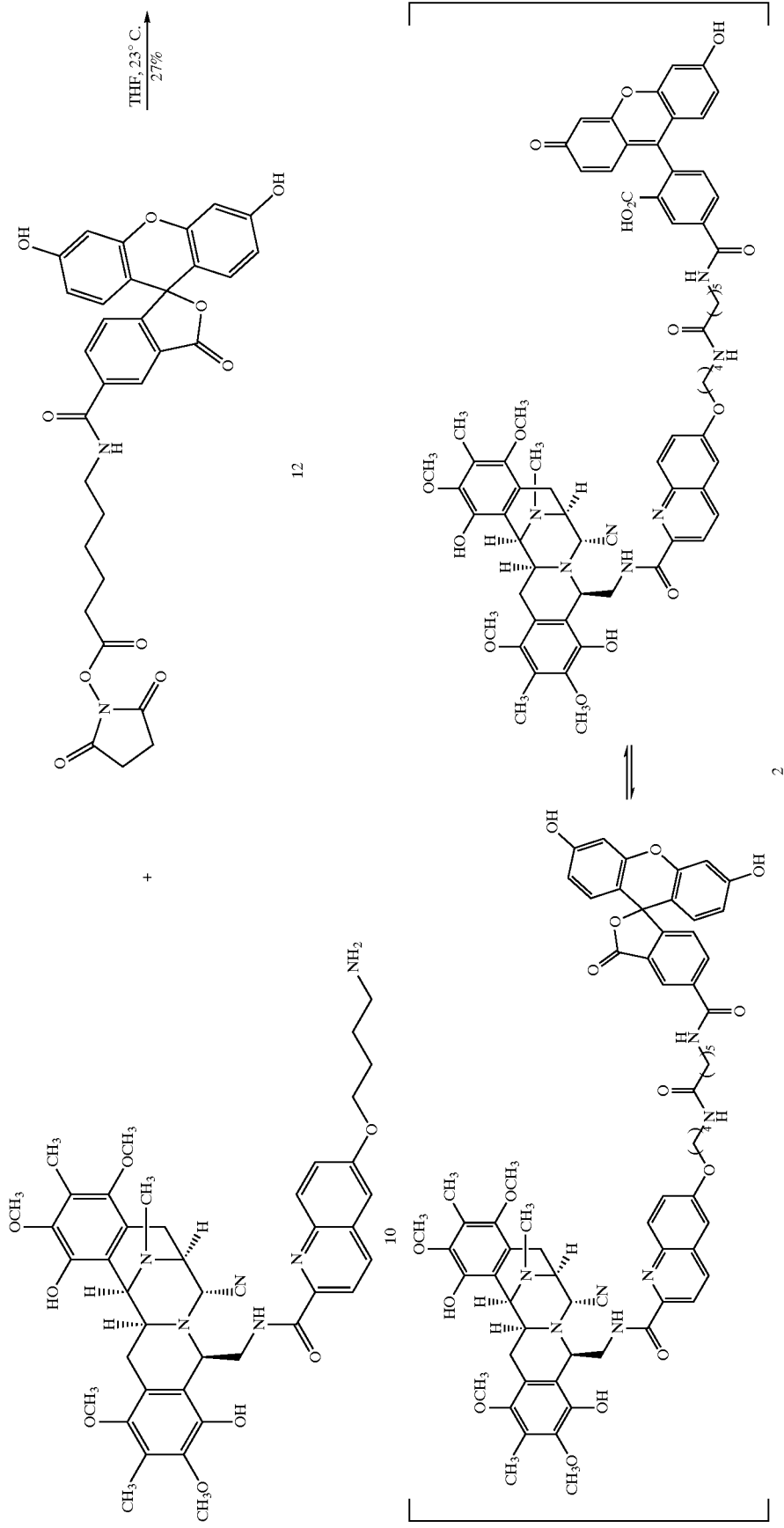

A solution of primary amine 10 (0.695 mg, 0.91 μmol, 1 equiv) and N-hydroxy-succinimidyl ester 12 (Molecular Probes, 0.560 mg, 0.96 μmol, 1.05 equiv) in tetrahydrofuran (0.2 mL) was stirred in the dark at 23° C. for 71 h. The yellow solution was concentrated. The solid residue was purified by HPLC (Beckman Ultrasphere ODS reverse phase column, 10 mm×25 mm, flow rate 2.0 mL/min, gradient elution from 5% to 60% acetonitrile in water over 40 min, injected crude product as a solution in 50% acetonitrile-water (200 μL), retention time 36 min). Fractions containing the desired product were pooled and were concentrated to remove acetonitrile. The residual aqueous solution was lyophilized, yielding fluorescein-labelled analog 2 (0.305 mg, 27%) as an orange solid: $R_f$ 0.49, 20% methanol-dichloromethane; $^1$H NMR (600 MHz, CD$_3$OD) δ 8.44 (br s, 1H, NHCOCCHCO$_2$), 8.16 (d, 1H, J=8.4 Hz, NCCHCH), 8.03 (br m, 1H, CO$_2$CCCHCHCCONH), 7.83 (d, 1H, J=9.0 Hz, NCCHCH), 7.54 (d, 1H, J=8.4 Hz, CHCHCOCH$_2$), 7.38 (dd, 1H, J=9.0, 2.4 Hz, CHCHCOCH$_2$), 7.29 (d, 1H, J=7.8 Hz, CO$_2$CCCHCHCCONH), 7.20 (d, 1H, J=3.0 Hz, CHCOCH$_2$), 6.58–6.67 (br m, 6H, CHCHCOHCH, CHCH-COHCH), 4.45 (d, 1H, J=2.4 Hz, CHC≡N), 4.37 (br s, 1H, CHCH$_2$NHCO), 4.19–4.21 (m, 1H, ArCHNCH$_3$), 4.11–4.14 (m, 2H, ArOCH$_2$), 3.94 (dd, 1H, J=13.2, 3.0 Hz, CHCH$_2$NHCO), 3.64 (s, 3H, ArOCH$_3$), 3.48 (dd, 1H, J=13.5, 3.3 Hz, CHCH$_2$NHCO), 3.44 (t, 2H, J=7.2 Hz, CH$_2$NHCO), 3.42 (s, 3H, ArOCH$_3$), 3.38 (s, 3H, ArOCH$_3$), 3.37 (s, 3H, ArOCH$_3$), 3.28 (t, 2H, J=7.2 Hz, CH$_2$NHCO), 3.09 (d of m, 1H, J=11.4 Hz, ArCHCHCH$_2$Ar), 3.02 (dd, 1H, J=18.6, 7.8 Hz, CH$_2$CHCHCE≡N), 2.60 (d, 1H, J=18.6 Hz, CH$_2$CHCHC≡N), 2.27 (dd, 1H, J=15.6, 11.4 Hz, ArCHCHCH$_2$Ar), 2.24 (t, 2H, J=7.2 Hz, CH$_2$CONH), 2.22 (s, 3H, NCH$_3$), 2.10 (s, 3H, ArCH$_3$), 1.85–1.90 (m, 2H, CH$_2$CH$_2$OAr), 1.83 (s, 3H, ArCH$_3$), 1.66–1.76 (m, 4H, CH$_2$CH$_2$NHCO, CH$_2$CH$_2$NHCO); LRMS (TOF MS ES+) m/z calcd for C$_{69}$H$_{72}$N$_7$O$_{15}$ (M+H)$^+$ 1239, found 1239.

IV, In vitro Activity:

a) Experimentals:

Cells and Cell Culture Conditions

The two cell lines used, A375 malignant melanoma and A-549 lung carcinoma, were purchased from American Type Culture Collection. These cells were cultured at 37° C. in a humidified atmosphere of 5% CO$_2$ in Dulbecco's Modified Eagle Medium (DMEM) supplemented with 10% fetal bovine serum (FBS), 0.1% glutamine and 0.1% penicillin-streptomycin. DMEM, FBS, glutamine and penicillin-streptomycin were purchased from Life Technologies (Grand Island, N.Y.).

Cell Growth Inhibition Assay

Exponentially growing cells were seeded at ~3000 (50 μl) cells per well in 96-well flat-bottomed microtiter plates and then incubated at 37° C. in a humidified atmosphere of 5% CO$_2$/95% air for 24 hr. An analogue was dissolved in dimethyl sulfoxide to give a concentration of 0.6 mg/ml, which was further diluted with the culture medium containing 10% fetal bovine serum. Nine three-fold dilutions were prepared with the maximum concentration being 1/300 of the original DMSO solution (i.e. 2000 ng/ml). This procedure was repeated for each analogue. Fifty microliters of the obtained dilutions were each transferred into the well of the above described culture, plate. The cell culture was then placed back into the incubator at 37° C. under the 5% CO$_2$ atmosphere for 72 hr. Cell proliferation was quantified by using the CellTiter 96 AQ$_{ueous}$ Assay (Promega). In this assay a mixture solution (20 μl) of MTS [Owen's reagent: 3-(4,5-dimethylthiazol-2-yl)-5-(3-carbomethoxyphenyl)-2-(4-sulfophenyl)-2H-tetrazolium inner salt] and phenazine methosulfate (PMS) was added to each well. The resulting mixtures were further incubated for 2.5 hr. The absorbance was measured with a microplate reader at a test wavelength of 540 nm and a reference wavelength of 655 nm to serve as an index of the number of viable cells. The inhibitory ratio of the test compound was calculated according to the following formula: inhibition ratio (%)=100×(C−T)/C, where T is an absorbance of the well containing a test compound and C is an absorbance of the well containing no test compound. The IC$_{50}$ was calculated by the least squares method.

b) Exemplary Data:

TABLE 1

(N = R$_1$ in generic structure, where m is 1)

| | IC$_{50}$, nM$^a$ | |
| --- | --- | --- |
| N = | A375 | A549 |
| Saframycin A (1) | 5.3 | 133 |
| 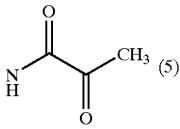 (5) | 4.5 | 160 |
| 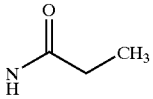 | 52 | 1400 |
| 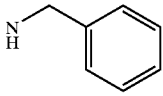 | 330 | 1100 |
| 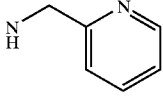 | 260 | 700 |
| N—(Pyr)$_2$ | >1400 | >1400 |
| 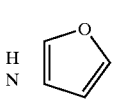 | 370 | 1100 |
| 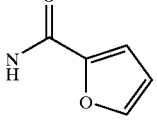 | 13 | 290 |
| 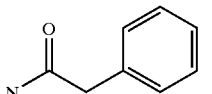 | 34 | 1200 |
| 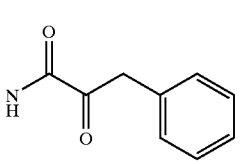 | 2.4 | 39 |

TABLE 1-continued
(N = R₁ in generic structure, where m is 1)
| N = | IC$_{50}$, nM[a] | |
|---|---|---|
| | A375 | A549 |
| 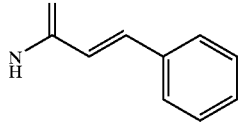 | 3.9 | 50 |
| 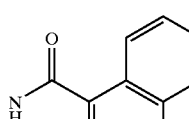 | | |
| R = NO$_2$ | 3.6 | 91 |
| R = CH$_3$ | 1.9 | 37 |
| R = Br | 1.7 | 25 |
| 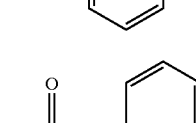 | 12 | 395 |
| 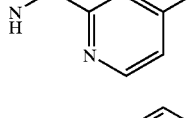 | 14 | 390 |
| 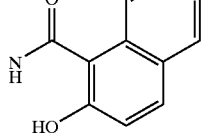 | 8.5 | 100 |
| 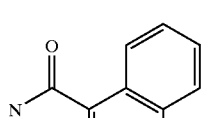 | 3.3 | 40 |
| 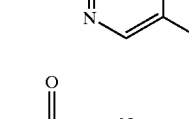 | 4.4 | 100 |
| 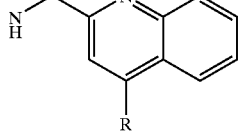 | 2.7 | 31 |
TABLE 1-continued
(N = R₁ in generic structure, where m is 1)
| N = | IC$_{50}$, nM[a] | |
|---|---|---|
| | A375 | A549 |
| 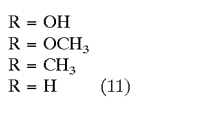 | 2.9 | 44 |
| (naphthalene-1-carboxamide) | 43 | 390 |
| (isoquinoline-1-carboxamide) | 2.5 | 32 |
| (3-hydroxynaphthalene-1-carboxamide) | 23 | 320 |
| (4-bromoisoquinoline-1-carboxamide) | 9.2 | 25 |
| 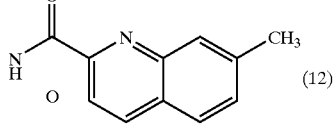 | | |
| R = OH | 11 | 91 |
| R = OCH$_3$ | 3.5 | 6.4 |
| R = CH$_3$ | 2.2 | 4.4 |
| R = H    (11) | 1.3 | 4.4 |
| (12) | 1.4 | 4.6 |
| 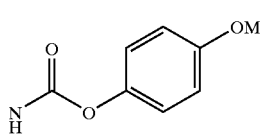 | 3.4 | 96 |

TABLE 1-continued
(N = R₁ in generic structure, where m is 1)
| N = | IC$_{50}$, nM[a] A375 | A549 |
|---|---|---|
| 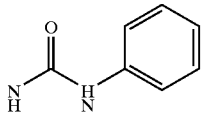 | 37 | 890 |
| 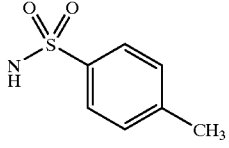 | 81 | 860 |
| 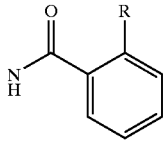 R = Phenyl<br>R = I<br>R = Cl<br>R = Me<br>R = H<br>R = F<br>R = OH  (7) | 34<br>23<br>11<br>7.6<br>4.1<br>2.5<br>1.4 | 330<br>790<br>340<br>350<br>91<br>37<br>14 |
| 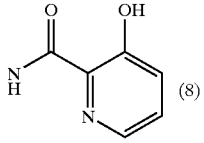 (8) | 1.2 | 11.3 |
| 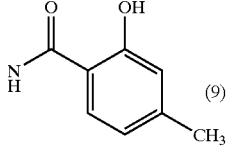 (9) | 1.2 | 6.5 |
| 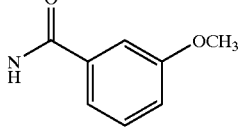 | 4.1 | 99 |
| 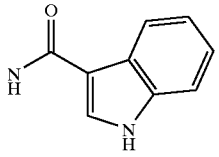 | 76 | 1200 |
| 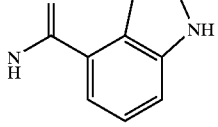 | 85 | 1100 |
TABLE 1-continued
(N = R₁ in generic structure, where m is 1)
| N = | IC$_{50}$, nM[a] A375 | A549 |
|---|---|---|
| 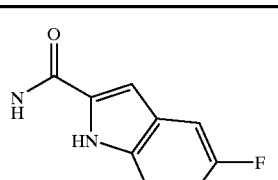 | 2.5 | 26 |
| 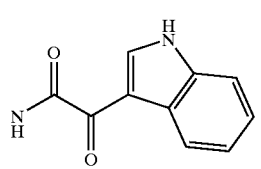 | 9.6 | 110 |
| 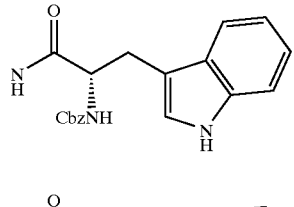 | 96 | 1100 |
| 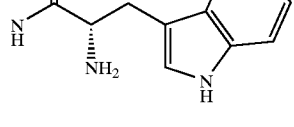 | 310 | >1400 |
| 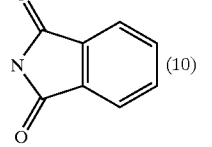 (10) | 1.7 | 9.2 |
| 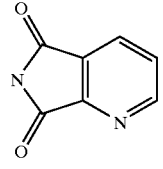 | >510 | >510 |
| 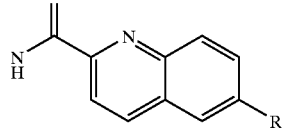<br>R = OH<br>R = OBu<br>R = CH₃<br>R = OCH₃  (13)<br>R = Cl  (14) | <br>29<br>4.7<br>2.5<br>2.0<br>1.5 | <br>120<br>13<br>4.0<br>3.5<br>4.1 |

TABLE 1-continued (N = R₁ in generic structure, where m is 1)

| N = | IC$_{50}$, nM[a] | |
|---|---|---|
| | A375 | A549 |
| 7-chloro-4-hydroxyquinoline-2-carboxamide | 7.5 | 42 |
| 6-chloro-4-hydroxyquinoline-2-carboxamide | 13 | 74 |
| quinoxaline-2-carboxamide (15) | 1.2 | 4.7 |

TABLE 1-continued (N = R₁ in generic structure, where m is 1)

| N = | IC$_{50}$, nM[a] | |
|---|---|---|
| | A375 | A549 |
| quinoline-2-(N-methyl)carboxamide (16)[10] | 3.6 | 78 |
| (S)-1,2,3,4-tetrahydroisoquinoline-3-carboxamide | 8.3 | 200 |
| 1,2,3,4-tetrahydroisoquinoline-1-carboxamide (diastereoisomers) | 34<br>42 | 975<br>1100 |

TABLE 2

| | IC$_{50}$ (nM) | |
|---|---|---|
| | Cell line | |
| | A375-Melanoma | A549-Lung |
| [complex ecteinascidin-like structure with OCH₃, OH, CH₃, CN, NHFmoc substituents] | 35 | 176 |

TABLE 2-continued
| | IC$_{50}$ (nM) Cell line | |
|---|---|---|
| | A375-Melanoma | A549-Lung |
| 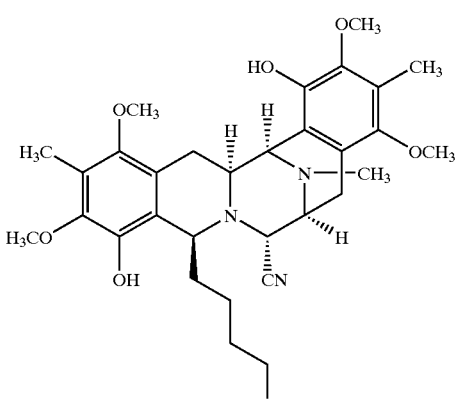 | 116 | 1400 |
| 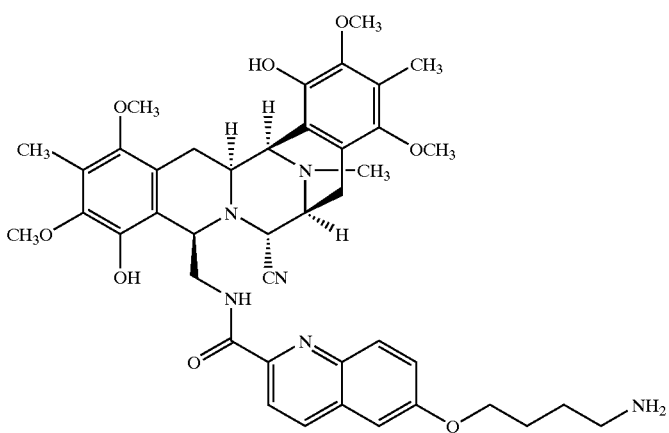 | 29 | 118 |
| Biotinylated derivative | 210 | 990 |
| Fluorescein derivative | 18 | 590 |

TABLE 3

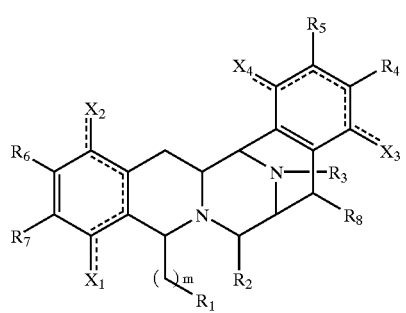

| X | IC$_{50}$ (nM) Cell line | |
|---|---|---|
| | A375-Melanoma | A549-Lung |
| OH | 0.9 | 13 |
| OCH$_3$ | 120 | 1100 |
| H | >9000 | >9000 |

V, In vivo Activity:

Although a variety of methods can be utilized, one exemplary method by which the in vivo activity of the inventive compounds is determined is by subcutaneously transplanting a desired tumor mass in mice. Drug treatment is then initiated when tumor mass reaches approximately 100 mm$^3$ after transplantation of the tumor mass. A suitable composition, as described in more detail above, is then administered to the mice, preferably in saline and also preferably administered once a day at doses of 5, 10 and 25 mg/kg, although it will be appreciated that other doses can also be administered. Body weight and tumor size are then measured daily and changes in percent ratio to initial values are plotted. In cases where the transplanted tumor ulcerates, the weight loss exceeds 25–30% of control weight loss, the tumor weight reaches 10% of the body weight of the cancer-bearing mouse, or the cancer-bearing mouse is dying, the animal is sacrificed in accordance with guidelines for animal welfare.

What is claimed is:

1. A compound having the structure (I):

(I)

wherein:

m is 0, 2, 3, 4, or 5;

R$_1$ is —NR$_A$R$_B$ wherein R$_A$ and R$_B$ are independently hydrogen, —(C=O)R$_C$, —NHR$_C$, —(SO$_2$)R$_C$, —OR$_C$, or an aliphatic, heteroaliphatic, aryl, or heteroaryl moiety, or R$_A$ and R$_B$, when taken together form an heteroaryl or cycloheteroaliphatic moiety, wherein each occurrence of R$_C$ is independently hydrogen, —OR$_D$, —SR$_D$, —NHR$_D$, —(C=O)R$_D$, or an aliphatic, heteroaliphatic, aryl, or heteroaryl moiety, wherein each occurrence of R$_D$ is independently hydrogen, or an aliphatic, heteroaliphatic, aryl, heteroaryl, acyl, alkoxy, aryloxy, alkylthio, arylthio, heteroaryloxy, or heteroarylthio moiety;

wherein R$_2$ is hydrogen, —OR$_E$, =O, —C(=O)R$_E$, —CO$_2$R$_E$, —CN, —SCN, halogen, —SR$_E$, —SOR$_E$, —SO$_2$R$_E$, —NO$_2$, —N(R$_E$)$_2$, —NHC(O)R$_E$, or an aliphatic, heteroaliphatic, aryl, or heteroaryl moiety, wherein each occurrence of R$_E$ is independently hydrogen, or an aliphatic, heteroaliphatic, aryl, heteroaryl, acyl, alkoxy, aryloxy, alkylthio, arylthio, heteroaryloxy, or heteroarylthio moiety;

wherein R$_3$ is hydrogen, —COOR$_F$, —COR$_F$, —CN, or an aliphatic, heteroaliphatic, aryl, or heteroaryl moiety, wherein each occurrence of R$_F$ is independently hydrogen, or an aliphatic, heteroaliphatic, aryl, heteroaryl, alkoxy, aryloxy, alkylthio, arylthio, heteroaryloxy, or heteroarylthio moiety;

wherein:

the foregoing aliphatic or heteroaliphatic moieties in R$_1$, R$_2$ and R$_3$ may independently be unsubstituted or substituted with one or more substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —NO$_2$, —CN, —SCN, —CF$_3$, —CHCF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —S(O)$_2$R$_x$, or —B(OR$_x$)$_2$ wherein each occurrence of R$_x$ independently is aliphatic, heteroaliphatic, aryl, heteroaryl, alkylaryl, or alkylheteroaryl where each of the foregoing aliphatic and heteroaliphatic moiety is unsubstituted; and each of the foregoing aryl, heteroaryl, or cycloheteroaliphatic moieties in R$_1$, R$_2$ and R$_3$ may independently be unsubstituted or substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —NO$_2$, —CN, —SCN, —CF$_3$, —CHCF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —N(R$_x$)$_2$, —S(O)$_2$R$_x$, —NR$_x$(CO)R$_x$, or —B(OR$_x$)$_2$ wherein each occurrence of R$_x$ independently is aliphatic, heteroaliphatic, aryl, heteroaryl, alkylaryl, or alkylheteroaryl where each of the foregoing aliphatic, heteroaliphatic, aryl, heteroaryl, alkylaryl, alkylheteroaryl, aryloxy, heteroaryloxy, arylthio, and heteroarylthio moiety is unsubstituted;

wherein R$_4$ and R$_6$ are each independently hydrogen, or an aliphatic, heteroaliphatic, aryl, heteroaryl, acyl, alkoxy, aryloxy, alkylthio, arylthio, heteroaryloxy, or heteroarylthio moiety where the foregoing aliphatic, heteroaliphatic, aryl, heteroaryl, aryloxy, arylthio, heteroaryloxy and heteroarylthio moieties in R$_4$ and R$_6$ are unsubstituted;

wherein R$_5$ and R$_7$ are each independently hydrogen, —OR$_G$, —C(=O)R$_G$, —CO$_2$R$_G$, —CN, —SCN, halogen, —SR$_G$, —SOR$_G$, —SO$_2$R$_G$, —NO$_2$, —N(R$_G$)$_2$, —NHC(O)R$_G$, or an aliphatic, heteroaliphatic, aryl or heteroaryl moiety, wherein each occurrence of R$_G$ is independently hydrogen, or an aliphatic, heteroaliphatic, aryl, heteroaryl, acyl, alkoxy, aryloxy, alkylthio, arylthio, heteroaryloxy, or heteroarylthio moiety where the each of the foregoing aliphatic, heteroaliphatic, aryl, heteroaryl, aryloxy, arylthio, heteroaryloxy and heteroarylthio moiety in R$_5$ and R$_6$ is unsubstituted;

wherein R$_8$ is hydrogen, alkyl, —OH, =O, —CN, —SCN, halogen, —SH, alkoxy, thioalkyl, amino, or alkylamino;

wherein X$_1$, X$_2$, X$_3$ and X$_4$ are each independently hydrogen, —OR$_H$, =O, —C(=O)R$_H$, —CO$_2$R$_H$, —CN, —SCN, halogen, —SR$_H$, —SOR$_H$, —SO$_2$R$_H$, —NO$_2$, —N(R$_H$)$_2$, —NHC(O)R$_H$, or an aliphatic, heteroaliphatic, aryl, or heteroaryl moiety, wherein each occurrence of R$_H$ is independently hydrogen, or an aliphatic, heteroaliphatic, aryl, heteroaryl, acyl, alkoxy, aryloxy, alkylthio, arylthio, heteroaryloxy, or heteroarylthio moiety where each of the foregoing aliphatic, heteroaliphatic, aryl, heteroaryl, aryloxy, arylthio, heteroaryloxy and heteroarylthio moiety in X$_1$, X$_2$, X$_3$ and X$_4$ is unsubstituted;

whereby if at least either X$_1$ and X$_2$ or X$_3$ and X$_4$ are doubly bonded to the 6-membered ring, then the dotted bonds in either or both of the 6-membered rings represent two single bonds and one double bond, and a quinone moiety is generated, or if at least either X$_1$ and X$_2$ or X$_3$ and X$_4$ are singly bonded to the 6-membered ring, then the dotted bonds in either or both of the 6-membered rings represent two double bonds and one single bond, and a hydroquinone moiety is generated; wherein:

each of foregoing acyl, alkoxy, alkylthio, thioalkyl, or alkylamino contains unsubstituted cyclic, acyclic, branched or unbranched alkyl of 1 to 10 carbon atoms;

each of the foregoing aliphatic moiety is cyclic, acyclic, branched or unbranched alkyl, alkenyl, or alkynyl containing 1 to 10 carbon atoms;

each of the foregoing heteroaliphatic moiety is cyclic, acyclic, branched or unbranched alkyl, alkenyl, or alkynyl containing 1 to 10 carbon atoms and which further contains one or more oxygen, sulfur, nitrogen, phosphorus or silicon atoms in place of the carbon atoms;

each of the foregoing cycloheteroaliphatic moiety is a cyclic heteroaliphatic;

each of the foregoing aryl is monocyclic or bicyclic carbocyclic ring system having one or two aromatic ring;

each of the foregoing heteroaryl is a cyclic aromatic radical having from five to ten ring atoms of which one ring atom is selected from S, O, and N; zero or two ring atoms are additional heteroatoms independently selected from S, O, and N; and the remaining ring atoms are carbon; and pharmaceutically acceptable salts thereof.

2. The compound of claim 1, wherein m is 0.
3. The compound of claim 1, wherein m is 2, 3, 4, or 5.
4. The compound of claim 2, wherein:
R$_2$ is —CN, —SCN, =O, —OH, H, or alkoxy;
R$_3$ is hydrogen, —CN, —CH$_2$CN, aliphatic, or aryl;
R$_4$ and R$_6$ are each unsubstituted alkyl;
R$_5$ and R$_7$ are each alkyloxy or thioalkyl;
R$_8$ is hydrogen, alkyl, —OH, =O, —CN, halogen, —SH, alkoxy, thioalkyl, amino, or alkylamino; and
X$_1$, X$_2$, X$_3$, and X$_4$ are each independently alkoxy, —OH, or =O.

5. The compound of claim 3 wherein:
R$_2$ is —CN, —SCN, =O, —OH, H, or alkoxy;
R$_3$ is hydrogen, —CN, —CH$_2$CN, aliphatic, or aryl;
R$_4$ and R$_6$ are each unsubstituted alkyl;
R$_5$ and R$_7$ are each alkyloxy or thioalkyl;
R$_8$ is hydrogen, alkyl, —OH, =O, —CN, halogen, —SH, alkoxy, thioalkyl, amino, or alkylamino; and
X$_1$, X$_2$, X$_3$, and X$_4$ are each independently alkoxy, —OH, or =O.

6. The compound of claim 1, wherein the compound has the structure:

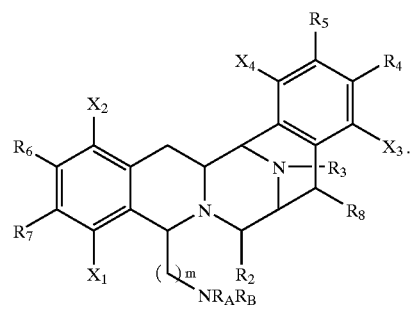

7. The compound of claim 6, wherein m is 0.
8. The compound of claim 6, wherein m is 2, 3, 4, or 5.
9. The compound of claim 7, wherein:
R$_A$ is hydrogen or unsubstituted lower alkyl;
R$_B$ is —COR$_C$ where R$_C$ is (heteroaliphatic)aryl, substitued heteroaryl, substituted (aliphatic)heteroaryl, or substituted (heteroaliphatic)heteroaryl moiety or R$_A$ and R$_B$, when taken together form cycloheteroaliphatic;
R$_2$ is —CN, —SCN, =O, —OH, H, or alkoxy;
R$_3$ is hydrogen, —CN, —CH$_2$CN, aliphatic, or aryl;
R$_4$ and R$_6$ are each unsubstituted alkyl;
R$_5$ and R$_7$ are each alkyloxy or thioalkyl;
R$_8$ is hydrogen, alkyl, —OH, =O, —CN, halogen, —SH, alkoxy, thioalkyl, amino, or alkylamino; and
X$_1$, X$_2$, X$_3$, and X$_4$ are each independently alkoxy, or —OH.

10. The compound of claim 9, wherein:
R$_C$ is:

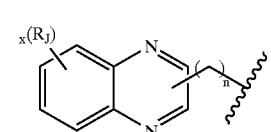

iii

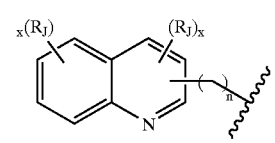

iv wherein each occurrence of $R_J$ is independently —$OR_K$, —C(=O)$R_K$, —$CO_2R_K$, —CN, —SCN, halogen, —$SR_K$, $SOR_K$, —$SO_2R_K$, $NO_2$, —N($R_K$)$_2$, —NHC(O)$R_K$, —B($OR_K$)$_2$, or an aliphatic, heteroaliphatic, aryl, or heteroaryl moiety, wherein each occurrence of $R_K$ is independently hydrogen, or an aliphatic, heteroaliphatic, aryl, or heteroaryl moiety, or wherein two occurrences of $R_K$, taken together form a cyclic aliphatic or heteroaliphatic moiety; wherein each occurrence of Y is independently O, S or NH; wherein each occurrence of x is independently 1–5; and wherein each occurrence of n is independently 0–3 wherein:

the foregoing aliphatic or heteroaliphatic is unsubstituted and each of the foregoing aryl or heteroaryl moieties may independently be unsubstituted or substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCF_3$, —$CHCl_2$, —$CH_2OH$, —$CH_2CH_2OH$, —$CH_2NH_2$, —$CH_2SO_2CH_3$, —C(O)$R_x$, —$CO_2$($R_x$), —CON($R_x$)$_2$, —OC(O)$R_x$, —$OCO_2R_x$, —OCON($R_x$)$_2$, —N($R_x$)$_2$, —S(O)$_2R_x$, —$NR_x$(CO)$R_x$, or —B(O$R_x$)$_2$ wherein each occurrence of wherein each occurrence of $R_x$ independently is aliphatic, heteroaliphatic, aryl, heteroaryl, alkylaryl, or alkylheteroaryl where each of the foregoing aliphatic, heteroaliphatic, heteroaryl, alkylaryl, alkylheteroaryl, aryloxy, heteroaryloxy, arylthio, and heteroarylthio is unsubstituted; and wherein:
each of the foregoing aliphatic moiety is cyclic, acyclic, branched or unbranched alkyl, alkenyl, or alkynyl containing 1 to 10 carbon atoms;

each of the foregoing heteroaliphatic moiety is cyclic, acyclic, branched or unbranched alkyl, alkenyl, or alkynyl containing 1 to 10 carbon atoms and which further contains one or more oxygen, sulfur, nitrogen, phosphorus or silicon atoms in place of the carbon atoms;

each of the foregoing aryl is monocyclic or bicyclic carbocyclic ring system having one or two aromatic ring;

each of the foregoing heteroaryl is a cyclic aromatic radical having from five to ten ring atoms of which one ring atom is selected from S, O, and N; zero or two ring atoms are additional heteroatoms independently selected from S, O, and N; and the remaining ring atoms are carbon.

11. The compound of claim 8, wherein:
$R_A$ is hydrogen or unsubstituted lower alkyl;
$R_B$ is —$COR_C$ where $R_C$ is (heteroaliphatic)aryl, substituted heteroaryl, substituted (aliphatic)heteroaryl, or substituted (heteroaliphatic)heteroaryl moiety or $R_A$ and $R_B$, when taken together form cycloheteroaliphatic;

R$_2$ is —CN, —SCN, =O, —OH, H, or alkoxy;

R$_3$ is hydrogen, —CN, —CH$_2$CN, aliphatic, or aryl;

R$_4$ and R$_6$ are each unsubstituted alkyl;

R$_5$ and R$_7$ are each alkyloxy or thioalkyl;

R$_8$ is hydrogen, alkyl, —OH, =O, —CN, halogen, —SH, alkoxy, thioalkyl, amino, or alkylamino; and X$_1$, X$_2$, X$_3$, and X$_4$ are each independently alkoxy or —OH.

12. The compound of claim 11, wherein:

R$_C$ is:

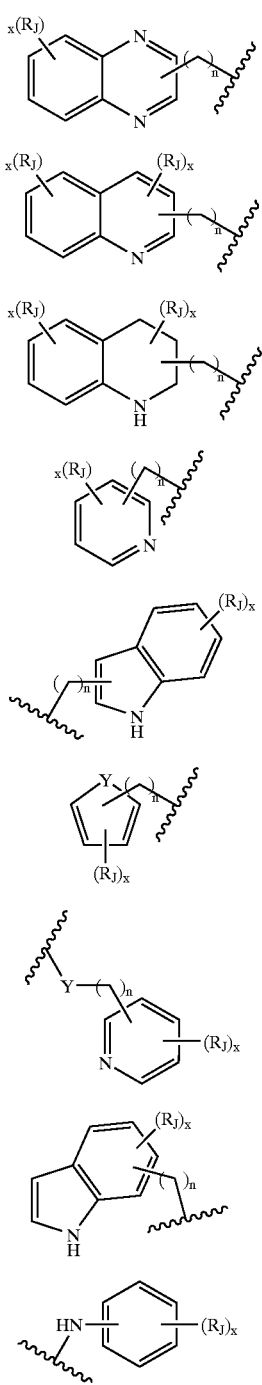

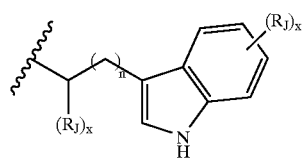

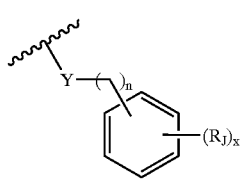

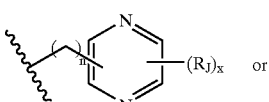

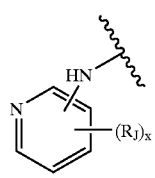

wherein each occurrence of R$_J$ is independently —OR$_K$, —C(=O)R$_K$, —CO$_2$R$_K$, —CN, —SCN, halogen, —SR$_K$, —SOR$_K$, —SO$_2$R$_K$, —NO$_2$, —N(R$_K$)$_2$, —NHC(O)R$_K$, —B(OR$_K$)$_2$, or an aliphatic, heteroaliphatic, aryl, or heteroaryl moiety, wherein each occurrence of R$_K$ is independently hydrogen, or an aliphatic, heteroaliphatic, aryl, or heteroaryl moiety, or wherein two occurrences of R$_K$, taken together form a cyclic aliphatic or heteroaliphatic moiety; wherein each occurrence of Y is independently O, S or NH; wherein each occurrence of x is independently 1–5; and wherein each occurrence of n is independently 0–3 wherein:

the foregoing aliphatic or heteroaliphatic is unsubstituted and each of the foregoing aryl or heteroaryl moieties may independently be unsubstituted or substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —NO$_2$, —CN, —SCN, —CF$_3$, —CHCF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —N(R$_x$)$_2$, —S(O)$_2$R$_x$, —NR$_x$(CO)R$_x$, or —B(OR$_x$)$_2$ wherein each occurrence of wherein each occurrence of R$_x$ independently is aliphatic, heteroaliphatic, aryl, heteroaryl, alkylaryl, or alkylheteroaryl where each of the foregoing aliphatic, heteroaliphatic, heteroaryl, alkylaryl, alkylheteroaryl, aryloxy, heteroaryloxy, arylthio, and heteroarylthio is unsubstituted; and wherein:

each of the foregoing aliphatic moiety is cyclic, acyclic, branched or unbranched alkyl, alkenyl, or alkynyl containing 1 to 10 carbon atoms;

each of the foregoing heteroaliphatic moiety is cyclic, acyclic, branched or unbranched alkyl, alkenyl, or alkynyl containing 1 to 10 carbon atoms and which further contains one or more oxygen, sulfur, nitrogen, phosphorus or silicon atoms in place of the carbon atoms;

each of the foregoing aryl is monocyclic or bicyclic carbocyclic ring system having one or two aromatic ring;

each of the foregoing heteroaryl is a cyclic aromatic radical having from five to ten ring atoms of which one ring atom is selected from S, O, and N; zero or two ring atoms are additional heteroatoms independently selected from S, O, and N; and the remaining ring atoms are carbon.

13. A compound having the structure (I):

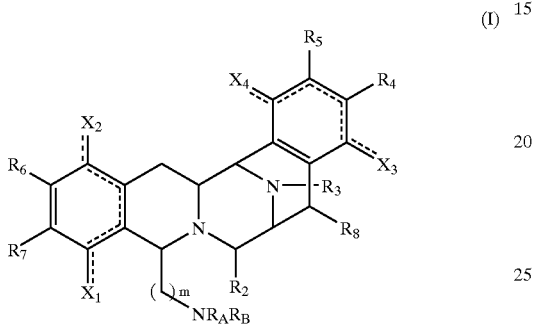

(I)

wherein:

m is 1;

$R_A$ is hydrogen or unsubstituted lower alkyl; and $R_B$ is —$COR_C$ where $R_C$ is (heteroaliphatic)aryl, substituted heteroaryl, substituted (aliphatic)heteroaryl, or substituted (heteroaliphatic)heteroaryl moiety or $R_A$ and $R_B$, when taken together form cycloheteroaliphatic;

wherein $R_2$ is hydrogen, —$OR_E$, =O, —$C(=O)R_E$, —$CO_2R_E$, —CN, —SCN, halogen, —$SR_E$, —$SOR_E$, —$SO_2R_E$, —$NO_2$, —$N(R_E)_2$, —$NHC(O)R_E$, or an aliphatic, heteroaliphatic, aryl, or heteroaryl moiety, wherein each occurrence of $R_E$ is independently hydrogen, or an aliphatic, heteroaliphatic, aryl, heteroaryl, acyl, alkoxy, aryloxy, alkylthio, arylthio, heteroaryloxy, or heteroarylthio moiety;

wherein $R_3$ is hydrogen, —$COOR_F$, —$COR_F$, —CN, or an aliphatic, heteroaliphatic, aryl, or heteroaryl moiety, wherein each occurrence of $R_F$ is independently hydrogen, or an aliphatic, heteroaliphatic, aryl, heteroaryl, alkoxy, aryloxy, alkylthio, arylthio, heteroaryloxy, or heteroarylthio moiety;

wherein:

the foregoing aliphatic or heteroaliphatic moieties in $R_A$, $R_B$, $R_2$ and $R_3$ may independently be unsubstituted or substituted with one or more substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCF_3$, —$CHCl_2$, —$CH_2OH$, —$CH_2CH_2OH$, —$CH_2NH_2$, —$CH_2SO_2CH_3$, —$C(O)R_x$, —$CO_2(R_x)$, —$CON(R_x)_2$, —$OC(O)R_x$, —$OCO_2R_x$, —$OCON(R_x)_2$, —$S(O)_2R_x$, or —$B(OR_x)_2$ wherein each occurrence of $R_x$ independently is aliphatic, heteroaliphatic, aryl, heteroaryl, alkylaryl, or alkylheteroaryl where each of the foregoing aliphatic and heteroaliphatic moiety is unsubstituted; and each of the foregoing aryl, heteroaryl, or cycloheteroaliphatic moieties in $R_A$, $R_B$, $R_2$ and $R_3$ may independently be unsubstituted or substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCF_3$, —$CHCl_2$, —$CH_2OH$, —$CH_2CH_2OH$, —$CH_2NH_2$, —$CH_2SO_2CH_3$, —$C(O)R_x$, —$CO_2(R_x)$, —$CON(R_x)_2$, —$OC(O)R_x$, —$OCO_2R_x$, —$OCON(R_x)_2$, —$N(R_x)_2$, —$S(O)_2R_x$, —$NR_x(CO)R_x$, or —$B(OR_x)_2$ wherein each occurrence of wherein each occurrence of $R_x$ independently is aliphatic, heteroaliphatic, aryl, heteroaryl, alkylaryl, or alkylheteroaryl where each of the foregoing aliphatic, heteroaliphatic, aryl, heteroaryl, alkylaryl, alkylheteroaryl, aryloxy, arylthio, heteroaryloxy and heteroarylthio moiety is unsubstituted; and wherein $R_4$ and $R_6$ are each independently hydrogen, or an aliphatic, heteroaliphatic, aryl, heteroaryl, acyl, alkoxy, aryloxy, alkylthio, arylthio, heteroaryloxy, or heteroarylthio moiety where the foregoing aliphatic, heteroaliphatic, aryl, heteroaryl, aryloxy, arylthio, heteroaryloxy and heteroarylthio moieties in $R_4$ and $R_6$ are unsubstituted;

wherein $R_5$ and $R_7$ are each independently hydrogen, —$OR_G$, —$C(=O)R_G$, —$CO_2R_G$, —CN, —SCN, halogen, —$SR_G$, —$SOR_G$, —$SO_2R_G$, —$NO_2$, —$N(R_G)_2$, —$NHC(O)R_G$, or an unsubstituted aliphatic, unsubstituted heteroaliphatic, unsubstituted aryl or unsubstituted heteroaryl moiety, wherein each occurrence of $R_G$ is independently hydrogen, or an aliphatic, heteroaliphatic, aryl, heteroaryl, acyl, alkoxy, aryloxy, alkylthio, arylthio, heteroaryloxy, or heteroarylthio moiety where each of the foregoing aliphatic, heteroaliphatic, aryl, heteroaryl, aryloxy, arylthio, heteroaryloxy and heteroarylthio moieties in $R_5$ and $R_7$ is unsubstituted;

wherein $R_8$ is hydrogen, alkyl, —OH, =O, —CN, —SCN, halogen, —SH, alkoxy, thioalkyl, amino, or alkylamino;

wherein $X_1$, $X_2$, $X_3$ and $X_4$ are each independently hydrogen, —$OR_H$, =O, —$C(=O)R_H$, —$CO_2R_H$, —CN, —SCN, halogen, —$SR_H$, —$SOR_H$, —$SO_2R_H$, —$NO_2$, —$N(R_H)_2$, —$NHC(O)R_H$, or an aliphatic, heteroaliphatic, aryl, or heteroaryl moiety, wherein each occurrence of $R_H$ is independently hydrogen, or an aliphatic, heteroaliphatic, aryl, heteroaryl, acyl, alkoxy, aryloxy, alkylthio, arylthio, heteroaryloxy, or heteroarylthio moiety where each of the foregoing aliphatic, heteroaliphatic, aryl, heteroaryl, aryloxy, arylthio, heteroaryloxy and heteroarylthio moiety in $X_1$, $X_2$, $X_3$ and $X_4$ is unsubstituted;

whereby if at least either $X_1$ and $X_2$ or $X_3$ and $X_4$ are doubly bonded to the 6-membered ring, then the dotted bonds in either or both of the 6-membered rings represent two single bonds and one double bond, and a quinone moiety is generated, or if at least either $X_1$ and $X_2$ or $X_3$ and $X_4$ are singly bonded to the 6-membered ring, then the dotted bonds in either or both of the 6-membered rings represent two double bonds and one single bond, and a hydroquinone moiety is generated;

wherein:

each of foregoing acyl, alkoxy, alkylthio, thioalkyl, or alkylamino contains unsubstituted cyclic, acyclic, branched or unbranched alkyl of 1 to 10 carbon atoms;

each of the foregoing aliphatic moiety is cyclic, acyclic, branched or unbranched alkyl, alkenyl, or alkynyl containing 1 to 10 carbon atoms;

each of the foregoing heteroaliphatic moiety is cyclic, acyclic, branched or unbranched alkyl, alkenyl, or alkynyl containing 1 to 10 carbon atoms and which further contains one or more oxygen, sulfur, nitrogen, phosphorus or silicon atoms in place of the carbon atoms;

each of the foregoing cycloheteroaliphatic moiety is a cyclic heteroaliphatic;

each of the foregoing aryl is monocyclic or bicyclic carbocyclic ring system having one or two aromatic ring;

each of the foregoing heteroaryl is a cyclic aromatic radical having from five to ten ring atoms of which one ring atom is selected from S, O, and N; zero or two ring atoms are additional heteroatoms independently selected from S, O, and N; and the remaining ring atoms are carbon; and pharmaceutically acceptable salts thereof provided that:

(i) it is not saframycin A, B, E, H, $Y_{d1}$, $Y_{d2}$, $Y_{2b}$, $Y_{2b-d}$, $AH_2$, $AH_2Ac$, $AH_1$, $AH_1Ac$, $AR_3$, $M_{x-1}$, and $M_{x-2}$;

(ii) $R_1$ is not —NHCOC(Me)(OMe)(OMe), —NHCOCH($NH_2$)$CH_3$, —NHCOCH(NH(acyl) $CH_3$, —NHCOCH($NH_2$)Ac, or —NHCOCH (NHCOOBn)(Me);

(iii) when $X_1$, $X_2$, $X_3$, and $X_4$ are each =O; when $R_2$ is —CN, or —OH; when $R_4$ and $R_6$ are each —$CH_3$; when $R_5$ and $R_7$ are each —$OCH_3$; when $R_8$ is H; and $R_1$ is —NH(C=O)$R_C$, then $R_C$ is not —CH($NR_WR_Y$)(CHR$_Z$) where $R_W$ and $R_Y$ are each independently hydrogen or $C_{1-7}$ alkyl, aryl($C_{1-4}$) alkyl, ($C_{1-4}$)alkylaryl, or a substituted sulfonyl (—S(O)$_2$—) group, or a substituted acyl group, and where $R_Z$ is hydrogen or $C_{1-4}$alkyl;

(iv) when $X_1$, $X_2$, $X_3$, and $X_4$ are each =O; when $R_2$ is —CN; when $R_4$ and $R_6$ are each —$CH_3$; when $R_5$ and $R_7$ are each —$OCH_3$; when $R_8$ is H; and $R_1$ is —NH(C=O)$R_C$, then $R_C$ is not —C(OH) (Me)$CH_2$(C=O)Me; and (v) when $R_2$ is H; and $R_1$ is —NH(C=O)$R_C$, then $R_C$ is not —CH(Me)NHC(=O)O($CH_2$)Ph.

14. The compound of claim 13, wherein the aliphatic and heteroaliphatic moieties in $R_1$, $R_2$, and $R_3$ are unsubstituted.

15. The compound of claim 14, wherein:

$R_2$ is —CN, —SCN, =O, —OH, H, or alkoxy;

$R_3$ is hydrogen, —CN, —$CH_2$CN, unsubstituted aliphatic, or aryl;

$R_4$ and $R_6$ are each alkyl;

$R_5$ and $R_7$ are each alkyloxy or thioalkyl;

$R_8$ is hydrogen, alkyl, —OH, =O, —CN, halogen, —SH, alkoxy, thioalkyl, amino, or alkylamino; and $X_1$, $X_2$, $X_3$, and $X_4$ are each independently alkoxy, —OH, or =O.

16. A compound that has the structure:

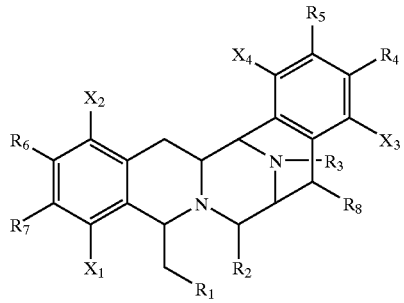

wherein:

$R_1$ is $NR_AR_B$ wherein $R_A$ is hydrogen or unsubstituted lower alkyl, $R_B$ is —$COR_C$ where $R_C$ is (heteroaliphatic)aryl, substitued heteroaryl, substituted (aliphatic)heteroaryl, or substituted (heteroaliphatic) heteroaryl moiety or $R_A$ and $R_B$, when taken together form cycloheteroaliphatic wherein:

the foregoing aliphatic or heteroaliphatic moieties in $R_1$ is unsubstituted;

the foregoing aryl moiety in $R_1$ may independently be unsubstituted or substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCF_3$, —$CHCl_2$, —$CH_2OH$, —$CH_2CH_2OH$, —$CH_2NH_2$, —$CH_2SO_2CH_3$, —C(O)$R_x$, —$CO_2(R_x)$, —CON($R_x$)$_2$, —OC(O)$R_x$, —$OCO_2R_x$, —OCON ($R_x$)$_2$, —N($R_x$)$_2$, —S(O)$_2R_x$, —$NR_x$ (CO)$R_x$, or —B(O$R_x$)$_2$ wherein each occurrence of $R_x$ independently is aliphatic, heteroaliphatic, aryl, heteroaryl, alkylaryl, or alkylheteroaryl where each of the foregoing aliphatic, heteroaliphatic, unsubstituted aryl, heteroaryl, alkylaryl, alkylheteroaryl, alkylaryl, alkylheteroaryl, aryloxy, heteroaryloxy, arylthio, and heteroarylthio is unsubstituted; and the foregoing heteroaryl moieties in $R_1$ is substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCF_3$, —$CHCl_2$, —$CH_2OH$, —$CH_2CH_2OH$, —$CH_2NH_2$, —$CH_2SO_2CH_3$, —C(O)$R_x$, —$CO_2(R_x)$, —CON($R_x$)$_2$, —OC(O)$R_x$, —$OCO_2R_x$, —OCON($R_x$)$_2$, —N($R_x$)$_2$, —S(O)$_2R_x$, —$NR_x$(CO)$R_x$, or —B(O$R_x$)$_2$ wherein each occurrence of wherein each occurrence of $R_x$ independently is aliphatic, heteroaliphatic, aryl, heteroaryl, alkylaryl, or alkylheteroaryl where each of the foregoing aliphatic, heteroaliphatic, aryl, heteroaryl, alkylaryl, alkylheteroaryl, aryloxy, heteroaryloxy, arylthio, and heteroarylthio is unsubstituted;

$R_2$ is —CN, —SCN, —OH, H, or alkoxy;

$R_3$ is hydrogen, aliphatic, or aryl;

$R_4$ and $R_6$ are each alkyl;

$R_5$ and $R_7$ are each alkyloxy or thioalkyl;

$R_8$ is hydrogen, alkyl, —OH, =O, —CN, halogen, —SH, alkoxy, thioalkyl, amino, or alkylamino;

$X_1$ and $X_4$ are each —OH; and $X_2$ and $X_3$ are each alkoxy or thioalkyl; and wherein:

each of foregoing alkoxy, alkylthio, thioalkyl, or alkylamino contains unsubstituted alkyl of 1 to 10 carbon atoms;

each of the foregoing aliphatic moiety is cyclic, acyclic, branched or unbranched alkyl, alkenyl, or alkynyl containing 1 to 10 carbon atoms;

each of the foregoing heteroaliphatic moiety is cyclic, acyclic, branched or unbranched alkyl, alkenyl, or alkynyl containing 1 to 10 carbon atoms and which further contains one or more oxygen, sulfur, nitrogen, phosphorus or silicon atoms in place of the carbon atoms;

each of the foregoing cycloheteroaliphatic moiety is a cyclic heteroaliphatic;

each of the foregoing aryl is monocyclic or bicyclic carbocyclic ring system having one or two aromatic ring;

each of the foregoing heteroaryl is a cyclic aromatic radical having from five to ten ring atoms of which one ring atom is selected from S, O, and N; zero or two ring atoms are additional heteroatoms independently selected from S, O, and N; and the remaining ring atoms are carbon; and pharmaceutically acceptable salts thereof.

17. The compound of claim 16, wherein $R_2$ is —CN, —OH, or H; $R_3$ is Me; $R_4$ and $R_6$ are each Me; $R_5$ and $R_7$ are each —OMe; $X_1$ and $X_4$ are each —OH; $R_8$ is hydrogen; and $X_2$ and $X_3$ are each —OMe.

18. A compound that has the structure:

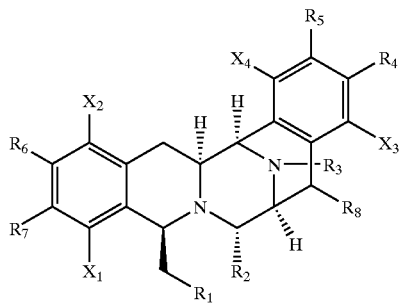

wherein:

$R_1$ is $NR_AR_B$ wherein $R_A$ is hydrogen or unsubstituted lower alkyl, $R_B$ is —$COR_C$ where $R_C$ is (heteroaliphatic)aryl, substituted heteroaryl, substituted (aliphatic)heteroaryl, or substituted (heteroaliphatic) heteroaryl moiety or $R_A$ and $R_B$, when taken together form cycloheteroaliphatic wherein:

the foregoing aliphatic or heteroaliphatic moieties in $R_1$ is unsubstituted;

the foregoing aryl moiety in $R_1$ may independently be unsubstituted or substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCF_3$, —$CHCl_2$, —$CH_2OH$, —$CH_2CH_2OH$, —$CH_2NH_2$, —$CH_2SO_2CH_3$, —$C(O)R_x$, —$CO_2(R_x)$, —$CON(R_x)_2$, —$OC(O)R_x$, —$OCO_2R_x$, —$OCON(R_x)_2$, —$N(R_x)_2$, —$S(O)_2R_x$, —$NR_x(CO)R_x$, or —$B(OR_x)_2$ wherein each occurrence of $R_x$ independently is aliphatic, heteroaliphatic, aryl, heteroaryl, alkylaryl, or alkylheteroaryl where each of the foregoing aliphatic, heteroaliphatic, unsubstituted aryl, heteroaryl, alkylaryl, alkylheteroaryl, alkylaryl, alkylheteroaryl, aryloxy, heteroaryloxy, arylthio, and heteroarylthio is unsubstituted; and the foregoing heteroaryl moieties in $R_1$ is substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCl_2$, —$CH_2OH$, —$CH_2CH_2OH$, —$CH_2NH_2$, —$CH_2SO_2CH_2$, —$C(O)R_x$, —$CO_2(R_x)$, —$CON(R_x)_2$, —$OC(O)R_x$, —$OCO_2R_x$, —$OCON(R_x)_2$, —$N(R_x)_2$, —$S(O)_2R_x$, —$NR_x(CO)R_x$, or —$B(OR_x)_2$ wherein each occurrence of wherein each occurrence of $R_x$ independently is aliphatic, heteroaliphatic, aryl, heteroaryl, alkylaryl, or alkylheteroaryl, where each of the foregoing aliphatic, heteroaliphatic, aryl, heteroaryl, alkylaryl, alkylheteroaryl, aryloxy, heteroaryloxy, arylthio, and heteroarylthio is unsubstituted;

$R_2$ is —CN, —SCN, OH, H, or alkoxy;

$R_3$ is hydrogen, aliphatic, or aryl;

$R_4$ and $R_6$ are each alkyl;

$R_5$ and $R_7$ are each alkyloxy or thioalkyl;

$R_8$ is hydrogen, alkyl, —OH, =O, CN, halogen, SH, alkoxy, thioalkyl, amino, or alkylamino;

$X_1$ and $X_4$ are each OH; and $X_2$ and $X_3$ are each alkoxy or thioalkyl; and wherein:

each of foregoing alkoxy, alkylthio, thioalkyl, or alkylamino contains unsubstituted alkyl of 1 to 10 carbon atoms;

each of the foregoing aliphatic moiety is cyclic, acyclic, branched or unbranched alkyl, alkenyl, or alkynyl containing 1 to 10 carbon atoms;

each of the foregoing heteroaliphatic moiety is cyclic, acyclic, branched or unbranched alkyl, alkenyl, or alkynyl containing 1 to 10 carbon atoms and which further contains one or more oxygen, sulfur, nitrogen, phosphorus or silicon atoms in place of the carbon atoms;

each of the foregoing cycloheteroaliphatic moiety is a cyclic heteroaliphatic;

each of the foregoing aryl is monocyclic or bicyclic carbocyclic ring system having one or two aromatic ring;

each of the foregoing heteroaryl is a cyclic aromatic radical having from five to ten ring atoms of which one ring atom is selected from S, O, and N; zero or two ring atoms are additional heteroatoms independently selected from S, O, and N; and the remaining ring atoms are carbon; and pharmaceutically acceptable salts thereof.

19. The compound of claim 18, wherein $R_2$ is —CN, —OH, or H; $R_3$ is Me; $R_4$ and $R_6$ are each Me; $R_5$ and $R_7$ are each OMe; $X_1$ and $X_4$ are each —OH; $R_8$ is hydrogen; and $X_2$ and $X_3$ are each OMe.

20. A compound that has the structure:

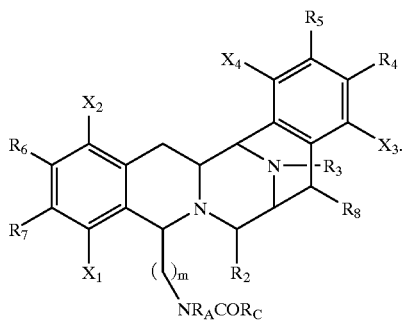

wherein:

$R_A$ is hydrogen or lower alkyl;

$R_C$ is:

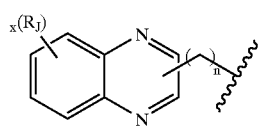   iii

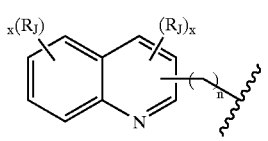   iv

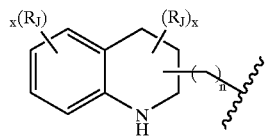   v

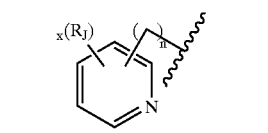   vii

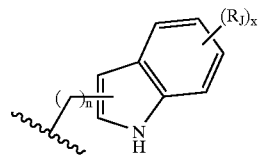   ix

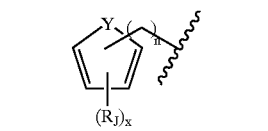   x

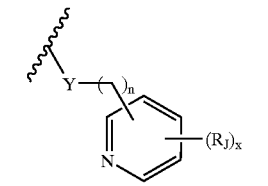   xi

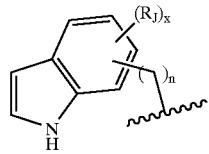   xii

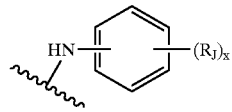   xiii

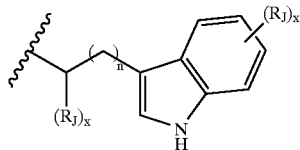   xiv

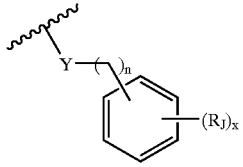   xv

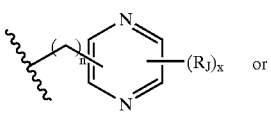   or   xvii

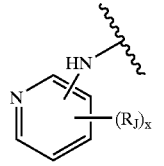   xviii wherein each occurrence of $R_J$ is independently —$OR_K$, —$C(=O)R_K$, —$CO_2R_K$, —CN, —SCN, halogen, —$SR_K$, —$SOR_K$, —$SO_2R_K$, —$NO_2$, —$N(R_K)_2$, —$NHC(O)R_K$, —$B(OR_K)_2$, or an aliphatic, heteroaliphatic, aryl, or heteroaryl moiety, wherein each occurrence of $R_K$ is independently hydrogen, or an aliphatic, heteroaliphatic, aryl, or heteroaryl moiety, or wherein two occurrences of $R_K$, taken together form a cyclic aliphatic or heteroaliphatic moiety; wherein each occurrence of Y is independently O, S or NH; wherein each occurrence of x is independently 1–5; and wherein each occurrence of n is independently 0–3 wherein:

the foregoing aliphatic or heteroaliphatic is unsubstituted and each of the foregoing aryl or heteroaryl moieties may independently be unsubstituted or substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCF_3$, —$CHCl_2$, —$CH_2OH$, —$CH_2CH_2OH$, —$CH_2NH_2$, —$CH_2SO_2CH_3$, —$C(O)R_x$, —$CO_2(R_x)$, —$CON(R_x)_2$, —$OC(O)R_x$, —$OCO_2R_x$, —$OCON(R_x)_2$, —$N(R_x)_2$, —$S(O)_2R_x$, —$NR_x(CO)R_x$, or —$B(OR_x)_2$ wherein each occurrence of wherein each occurrence of $R_x$ independently is aliphatic, heteroaliphatic, aryl, heteroaryl, alkylaryl, or alkylheteroaryl where each of the foregoing aliphatic, heteroaliphatic, heteroaryl, alkylaryl, alkylheteroaryl, aryloxy, heteroaryloxy, arylthio, and heteroarylthio is unsubstituted; and wherein:

each of the foregoing aliphatic moiety is cyclic, acyclic, branched or unbranched alkyl, alkenyl, or alkynyl containing 1 to 10 carbon atoms;

each of the foregoing heteroaliphatic moiety is cyclic, acyclic, branched or unbranched alkyl, alkenyl, or alkynyl containing 1 to 10 carbon atoms and which further contains one or more oxygen, sulfur, nitrogen, phosphorus or silicon atoms in place of the carbon atoms;

each of the foregoing aryl is monocyclic or bicyclic carbocyclic ring system having one or two aromatic ring;

each of the foregoing heteroaryl is a cyclic aromatic radical having from five to ten ring atoms of which one ring atom is selected from S, O, and N; zero or two ring atoms are additional heteroatoms independently selected from S, O, and N; and the remaining ring atoms are carbon; and pharmaceutically acceptable salts.

21. The compound of claim 20, wherein $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, and $R_8$ is H.

22. The compound of claim 21 wherein $R_C$ is:

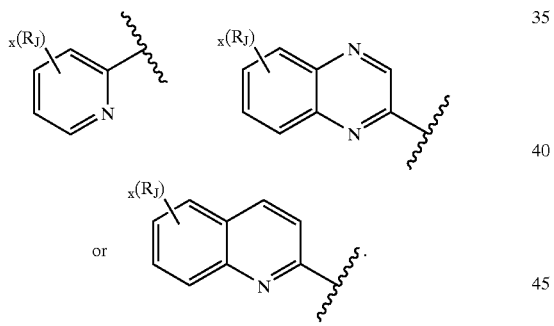

wherein $R_j$ is hydrogen, halogen, —OH, lower alkyl or lower alkoxy and x is 1 or 2.

23. A compound that has the structure:

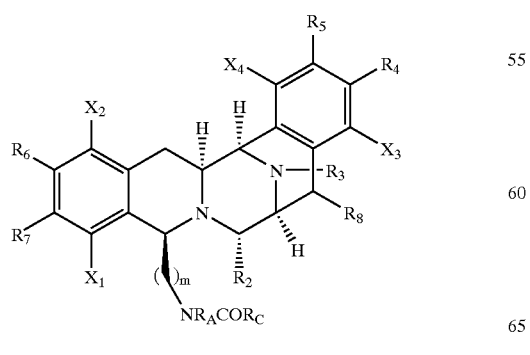

wherein:

$R_A$ is hydrogen or lower alkyl;

$R_C$ is:

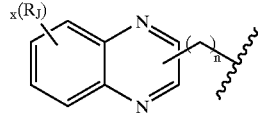   iii

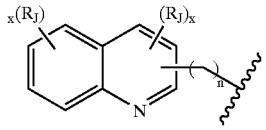   iv

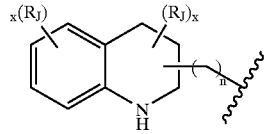   v

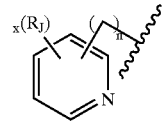   vii

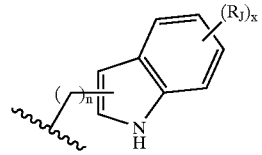   ix

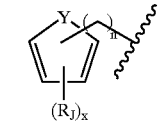   x

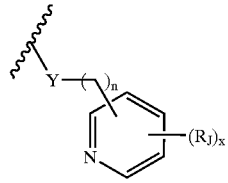   xi

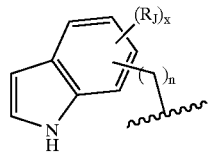   xii

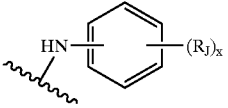   xiii

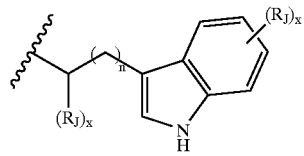   xiv

-continued

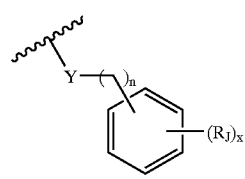
xv

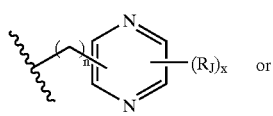
xvii or

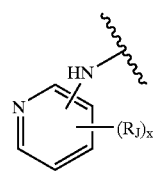
xviii wherein each occurrence of $R_J$ is independently —$OR_K$, —C(=O)$R_K$, —$CO_2R_K$, —CN, —SCN, halogen, —$SR_K$, —$SOR_K$, —$SO_2R_K$, —$NO_2$, —$N(R_K)_2$, —NHC(O)$R_K$, —B(O$R_K$)$_2$, or an aliphatic, heteroaliphatic, aryl, or heteroaryl moiety, wherein each occurrence of $R_K$ is independently hydrogen, or an aliphatic, heteroaliphatic, aryl, or heteroaryl moiety, or wherein two occurrences of $R_K$, taken together form a cyclic aliphatic or heteroaliphatic moiety; wherein each occurrence of Y is independently O, S or NH; wherein each occurrence of x is independently 1–5; and wherein each occurrence of n is independently 0–3 wherein:

the foregoing aliphatic or heteroaliphatic is unsubstituted and each of the foregoing aryl or heteroaryl moieties may independently be unsubstituted or substituted with one, two or three substitutents independently selected from aliphatic, heteroaliphatic, aryl, heteroaryl, alkylaryl, alkylheteroaryl, alkoxy, aryloxy, heteroaryloxy, alkylthio, arylthio, heteroarylthio, F, Cl, Br, I, —OH, —$NO_2$, —CN, —SCN, —$CF_3$, —$CHCF_3$, —$CHCl_2$, —$CH_2OH$, —$CH_2CH_2OH$, —$CH_2NH_2$, —$CH_2SO_2CH_3$, —C(O)$R_x$, —$CO_2(R_x)$, —CON($R_x$)$_2$, —OC(O)$R_x$, —$OCO_2R_x$, —OCON($R_x$)$_2$, —N($R_x$)$_2$, —S(O)$_2R_x$, —$NR_x$ (CO)$R_x$, or —B(O$R_x$)$_2$ wherein each occurrence of wherein each occurrence of $R_x$ independently is aliphatic, heteroaliphatic, aryl, heteroaryl, alkylaryl, or alkylheteroaryl where each of the foregoing aliphatic, heteroaliphatic, heteroaryl, alkylaryl, alkylheteroaryl, aryloxy, heteroaryloxy, arylthio, and heteroarylthio is unsubstituted; and wherein:

each of the foregoing aliphatic moiety is cyclic, acyclic, branched or unbranched alkyl, alkenyl, or alkynyl containing 1 to 10 carbon atoms;

each of the foregoing heteroaliphatic moiety is cyclic, acyclic, branched or unbranched alkyl, alkenyl, or alkynyl containing 1 to 10 carbon atoms and which further contains one or more oxygen, sulfur, nitrogen, phosphorus or silicon atoms in place of the carbon atoms;

each of the foregoing aryl is monocyclic or bicyclic carbocyclic ring system having one or two aromatic ring;

each of the foregoing heteroaryl is a cyclic aromatic radical having from five to ten ring atoms of which one ring atom is selected from S, O, and N; zero or two ring atoms are additional heteroatoms independently selected from S, O, and N; and the remaining ring atoms are carbon; and pharmaceutically acceptable salts.

24. The compound of claim 23, wherein $X_1$ is OH, $X_2$ is $OCH_3$, $X_3$ is $OCH_3$, $X_4$ is OH, $R_2$ is CN, H or OH, $R_3$ is Me, $R_4$ is $CH_3$, $R_5$ is $OCH_3$, $R_6$ is $CH_3$, $R_7$ is $OCH_3$, and $R_8$ is H.

25. The compound of claim 24, wherein $R_C$ is:

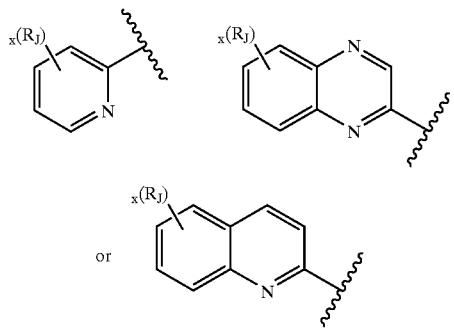

or wherein $R_J$ is hydrogen, halogen, —OH, lower alkyl or lower alkoxy and x is 1 or 2.

26. A compound selected from the group consisting of:

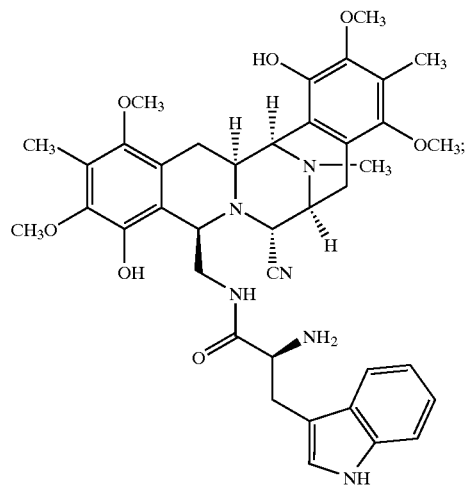

181
-continued
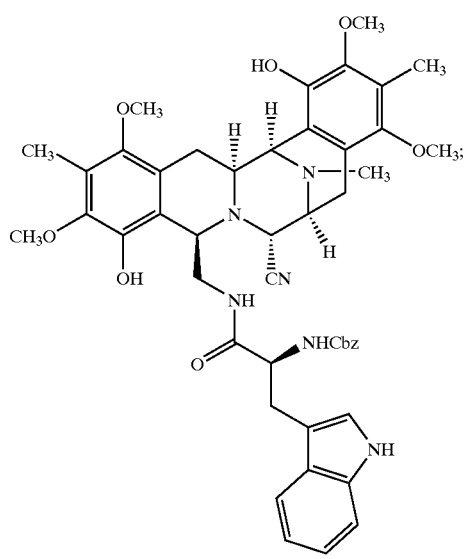
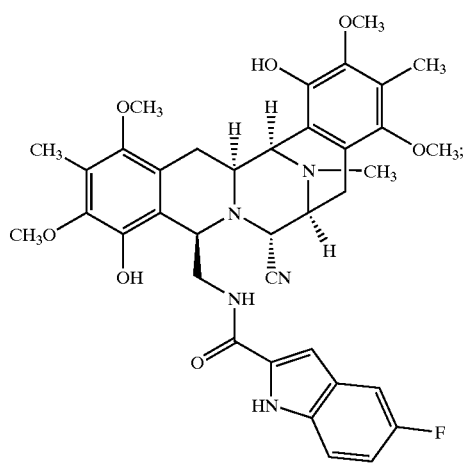
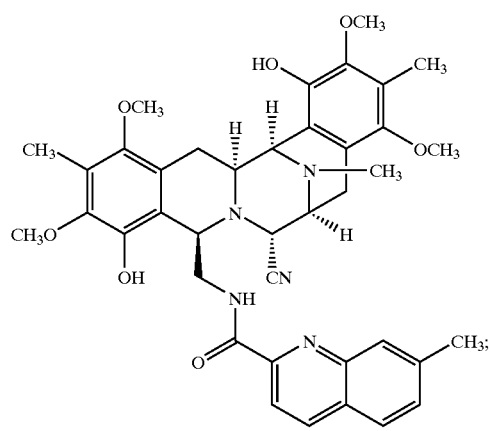
182
-continued
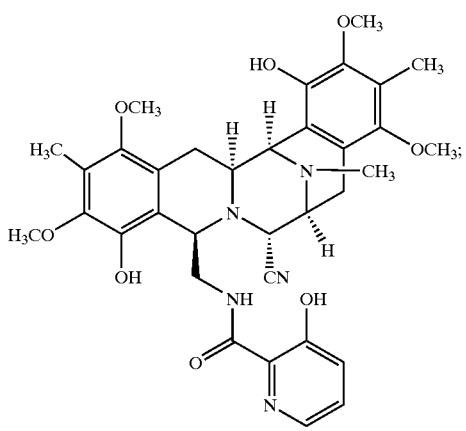
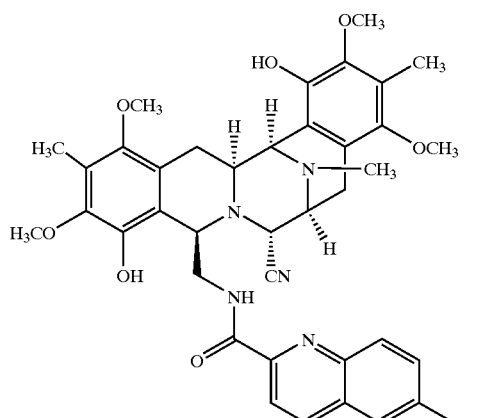
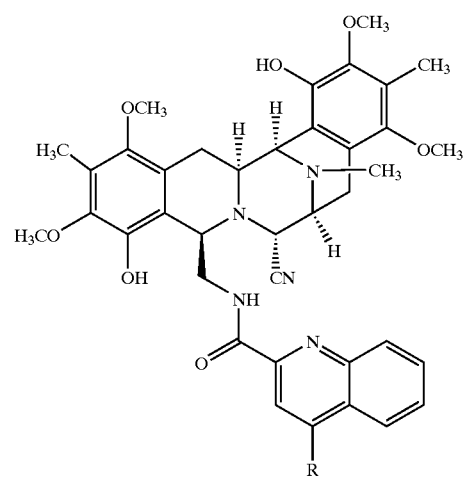
R = H, OH, OCH₃, or CH₃;

-continued
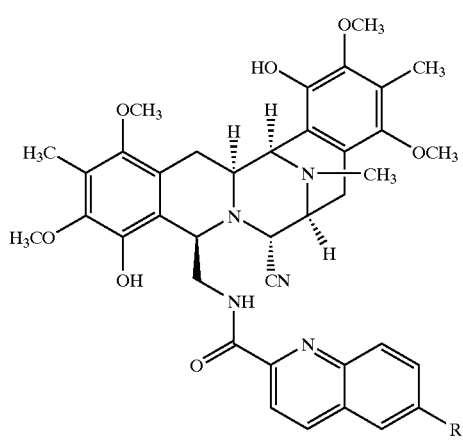
R = OH, OBu, CH₃, OCH₃, or Cl;
-continued
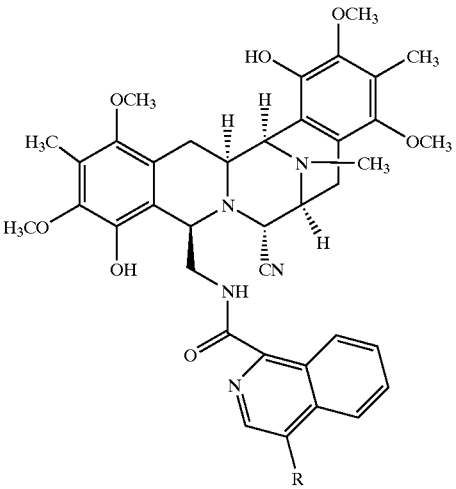
R = H or Br;
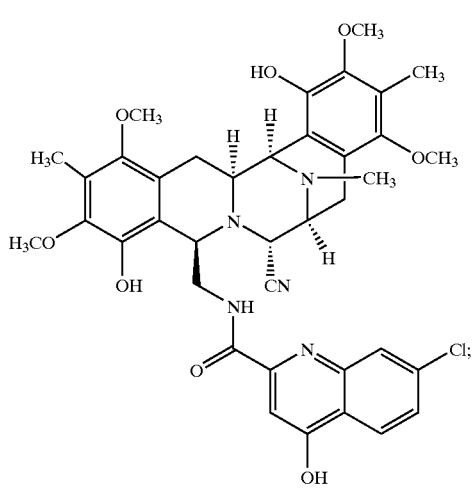
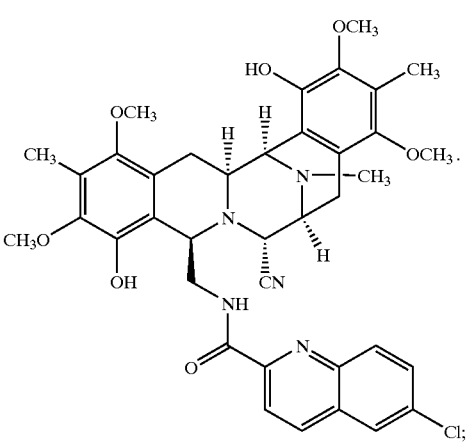
and
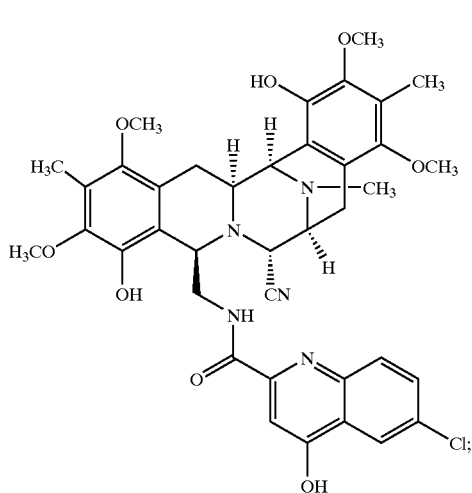
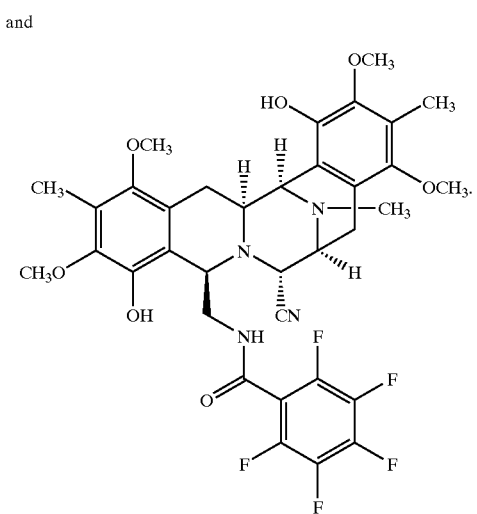

27. A compound selected from the group consisting of:
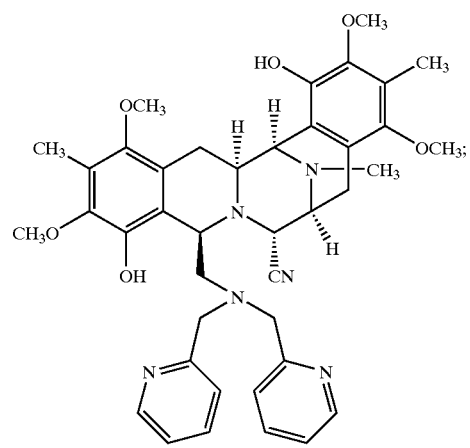
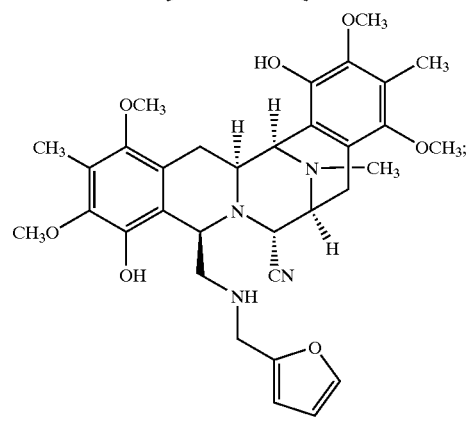
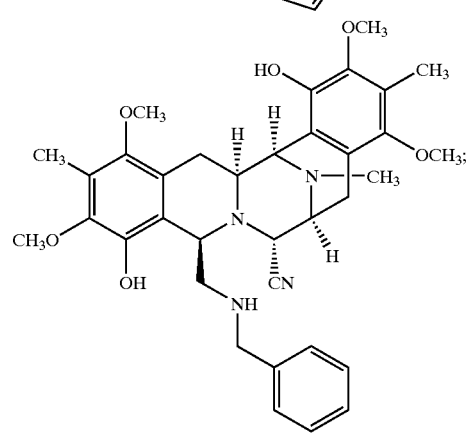
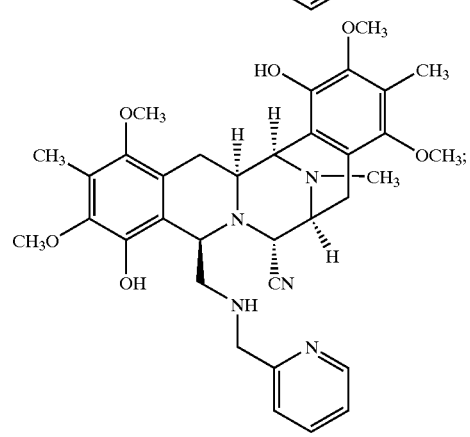
-continued
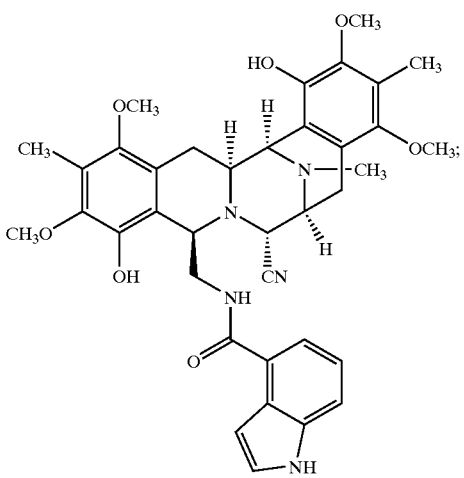
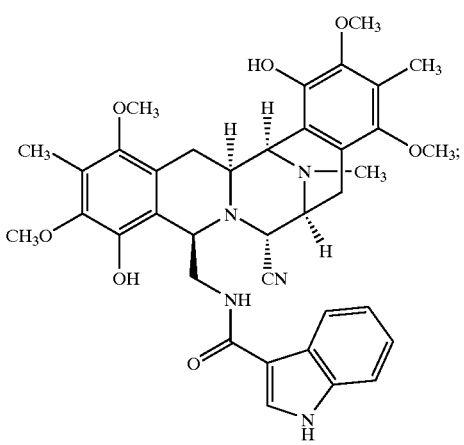
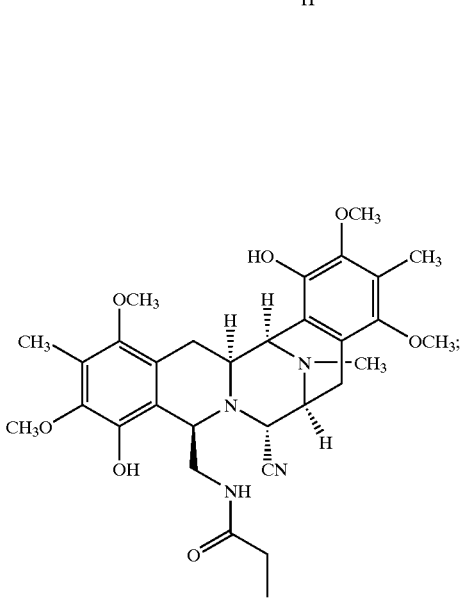

187
-continued
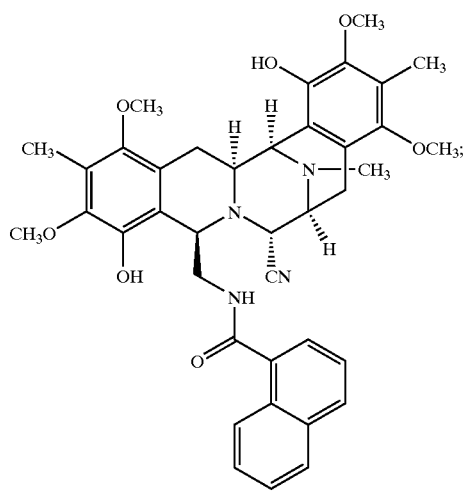
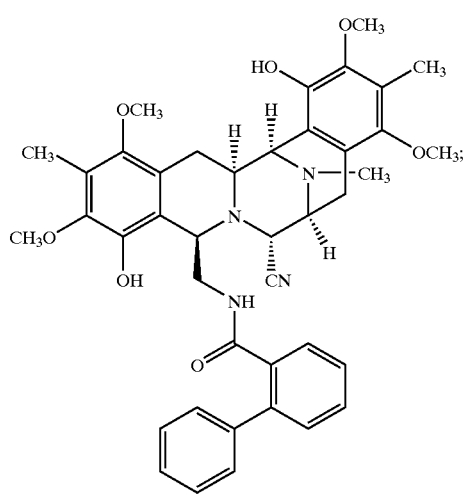
188
-continued
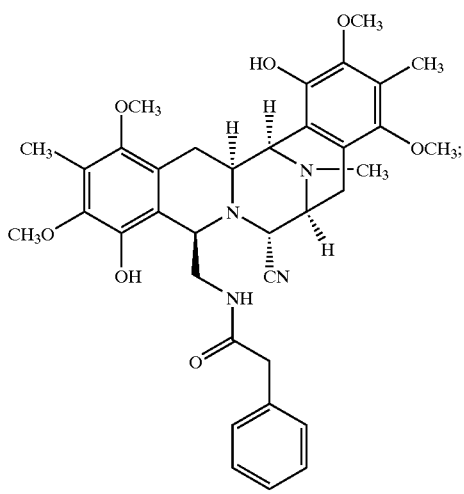
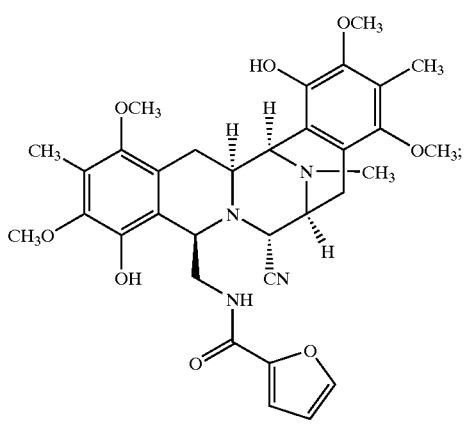

189
-continued
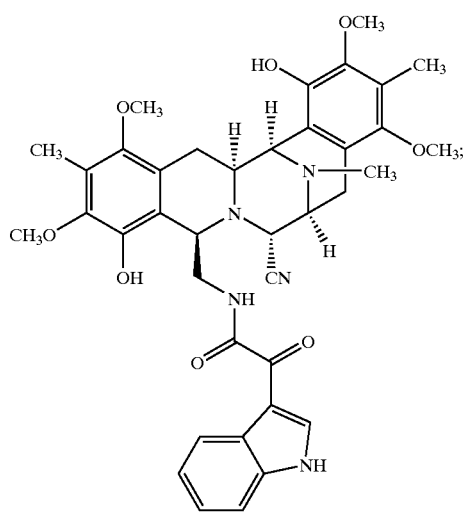
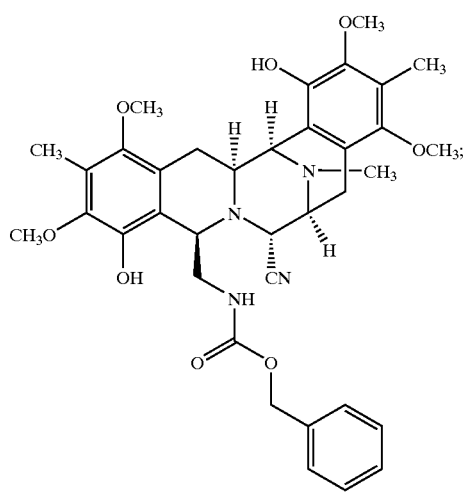
190
-continued
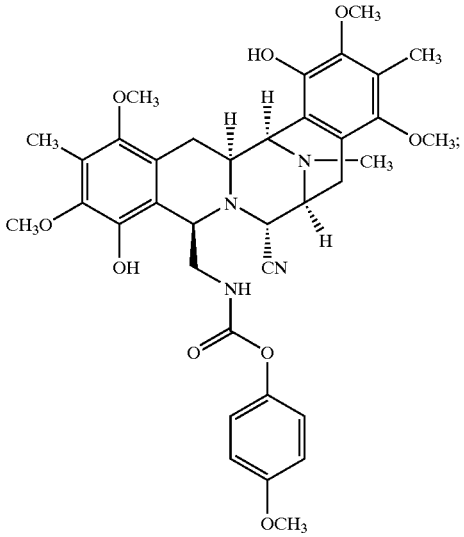
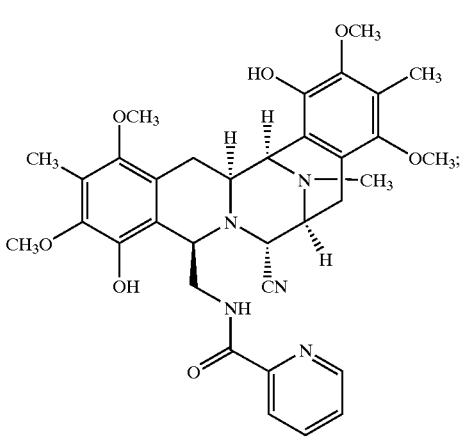
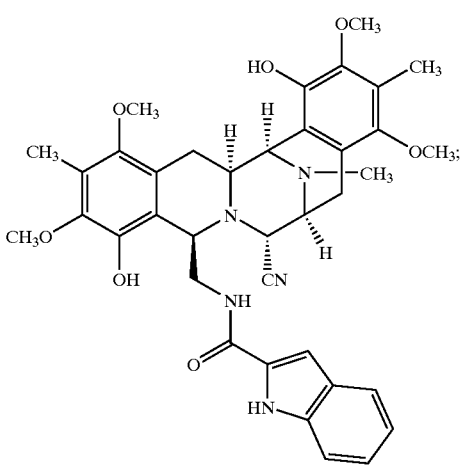

-continued

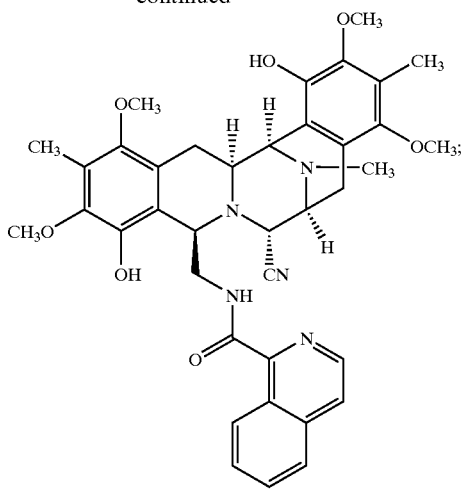

and

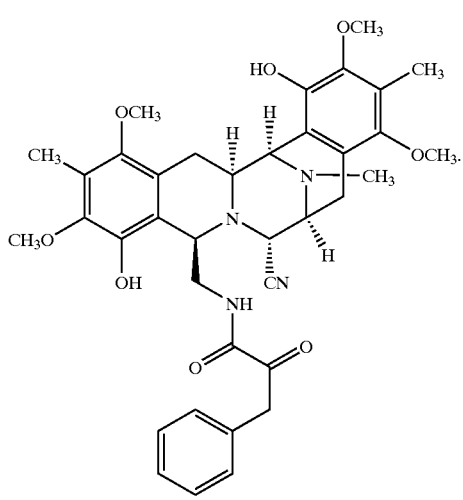

28. A pharmaceutical composition comprising a compound of any one of the claims 1–3, 7, 8, 10, 12, 13, 16, 18, 20, and 23.

29. A method for inhibiting the growth of or killing cancer cells comprising contacting the cells with an amount of a composition effective to inhibit the growth of or to kill cancer cells, the composition comprising a compound of any one of the claims 1–3, 7, 8, 10, 12, 13, 16, 18, 20, and 23.

30. The method of claim 29, wherein the cancer cells comprise melanoma cancer cells or lung cancer cells.

31. A method for treating cancer comprising:

administering to a subject in need thereof a therapeutically effective amount of a composition comprising a compound of any one of the claims 1–3, 7, 8, 10, 12, 13, 16, 18, 20, and 23.

32. The method of claim 31 wherein said composition comprises one or more cytotoxic agents.

33. The method of claim 31, wherein the cancer cells comprise melanoma cancer cells or lung cancer cells.

* * * * *

UNITED STATES PATENT AND TRADEMARK OFFICE
CERTIFICATE OF CORRECTION

PATENT NO. : 6,809,099 B2
DATED : October 26, 2004
INVENTOR(S) : Myers et al.

It is certified that error appears in the above-identified patent and that said Letters Patent is hereby corrected as shown below:

Title page,
Item [75], Inventors, please replace "Andrew G. Myers, Boston, MA (US); Alleyn T. Plowright, Didsbury, (GB); Daniel W. Kung, Salem, CT (US); Brian Lanman, Cambrige, MA (US)" with -- Andrew G. Myers, Boston, MA (US); Alleyn T. Plowright, Didsbury, (GB) --

Signed and Sealed this

Fifteenth Day of February, 2005

JON W. DUDAS
*Director of the United States Patent and Trademark Office*